United States Patent
Vankayalapati et al.

(10) Patent No.: US 11,407,729 B2
(45) Date of Patent: Aug. 9, 2022

(54) QUINOLINE AND QUINAZOLINE COMPOUNDS AND METHODS OF USE THEREOF

(71) Applicant: Stingray Therapeutics, Inc., Houston, TX (US)

(72) Inventors: Hariprasad Vankayalapati, Draper, UT (US); Sunil Sharma, Phoenix, AZ (US); Mohan Rao Kaadige, Scottsdale, AZ (US); Alexis Weston, Phoenix, AZ (US)

(73) Assignee: STINGRAY THERAPEUTICS, INC., Houston, TX (US)

( * ) Notice: Subject to any disclaimer, the term of this patent is extended or adjusted under 35 U.S.C. 154(b) by 0 days.

(21) Appl. No.: 16/821,098

(22) Filed: Mar. 17, 2020

(65) Prior Publication Data

US 2020/0299258 A1    Sep. 24, 2020

Related U.S. Application Data

(60) Provisional application No. 62/820,672, filed on Mar. 19, 2019.

(51) Int. Cl.
*C07D 401/04* (2006.01)
*C07D 413/14* (2006.01)
*A61P 35/00* (2006.01)
*C07D 401/14* (2006.01)

(52) U.S. Cl.
CPC ........ *C07D 401/04* (2013.01); *C07D 401/14* (2013.01); *C07D 413/14* (2013.01)

(58) Field of Classification Search
CPC ...... C07D 401/04; C07D 413/14; A61P 35/00
See application file for complete search history.

(56) References Cited

FOREIGN PATENT DOCUMENTS

WO    WO-2019046778 A1 *  3/2019  ........... C07D 471/04

OTHER PUBLICATIONS

Jackson et al. Hypertension, 2017, vol. 69, No. 3, pp. 484-493.*

* cited by examiner

*Primary Examiner* — Samira J Jean-Louis
(74) *Attorney, Agent, or Firm* — Wood, Phillips, Katz, Clark & Mortimer

(57) ABSTRACT

Compounds and methods for their preparation and use as therapeutic or prophylactic agents, for example for treatment of cancer, bacterial or viral diseases by targeting Ectonucleotide Pyrophosphatase/Phosphodiesterase-1 (ENPP1).

3 Claims, No Drawings

QUINOLINE AND QUINAZOLINE COMPOUNDS AND METHODS OF USE THEREOF

FIELD OF THE INVENTION

The present invention generally relates to the substituted quinolin and quinazoline derivatives as inhibitors of ENPP1. The invention is directed to pharmaceutical compositions containing the Formula 1 compounds and methods of using the compounds or compositions to treat various types of human cancers where the ENPP1 is overexpressed, cardiovascular, diabetes, obesity, antiviral, antibacterial and anti-fibrotic therapeutics. The invention is also directed to methods of making the compounds and its pharmaceuticals salts.

BACKGROUND OF THE INVENTION

Ectonucleotide Pyrophophatase/Phosphodiesterase (ENPP) family members include seven isoforms, ENPP1-7, which are type II transmembrane glycoproteins or ectoenzymes. Mass spectrometry and proteomics analysis from more than 370 protein targets led to the identification of an extracellular protein ENPP1 as one of the top hit which exhibited high hydrolytic activity. ATP is an identified substrate of ENPP1, which is hydrolyzed to AMP and PPi. CD73 converts AMP to adenosine and inorganic phosphate (Pi). The kinetic experimental data indicates that the ENPP1 is capable of hydrolyzing ATP. These ectonucleotide enzymes are involved in the hydrolysis of pyrophosphate (PPi) and phosphodiester bonds in extracellular nucleotides; such as triphosphates, oligonucleotides and that generates nucleoside 5'-monophosphates. One of the key isoforms, ENPP1 (Plasma cell membrane glycoprotein-1, PC-1), is involved in a number of physiological processes, such as development, formation and trafficking, as well as in pathophysiological conditions. Aberrant ENPP1 expression has been detected in breast cancers relative to normal mammary epithelium, an evidence of its potential in the development of bone metastasis (occurs in approximately 80% cases), Hodgkin's lymphoma, hepatocellular carcinoma, follicular lymphoma, glioblastoma and in other malignant tumor tissues.

Recent reports suggest that the cyclic dinucleotides (CDNs), a substrate for ENPP1, stimulate innate immunity via STING-dependent activation of interferon genes. ENPP1 inhibition of STING pathway activation is critical for tumor control, similar to that of checkpoint inhibitors such as anti PD-1 or PD-L1 which are promising immunotherapeutics for various cancers. In addition, mutations in ENPP1 were associated with several disorders including infantile arterial calcification (generalized arterial calcification of infancy or GACI), ossification of the posterior longitudinal ligament of the spine and insulin signaling and resistance. ENPP1 expression is high in bone and cartilage and is implicated in lung and kidney fibrosis. A correlation was also found between expression of ENPP1 and the grade of astrocytic tumor. Another study reported that ENPP1 was required to maintain the undifferentiated and proliferative state of glioblastoma stem-like cells. Therefore, ENPP1 is an attractive druggable target for the development of novel anticancer, cardiovascular, diabetes, obesity and anti-fibrotic therapeutics.

Importance of ENPP1 activity was further investigated from both direct binding assay and in vitro cellular efficacy on MDA-MB231 cells. The siRNA-based knock down of ENPP1 significantly reduced its catalytic activity both in cell specific and in vivo experiments. These experiments demonstrated that the ENPP1 activity was abolished on treatment with siRNA. This further supports the validity of this target in certain diseases. It has been shown recently that the bisphosphothionate analog of endogenous cGAMP is resistant to hydrolysis by ENPP1 phosphodiesterase, and particularly the cyclic dinucleotides (CDNs) are more potent at inducing IFN-β secretion in human THP1 cells by a mechanism of inhibiting the ENPP1 activity and simultaneous STING activation responses.

There is ample evidence that ENPP1 expression is prominent in human primary breast tumors relative to normal mammary epithelium, with highest levels observed in breast-bone metastasis. These data not only support a potential role for ENPP1 in breast-bone metastasis, but also support as a potential prognostic marker for breast cancer. These results from target validation experiments clearly support the pharmacological role of ENPP1 for the development of novel immunotherapeutics for cancers.

Furthermore, ENPP1 activity has also been implicated in diseases caused by bacteria and/or viruses, and therefore modulators of ENPP1 can be used to treat bacterial and/or viral diseases and conditions.

SUMMARY OF THE INVENTION

The invention, in one aspect, relates to compounds of Formula 1:

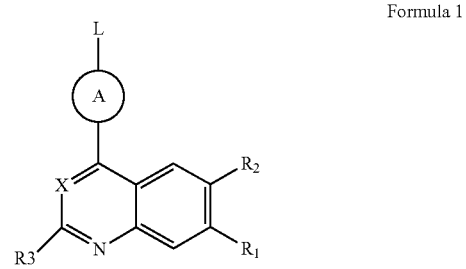

Formula 1 wherein

X is selected from the group consisting of —C and —N;

is selected from group consisting of

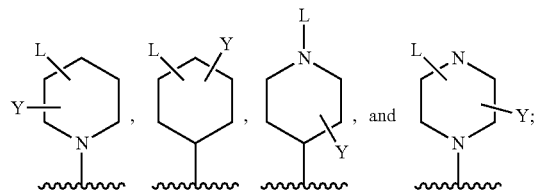

L is selected from the group consisting of

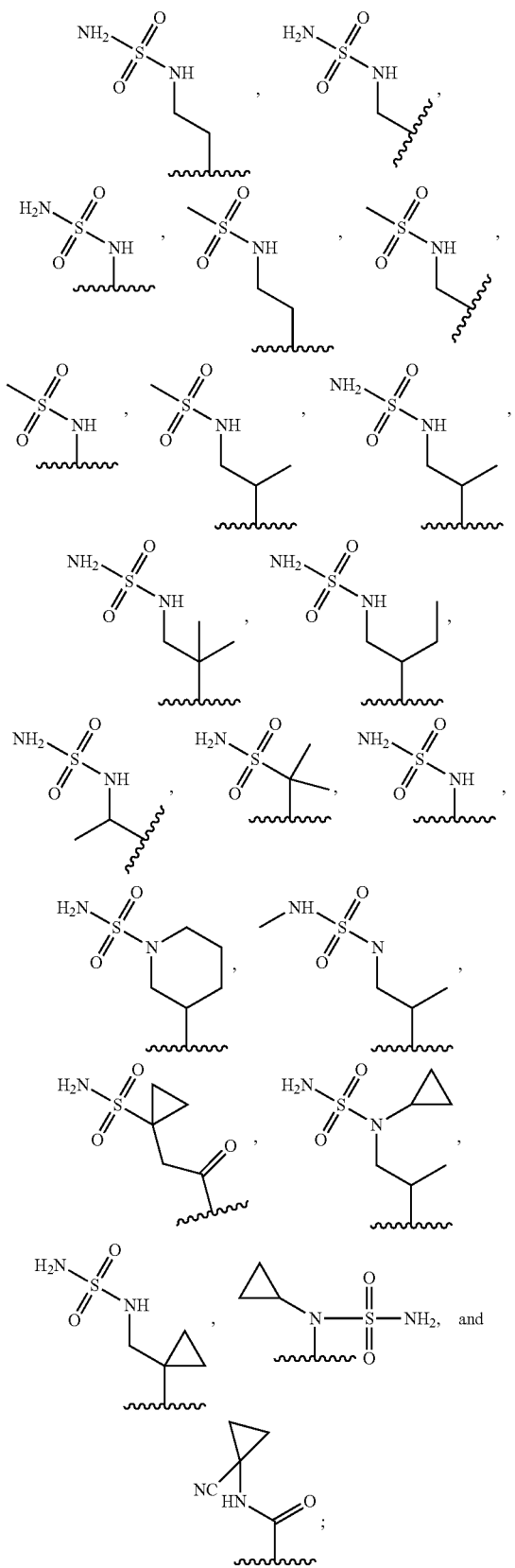

Y is selected from the group consisting of H and alkyl;
$R_1$ is selected from the group consisting of —H, alkyl, O-alkyl, —OCF$_3$, —OP═(O)(ONa)$_2$, and —CH$_2$OP═(OXONa)$_2$;
$R_2$ is selected from the group consisting of —H, alkyl, —Oalkyl, —OH, —OCF$_3$, —OCH$_2$CH$_2$OH, —OCH$_2$CH$_2$OCH$_3$, —OCH$_2$OCH$_3$, —OP—(O)(ONa)$_2$, —CH$_2$—OP═(OXONa)$_2$; and

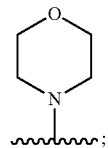

$R_3$ is selected from the group consisting of —H, —NH$_2$, and —CH$_3$;
or an isomer, hydrate, solvate, polymorph, tautomer or a pharmaceutically acceptable salt thereof.

In one preferred embodiment, $R_1$ is selected from the group consisting of —H, —CH$_3$, —OCH$_3$, —OCF$_3$, —OP—(O)(ONa)$_2$, and —CH$_2$OP═(O)(ONa)$_2$.

In one preferred embodiment, $R_1$ is OCH$_3$.

In another preferred embodiment, $R_2$ is selected from the group consisting of —H, —CH$_3$, —OCH$_3$, —OH, —OCF$_3$, —OCH$_2$CH$_2$OH, —OCH$_2$CH$_2$OCH$_3$, —OCH$_2$OCH$_3$, —OP═(O)(ONa)$_2$, —CH$_2$OP═(O)(ONa)$_2$, and

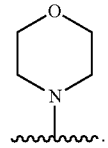

In another preferred embodiment, Y is selected from the group consisting of H and CH$_3$.
In one preferred embodiment, Y is H.
In one preferred embodiment,

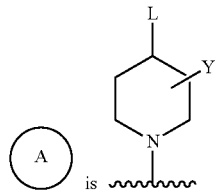

$R_1$ is OCH$_3$.
In one preferred embodiment,
X is N;

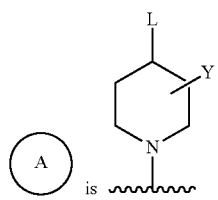

L is selected from the group consisting of

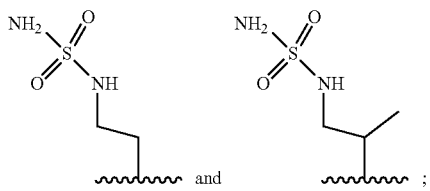

Y is H;
R₁ is selected from the group consisting of —H, —CH₃, and —OCH₃;
R₂ is selected from the group consisting of —H, —CH₃, —OCH₃, OP═(O)(ONa)₂, —CH₂—OP═(O)(ONa)₂, —OH, —OCH₂CH₂OH, —OCH₂CH₂OCH₃, —OCH₂OCH₃, and

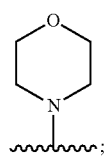

R₃ is selected from the group consisting of —H, —NH₂, and —CH₃.

In another preferred embodiment,
X is C;

is selected from the group consisting of

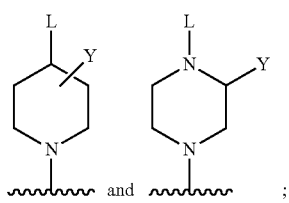

L is selected from the group consisting of

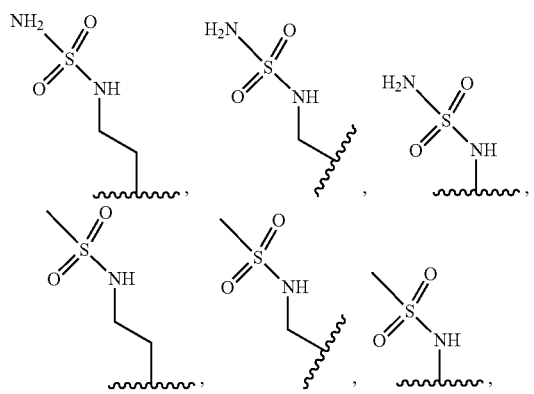

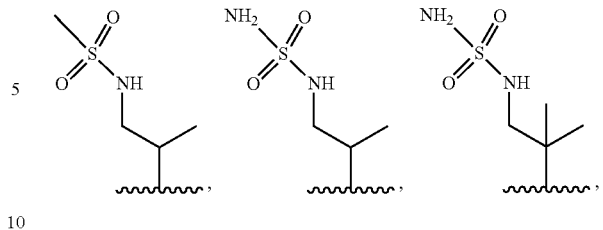

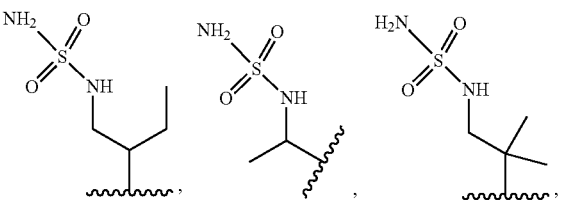

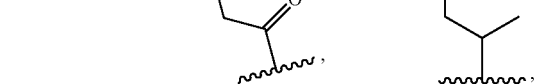

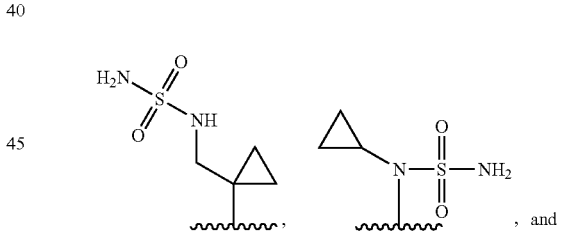

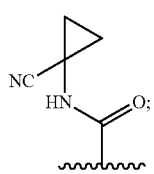

R₁ is selected from the group consisting of —H, —CH₃, and —OCH₃;
R₂ is selected from the group consisting of —H, —CH₃, —OCH₃, —OH, —OCF₃, —OCH₂CH₃, —OCH₂CH₂OH, —OCH₂CH₂OCH₃, —OP—(OXONa)₂, —CH₂OP(O)(ONa)₂; and
R₃ is selected from the group consisting of —H, —NH₂, and —CH₃.

Examples of the provided compounds include:
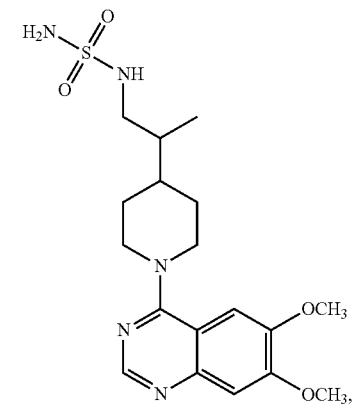
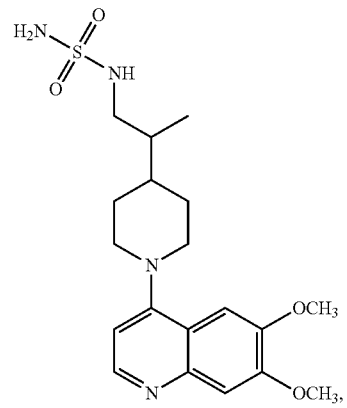
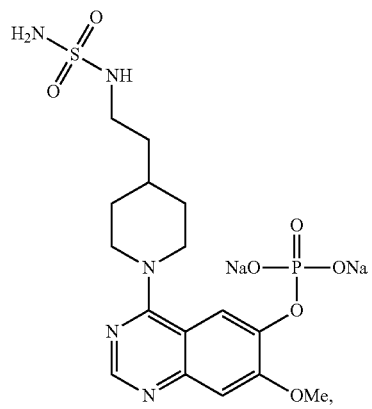
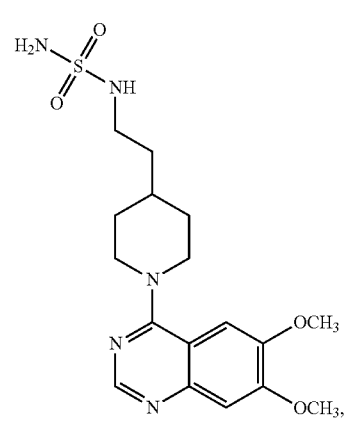
-continued
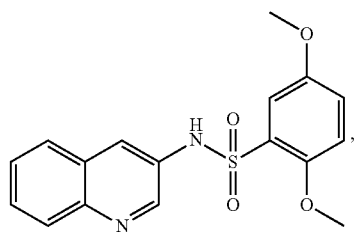
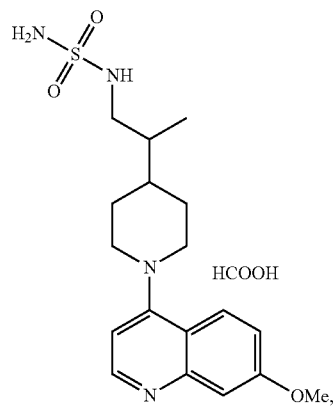
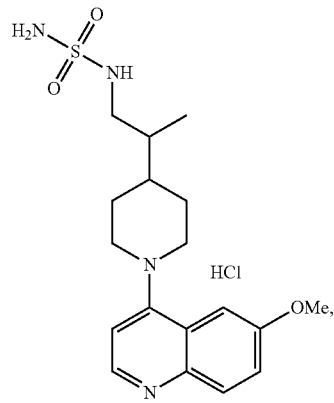
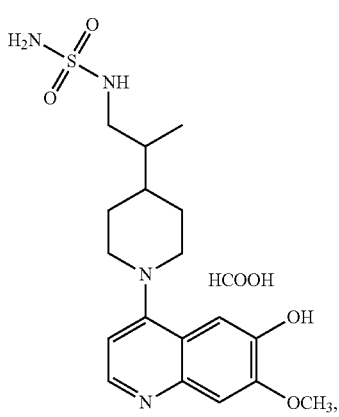

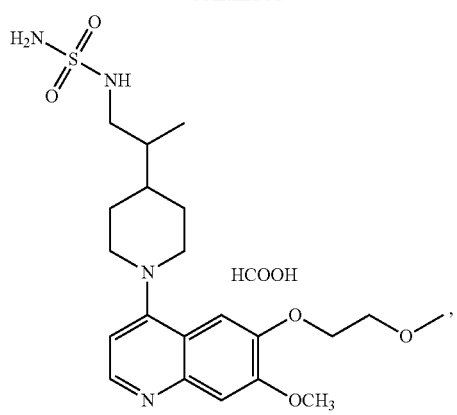
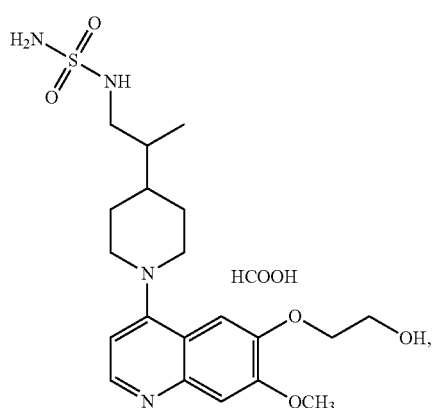
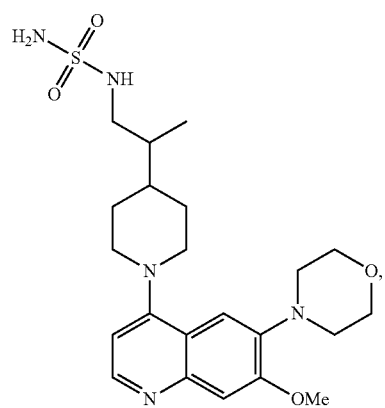
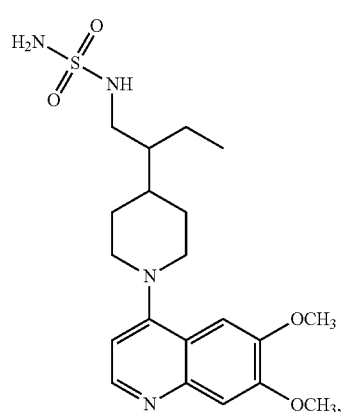
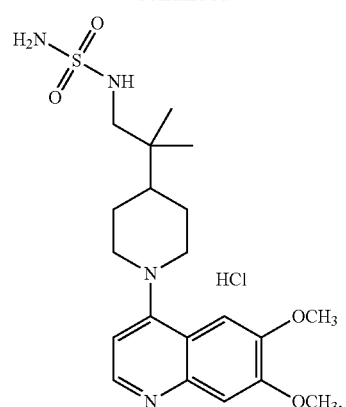
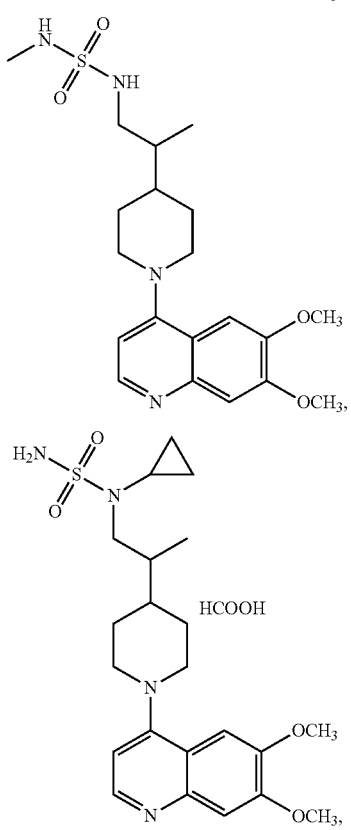
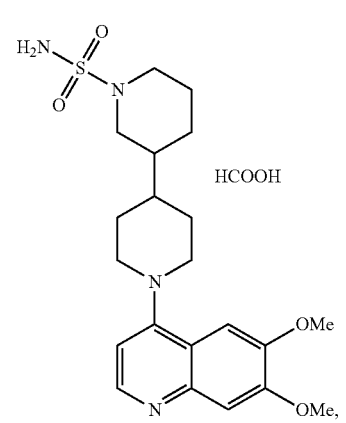

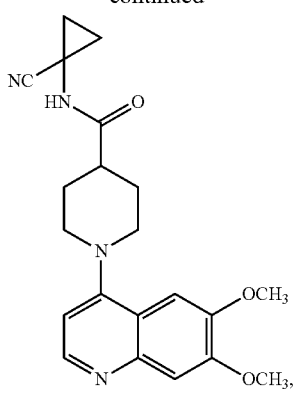
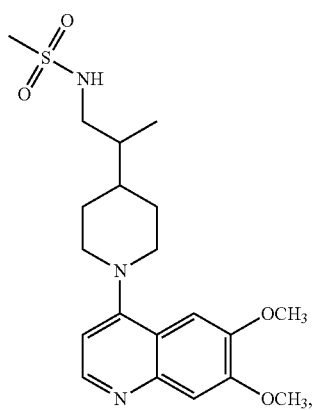
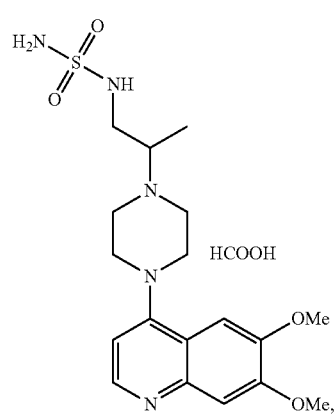
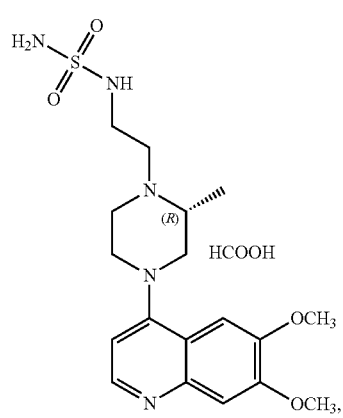
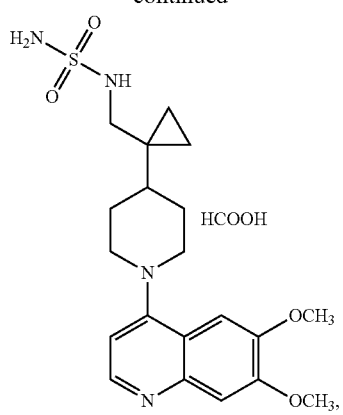
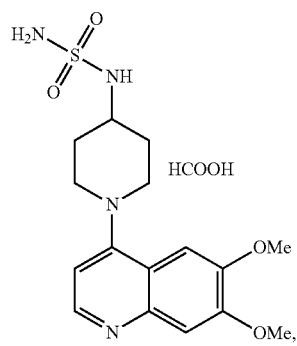
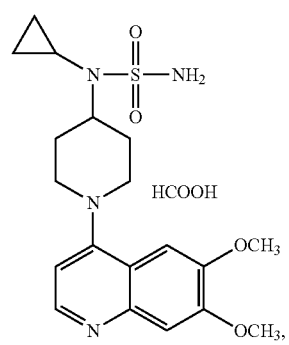
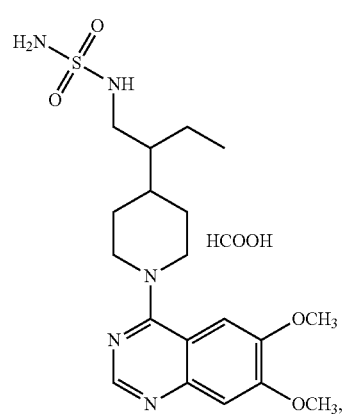

-continued
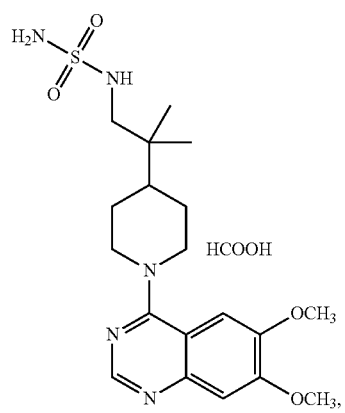
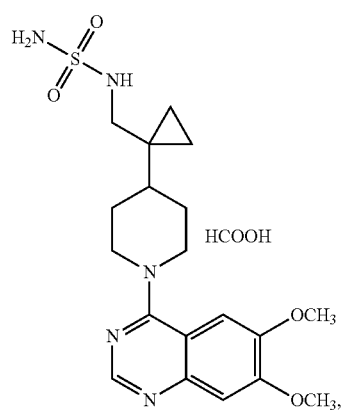
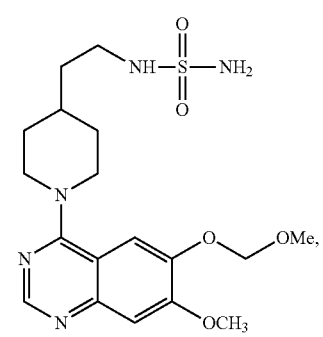
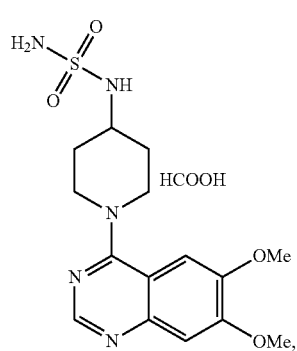
-continued
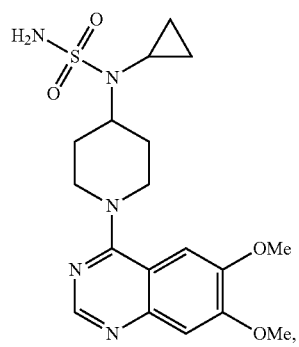
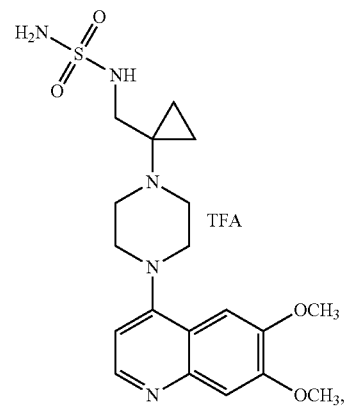
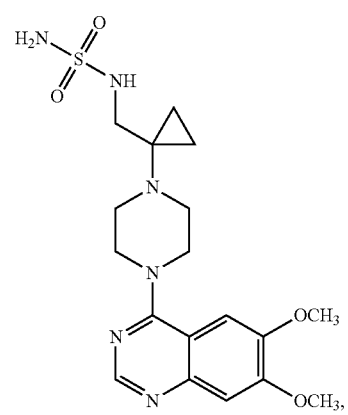
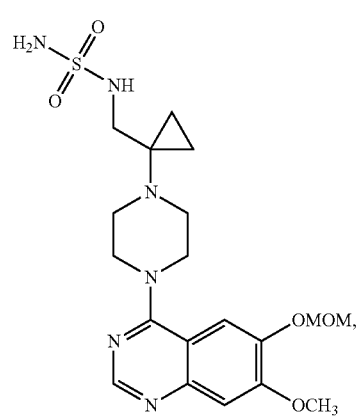

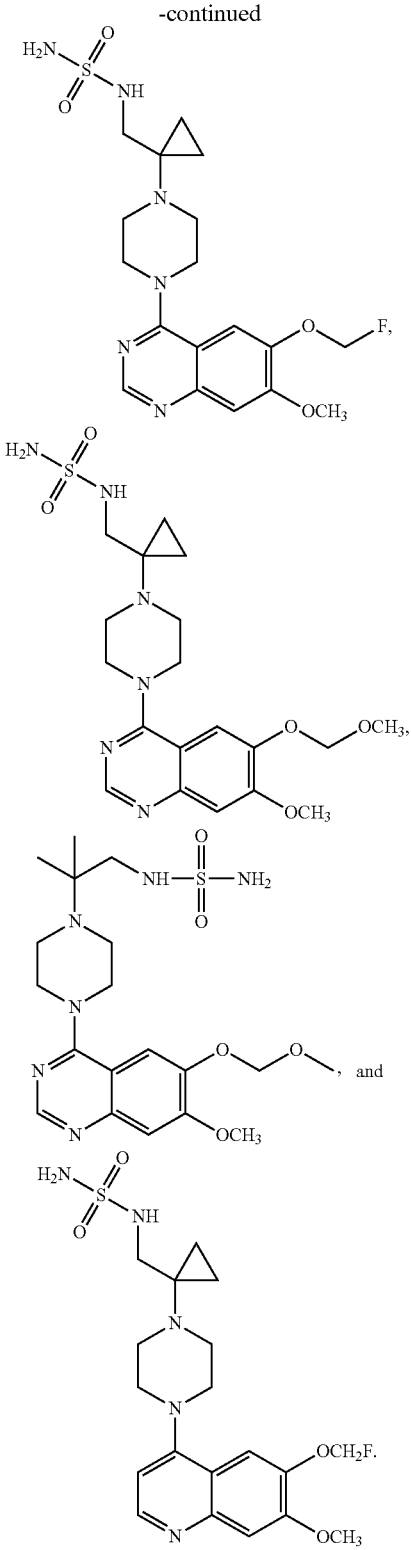

The invention also includes hydrates, solvates, polymorphs, isomers, tautomers of the compounds, pharmaceutically acceptable salts of the compounds and pharmaceutically acceptable salts of the tautomers.

The invention also provides pharmaceutical formulations, medicaments including the compounds, methods of preparing pharmaceuticals formulations, medicaments, compounds, and methods of treating patients with the provided pharmaceutical formulations and compounds.

The compounds of the invention were identified by structure-based, computational docking and binding free energies.

Also disclosed are pharmaceutical compositions comprising a therapeutically effective amount of a disclosed compound and a pharmaceutically acceptable carrier.

Also disclosed are synthetic methods for making the disclosed compounds. In a further aspect, disclosed are the products of the disclosed synthetic methods.

Also disclosed are methods for the treatment of a disorder associated with an ENPP1 activity dysfunction in a mammal comprising the step of administering to the mammal a therapeutically effective amount of a disclosed compound, or a pharmaceutically acceptable salt, tautomer, isomer, hydrate, solvate, or polymorph thereof.

Also disclosed are methods for inhibition of ENPP1 activity in a mammal comprising the step of administering to the mammal a therapeutically effective amount of least one disclosed compound, or a pharmaceutically acceptable salt, tautomer, isomer, hydrate, solvate, or polymorph thereof.

Also disclosed are methods for inhibiting ENPP1 activity in at least one cell, comprising the step of contacting the at least one cell with an effective amount of least one disclosed compound, or a pharmaceutically acceptable salt, tautomer, isomer, hydrate, solvate, or polymorph thereof.

Also disclosed are methods for treating a disorder associated with an ENPP1 activity dysfunction in a mammal through eliciting an immunotherapeutic response in the mammal, comprising administering to the mammal a therapeutically effective amount of a disclosed compound, or a pharmaceutically acceptable salt, tautomer, isomer, hydrate, solvate, or polymorph thereof, wherein this compound causes an immunotherapeutic response beneficial in the treatment of the disorder associated with an ENPP1 activity. Such disorder can be, but is not limited to, any type of cancer or any disease caused by bacteria and/or viruses wherein ENPP1 activity has been implicated.

Also disclosed are pharmaceutical compositions comprising a pharmaceutically acceptable carrier and an effective amount of a disclosed compound, or a pharmaceutically acceptable salt, tautomer, isomer, hydrate, solvate, or polymorph thereof.

Also disclosed are kits comprising at least one disclosed compound, or a pharmaceutically acceptable salt, tautomer, isomer, hydrate, solvate, or polymorph thereof.

Also disclosed are methods for manufacturing a medicament comprising, combining at least one disclosed compound or at least one disclosed product with a pharmaceutically acceptable carrier or diluent. In a further aspect, the invention relates to the use of a disclosed compound in the manufacture of a medicament for the treatment of a disorder associated with an ENPP1 activity dysfunction. In a further aspect, the invention relates to the uses of disclosed compounds in the manufacture of a medicament for the treatment of a disorder of uncontrolled cellular proliferation.

Also disclosed are uses of a disclosed compound or a disclosed product in the manufacture of a medicament for the treatment of a disorder associated with an ENPP1 dysfunction in a mammal.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

DETAILED DESCRIPTION OF THE INVENTION

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as ChemDraw™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the term "ENPP1" refers to Ectonucleotide Pyrophophatase/Phosphodiesterase.

As used herein, the terms "optional" or "optionally" means that the subsequently described event or circumstance can or can not occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of a disorder of uncontrolled cellular proliferation associated with an ENPP1 dysfunction prior to the administering step. In some aspects of the disclosed method, the subject has been diagnosed with a need for inhibition of ENPP1 prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, zebra fish etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder of uncontrolled cellular proliferation" means having been subjected to a physical examination by a person of skill, for example, a physician, and found to have a condition that can be diagnosed or treated by a compound or composition that can inhibit ENPP1. As a further example, "diagnosed with a need for inhibition of ENPP1" refers to having been subjected to a physical examination by a person of skill, for example, a physician, and found to have a condition characterized by an ENPP1 dysfunction. Such a diagnosis can be in reference to a disorder, such as a disorder of uncontrolled cellular proliferation, cancer and the like, as discussed herein. For example, "diagnosed with a need for treatment of one or more disorders of uncontrolled cellular proliferation associated with an ENPP1 dysfunction" means having been subjected to a physical examination by a person of skill, for example, a physician, and found to have one or more disorders of uncontrolled cellular proliferation associated with an ENPP1 dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to a dysfunction of ENPP1) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, intraurethral administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex, and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration of a substance (e.g., a compound or a drug) that is required for 50% agonism or activation of a biological process, or component of a process, including a protein, subunit, organelle, ribonucleoprotein, etc. In one aspect, an $EC_{50}$ can refer to the concentration of a substance that is required for 50% agonism or activation in vivo, as further defined elsewhere herein. In a further aspect, $EC_{50}$ refers to the concentration of agonist or activator that provokes a response halfway between the baseline and maximum response.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. For example, an $IC_{50}$ can refer to the concentration of a substance that is required for 50% inhibition in vivo or the inhibition is measured in vitro, as further defined elsewhere herein. Alternatively, $IC_{50}$ refers to the half maximal (50%) inhibitory concentration (IC) of a substance. The inhibition can be measured in a cell-line such as AN3 CA, BT-20, BT-549, HCT 116, HER218, MCF7, MDA-MB-231, MDA-MB-235, MDA-MB-435S, MDA-MB-468, PANC-1, PC-3, SK-N-MC, T-47D, and U-87 MG.

The term "pharmaceutically acceptable" describes a material that is not biologically or otherwise undesirable, i.e., without causing an unacceptable level of undesirable biological effects or interacting in a deleterious manner.

The term "stable," as used herein, refers to compounds that are not substantially altered when subjected to conditions to allow for their production, detection, and, in certain aspects, their recovery, purification, and use for one or more of the purposes disclosed herein.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

For example, a "C1-C3 alkyl" group can be selected from methyl, ethyl, n-propyl, i-propyl, and cyclopropyl, or from a subset thereof. In certain aspects, the "C1-C3 alkyl" group can be optionally further substituted. As a further example, a "C1-C4 alkyl" group can be selected from methyl, ethyl, n-propyl, i-propyl, cyclopropyl, n-butyl, i-butyl, s-butyl, t-butyl, and cyclobutyl, or from a subset thereof. In certain aspects, the "C1-C4 alkyl" group can be optionally further substituted. As a further example, a "C1-C6 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, and cyclohexane, or from a subset thereof. In certain aspects, the "C1-C6 alkyl" group can be optionally further substituted. As a further example, a "C1-C8 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, cyclohexane, heptane, cycloheptane, octane, and cyclooctane, or from a subset thereof. In certain aspects, the "C1-C8 alkyl" group can be optionally further substituted. As a further example, a "C1-C12 alkyl" group can be selected from methyl, ethyl, n-propyl, i-propyl, cyclopropyl, n-butyl, i-butyl, s-butyl, i-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, cyclohexane, heptane, cycloheptane, octane, cyclooctane, nonane, cyclononane, decane, cyclodecane, undecane, cycloundecane, dodecane, and cyclododecane, or from a subset thereof. In certain aspects, the "C1-C12 alkyl" group can be optionally further substituted.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, nitrile, sulfonamide, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, nitrile, sulfonamide, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The terms "halogen," "halide," and "halo," as used herein, refer to the halogens fluorine, chlorine, bromine, and iodine. It is also contemplated that, in various aspects, halogen can be selected from fluoro, chloro, bromo, and iodo. For example, halogen can be selected from fluoro, chloro, and bromo. As a further example, halogen can be selected from fluoro and chloro. As a further example, halogen can be selected from chloro and bromo. As a further example, halogen can be selected from bromo and iodo. As a further example, halogen can be selected from chloro, bromo, and iodo. In one aspect, halogen can be fluoro. In a further aspect, halogen can be chloro. In a still further aspect, halogen is bromo. In a yet further aspect, halogen is iodo.

It is also contemplated that, in certain aspects, pseudohalogens (e.g. triflate, mesylate, tosylate, brosylate, etc.) can be used in place of halogens. For example, in certain aspects, halogen can be replaced by pseudohalogen. As a further example, pseudohalogen can be selected from triflate, mesylate, tosylate, and brosylate. In one aspect, pseudohalogen is triflate. In a further aspect, pseudohalogen is mesylate. In a further aspect, pseudohalogen is tosylate. In a further aspect, pseudohalogen is brosylate.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

Compounds described herein can contain one or more double bonds and, thus, potentially give rise to cis/trans (E/Z) isomers, as well as other conformational isomers.

Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture.

Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

It is also appreciated that certain compounds described herein can be present as an equilibrium of tautomers. For example, ketones with an α-hydrogen can exist in an equilibrium of the keto form and the enol form.

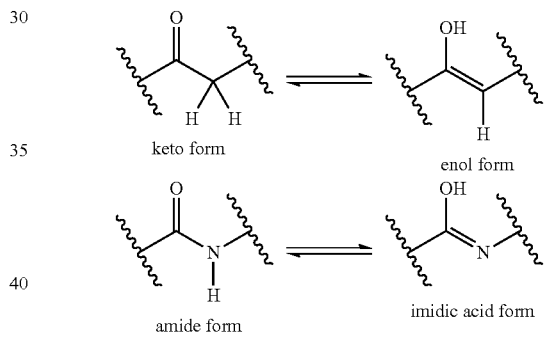

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

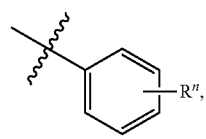

which is understood to be equivalent to a formula:

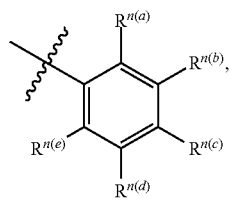

wherein n is typically an integer. That is, $R''$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Sigma-Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as *Fieser and Fieser's Reagents for Organic Synthesis*, Volumes 1-17 (John Wiley and Sons, 1991); *Rodd's Chemistry of Carbon Compounds*, Volumes 1-5 and Supplementals (Elsevier Science Publishers, 1989); *Organic Reactions*, Volumes 1-40 (John Wiley and Sons, 1991); March's *Advanced Organic Chemistry*, (John Wiley and Sons, 4th Edition); and Larock's *Comprehensive Organic Transformations* (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful as inhibitors of ENPP1. Moreover, in one aspect, the compounds of the invention are useful in the treatment of disorders of uncontrolled cellular proliferations. In a further aspect, the disorder of uncontrolled cellular proliferation is a cancer or a tumor. In a still further aspect, the disorder of uncontrolled cellular proliferation is associated with an ENPP1 dysfunction, as further described herein.

In another aspect, the compounds of the invention are useful in the treatment of diseases of bacterial or viral origin. Accordingly, in one aspect, the invention provides a method of treating a disease caused by bacteria or viruses, comprising administering to a subject a therapeutically effective amount of a compound of the invention.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a compound of Formula 1:

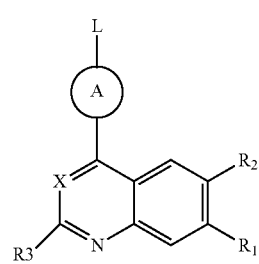

Formula 1 wherein

X is selected from the group consisting of —C and —N;

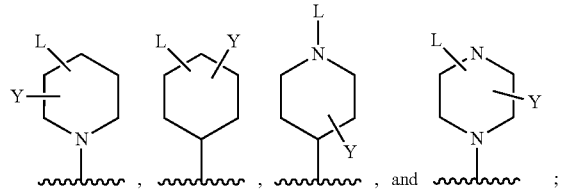

is selected from group consisting of

L is selected from the group consisting of

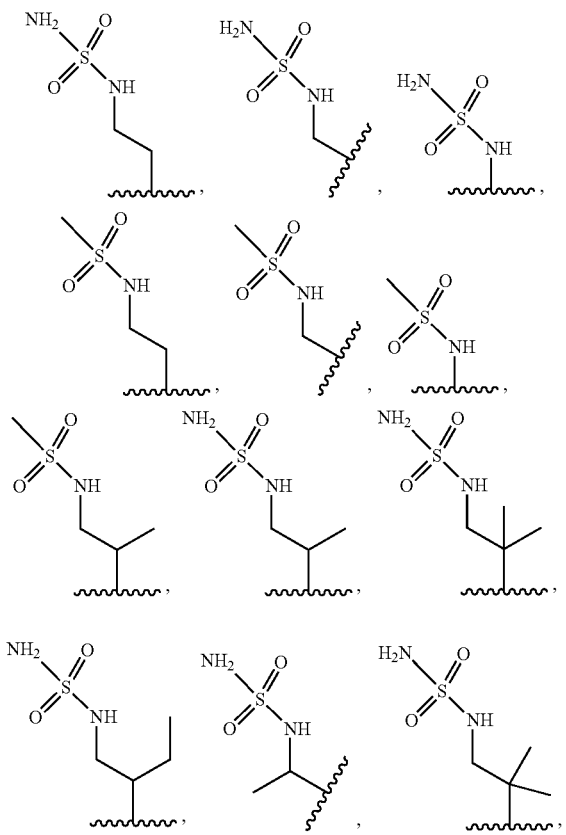

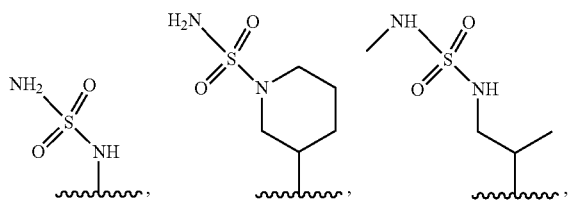

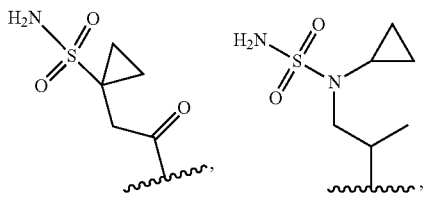

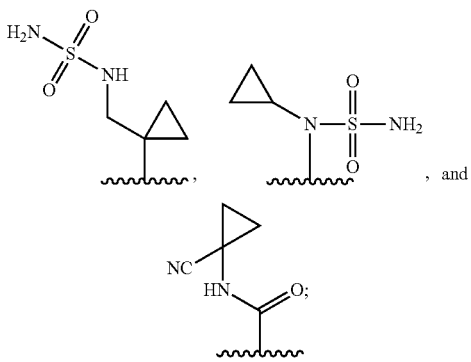

Y is selected from the group consisting of H and alkyl;

R$_1$ is selected from the group consisting of —H, alkyl, O-alkyl, —OCF$_3$, —OP—(OXONa)$_2$, and —CH$_2$OP(OXONa)$_2$;

R$_2$ is selected from the group consisting of —H, alkyl, —Oalkyl, —OH, —OCF$_3$, —OCH$_3$CH$_2$OCH$_3$, —OCH$_3$CH$_2$CH$_2$OH, —OCH$_3$CH$_2$CH$_2$OCH$_3$, —OP═(OXONa)$_2$, —CH$_2$—OP—(OXONa)$_2$, and

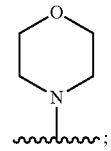 [SMILES: *N1CCOCC1]

R$_3$ is selected from the group consisting of —H, —NH$_2$, and —CH$_3$;

or an isomer, hydrate, solvate, polymorph, tautomer or a pharmaceutically acceptable salt thereof.

In one preferred embodiment, R$_1$ is selected from the group consisting of —H, —CH$_3$, —OCH$_3$, —OCF$_3$, —OP═(O)(ONa)$_2$, and —CH$_2$OP═(O)(ONa)$_2$.

In one preferred embodiment, R$_1$ is OCH$_3$.

In another preferred embodiment, R$_2$ is selected from the group consisting of —H, —CH$_3$, —OCH$_3$, —OH, —OCF$_3$, —OCH$_2$CH$_2$OH, —OCH$_2$CH$_2$OCH$_3$, —OCH$_2$OCH$_3$, —OP═(O)(ONa)$_2$, —CH$_2$OP═(O)(ONa)$_2$; and

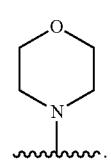

In another preferred embodiment, Y is selected from the group consisting of H and CH$_3$.

In one preferred embodiment, Y is H.

In one preferred embodiment,
X is N;

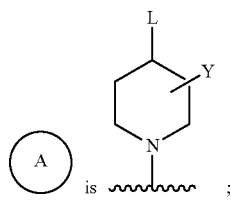 is ;

L is selected from the group consisting of

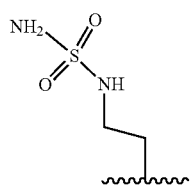 and 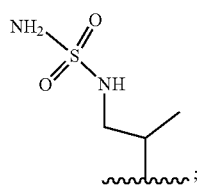 ;

Y is H;
R$_1$ is selected from the group consisting of —H, —CH$_3$, and —OCH$_3$;
R$_2$ is selected from the group consisting of —H, —CH$_3$, —OCH$_3$, OP=(O)(ONa)$_2$, —CH$_2$—OP=(O)(ONa)$_2$, —OH, —OCH$_2$CH$_2$OH, —OCH$_2$CH$_2$OCH$_3$, —OCH$_2$OCH$_3$, and

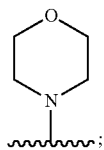 ;

R$_3$ is selected from the group consisting of —H, —NH$_2$, and —CH$_3$.

In another preferred embodiment:
X is C;

is selected from the group consisting of

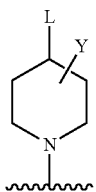 and 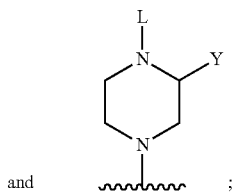 ;

L is selected from the group consisting of

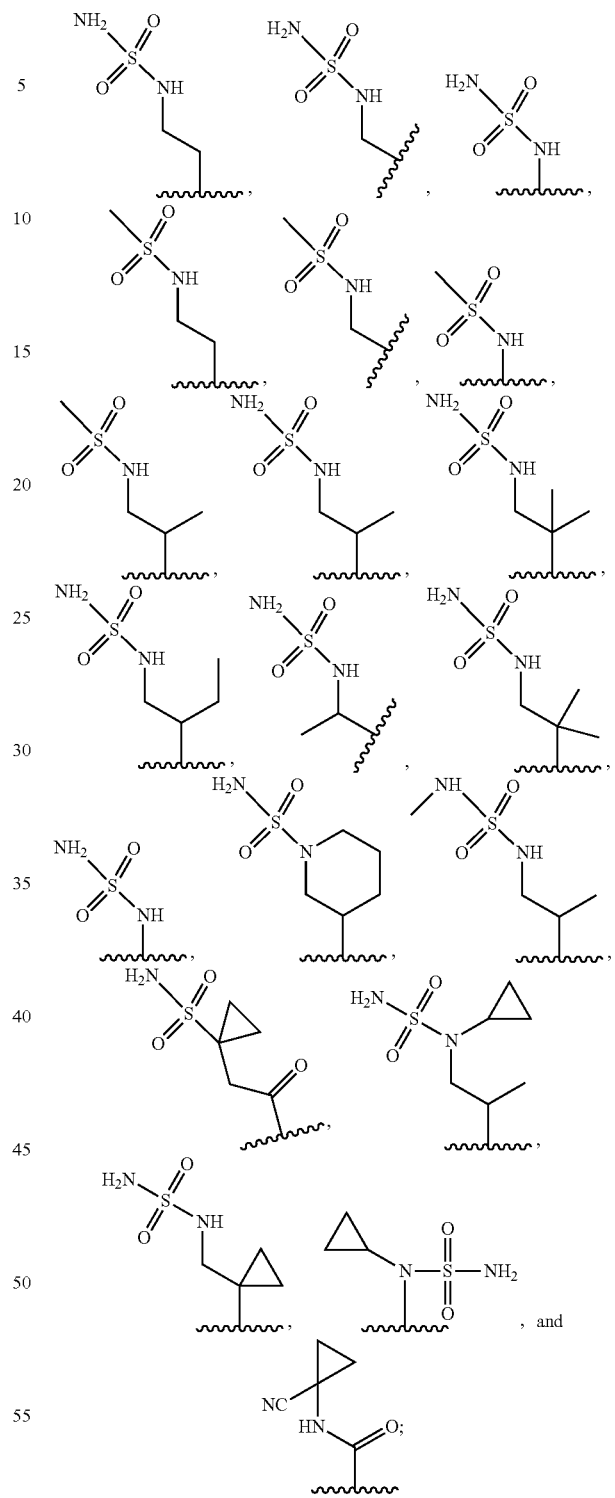

R$_1$ is selected from the group consisting of —H, —CH$_3$, and —OCH$_3$;
R$_2$ is selected from the group consisting of —H, —CH$_3$, —OCH$_3$, —OH, —OCF$_3$, —OCH$_2$CH$_2$OH, —OCH$_2$CH$_2$OCH$_3$, —OCH$_2$OCH$_3$, —OP—(O)(ONO)$_2$, and —CH$_2$OP=(O)(ONa)$_2$; and
R$_3$ is selected from the group consisting of —H, —NH$_3$, and —CH$_3$.

Examples of the provided compounds include:
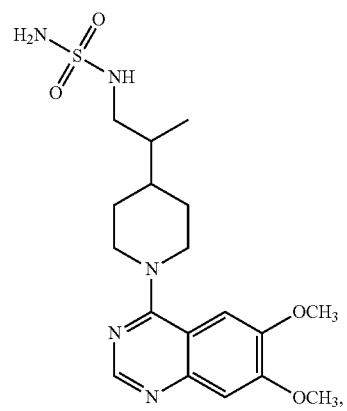
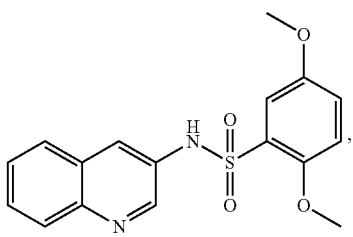
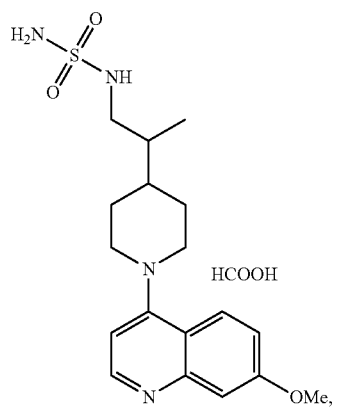
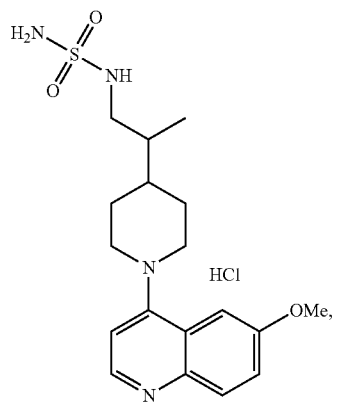
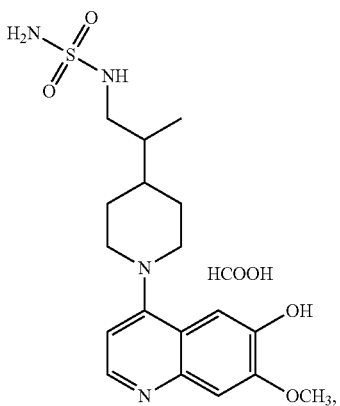

-continued
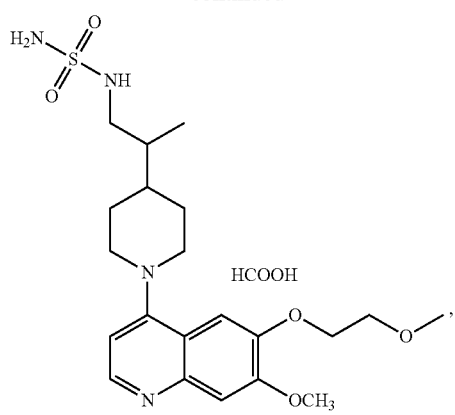
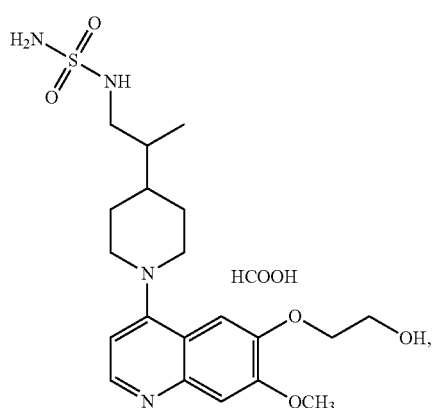
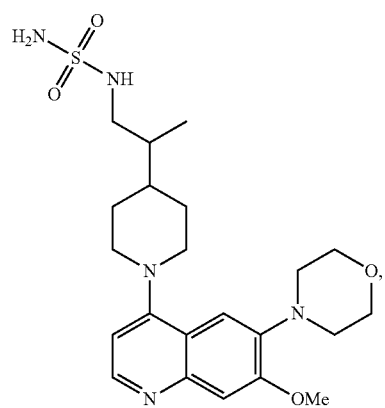
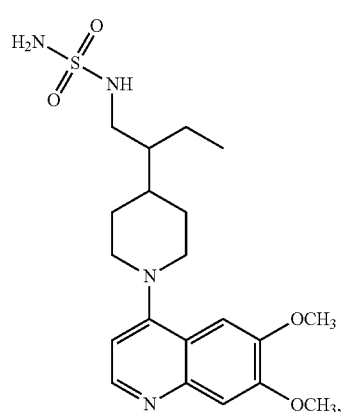
-continued
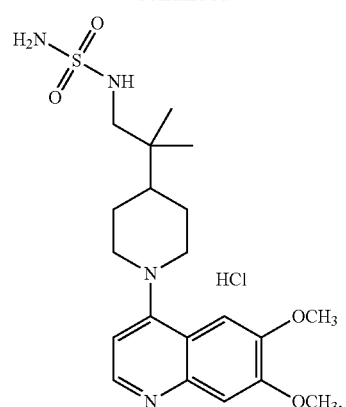
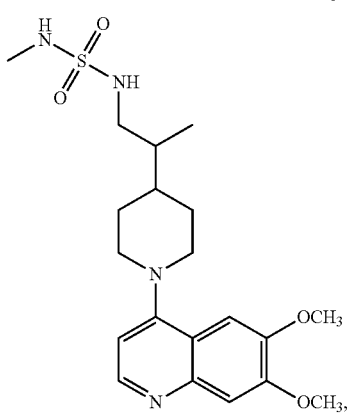
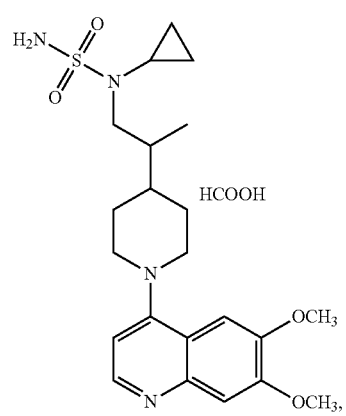
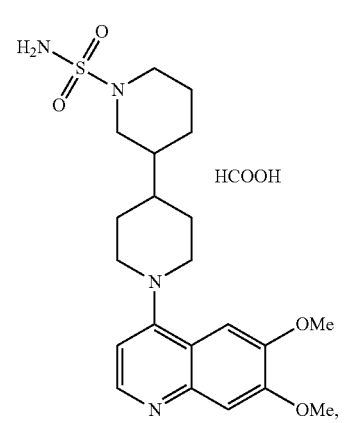

-continued
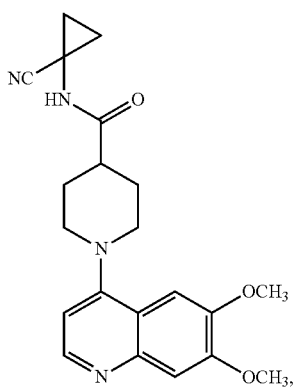
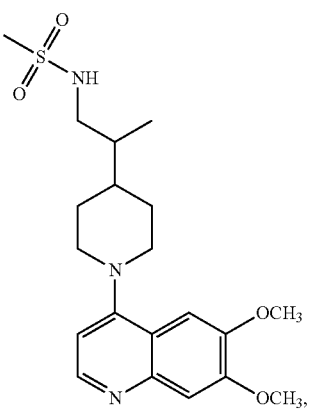
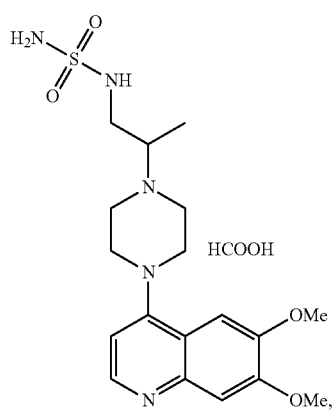
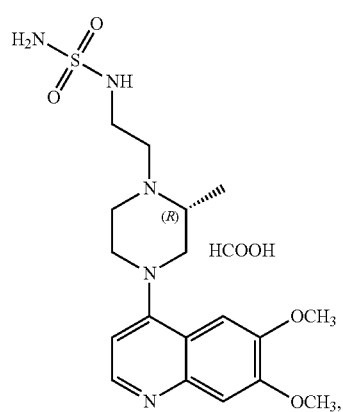
-continued
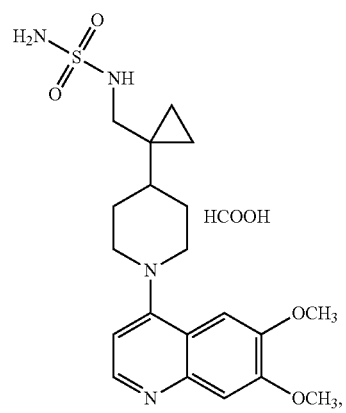
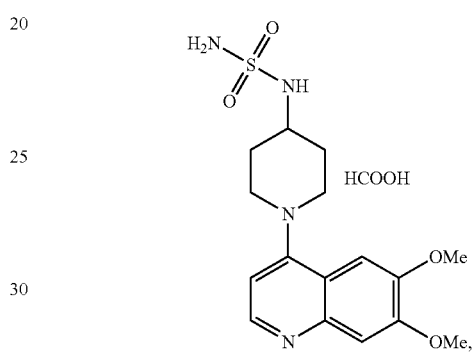
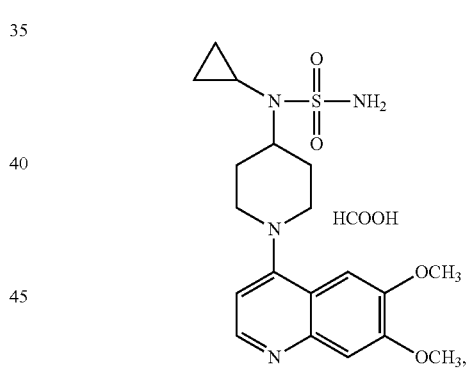
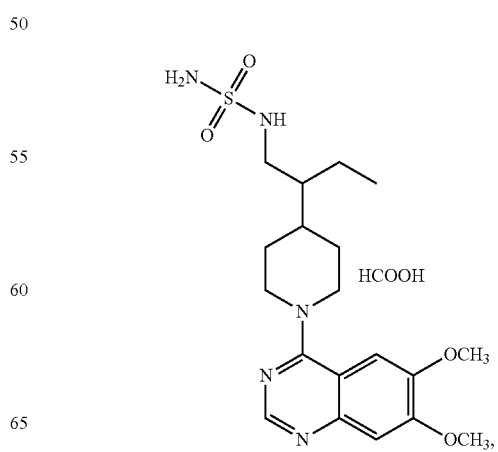

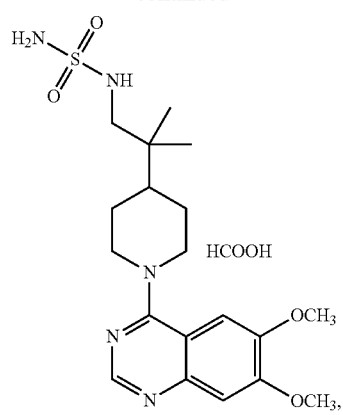
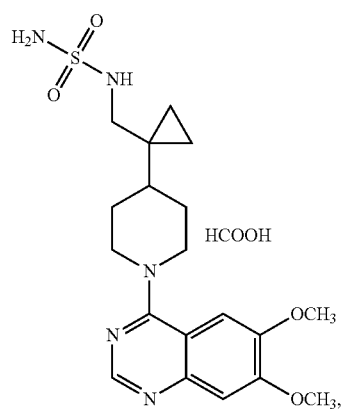
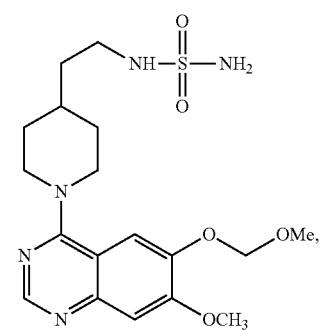
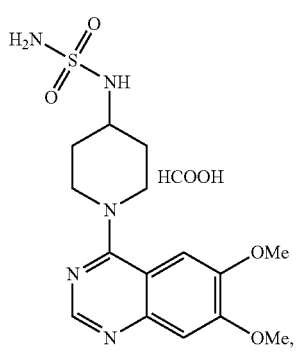
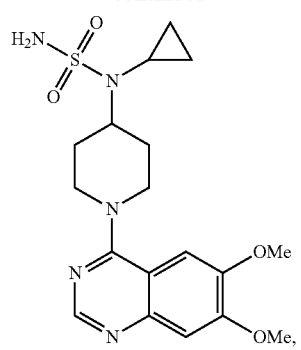
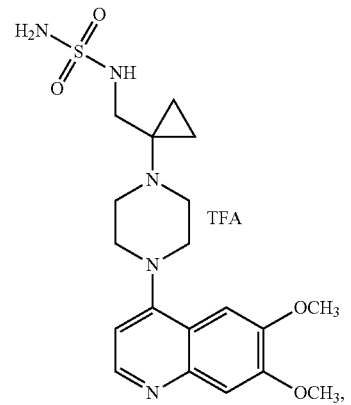
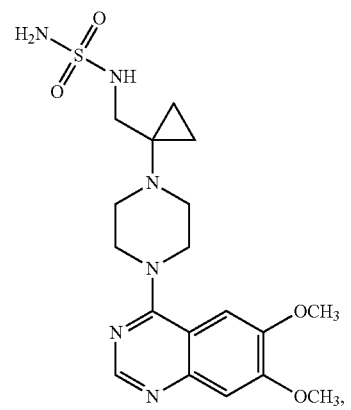
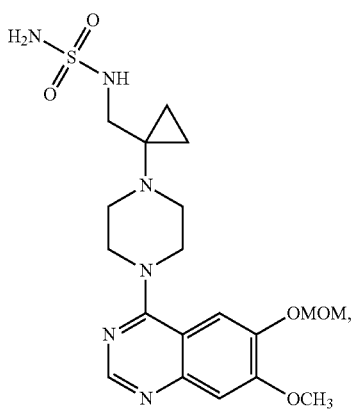

-continued

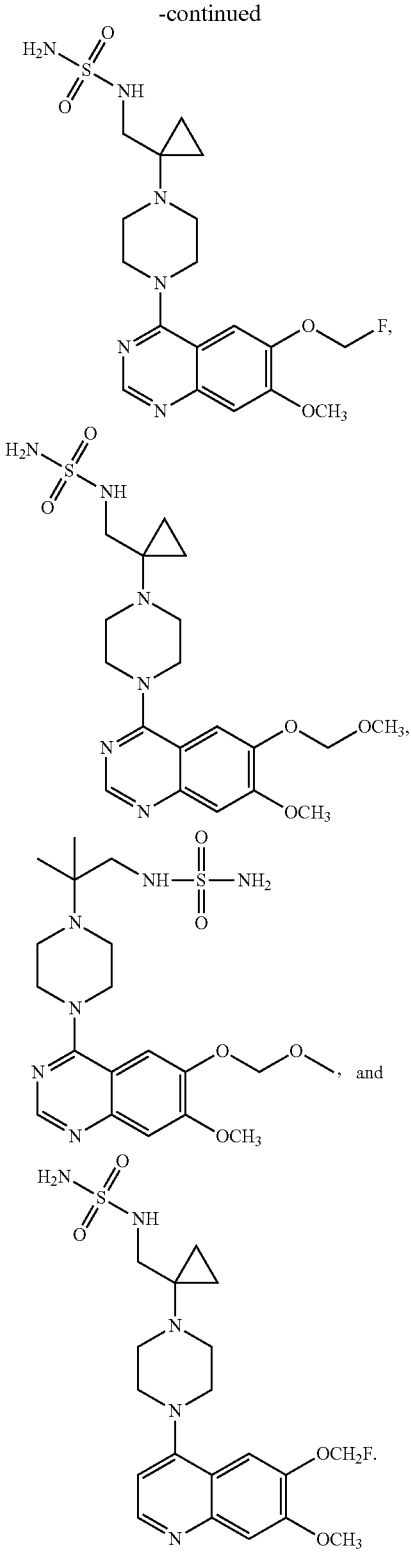

The invention also provides a pharmaceutical composition comprising a therapeutically effective amount of any of a compound of the invention and a pharmaceutically acceptable carrier.

The invention also provides a method for the treatment of a disorder of uncontrolled cellular proliferation in a mammal, the method comprising the step of administering to the mammal an effective amount of any of the compounds of the invention.

The invention also provides a method for decreasing ENPP1 activity in a mammal, the method comprising the step of administering to the mammal an effective amount of any of the compounds of the invention.

The invention also provides a method for inhibiting ENPP1 activity in a mammal, the method comprising the step of administering to the mammal an effective amount of any of the compounds of the invention.

C. Methods of Making the Compounds

In one aspect, the invention relates to methods of making compounds useful as inhibitors of ENPP1. In a further aspect, the products of disclosed methods of making are modulators of ENPP1 activity.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, in addition to other standard manipulations known in the literature or to one skilled in the art. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

Where reaction conditions and amounts of ingredients are not stated, it is believed that it is within a skill in the art to determine them. It is contemplated that each disclosed methods can further comprise additional steps, manipulations, and/or components. It is also contemplated that any one or more step, manipulation, and/or component can be optionally omitted from the invention. It is understood that a disclosed methods can be used to provide the disclosed compounds. It is also understood that the products of the disclosed methods can be employed in the disclosed methods of using.

D. Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In a further aspect, the invention relates to pharmaceutical compositions comprising a pharmaceutically acceptable carrier and an effective amount of the product of a disclosed synthetic method. In a further aspect, the effective amount is a therapeutically effective amount. In a further aspect, the effective amount is a prophylactically effective amount. In a further aspect, the compound is a disclosed compound.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require inhibition or negative modulation of ENPP1 protein activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for inhibiting or negatively modulating ENPP1 protein activity (e.g., treatment of a disorder of uncontrolled cellular proliferation, or one or more neurodegenerative disorders associated with ENPP1 dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

E. Methods of Using the Compounds and Compositions

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of disorders wherein the patient or subject would benefit from inhibition or negative modulation of ENPP1. In one aspect, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more disorders, for which ENPP1 inhibition is predicted to be beneficial, in a subject comprising the step of administering to the subject at least one disclosed compound; at least one disclosed pharmaceutical composition; and/or at least one disclosed product in a dosage and amount effective to treat the disorder in the subject.

In one aspect, provided is a method for treating a disorder of uncontrolled cellular proliferation, comprising: administering to a subject at least one disclosed compound; at least one disclosed pharmaceutical composition; and/or at least one disclosed product in a dosage and amount effective to treat the disorder in the subject. In a further aspect, provided is a method for treating or preventing a neurodegenerative disorder, comprising: administering to a subject at least one disclosed compound; at least one disclosed pharmaceutical composition; and/or at least one disclosed product in a dosage and amount effective to treat the disorder in the subject. Also provided is a method for the treatment of a disorder in a mammal comprising the step of administering to the mammal at least one disclosed compound, composition, or medicament.

The invention is directed at the use of described chemical compositions to treat diseases or disorders in patients (preferably human) wherein ENPP1 inhibition would be predicted to have a therapeutic effect, such as disorders of uncontrolled cellular proliferation (e.g. cancers) and neurodegenerative disorders such as Alzheimer's disease, Huntington's disease, and Parkinson's disease, diseases caused by bacteria and/or viruses, by administering one or more disclosed compounds or products.

The compounds of the invention can also be used for immunotherapy. In one embodiment, the compounds of the invention treat disorders of uncontrolled cellular proliferation, and/or diseases caused by bacteria and/or viruses through immunotherapy, meaning that the compounds elicit immunotherapeutic response which results in the treatment of these diseases.

The compounds disclosed herein are useful for treating, preventing, ameliorating, controlling or reducing the risk of a variety of disorders of uncontrolled cellular proliferation.

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

Examples of disorders treatable with the provided compounds include a disorder of uncontrolled cellular proliferation. In a yet further aspect, the disorder of uncontrolled cellular proliferation is cancer. In a yet further aspect, the cancer is a leukemia. In an even further aspect, the cancer is a sarcoma. In a still further aspect, the cancer is a solid tumor. In a yet further aspect, the cancer is a lymphoma.

It is understood that cancer refer to or describe the physiological condition in mammals that is typically characterized by unregulated cell growth. The cancer may be multi-drug resistant (MDR) or drug-sensitive. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various aspects, further examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma. In a still further aspect, the cancer is selected from chronic lymphocytic leukemia, small lymphocytic lymphoma, B-cell non-Hodgkin lymphoma, and large B-cell lymphoma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In one aspect, the cancer can be a cancer selected from cancers of the blood, brain, genitourinary tract, gastrointestinal tract, colon, rectum, breast, kidney, lymphatic system, stomach, lung, pancreas, and skin. In a further aspect, the cancer is selected from prostate cancer, glioblastoma multiforme, endometrial cancer, breast cancer, and colon cancer. In a further aspect, the cancer is selected from a cancer of the breast, ovary, prostate, head, neck, and kidney. In a still further aspect, the cancer is selected from cancers of the blood, brain, genitourinary tract, gastrointestinal tract, colon, rectum, breast, livery, kidney, lymphatic system, stomach, lung, pancreas, and skin. In a yet further aspect, the cancer is selected from a cancer of the lung and liver. In an even further aspect, the cancer is selected from a cancer of the breast, ovary, testes and prostate. In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

In various aspects, disorders associated with an ENPP1 dysfunction include neurodegenerative disorders. In a further aspect, the neurodegenerative disease is selected from Alzheimer's disease, Parkinson's disease, and Huntington's disease.

The compounds are further useful in a method for the prevention, treatment, control, amelioration, or reducation of risk of the diseases, disorders and conditions noted herein. The compounds are further useful in a method for the prevention, treatment, control, amelioration, or reduction of risk of the aforementioned diseases, disorders and conditions in combination with other agents.

The present invention is further directed to administration of an ENPP1 inhibitor for improving treatment outcomes in the context of disorders of uncontrolled cellular proliferation, including cancer. That is, in one aspect, the invention relates to a cotherapeutic method comprising the step of administering to a mammal an effective amount and dosage of at least one compound of the invention in connection with cancer therapy.

In a further aspect, administration improves treatment outcomes in the context of cancer therapy. Administration in connection with cancer therapy can be continuous or intermittent. Administration need not be simultaneous with therapy and can be before, during, and/or after therapy. For example, cancer therapy can be provided within 1, 2, 3, 4, 5, 6, 7 days before or after administration of the compound. As a further example, cancer therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present invention.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In one aspect, the compound can be employed in combination with anti-cancer therapeutic agents or other known therapeutic agents.

In the treatment of conditions which require inhibition or negative modulation of ENPP1, an appropriate dosage level will generally be about 0.01 to 1000 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the invention relates to methods for inhibiting or negatively modulating ENPP1 in at least one cell, comprising the step of contacting the at least one cell with at least one compound of the invention, in an amount effective to modulate or activate ENPP1 activity response, e.g. in the at least one cell. In a further aspect, the cell is mammalian, for example human. In a further aspect, the cell has been isolated from a subject prior to the contacting step. In a further aspect, contacting is via administration to a subject.

a. Treatment of a Disorder of Uncontrolled Cellular Proliferation

In one aspect, the invention relates to a method for the treatment of a disorder of uncontrolled cellular proliferation in a mammal, the method comprising the step of administering to the mammal an effective amount of least one disclosed compound or a product of a disclosed method of making a compound, or a pharmaceutically acceptable salt, hydrate, solvate, or polymorph thereof, thereby treating the disorder of uncontrolled cellular proliferation.

In a still further aspect, the effective amount is a therapeutically effective amount. In a yet still further aspect, the effective amount is a prophylactically effective amount.

In a further aspect, the mammal is a human. In a yet further aspect, the method further comprises the step of identifying a mammal in need of treatment of a disorder of uncontrolled cellular proliferation. In a still further aspect, the mammal has been diagnosed with a need for treatment of a disorder of uncontrolled cellular proliferation prior to the administering step.

In a further aspect, the disorder of uncontrolled cellular proliferation is a cancer. In a yet further aspect, the cancer is a leukemia. In an even further aspect, the cancer is a sarcoma. In a still further aspect, the cancer is a solid tumor. In a yet further aspect, the cancer is a lymphoma. In an even further aspect, the cancer is selected from chronic lymphocytic leukemia, small lymphocytic lymphoma, B-cell non-Hodgkin lymphoma, and large B-cell lymphoma. In a still further aspect, the cancer is selected from cancers of the blood, brain, genitourinary tract, gastrointestinal tract, colon, rectum, breast, livery, kidney, lymphatic system, stomach, lung, pancreas, and skin. In a yet further aspect, the cancer is selected from a cancer of the lung and liver. In an even further aspect, the cancer is selected from a cancer of the breast, ovary, testes and prostate. In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

EXAMPLES

F. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

Some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

Experimental Chemistry

Synthesis Schemes, Methods and Procedures

Synthesis of N-(2-(1-(6,7-dimethoxyquinazolin-4-yl)piperidin-4-yl)propyl)sulfonamide urea (I-01)

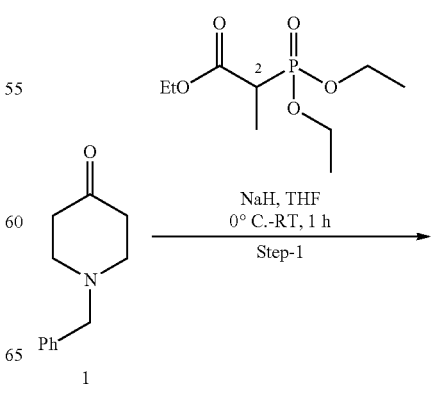

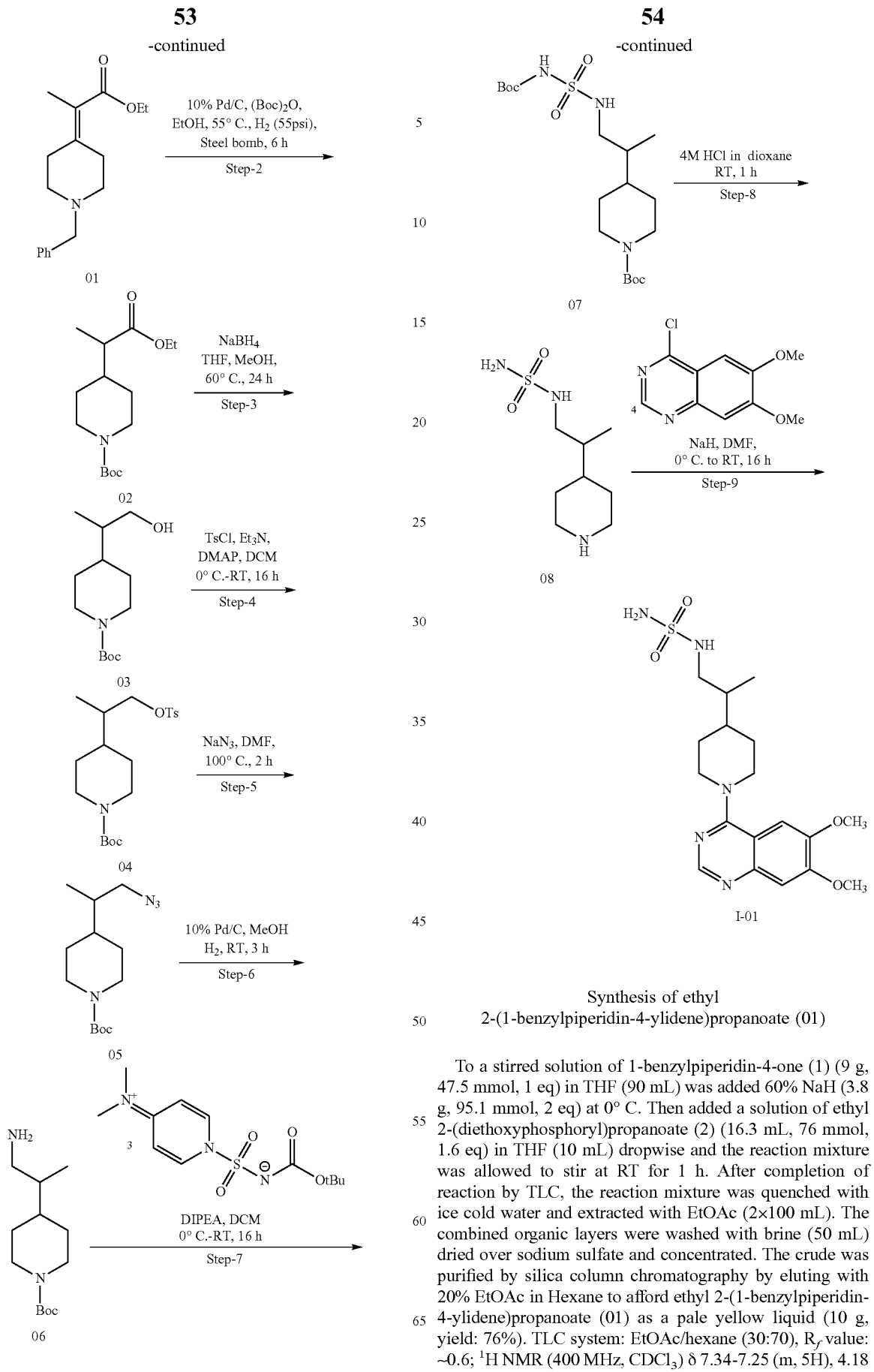

Synthesis of ethyl 2-(1-benzylpiperidin-4-ylidene)propanoate (01)

To a stirred solution of 1-benzylpiperidin-4-one (1) (9 g, 47.5 mmol, 1 eq) in THF (90 mL) was added 60% NaH (3.8 g, 95.1 mmol, 2 eq) at 0° C. Then added a solution of ethyl 2-(diethoxyphosphoryl)propanoate (2) (16.3 mL, 76 mmol, 1.6 eq) in THF (10 mL) dropwise and the reaction mixture was allowed to stir at RT for 1 h. After completion of reaction by TLC, the reaction mixture was quenched with ice cold water and extracted with EtOAc (2×100 mL). The combined organic layers were washed with brine (50 mL) dried over sodium sulfate and concentrated. The crude was purified by silica column chromatography by eluting with 20% EtOAc in Hexane to afford ethyl 2-(1-benzylpiperidin-4-ylidene)propanoate (01) as a pale yellow liquid (10 g, yield: 76%). TLC system: EtOAc/hexane (30:70), $R_f$ value: ~0.6; $^1$H NMR (400 MHz, CDCl$_3$) δ 7.34-7.25 (m, 5H), 4.18

(d, J=7.2 Hz, 2H), 3.51 (s, 2H), 2.64-2.57 (m, 2H), 2.49-2.44 (m, 4H), 2.37-2.35 (m, 2H), 1.85 (s, 3H), 1.29 (t, J=7.2 Hz, 3H).

Synthesis of tert-butyl 4-(1-ethoxy-1-oxopropan-2-yl)piperidine-1-carboxylate (02)

To a stirred solution of ethyl 2-(1-benzylpiperidin-4-ylidene)propanoate (01) (2 g, 7.06 mmol, 1 eq) in ethanol (30 mL) was added (Boc)$_2$O (1.54 mL, 7.06 mmol, 1 eq) followed by 10% Pd/C (200 mg). The reaction mixture was stirred at 55° C. for 6 h in a steel bomb under H$_2$ (55 psi). After completion of reaction by TLC, the reaction mixture was filtered through Celite pad. The obtained filtrate was evaporated under reduced pressure to afford tert-butyl 4-(1-ethoxy-1-oxopropan-2-yl)piperidine-1-carboxylate (02) (2 g, yield: 99%) as pale yellow liquid. TLC system: EtoAc:Hexane (10:90; KMnO$_4$ stain), R$_f$ value: ~0.3; $^1$H NMR (400 MHz, CDCl$_3$) δ 4.17-4.07 (m, 4H), 2.66 (t, J=12 Hz, 2H), 2.26 (p, J=7.2 Hz, 1H), 1.72-1.66 (m, 2H), 1.64-1.52 (m, 3H), 1.41 (s, 9H), 1.27 (t, J=7.2 Hz, 3H), 1.09 (d, J=7.2 Hz, 3H).

Synthesis of tert-butyl 4-(1-hydroxypropan-2-yl)piperidine-1-carboxylate (03)

To a stirred solution of tert-butyl 4-(1-ethoxy-1-oxopropan-2-yl)piperidine-1-carboxylate (02) (2 g, 7 mmol, 1 eq) in THF:MeOH (8:2) (20 mL) at 0° C. was added NaBH$_4$ (1.58 g, 42 mmol, 6 eq) The reaction mixture was stirred at 80° C. for 24 h, After completion of reaction by TLC, the reaction mixture was quenched with ice cold water and extracted with ethyl acetate (2×100 mL). The combined organic layer was washed with water (50 mL), brine (50 mL), dried over sodium sulfate, and concentrated to provide crude. The crude compound was purified by 100-200 mesh silica gel column chromatography by eluting with 20% EtOAc in Hexane to afford tert-butyl 4-(1-hydroxypropan-2-yl)piperidine-1-carboxylate (03) (1.5 g, yield: 88%) as gummy liquid. TLC system EtoAc:Hexane (30:70; KMnO$_4$ stain), R$_f$ value: 0.3; LCMS (m/z): 188.2 (M+H-tBu)$^+$; $^1$HNMR (400 MHz, DMSO-d$_6$) δ 4.37 (t, J=5.2 Hz, 1H), 3.97-3.94 (m, 2H), 3.25-3.22 (m, 2H), 2.51-2.49 (m, 2H), 1.55-1.52 (m, 2H), 1.45-1.42 (m, 2H), 1.38 (s, 9H), 1.11-0.98 (m, 2H), 0.78 (d, J=6.8 Hz, 3H).

Synthesis of tert-butyl 4-(1-(tosyloxy)propan-2-yl)piperidine-1-carboxylate (04)

To a stirred solution of tert-butyl 4-(1-hydroxypropan-2-yl)piperidine-1-carboxylate (03) (1.5 g, 6.1 mmol, 1 eq) in DCM (10 mL) cooled to 0° C., added TEA (2.64 mL, 18.3 mmol, 3 eq), tosyl chloride (1.75 g, 9.2 mmol, 1.5 eq), The reaction mixture was stirred at room temperature for 16 h. After completion of reaction by TLC, the reaction mixture was quenched with water and extracted with DCM (2×100 mL). The combined organic layer was washed with water (50 mL), brine (40 mL), dried over sodium sulfate, and concentrated to provide crude. The crude compound was purified by 100-200 mesh silica gel column by eluting with 20% EtOAc in Hexane to afford tert-butyl 4-(1-(tosyloxy)propan-2-yl)piperidine-1-carboxylate (04) (1.5 g, yield: 60%) as gummy liquid. TLC system EtoAc:Hexane (30:70), R$_f$ value: 0.5; LCMS (m/z): 298.2 (M+H-Boc)+; $^1$HNMR (400 MHz, CDCl$_3$) δ 7.79 (d, J=7.6 Hz, 2H), 7.34 (d, J=7.6 Hz, 2H), 4.07 (brs, 2H), 3.93-3.87 (m, 2H), 2.61-2.45 (brs, 2H), 2.43 (s, 3H), 1.69-1.66 (m, 1H), 1.55-1.47 (m, 3H), 1.45 (s, 9H), 1.20-1.08 (m, 2H), 0.87 (d, J=6.8 Hz, 3H).

Synthesis of tert-butyl 4-(1-azidopropan-2-yl)piperidine-1-carboxylate (05)

To a stirred solution of tert-butyl 4-(1-(tosyloxy)propan-2-yl)piperidine-1-carboxylate (04) (1.5 g, 3.7 mmol, 1 eq), in DMF (12 mL) was added NaN$_3$ (1.2 g, 18.8 mmol, 5 eq), The reaction mixture was stirred at 100° C. for 2 h. After completion of reaction by TLC, reaction mixture was quenched with cold water, extracted with Diethyl ether (2×50 mL). The combined organic layer was washed with cold water (50 mL), brine (20 mL), dried over sodium sulfate, and concentrated to afford tert-butyl 4-(1-azidopropan-2-yl)piperidine-1-carboxylate (05) (910 mg, yield: 90%) as gummy liquid. TLC system EtoAc:Hexane (20:80; KMnO$_4$ stain), R$_f$ value: 0.8; $^1$HNMR (400 MHz, CDCl$_3$) δ 4.14 (brs, 2H), 3.31 (ABq, J=6.8 Hz, 1H), 3.19 (ABq, J=6.8 Hz, 1H), 2.66-2.64 (m, 2H), 1.63-1.57 (m, 2H), 1.45 (s, 9H), 1.28-1.14 (m, 4H), 0.94 (d, J=7.2 Hz, 3H).

Synthesis of tert-butyl 4-(1-aminopropan-2-yl)piperidine-1-carboxylate (06)

To a stirred solution of tert-butyl 4-(1-azidopropan-2-yl)piperidine-1-carboxylate (05) (900 mg, 3.35 mmol, 1 eq) in methanol (9 mL) was added 10% Pd/C (450 mg). The reaction mixture was stirred at RT for 3 h. The reaction mixture was filtered through Celite pad and filtrate was evaporated under reduced pressure to afford tert-butyl 4-(1-aminopropan-2-yl)piperidine-1-carboxylate (06) (800 mg, yield: 98%) as liquid. TLC system MeOH:DCM (10:90; ninhydrin stain), R$_f$ value: 0.2; $^1$HNMR (400 MHz, DMSO-d$_6$) δ 3.97-3.94 (m, 2H), 2.66-2.49 (m, 3H), 2.36 (ABq, J=7.2 Hz, 1H), 1.53-1.44 (m, 5H), 1.42 (s, 9H), 1.09-0.97 (m, 3H), 0.78 (d, J=6.8 Hz, 3H).

Synthesis of tert-butyl 4-(1-((N-(tert-butoxycarbonyl)sulfamoyl)amino)propan-2-yl)piperidine-1-carboxylate (07)

To a stirred solution of tert-butyl 4-(1-aminopropan-2-yl)piperidine-1-carboxylate (06) (500 mg, 2.05 mmol, 1 eq), in DCM (10 mL) cooled to 0° C. was added DIPEA (0.56 mL, 3.07 mmol, 1.5 eq), and (tert-butoxycarbonyl)((4-(dimethyliminio)pyridin-1(4H)-yl)sulfonyl)amide (3) (805 mg, 2.67 mmol, 1.3 eq), The reaction mixture was stirred at room temperature for 16 h. After completion of reaction, reaction mixture was diluted with water and extracted with DCM (2×50 mL). The combined organic layer was washed with cold water (40 mL), brine (20 mL), dried over sodium sulfate, and concentrated to afford crude. Obtained crude was purified by reverse phase Grace column purification to afford tert-butyl 4-(1-((N-(tert-butoxycarbonyl)sulfamoyl)amino)propan-2-yl)piperidine-1-carboxylate (07) (440 mg, yield: 50%) as gummy liquid. TLC system MeOH:DCM (10:90; KMnO$_4$ stain), R$_f$ value: 0.8; $^1$HNMR (400 MHz, DMSO-d$_6$) δ 10.76 (s, 1H), 7.53 (t, J=5.6 Hz, 1H), 3.97-3.94 (m, 2H), 2.89-2.85 (m, 1H), 2.71-2.62 (m, 3H), 1.52-1.46 (m, 4H), 1.42 (s, 9H), 1.38 (s, 9H), 1.15-0.95 (m, 2H), 0.79 (d, J=6.8 Hz, 3H).

Synthesis of N-(2-(piperidin-4-yl)propyl)sulfonamide urea hydrochloride (08)

To a stirred solution of tert-butyl 4-(1-((N-(tert-butoxycarbonyl)sulfamoyl)amino)propan-2-yl)piperidine-1-carboxylate (07) (440 mg, 1.04 mmol, 1 eq) in 1,4 Dioxane (1 mL) at 0° C. was added 4M Dioxane. HCl (3 mL). The reaction mixture was stirred at room temperature for 1 h and concentrated under reduced pressure to afford N-(2-(piperidin-4-yl)propyl)sulfonamide urea hydrochloride (08) (230 mg, yield: 85%) as gummy solid. ¹HNMR (400 MHz, DMSO-$d_6$) δ 8.91 (s, 1H), 8.66 (s, 1H), 6.49 (s, 3H), 3.26-3.23 (m, 2H), 2.86-2.69 (m, 4H), 1.69-1.66 (m, 2H), 1.59-1.35 (m, 4H), 0.81 (d, J=6.8 Hz, 3H).

Synthesis of N-(2-(1-(6,7-dimethoxyquinazolin-4-yl)piperidin-4-yl)propyl)sulfonamide urea (I-01)

To a stirred solution of 4-chloro-6,7-dimethoxyquinazoline (4) (200 mg, 0.89 mmol, 1 eq) in DMF (2 mL) at 0° C. was added NaH (89 mg, 2.23 mmol, 2.5 eq) and N-(2-(piperidin-4-yl)propyl)sulfonamide urea hydrochloride (I-01) (228 mg, 0.89 mmol, 1 eq) and stirred at room temperature for 16 h. The reaction mixture was quenched with ice cold water and extracted with EtOAc (2×50 mL). The combined organic layer was washed with cold water (40 mL), brine (20 mL), dried over sodium sulfate, and concentrated to afford crude. Crude compound was purified by prep-HPLC to afford N-(2-(1-(6,7-dimethoxyquinazolin-4-yl)piperidin-4-yl)propyl)sulfonamide urea (I-01) (80 mg, yield: 21%) as white solid. TLC system MeOH:DCM (10:90), $R_f$ value: 0.4; LCMS (m/z): 410.4 (M+H)⁺; ¹HNMR (400 MHz, DMSO-$d_6$) δ 8.51 (s, 1H), 7.20 (s, 1H), 7.11 (s, 1H), 6.46 (s, 3H), 4.21 (d, J=12.8 Hz, 2H), 3.92 (s, 3H), 3.91 (s, 3H), 3.03-2.95 (m, 3H), 2.76-2.71 (m, 1H), 1.70-1.40 (s, 6H), 0.88 (d, J=6.8 Hz, 3H).

Scheme for the Synthesis of N-(2-(1-(6,7-dimethoxyquinolin-4-yl)piperidin-4-yl)propyl)sulfamoylcarbamate (I-02)

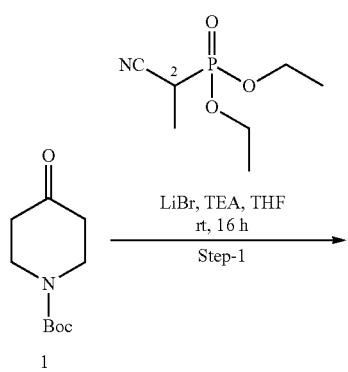

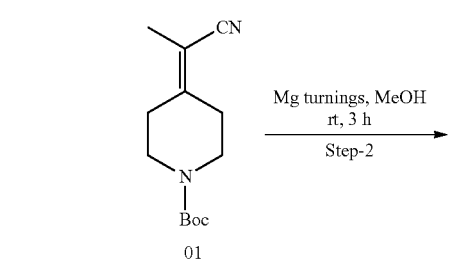

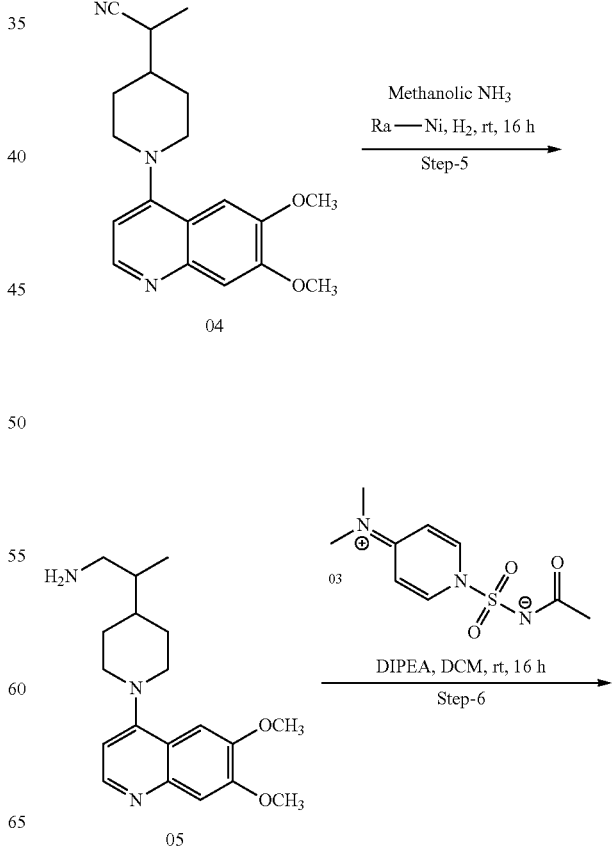

-continued

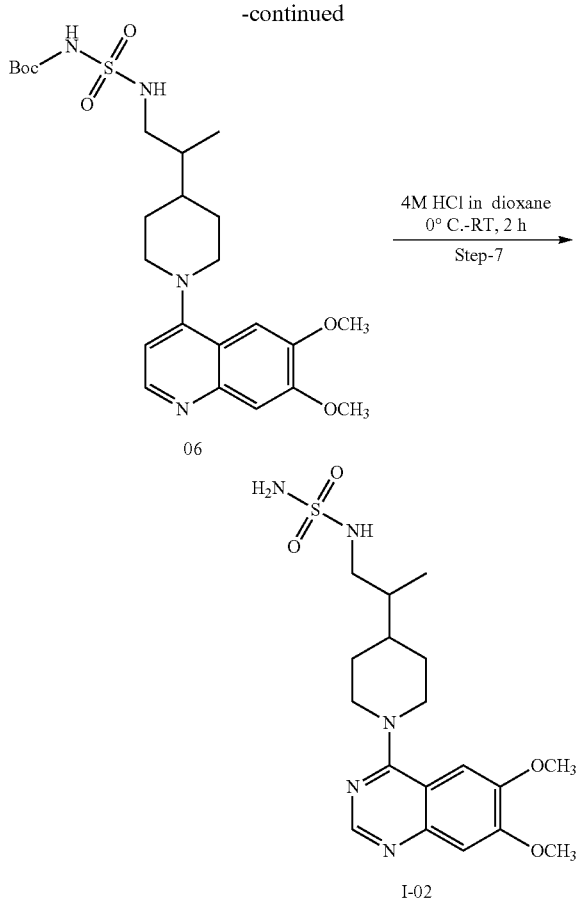

Synthesis of tert-butyl 4-(1-cyanoethylidene)piperidine-1-carboxylate (01)

To a stirred solution of tert-butyl 4-oxopiperidine-1-carboxylate (1) (1.5 g, 7.5 mmol, 1 eq) in THF (15 mL) at 0° was added diethyl (1-cyanoethyl)phosphonate (2) (2.15 g, 11.3 mmol, 1.5 eq), LiBr (0.72 g, 9 mmol, 1.2 eq) and TEA (2 mL, 15 mmol, 2 eq). The reaction mixture was allowed to stir at room temperature for 16 h. After completion of reaction by TLC, the reaction mixture was diluted with water and extracted with EtOAc (3×30 mL). The combined organic layers were washed with brine (30 mL) dried over sodium sulfate and concentrated. The crude was purified by silica column chromatography by eluting with 20% EtOAc in Hexane to afford tert-butyl-4-(1-cyanoethylidene)piperidine-1-carboxylate (01) as a white solid (1.2 g, yield: 70%). TLC system: EtOAc/hexane (30:70; Ninhydrin stain), $R_f$ value: ~0.6; $^1$H NMR (400 MHz, CDCl$_3$) δ 3.51-3.45 (m, 4H), 2.58 (t, J=5.6 Hz, 2H), 2.35 (t, J=5.6 Hz, 2H), 1.91 (s, 3H), 1.47 (s, 9H).

Synthesis of Tert-butyl 4-(1-cyanoethyl)piperidine-1-carboxylate (02)

To a stirred solution of tert-butyl 4-(1-cyanoethylidene) piperidine-1-carboxylate (01) (1.2 g, 5 mmol, 1 eq) in dry methanol (70 mL) was added Mg turnings (4.8 g, 0.2 mol, 40 eq). The reaction mixture was stirred at room temperature for 3 h. After completion of reaction by TLC, the reaction mixture was quenched with 6N HCl and extracted with EtOAc (2×50 mL). The combined organic layers were washed with brine (20 mL) dried over sodium sulfate and concentrated under reduced pressure to afford tert-butyl 4-(1-cyanoethyl)piperidine-1-carboxylate (02) (1.2 g, yield: 99%) as gummy liquid. TLC system: EtoAc:Hexane (20:80; Ninhydrin stain), $R_f$ value: ~0.5; $^1$H NMR (400 MHz, CDCl$_3$) δ 4.14 (brs 2H), 2.67 (brs, 2H), 2.53 (p, J=6.8 Hz, 1H), 1.88-1.83 (m, 1H), 1.73-1.69 (m, 1H), 1.63-1.55 (m, 2H), 1.46 (s, 9H), 1.32 (d, J=6.8 Hz, 3H), 1.31-1.29 (m, 1H)

Synthesis of 2-(piperidin-4-yl)propanenitrile hydrochloride (03)

A solution of tert-butyl 4-(1-cyanoethyl)piperidine-1-carboxylate (02) (1.2 g, 5 mmol, 1 eq) in 4M Dioxane.HCl (12 mL) was stirred at room temperature for 1 h, After completion of reaction by TLC, the reaction mixture was concentrated under reduced pressure to afford 2-(piperidin-4-yl) propanenitrile hydrochloride (03) (0.88 g, yield: 99%) as gummy solid. TLC system EtoAc (100%, KMnO$_4$ stain), $R_f$ value: 0.1; $^1$HNMR (400 MHz, DMSO-d$_6$) 9.22 (s, 1H), 8.71 (s, 1H), 3.31-3.25 (m, 2H), 2.91-2.81 (m, 3H), 1.92-1.79 (m, 2H), 1.77-1.72 (m, 1H), 1.53-1.46 (m, 2H), 1.22 (d, J=7.2 Hz, 3H).

Synthesis of 2-(1-(6,7-dimethoxyquinolin-4-yl)piperidin-4-yl)propanenitrile (04)

To a stirred solution of 4-chloro-6,7-dimethoxyquinoline (3) (1 g, 4.46 mmol, 1 eq) in 1,4 Dioxane (10 mL) was added 2-(piperidin-4-yl)propanenitrile hydrochloride (03) (0.73 g, 5.35 mmol, 1.2 eq) degassed for 10 mins, added Cs$_2$CO$_3$ (4.34 g, 13.3 mmol, 3 eq), Pd$_2$(dba)$_3$ (0.4 g, 0.44 mmol, 0.1 eq), X-Phos (0.42 g, 0.89 mmol, 0.2 eq). The reaction mixture was stirred at 110° C. for 16 h in a sealed tube. After completion of reaction by TLC, the reaction mixture was filtered through Celite pad and concentrated to provide crude. The crude compound was purified by 100-200 mesh silica gel column by eluting with 3% MeOH in DCM to afford 2-(1-(6,7-dimethoxyquinolin-4-yl)piperidin-4-yl)propanenitrile (04) (0.5 g, yield: 34%) as white solid. TLC system MeOH:DCM (10:90), $R_f$ value: 0.5; LCMS (m/z): 326.3 (M+H)$^+$; $^1$HNMR (400 MHz, DMSO-d$_6$) δ 8.49 (d, J=5.2 Hz, 1H), 7.31 (s, 1H), 7.15 (s, 1H), 6.87 (d, J=5.2 Hz, 1H), 3.91 (s, 6H), 3.58 (t, J=11.6 Hz, 2H), 2.92 (p, J=6.8 Hz, 1H), 2.76 (t, J=11.6 Hz, 2H), 2.00-1.89 (m, 2H), 1.71-1.57 (m, 3H), 1.29 (d, J=6.8 Hz, 3H).

Synthesis of 2-(1-(6,7-dimethoxyquinolin-4-yl)piperidin-4-yl)propan-1-amine (05)

To a stirred solution of 2-(1-(6,7-dimethoxyquinolin-4-yl)piperidin-4-yl)propanenitrile (04) (500 mg, 1.53 mmol, 1 eq), in 7M methanolic.NH$_3$ (10 mL) was added Ra—Ni (250 mg). The reaction mixture was stirred at room temperature for 16 h under H$_2$ balloon pressure. After completion of reaction by TLC, reaction mixture was filtered through Celite pad and concentrated to afford 2-(1-(6,7-dimethoxyquinolin-4-yl)piperidin-4-yl)propan-1-amine (05) (500 mg, yield: 99%) as off-white solid. TLC system MeOH:DCM (10:90), $R_f$ value: 0.1; $^1$HNMR (400 MHz, DMSO-d$_6$) 8.48 (s, 1H), 7.30 (s, 1H), 7.18 (s, 1H), 6.86 (d, J=4.8 Hz, 1H), 3.91 (s, 6H), 3.56-3.54 (m, 2H), 3.41-3.37 (m, 2H), 2.89 (br, 1H), 2.73-2.72 (m, 2H), 1.78-1.76 (m, 1H), 1.55-1.53 (m, 3H), 1.09 (t, J=6.8 Hz, 1H), 0.98 (brs, 3H).

Synthesis of tert-butyl N-(2-(1-(6,7-dimethoxyquinolin-4-yl)piperidin-4-yl)propyl)sulfamoylcarbamate (06)

To a stirred solution of 2-(1-(6,7-dimethoxyquinolin-4-yl)piperidin-4-yl)propan-1-amine (05) (400 mg, 1.21 mmol, 1.0 eq) in DCM (8 mL) was added DIPEA (0.32 mL, 1.82 mmol, 1.5 eq), acetyl((4-(dimethyliminio)pyridin-1(4H)-yl)sulfonyl)amide (03) (475 mg, 1.58 mmol, 1.3 eq). The reaction mixture was stirred at RT for 16 h. After completion of reaction, the reaction mixture was diluted with water and extracted with DCM (2×50 mL). The combined organic layers were washed with brine (20 mL) dried over sodium sulfate and concentrated under reduced pressure to afford crude. The crude compound was purified by prep HPLC to afford tert-butyl N-(2-(1-(6,7-dimethoxyquinolin-4-yl)piperidin-4-yl)propyl) sulfamoylcarbamate (06) (100 mg, yield: 16%) as off-white solid. TLC system MeOH:DCM (5:95), $R_f$ value: 0.5; LCMS (m/z): 509.3 (M+H)$^+$; $^1$HNMR (400 MHz, DMSO-$d_6$) δ 8.48 (d, J=4.4 Hz, 1H), 8.17 (s, 1H), 7.46 (brs, 1H), 7.30 (s, 1H), 7.16 (s, 1H), 6.84 (d, J=4.4 Hz, 1H), 3.90 (s, 6H), 3.02-2.96 (m, 2H), 2.78-2.72 (m, 4H), 1.76-1.74 (m, 2H), 1.62-1.52 (m, 4H), 1.43 (s, 9H), 0.92 (d, J=5.2 Hz, 3H).

Synthesis of (I-02)

A solution of tert-butyl N-(2-(1-(6,7-dimethoxyquinolin-4-yl)piperidin-4-yl)propyl) sulfamoylcarbamate (06) (60 mg, 2.05 mmol, 1 eq), in 4M Dioxane.HCl (1 mL) was stirred at room temperature for 2 h. After completion of reaction by TLC, reaction mixture was concentrated and triturated with pentane to afford (I-02) (60 mg, yield: 75%) as an off-white solid. TLC system MeOH:DCM (10:90), $R_f$ value: 0.3; LCMS (m/z): 409.4 (M+H)$^+$; $^1$HNMR (400 MHz, DMSO-$d_6$) δ 8.51 (d, J=6.8 Hz, 1H), 7.37 (s, 1H), 7.241 (s, 1H), 7.1 (d, J=6.8 Hz, 1H), 6.52-6.48 (m, 3H), 4.11 (d, J=12.8 Hz, 2H), 3.97, 3.96 (2 s, 6H), 3.28-3.26 (m, 2H), 2.95-2.92 (m, 1H), 2.78-2.75 (m, 1H), 1.82-1.76 (m, 3H), 1.64-1.44 (m, 3H), 0.89 (d, J=6.8 Hz, 3H).

Scheme for the synthesis of sodium 7-methoxy-4-(4-(2-(sulfamoylamino)ethyl)piperidin-1-yl)quinazolin-6-yl phosphate (I-03)

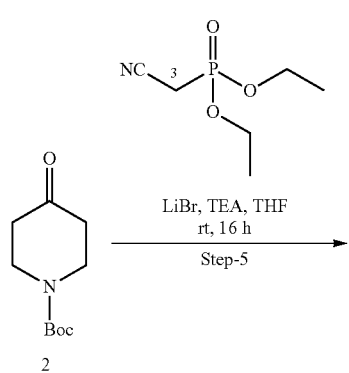

-continued

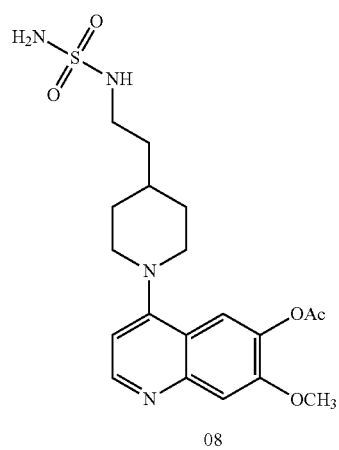 [SMILES: COc1cc2ncnc(N3CCC(C(C)CNS(N)(=O)=O)CC3)c2cc1OC]
08

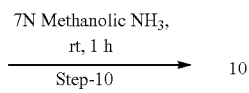
7N Methanolic NH₃,
rt, 1 h
Step-10

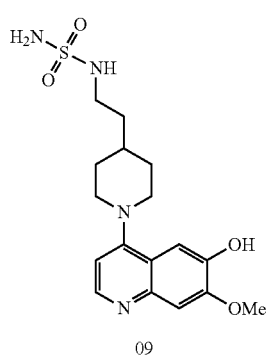
09

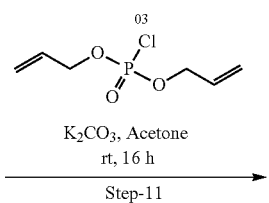
K₂CO₃, Acetone
rt, 16 h
Step-11

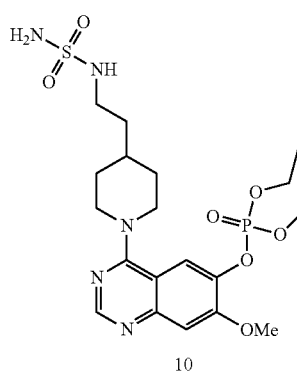
10

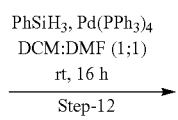
PhSiH₃, Pd(PPh₃)₄
DCM:DMF (1;1)
rt, 16 h
Step-12

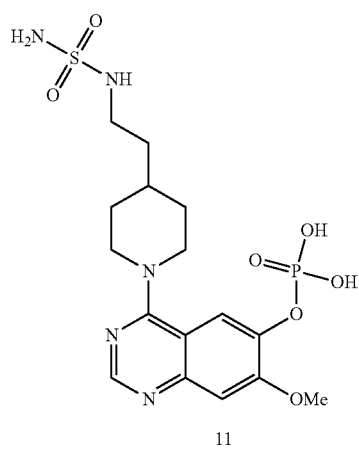
11

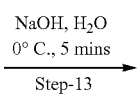
NaOH, H₂O
0° C., 5 mins
Step-13

-continued

I-03

Synthesis of 6,7-dimethoxyquinazolin-4-ol (01)

To a stirred solution of 4-chloro-6,7-dimethoxyquinazoline (1) (10 g, 44.64 mmol, 1 eq) in THF (100 mL) was added KOH in H₂O (50 mL) (8.2 g, 147.3 mmol, 3.3 eq), and the reaction mixture was stirred at 75° C. for 24 h. After completion of reaction by TLC, reaction mixture was cooled to 0° C. and added acetic acid. The precipitated solid was filtered under vacuum and dried to afford 6,7-dimethoxyquinazolin-4-ol (01) as pale yellow solid (7 g, yield: 76%). TLC system: EtOAc (100), $R_f$ value: ~0.1; LCMS (m/z): 207.1 (M+H)⁺; ¹HNMR (400 MHz, DMSO-d₆) δ 12.1 (brs, 1H), 7.98 (s, 1H), 7.44 (s, 1H), 7.13 (s, 1H), 3.9 (s, 3H), 3.87 (s, 3H).

Synthesis of 4-hydroxy-7-methoxyquinazolin-6-yl acetate (02)

To a stirred solution of 6,7-dimethoxyquinazolin-4-ol (01) (7 g, 36.2 mmol, 1 eq) in Methane sulphonic acid (60 mL) was added DL-methionine (8.6 g, 57.9 mmol, 1.6 eq). The reaction mixture was stirred at 120° C. for 24 h, After completion of reaction by TLC, The reaction mixture was cooled to 0° C. and added 2M NaOH to precipitate, solid was filtered and dried. The resulting solid was dissolved in (Ac)₂O (24 mL) and added pyridine (5.3 mL, 67.6 mmol, 2 eq). The reaction mixture was stirred at 100° C. for 24 h, After completion of reaction by TLC, the reaction mixture diluted with cold water, precipitate solid filtered and dried under vacuum to afford 4-hydroxy-7-methoxyquinazolin-6-yl acetate (02) (5.5 g, yield: 69%) as an off-white solid. TLC system: EtOAc (100), $R_f$ value: ~0.2; LCMS (m/z): 235.0 (M+H)⁺; ¹HNMR (400 MHz, DMSO-d₆) δ 12.2 (brs, 1H), 8.08 (s, 1H), 7.74 (s, 1H), 7.27 (s, 1H), 3.9 (s, 3H), 2.29 (s, 3H).

Synthesis of 4-chloro-7-methoxyquinazolin-6-yl acetate (03)

To a stirred solution of 4-hydroxy-7-methoxyquinazolin-6-yl acetate (02) (2 g, 8.54 mmol, 1 eq) in thionyl chloride (18 mL) was added catalytic DMF (1 mL), The reaction mixture was stirred at 80° C. for 2 h, After completion of reaction by TLC, the reaction mixture was diluted with toluene and evaporated under reduced pressure to afford crude. The crude was purified by silica column chromatography by eluting with 20% EtOAc in Hexanes to afford 4-chloro-7-methoxyquinazolin-6-yl acetate (03) (1.2 g, yield: 57%) as cream color solid. TLC system: EtOAc in Hexanes (50:50), $R_f$ value: 0.5; LCMS (m/z): 253.1 (M+H)⁺; ¹HNMR (400 MHz, CDCl₃) δ 8.95 (s, 1H), 7.90 (s, 1H), 7.43 (s, 1H), 4.02 (s, 3H), 2.39 (s, 3H).

Synthesis of tert-butyl 4-(cyanomethylene)piperidine-1-carboxylate (04)

To a stirred solution of tert-butyl 4-oxopiperidine-1-carboxylate (2) (5 g, 25.1 mmol, 1 eq) in THF (50 mL) was added diethyl (cyanomethyl)phosphonate (3) (6.67 mL, 37.6 mmol, 1.5 eq) at 0° C. Then added LiBr (2.58 g, 30.1 mmol, 1.2 eq), TEA (7.2 mL, 50.2 mmol, 2 eq), and the reaction mixture was allowed to stirred at room temperature for 16 h. After completion of reaction by TLC, the reaction mixture was diluted with water and extracted with EtOAc (3×50 mL). The combined organic layers were washed with brine (50 mL) dried over sodium sulfate and concentrated. The crude was purified by silica column chromatography by eluting with 20% EtOAc in Hexane to afford tert-butyl 4-(cyanomethylene)piperidine-1-carboxylate (04) as a white solid (5 g, yield: 89%). TLC system: EtOAc/hexane (20:80), $R_f$ value: ~0.6, PMA stain; ¹H NMR (400 MHz, CDCl₃) δ 5.19 (s, 1H), 3.51 (m, 4H), 2.56 (t, =5.6 Hz, 2H), 2.33 (t, J=5.6 Hz, 2H), 1.47 (s, 9H).

Synthesis of tert-butyl 4-(2-aminoethyl)piperidine-1-carboxylate (05)

To a stirred solution of tert-butyl 4-(cyanomethylene) piperidine-1-carboxylate (04) (5 g, 22.5 mmol, 1 eq) in 1,4 Dioxane:H₂O (3:1) (130 mL) was added 10% Pd/C (1.5 g), Re—Ni (5 g), LiOH.H₂O (1.9 g, 48.3 mmol, 2.1 eq), The reaction mixture was stirred at room temperature for 16 h under H₂ atmosphere (50 psi) in a steel bomb. After completion of reaction by TLC, the reaction mixture was filtered through Celite pad and filtrate was concentrated under reduced pressure to afford tert-butyl 4-(2-aminoethyl)piperidine-1-carboxylate (05) (5 g (crude)) as gummy liquid. TLC system MeOH:DCM (10:90; Ninhydrin stain), $R_f$ value: ~0.1; ¹H NMR (400 MHz, DMSO-d₆) δ 3.91-3.88 (m, 2H), 2.67-2.65 (m, 2H), 1.69-1.57 (m, 2H), 1.39-1.38 (m, 11H), 1.29-1.24 (m, 2H), 1.14-1.09 (m, 1H), 0.97-1.85 (m, 2H). Desired protons were observed by NMR along with impurity peaks.

Synthesis of Tert-butyl 4-(2-((N-(tert-butoxycarbonyl)sulfamoyl)amino)ethyl)piperidine-1-carboxylate (06)

To a stirred solution of tert-butyl 4-(2-aminoethyl)piperidine-1-carboxylate (05) (5 g, crude 21.9 mmol, 1 eq) in DCM (50 mL) was added DIPEA (6 mL, 32.8 mmol, 1.5 eq), (tert-butoxycarbonyl)((4-(dimethyliminio)pyridin-1(4H)-yl) sulfonyl)amide (03) (7.9 g, 26.2 mmol, 1.2 eq) at 0° C., The reaction mixture was stirred at room temperature for 16 h, After completion of reaction by TLC, the reaction mixture was diluted with water and extracted with DCM (2×100 mL). The combined organic layers were washed with brine (30 mL) dried over sodium sulfate and concentrated under reduced pressure to afford tert-butyl 4-(2-((N-(tert-butoxycarbonyl)sulfamoyl)amino)ethyl)piperidine-1-carboxylate (06) (2.5 g, yield: 28%) as white color solid. TLC system MeOH:DCM (10:90; Ninhydrin stain), $R_f$ value: 0.6; ¹HNMR (400 MHz, DMSO-d₆) δ 10.79 (s, 1H), 7.54 (s, 1H), 3.95-3.88 (m, 2H), 2.93-2.88 (m, 2H), 2.67-2.50 (br, 2H), 1.69-1.51 (m, 4H), 1.38 (s, 9H), 1.34 (s, 9H), 1.11-1.07 (m, 1H), 0.96-0.90 (m, 2H).

Synthesis of 4-(2-((N-(sulfamoyl)amino)ethyl)piperidine-1-carboxylate (07)

A solution of tert-butyl 4-(2-((N-(tert-butoxycarbonyl) sulfamoyl)amino)ethyl)piperidine-1-carboxylate (06) (2.5 g, 6.1 mmol, 1 eq) in 4M Dioxane.HCl (25 mL) was stirred at room temperature for 2 h. After completion of reaction by TLC, the reaction mixture was concentrated under reduced pressure to afford 4-(2-((N-(sulfamoyl)amino)ethyl)piperidine-1-carboxylate (07) (1.4 g, yield: 99%) as gummy solid. TLC system MeOH:DCM (10:90; Ninhydrin stain), $R_f$ value: ~0.1; ¹HNMR (400 MHz, DMSO-d₆) δ 8.52-8.51 (br, 2H), 6.52-6.44 (m, 3H), 3.28-3.20 (m, 2H), 2.91-2.78 (m, 4H), 1.85-1.75 (m, 2H), 1.64-1.61 (m, 1H), 1.45-1.38 (m, 2H), 1.32-1.26 (m, 2H).

Synthesis of 7-methoxy-4-(4-(2-(sulfamoylamino) ethyl)piperidin-1-yl)quinazolin-6-yl acetate (08)

To a stirred solution of 4-chloro-7-methoxyquinazolin-6-yl acetate (03) (1 g, 3.9 mmol, 1 eq), and 4-(2-((N-(sulfamoyl)amino)ethyl)piperidine-1-carboxylate (07) (0.97 g, 4.7 mmol, 1.2 eq) in IPA (10 mL), DMF (2 mL) at 0° C., was added DIPEA (1.74 mL, 9.75 mmol, 2.5 eq), The reaction mixture was stirred at 40° C. for 2 h, After completion of reaction by TLC, the reaction mixture was diluted with water and extracted with EtOAc (2×50 mL). The combined organic layers were washed with brine (10 mL) dried over sodium sulfate and concentrated under reduced pressure to afford crude compound. The crude was purified by silica column chromatography by eluting with 10% MeOH in DCM to afford 7-methoxy-4-(4-(2-(sulfamoylamino)ethyl) piperidin-1-yl)quinazolin-6-yl acetate (08) as white solid (450 mg, yield: 28%). TLC system: MeOH/DCM (10:90), $R_f$ value: 0.4; LCMS (m/z): 424.4 (M+H)⁺; ¹HNMR (400 MHz, DMSO-d₆) δ 8.55 (s, 1H), 7.62 (s, 1H), 7.32 (s, 1H), 6.48-6.44 (m, 3H), 4.17 (d, J=13.2 Hz, 2H), 3.94 (s, 3H), 3.08 (t, J=12.4 Hz, 2H), 2.97-2.92 (m, 2H), 2.32 (s, 3H), 1.79-1.75 (m, 3H), 1.49-1.46 (m, 2H), 1.34-1.31 (m, 2H).

Synthesis of (09)

A solution of 7-methoxy-4-(4-(2-(sulfamoylamino)ethyl) piperidin-1-yl)quinazolin-6-yl acetate (08) (450 mg, 1.06 mmol, 1 eq) in 7M Methanolic.NH₃ (5 mL) was stirred at room temperature for 1 h. After completion of reaction by TLC, reaction mixture was concentrated and triturated with diethyl ether to afford (09) (400 mg, yield: 99%) as off-white solid. TLC system MeOH:DCM (10:90), $R_f$ value: 0.3; LCMS (m/z): 382.2 (M+H)⁺; ¹HNMR (400 MHz, DMSO-d₆) δ 9.98-9.99 (br, 1H), 8.45 (s, 1H), 7.19 (s, 1H), 7.16 (s, 1H), 6.48-6.46 (m, 3H), 4.06 (t, J=13.2 Hz, 2H), 3.92 (s, 3H), 2.98-2.92 (m, 4H), 1.81-1.75 (m, 2H), 1.70-1.68 (br, 1H), 1.52-1.46 (m, 2H), 1.35-1.29 (m, 2H).

Synthesis of Diallyl (7-methoxy-4-(4-(2-(sulfamoylamino)ethyl)piperidin-1-yl)quinazolin-6-yl) phosphate (10)

To a stirred solution of (09) (400 mg, 1.04 mmol, 1 eq), in acetone (8 mL) at 0° C., was added K₂CO₃ (215 mg, 1.56 mmol, 1.5 eq), diallyl phosphorochloridate (03) (244 mg, 1.24 mmol, 1.2 eq), The reaction mixture was stirred at room temperature for 16 h. After completion of reaction by TLC, the reaction mixture was quenched with water and extracted with EtOAc (2×30 mL). The combined organic layers were washed with brine (20 mL) dried over sodium sulfate and concentrated to afford Diallyl (7-methoxy-4-(4-(2-(sulfamoylamino)ethyl)piperidin-1-yl)quinazolin-6-yl) phosphate (10) (400 mg (crude)) as gummy liquid. TLC system MeOH: DCM (10:90), $R_f$ value: 0.5; LCMS (m/z): 542.3 (M+H)$^+$.

Synthesis of 7-methoxy-4-(4-(2-(sulfamoylamino)ethyl)piperidin-1-yl)quinazolin-6-yl dihydrogen phosphate (11)

To a stirred solution of Diallyl (7-methoxy-4-(4-(2-(sulfamoylamino)ethyl)piperidin-1-yl)quinazolin-6-yl) phosphate (10) (crude) (400 mg, 0.73 mmol, 1 eq), in DCM:DMF (1:1) (10 mL) degassed for 10 mins and added Phenyl silane (0.45 mL, 3.65 mmol, 5 eq), Pd(PPh$_3$)$_4$ (84 mg, 0.073 mmol, 0.1 eq), The reaction mixture was stirred at room temperature for 16 h. After completion of reaction by TLC, reaction mixture was concentrated and triturated with DCM to afford crude. Crude compound was purified by prep HPLC to afford 7-methoxy-4-(4-(2-(sulfamoylamino)ethyl)piperidin-1-yl)quinazolin-6-yl dihydrogen phosphate (11) (30 mg, yield: 9%) as white solid. TLC system MeOH:DCM (20:80), $R_f$ value: ~0.05; LCMS (m/z): 462.4 (M+H)$^+$; $^1$HNMR (400 MHz, DMSO-d$_6$) δ 8.53 (s, 1H), 7.95 (s, 1H), 7.14 (s, 1H), 6.49-6.46 (m, 3H), 4.37-4.34 (m, 2H), 3.88 (s, 3H), 3.19-3.13 (m, 2H), 2.95-2.93 (m, 2H), 1.84-1.76 (m, 3H), 1.50-1.45 (m, 2H), 1.37-1.31 (m, 2H).

Synthesis of sodium 7-methoxy-4-(4-(2-(sulfamoylamino)ethyl)piperidin-1-yl)quinazolin-6-yl phosphate (I-03)

To a stirred suspension of 7-Methoxy-4-(4-(2-(sulfamoylamino)ethyl)piperidin-1-yl)quinazolin-6-yl dihydrogen phosphate (11) (20 mg, 0.043 mmol, 1 eq) in H$_2$O (0.5 mL), cooled to 0° C. and added NaOH solution (3.4 mg, 0.086 mmol, 2 eq) The reaction mixture was stirred at 0° C. for 5 mins. Reaction mixture was kept under lyophilization to afford (I-03) (21 mg, yield: 99%) as white solid. LCMS (m/z): 462.2 ([M−2Na]+H)$^+$; $^1$HNMR (400 MHz, D$_2$O) δ 8.28 (s, 1H), 7.96 (s, 1H), 7.11 (s, 1H), 4.20 (d, J=13.2 Hz, 2H), 3.92 (s, 3H), 3.16 (t, J=11.6 Hz, 2H), 3.02 (t, J=7.2 Hz, 2H), 1.80 (d, J=12.8 Hz, 2H), 1.71-1.67 (m, 1H), 1.53-1.48 (m, 2H), 1.41-1.38 (m, 2H).

Synthesis of I-04

Synthesis of tert-butyl (2-(1-(6,7-dimethoxyquinazolin-4-yl)piperidin)ethyl)carbamate)(01)

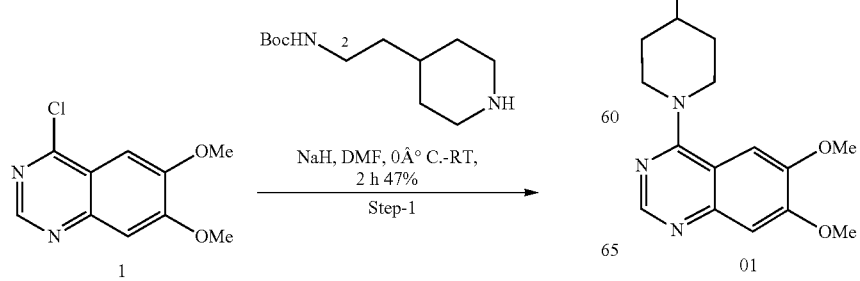

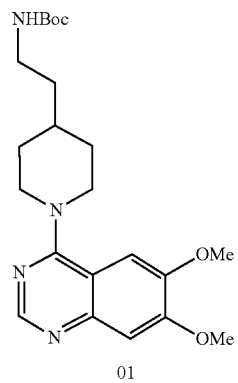

To a stirred solution of NaH (875 mg, 21.90 mmol, 2.5 eq) in DMF (10 mL) at 0° C. was added 4-chloro-6,7-dimethoxyquinazoline (1) (1.96 g, 8.76 mmol, 1.0 eq) and tert-butyl (2-(piperidin-4-yl) ethyl) carbamate (2) (2.0 g, 8.76 mmol, 1.0 eq). The reaction mixture was stirred at room temperature for 2 h. After completion of reaction by TLC, the reaction mixture was quenched with ice-cold water and extracted with EtOAc (2×100 mL). The combined organic layer was washed with brine (50 mL), dried over sodium sulfate and concentrated to obtain crude product. The crude was purified by silica (60-120 mesh) column chromatography [gradient elution with 60% Ethyl acetate/Hexane] to afford tert-butyl (2-(1-((6,7-dimethoxyquinazolin-4-yl) methyl) piperidin-4-yl)ethyl)carbamate (01) (1.8 g, yield: 47%). TLC system: EtOAc/Hexane (70:30), $R_f$ value: ~0.1; LCMS (m/z): 417.3 (M+H)$^+$; $^1$H NMR (400 MHz, DMSO-d$_6$) δ 8.51 (s, 1H), 7.19 (s, 1H), 7.10 (s, 1H). 6.82-6.79 (brs, 1H), 4.13 (d, J=12.8 Hz, 2H), 3.95 (s, 3H), 3.94 (s, 3H), 3.02-2.96 (m, 4H), 1.81 (d, J=10.8 Hz, 2H), 1.59-1.57 (m, 1H), 1.42-1.31 (m, 13H).

Synthesis of 2-(1-(6,7-dimethoxyquinazolin-4-yl)piperidin-4-yl)ethan-1-amine hydrochloride (02)

-continued

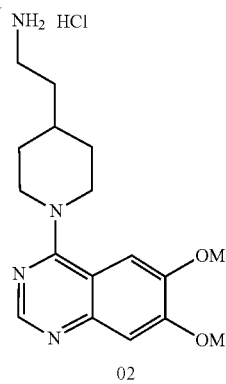

A solution of tert-butyl (2-(1-(6,7-dimethoxyquinazolin-4-yl)piperidin-4-yl)ethyl) carbamate (01) (1.0 g, 2.40 mmol, 1.0 eq) in 4 M HCl in dioxane (5.0 mL; 5 vol) under N₂ was stirred at RT for 2 h. The volatiles were evaporated and triturated with diethyl ether to afford 2-(1-(6,7-dimethoxyquinazolin-4-yl)piperidin-4-yl)ethan-1-amine hydrochloride (02) as an off-white solid (580 mg, yield: 76%). TLC system: MeOH:DCM (10:90), $R_f$ value: ~0.1; (400 MHz, DMSO-$d_6$) δ 8.75 (s, 1H), 8.04 (brs, 3H), 7.39 (s, 1H), 7.32 (s, 1H), 4.68 (d, J=13.2 Hz, 2H), 3.97 (s, 3H), 3.95 (s, 3H), 3.49-3.38 (m, 2H), 2.87-2.82 (m, 2H), 1.96-86 (m, 3H), 1.60-1.56 (m, 2H), 1.39-1.35 (m, 2H).

Synthesis of (tert-butoxycarbonyl)((4-(dimethyliminio)pyridin-1(4H)-yl)sulfonyl)amide (03)

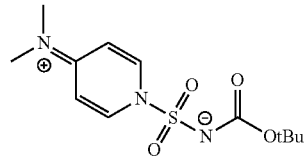

To a stirred solution of tBuOH (1.3 mL, 13.5 mmol, 2.0 eq) in DCM (10 mL) at 0° C. was added chlorosulfonyl isocyanate (4) (1.2 mL, 13.8 mmol, 1.0 eq) over 15 minutes. The mixture was stirred at 0° C. for 10 minutes and DMAP (3) (3.45 g, 28.3 mmol, 1.0 eq) was added. The reaction mixture was stirred at room temperature for 1 h. The thick slurry was diluted with DCM (60 mL) and washed with water (30 mL). The organic layer was concentrated in vacuo and the residue was crystallized from DCM (30 mL) to afford (tert-butoxycarbonyl)((4-(dimethyliminio)pyridin-1(4H)-yl)sulfonyl)amide (03) (2.3 g, 55%). ¹H NMR (400 MHz, DMSO-$d_6$) δ 8.22 (d, J=7.6 Hz, 2H), 6.99 (d, J=7.6 Hz, 2H), 3.19 (s, 6H), 1.36 (s, 9H).

Synthesis of tert-butyl (N-(2-(1-(6,7-dimethoxyquinazolin-4-yl)piperidin-4-yl)ethyl)sulfamoyl)carbamate (04)

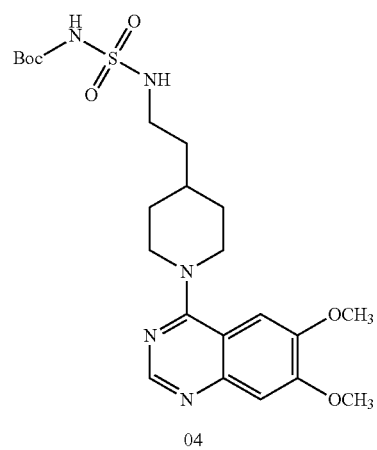

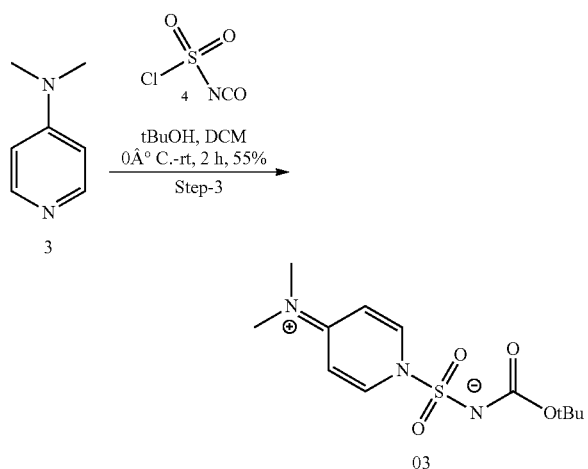

To a stirred solution of 2-(1-(6,7-dimethoxyquinazolin-4-yl)piperidin-4-yl)ethan-1-amine hydrochloride (02) (500 mg, 1.58 mmol, 1.0 eq) in DCM (5 mL) at RT, was added DIPEA (0.6 ml, 3.16 mmol, 2.0 eq) and (tert-butoxycarbonyl)((4-(dimethyliminio)pyridin-1(4H)-yl)sulfonyl)amide (03) (619 mg, 2.05 mmol, 1.3 eq) and stirred at room temperature for 16 h. After completion of reaction by TLC, the reaction mixture was diluted with water and extracted with Ethyl acetate (2×60 mL). The combined organic layer was washed with brine (20 mL), dried over sodium sulfate and concentrated to obtain crude product. The crude was purified by Grace column chromatography [gradient elution with 10% to 15% MeOH/DCM] to afford tert-butyl (N-(2-(1-(6,7-dimethoxyquinazolin-4-yl)piperidin-4-yl)ethyl)sulfamoyl)carbamate (04) (450 mg, yield: 57%). TLC system: MeOH:DCM (10:90), $R_f$ value: ~0.2; LCMS (m/z): 496.3 (M+H)⁺; ¹H NMR (400 MHz, CDCl₃) δ 8.65 (s, 1H), 7.25 (s, 1H), 7.08 (s, 1H), 5.11 (t, J=6.0 Hz, 1H), 4.20-4.17 (m, 2H), 4.02 (s, 3H), 3.99 (s, 3H), 3.19-3.15 (m, 2H), 3.07-3.04 (m, 2H), 1.89-1.86 (m, 3H), 1.79-1.73 (m, 2H), 1.66-1.64 (m, 2H), 1.51 (s, 9H). exchangeable proton was not clearly evident from the spectrum.

Synthesis of N-(2-(1-(6,7-dimethoxyquinazolin-4-yl)piperidin-4-yl)ethyl)sulfonamide (I-04)

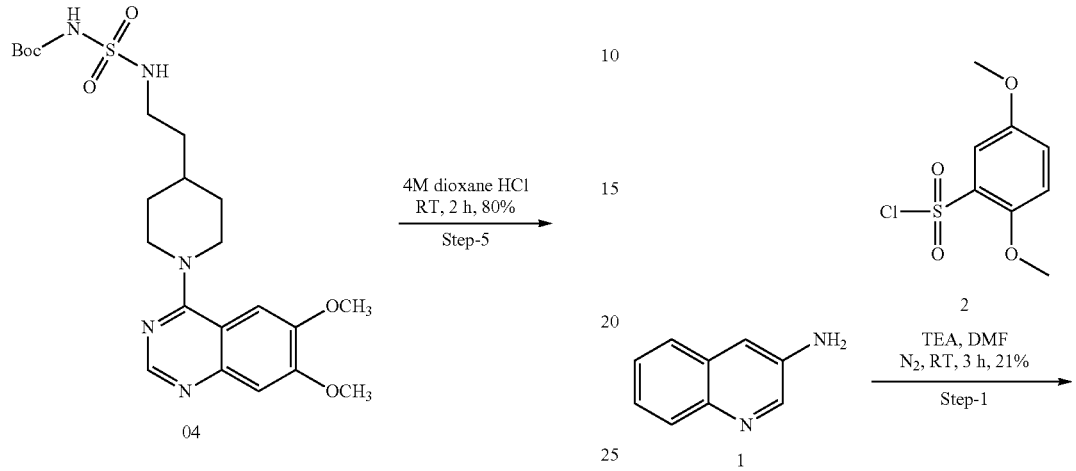

Synthesis of I-06

Synthesis of 2,5-dimethoxy-N(quinoline-3-yl) benzene sulfonamide (I-06)

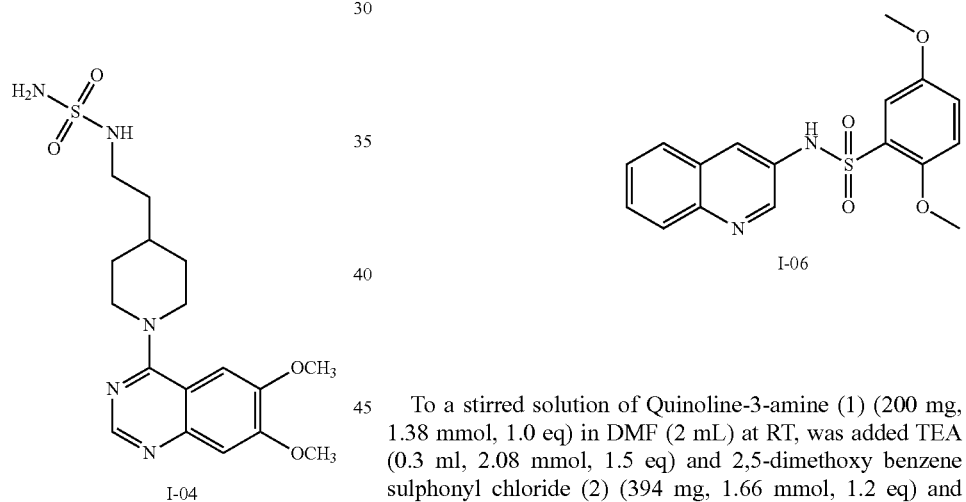

A solution of tert-butyl N-(2-(1-(6,7-dimethoxyquinazolin-4-yl)piperidin-4-yl)ethyl)sulfamoylcarbamate (04) (80 mg, 0.16 mmol, 1.0 eq) in 4M HCl in dioxane (1.0 mL; 10 vol) was stirred for 2 h at room temperature under nitrogen flush. The volatiles were evaporated and triturated with diethyl ether followed by lyophilization afforded N-(2-(1-(6,7-dimethoxyquinazolin-4-yl)piperidin-4-yl)ethyl)sulfonamide (I-04) as an off white solid (34 mg, yield: 80%). LCMS (m/z): 396.2 (M+H)$^+$; $^1$H NMR (400 MHz, DMSO-$d_6$) δ 8.73 (s, 1H), 7.31 (s, 1H), 7.28 (s, 1H), 6.49 (s, 3H), 4.67 (d, J=12.8 Hz, 2H), 3.98 (s, 3H), 3.95 (s, 3H), 3.48-3.42 (m, 2H), 2.95-2.94 (m, 2H), 1.92-1.89 (m, 3H), 1.50-1.45 (m, 2H), 1.37-1.33 (m, 2H).

To a stirred solution of Quinoline-3-amine (1) (200 mg, 1.38 mmol, 1.0 eq) in DMF (2 mL) at RT, was added TEA (0.3 ml, 2.08 mmol, 1.5 eq) and 2,5-dimethoxy benzene sulphonyl chloride (2) (394 mg, 1.66 mmol, 1.2 eq) and stirred at room temperature for 3 h. After completion of reaction by TLC, the reaction mixture was diluted with water and extracted with Ethyl acetate (2×50 mL). The combined organic layer was washed with brine (20 mL), dried over sodium sulfate and concentrated to obtain crude product. The crude compound was purified by Reverse phase Grace column chromatography [gradient elution with 38% of 0.1%% FA in Water and ACN] provided 150 mg of I-06 with 89% purity which was further purified by silica gel column chromatography [gradient elution with 80% Ethyl acetate/Hexane] to afford 2,5-dimethoxy-N-(quinolin-3-yl) benzenesulfonamide (I-06) (100 mg, yield: 21%). TLC system: EtOAc (100%; with a drop of TEA), $R_f$ value: ~0.6; LCMS (m/z): 345.2 (M+H)$^+$; $^1$H NMR (400 MHz, CDCl$_3$) δ 8.54 (d, J=2.8 Hz, 1H), 8.03 (d, J=2.4 Hz, 1H), 7.99 (d, J=8.0 Hz, 1H), 7.75 (d, J=8.0 Hz, 1H), 7.65-7.61 (m, 1H), 7.54-7.50 (m, 1H), 7.31 (d, J=2.8 Hz, 1H), 7.27 (brs, 1H), 7.01-6.94 (m, 2H), 4.03 (s, 3H), 3.70 (s, 3H).

Synthesis of I-07

Synthesis of 2-(1-(7-methoxyquinolin-4-yl)piperidin-4-yl)propanenitrile (01)

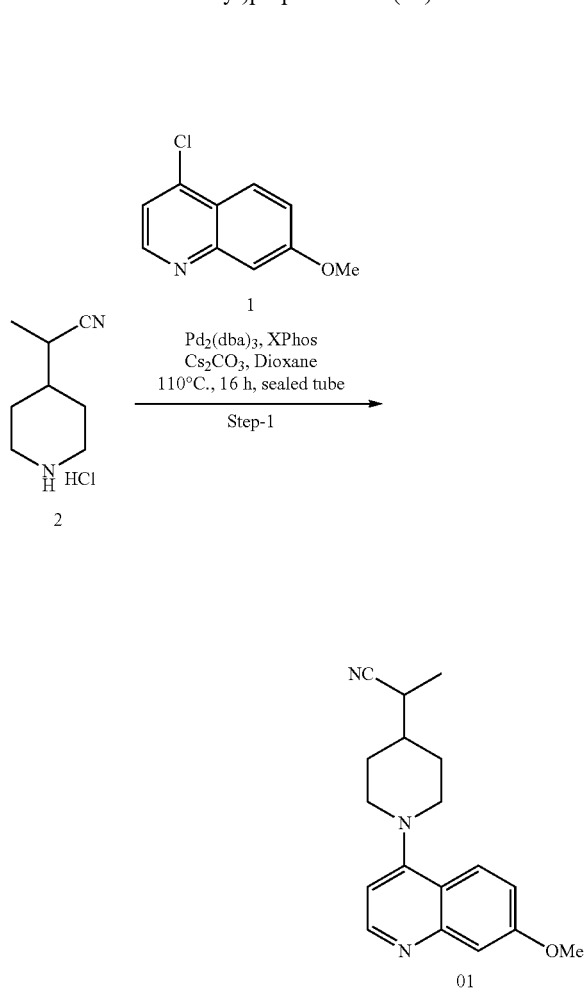

To a stirred solution of 4-chloro-7-methoxyquinoline (1) (1 g, 5.16 mmol, 1 eq) in 1,4 Dioxane (10 mL) was added 2-(piperidin-4-yl)propanenitrile hydrochloride (2) (0.85 g, 6.19 mmol, 1.2 eq) and degassed for 10 mins. Then added $Cs_2CO_3$ (5 g, 15.4 mmol, 3 eq), $Pd_2(dba)_3$ (0.47 g, 0.51 mmol, 0.1 eq) and X-Phos (0.49 g, 1.0 mmol, 0.2 eq). The reaction mixture was stirred at 110° C. for 16 h in a sealed tube. After completion of reaction by TLC, the reaction mixture was filtered through Celite pad and concentrated to provide crude. The crude compound was purified by 100-200 mesh silica gel column by eluting with 3% MeOH in DCM to afford 2-(1-(7-methoxyquinolin-4-yl)piperidin-4-yl)propanenitrile (01) (0.7 g, yield: 50%) as yellow solid. TLC system MeOH:DCM (10:90), $R_f$ value: 0.5; LCMS (m/z): 296.2 (M+H)$^+$; $^1$HNMR (400 MHz, DMSO-d$_6$) δ 8.63 (d, J=5.2 Hz, 1H), 7.87 (d, J=9.2 Hz, 1H), 7.40-7.39 (m, 1H), 7.14 (dd, J=9.2 Hz, 2.4 Hz, 1H), 6.73 (d, J=5.2 Hz, 1H), 3.94 (s, 3H), 3.70-3.64 (m, 2H), 2.85-2.69 (m, 2H), 2.68-2.65 (m, 1H), 2.09-2.06 (m, 2H), 1.95-1.92 (m, 1H), 1.81-1.76 (m, 2H), 1.40 (d, J=7.2 Hz, 3H).

Synthesis of 2-(1-(7-methoxyquinolin-4-yl)piperidin-4-yl)propan-1-amine (02)

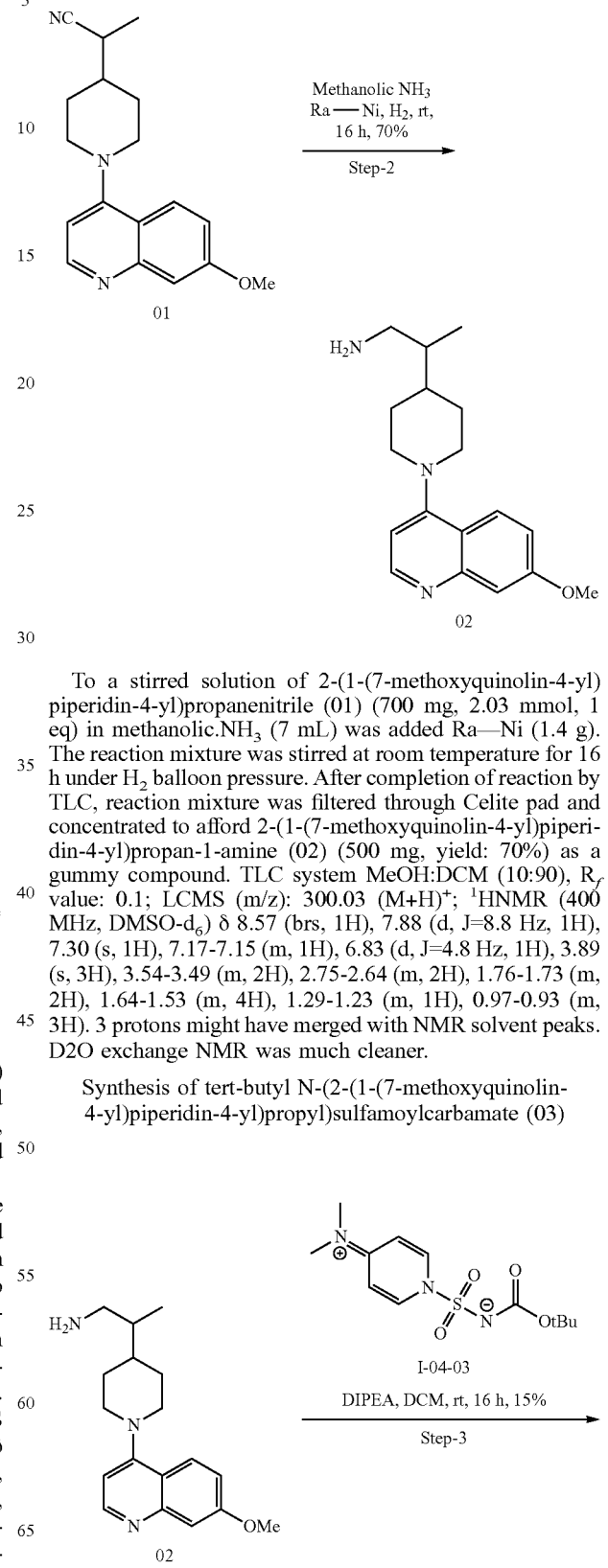

To a stirred solution of 2-(1-(7-methoxyquinolin-4-yl)piperidin-4-yl)propanenitrile (01) (700 mg, 2.03 mmol, 1 eq) in methanolic.NH$_3$ (7 mL) was added Ra—Ni (1.4 g). The reaction mixture was stirred at room temperature for 16 h under H$_2$ balloon pressure. After completion of reaction by TLC, reaction mixture was filtered through Celite pad and concentrated to afford 2-(1-(7-methoxyquinolin-4-yl)piperidin-4-yl)propan-1-amine (02) (500 mg, yield: 70%) as a gummy compound. TLC system MeOH:DCM (10:90), $R_f$ value: 0.1; LCMS (m/z): 300.03 (M+H)$^+$; $^1$HNMR (400 MHz, DMSO-d$_6$) δ 8.57 (brs, 1H), 7.88 (d, J=8.8 Hz, 1H), 7.30 (s, 1H), 7.17-7.15 (m, 1H), 6.83 (d, J=4.8 Hz, 1H), 3.89 (s, 3H), 3.54-3.49 (m, 2H), 2.75-2.64 (m, 2H), 1.76-1.73 (m, 2H), 1.64-1.53 (m, 4H), 1.29-1.23 (m, 1H), 0.97-0.93 (m, 3H). 3 protons might have merged with NMR solvent peaks. D2O exchange NMR was much cleaner.

Synthesis of tert-butyl N-(2-(1-(7-methoxyquinolin-4-yl)piperidin-4-yl)propyl)sulfamoylcarbamate (03)

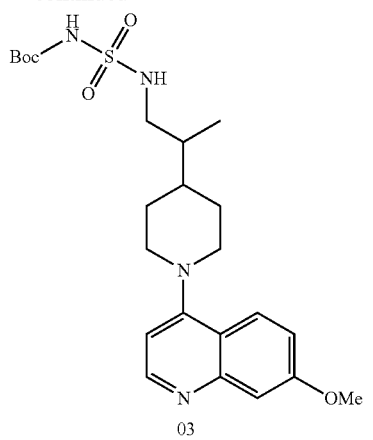

03

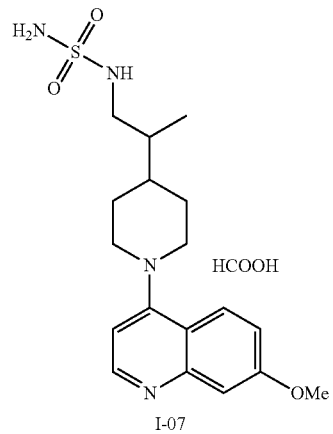

I-07

To a stirred solution of 2-(1-(7-methoxyquinolin-4-yl)piperidin-4-yl)propan-1-amine (02) (500 mg, 1.67 mmol, 1 eq) in DCM (14 mL) was added DIPEA (0.46 mL, 2.50 mmol, 1.5 eq), (tert-butoxycarbonyl)((4-(dimethyliminio)pyridin-1 (4H)-yl)sulfonyl)amide (I-04-03) (654 mg, 2.17 mmol, 1.3 eq). The reaction mixture was stirred at RT for 16 h. After completion of reaction, the reaction mixture was diluted with water and extracted with DCM (2×20 mL). The combined organic layers were washed with brine (10 mL) dried over sodium sulfate and concentrated under reduced pressure to afford crude. The crude compound was purified by prep HPLC to afford tert-butyl N-(2-(1-(7-methoxyquinolin-4-yl)piperidin-4-yl)propyl)sulfamoylcarbamate (03) (120 mg, yield: 15%) as off-white solid. TLC system MeOH:DCM (5:95), $R_f$ value: 0.5; LCMS (m/z): 479.4 (M+H)$^+$; $^1$HNMR (400 MHz, DMSO-d$_6$) δ 8.57 (d, J=5.2 Hz, 1H), 7.87 (d, J=9.2 Hz, 1H), 7.57 (t, J=5.6 Hz, 1H), 7.29 (d, J=2.4 Hz, 1H), 7.16 (dd, J=9.2 Hz, 2.4 Hz, H), 6.83 (d, J=5.2 Hz, 1H), 3.89 (s, 3H), 3.56-3.53 (m, 2H), 2.99-2.96 (m, 1H), 2.79-2.74 (m, 4H), 1.73-1.70 (m, 2H), 1.62-1.57 (m, 4H), 1.43 (s, 9H), 0.9 (d, J=6.8 Hz, 3H).

Synthesis of N-(2-(1-(7-methoxyquinolin-4-yl)piperidin-4-yl)propyl)aminosulfonamide (I-07)

A solution of tert-butyl N-(2-(1-(7-methoxyquinolin-4-yl)piperidin-4-yl)propyl)sulfamoylcarbamate (03) (120 mg, 0.25 mmol, 1 eq) in 4M Dioxane.HCl (2 mL) was stirred at room temperature for 2 h. After completion of reaction by TLC, volatiles were evaporated, The crude compound was purified by prep HPLC to afford N-(2-(1-(7-methoxyquinolin-4-yl)piperidin-4-yl)propyl)aminosulfonamide (I-07) (45 mg, yield: 47%) as an off-white solid. TLC system MeOH:DCM (10:90), $R_f$ value: 0.3; LCMS (m/z): 379.2 (M+H)$^+$; $^1$HNMR (400 MHz, DMSO-d$_6$) δ 8.56 (d, J=5.2 Hz, 1H), 8.13 (formic acid proton), 7.91 (d, J=9.2 Hz, 1H), 7.29 (d, J=2.8 Hz, 1H), 7.19 (dd, J=9.2 Hz, 2.8 Hz, 1H), 6.88 (d, J=5.6 Hz, 1H), 6.49-6.47 (m, 3H), 3.91 (s, 3H), 3.70-3.67 (m, 2H), 2.98-2.91 (m, 3H), 2.78-2.72 (m, 1H), 1.76-1.73 (m, 2H), 1.62-1.49 (m, 4H), 0.90 (d, J=6.4 Hz, 3H).

Synthesis of I-08

Synthesis of 2-(1-(6-methoxyquinolin-4-yl)piperidin-4-yl)propanenitrile (01)

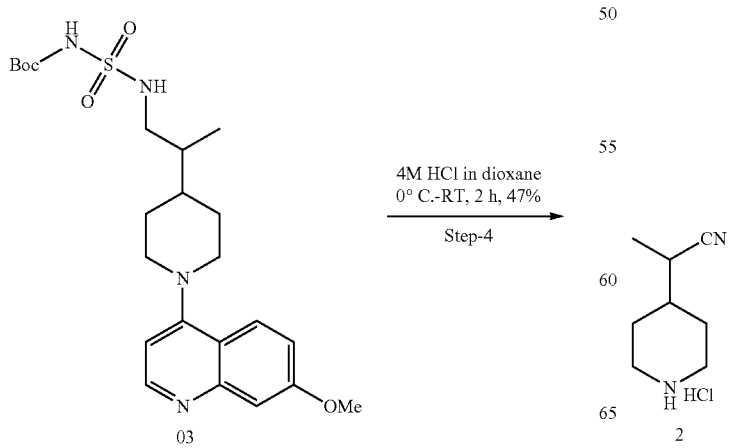

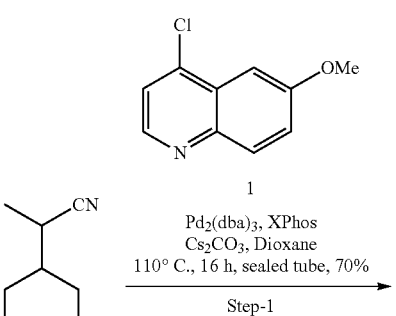

-continued

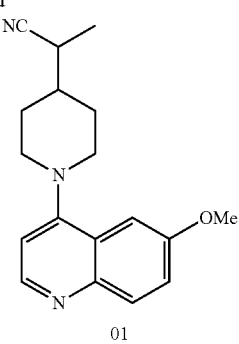

To a stirred solution of 4-chloro-7-methoxyquinoline (1) (0.6 g, 3.18 mmol, 1 eq) in 1,4 Dioxane (10 mL) was added 2-(piperidin-4-yl)propanenitrile hydrochloride (2) (0.51 g, 3.73 mmol, 1.2 eq) and degassed for 10 mins. Then added $Cs_2CO_3$ (3.0 g, 9.32 mmol, 3 eq), $Pd_2(dba)_3$ (0.28 g, 0.31 mmol, 0.1 eq) and X-Phos (0.29 g, 0.62 mmol, 0.2 eq). The reaction mixture was stirred at 110° C. for 16 h in a sealed tube. After completion of reaction by TLC, the reaction mixture was filtered through Celite pad and concentrated to provide crude. The crude compound was purified by 100-200 mesh silica gel column by eluting with 3% MeOH in DCM to afford 2-(1-(6-methoxyquinolin-4-yl)piperidin-4-yl)propanenitrile (01) (0.7 g, yield: 70%) as white solid. TLC system MeOH:DCM (10:90), $R_f$ value: 0.5; LCMS (m/z): 296.2 (M+H)$^+$; $^1$HNMR (400 MHz, DMSO-d$_6$) δ 8.60 (d, J=6.0 Hz, 1H), 7.94 (d, J=9.2 Hz, 1H), 7.56-7.49 (m, 1H), 7.28-7.27 (m, 1H), 7.12 (d, J=6.0 Hz, 1H), 3.94 (s, 3H), 3.92-3.90 (m, 2H), 3.15-3.09 (m, 2H), 2.96-2.89 (m, 1H), 2.03-1.92 (m, 2H), 1.85-1.83 (m, 1H), 1.64-1.56 (m, 2H), 1.29 (d, J=6.8 Hz, 3H).

Synthesis of 2-(1-(6-methoxyquinolin-4-yl)piperidin-4-yl)propan-1-amine (02)

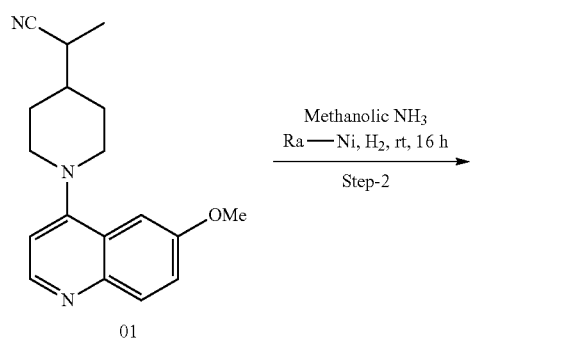

To a stirred solution of 2-(1-(6-methoxyquinolin-4-yl)piperidin-4-yl)propanenitrile (01) (600 mg, 2.03 mmol, 1 eq) in Methanolic.NH$_3$ (6 mL) was added Re—Ni (1.4 g). The reaction mixture was stirred at room temperature for 16 h under H$_2$ balloon pressure. After completion of reaction by TLC, reaction mixture was filtered through Celite pad and concentrated to afford 2-(1-(6-methoxyquinolin-4-yl)piperidin-4-yl)propan-1-amine (02) (700 mg, yield: 98%) as a gummy compound. TLC system MeOH:DCM (10:90), $R_f$ value: 0.1; LCMS (m/z): 300.03 (M+H)$^+$;

Synthesis of tert-butyl N-(2-(1-(6-methoxyquinolin-4-yl)piperidin-4-yl)propyl)sulfamoylcarbamate (03)

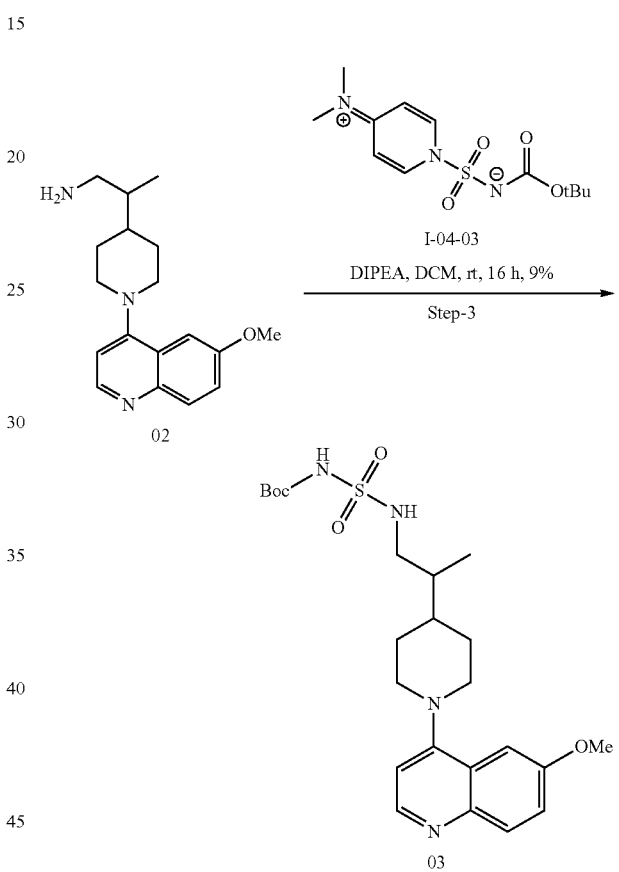

To a stirred solution of 2-(1-(6-methoxyquinolin-4-yl)piperidin-4-yl)propan-1-amine (02) (700 mg, 2.37 mmol, 1 eq) in DCM (14 mL) was added DIPEA (0.65 mL, 3.55 mmol, 1.5 eq), (tert-butoxycarbonyl)((4-(dimethyliminio)pyridin-1(4H)-yl)sulfonyl)amide (I-04-03) (928 mg, 3.08 mmol, 1.3 eq). The reaction mixture was stirred at RT for 16 h. After completion of reaction, the reaction mixture was quenched with water and extracted with DCM (2×50 mL). The combined organic layers were washed with brine (20 mL) dried over sodium sulfate and concentrated under reduced pressure to afford crude. The crude compound was purified by prep HPLC to afford tert-butyl N-(2-(1-(6-methoxyquinolin-4-yl)piperidin-4-yl)propyl)sulfamoyl carbamate (03) (100 mg, yield: 9%) as off-white solid. TLC system MeOH:DCM (5:95), $R_f$ value: 0.5; LCMS (m/z): 479.3 (M+H)$^+$; $^1$HNMR (400 MHz, DMSO-d$_6$) 8.54 (d, J=5.2 Hz, 1H), 7.86 (d, J=8.8 Hz, 1H), 7.59 (t, J=6.0 Hz, 1H), 7.36 (dd, J=8.8 Hz, 2.8 Hz, 1H), 7.23-7.22 (m, 1H), 6.95 (d, J=5.2 Hz, 1H), 6.47 (s, 1H), 3.90 (s, 3H), 3.58-3.55

(m, 2H), 3.02-2.96 (m, 1H), 2.81-2.70 (m, 3H), 1.77-1.75 (m, 2H), 1.64-1.53 (m, 4H), 1.44 (s, 9H), 0.92 (d, J=6 Hz 3H).

Synthesis of N-(2-(1-(6-methoxyquinolin-4-yl)piperidin-4-yl)propyl)aminosulfonamide (I-08)

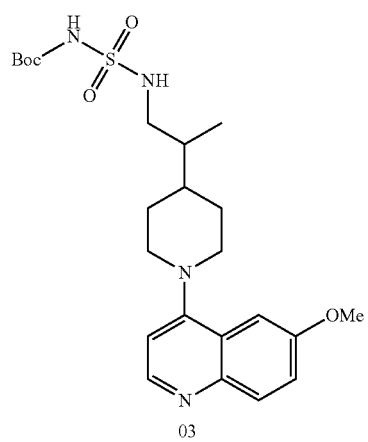

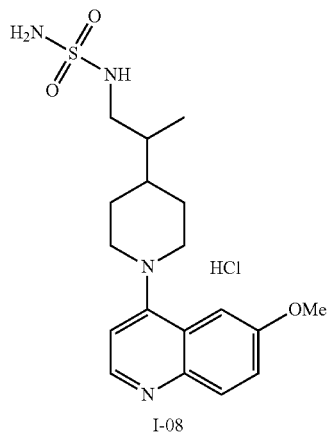

A solution of tert-butyl N-(2-(1-(6-methoxyquinolin-4-yl) piperidin-4-yl)propyl)sulfamoylcarbamate (03) (100 mg, 0.20 mmol, 1 eq) in 4M Dioxane.HCl (2 mL) was stirred at room temperature for 2 h. After completion of reaction by TLC, volatiles were evaporated, triturated with diethyl ether and dried to afford N-(2-(1-(6-methoxyquinolin-4-yl)piperidin-4-yl)propyl)aminosulfonamide (I-08) (50 mg, yield: 56%) as an off-white solid. TLC system MeOH:DCM (10: 90), $R_f$ value: 0.3; LCMS (m/z): 379.3 (M+H)$^+$; $^1$HNMR (400 MHz, DMSO-d) δ 14.8-14.6 (br, 1H), 8.59 (d, J=6.8 Hz, 1H), 8.02 (d, J=8.8 Hz, 1H), 7.65 (dd, J=8.8 Hz, 2.4 Hz, 1H), 7.31 (d, J=2.4 Hz, 1H), 7.18 (d, J=6.8 Hz, 1H), 6.52-6.48 (m, 3H), 4.17-4.13 (m, 2H), 3.95 (s, 3H), 3.31-3.29 (m, 2H), 2.97-2.91 (m, 1H), 2.79-2.73 (m, 1H), 1.83-1.79 (m, 3H), 1.66-1.47 (m, 3H), 0.89 (d, J=6.8 Hz, 3H).

Synthesis of I-09

Synthesis of 4-chloro-7-methoxy-6-(methoxymethoxy)quinoline (01)

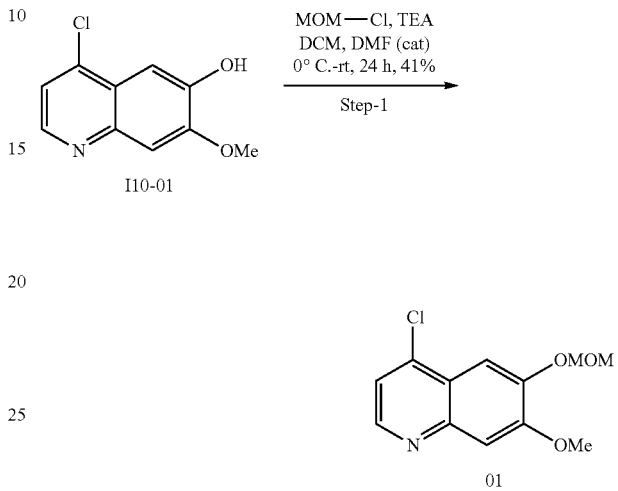

To a stirred solution of 4-chloro-7-methoxyquinolin-6-ol (I-10-01) (1.2 g, 5.74 mmol, 1 eq) in DCM (15 mL) cooled to 0° C., added TEA (0.48 mL, 34.4 mmol, 6 eq), MOM-Cl (2.17 mL, 28.7 mmol, 5 eq) and catalytic amount of DMF. The reaction mixture was stirred at room temperature for 24 h. After completion of reaction by TLC, the reaction mixture was poured into ice water and extracted with DCM (2×80 mL). The combined organic layer was washed with brine (50 mL), dried over sodium sulfate and concentrated under reduced pressure to afford crude. The crude compound was purified by silica gel (100-200 mesh) column purification [eluted with 2% MeOH in DCM] to afford 4-chloro-7-methoxy-6-(methoxymethoxy)quinoline (01) (600 mg, yield: 41%) as Gummy solid. TLC system EtOAc:Hexane (60:40), $R_f$ value: 0.4; LCMS (m/z): 254.1 (M+H)$^+$.

Synthesis of 2-(1-(7-methoxy-6-(methoxymethoxy)quinolin-4-yl)piperidin-4-yl)propanenitrile (02)

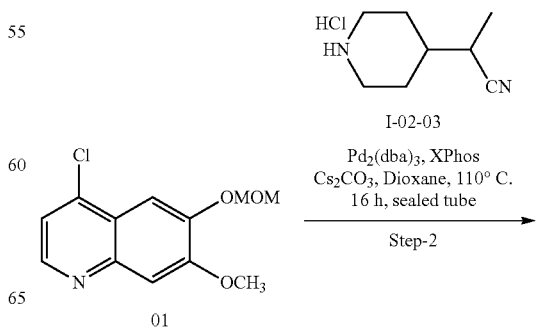

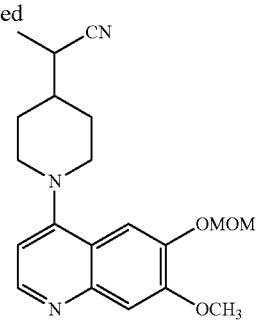

02

To a stirred solution of 4-chloro-7-methoxy-6-(methoxymethoxy)quinoline (01) (600 mg, 2.37 mmol, 1 eq) in 1,4 Dioxane (6 mL) was added 2-(piperidin-4-yl)propanenitrile hydro chloride (I-02-03) (0.49 g, 2.84 mmol, 1.2 eq) and degassed for 10 mins. Then added $Cs_2CO_3$ (2.3 g, 7.11 mmol, 3 eq), $Pd_2(dba)_3$ (0.21 g, 0.23 mmol, 0.1 eq) and X-Phos (0.21 g, 0.46 mmol, 0.2 eq). The reaction mixture was stirred at 110° C. for 16 h in a sealed tube. After completion of reaction by TLC, the reaction mixture was filtered through Celite pad, washed with ethyl acetate and filtrate was concentrated to provide crude. The crude compound was purified by silica gel (100-200 mesh) column chromatography [eluted with 2% MeOH in DCM] to afford 2-(1-(7-methoxy-6-(methoxymethoxy)quinolin-4-yl)piperidin-4-yl)propanenitrile (02) (450 mg) as gummy solid with 66% purity. TLC system MeOH:DCM (5:95), $R_f$ value: 0.2; LCMS (m/z): 356.3 $(M+H)^+$. The material was taken forward to next step without further purification.

Synthesis of 2-(1-(7-methoxy-6-(methoxymethoxy) quinolin-4-yl)piperidin-4-yl)propan-1-amine (03)

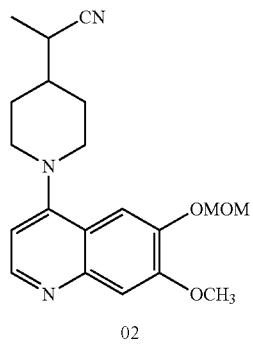

To a stirred solution of 2-(1-(7-methoxy-6-(methoxymethoxy)quinolin-4-yl)piperidin-4-yl)propanenitrile (02) (450 mg, 2.03 mmol, 1 eq) in 7M methanolic.$NH_3$ (5 mL) was added Raney-Ni (1 g). The reaction mixture was stirred at room temperature for 16 h under $H_2$ balloon pressure. After completion of reaction by TLC, reaction mixture was filtered through Celite pad, washed with methanol and filtrate was concentrated under reduced pressure to afford 2-(1-(7-methoxy-6-(methoxymethoxy)quinolin-4-yl) piperidin-4-yl)propan-1-amine (03) (450 mg) as a gummy material. TLC system MeOH:DCM (10:90), $R_f$ value: 0.1; LCMS (m/z): 360.3 $(M+H)^+$.

Synthesis of tert-butyl (N-(2-(1-(7-methoxy-6-(methoxymethoxy)quinolin-4-yl)piperidin-4-yl)propyl)sulfamoyl)carbamate (04)

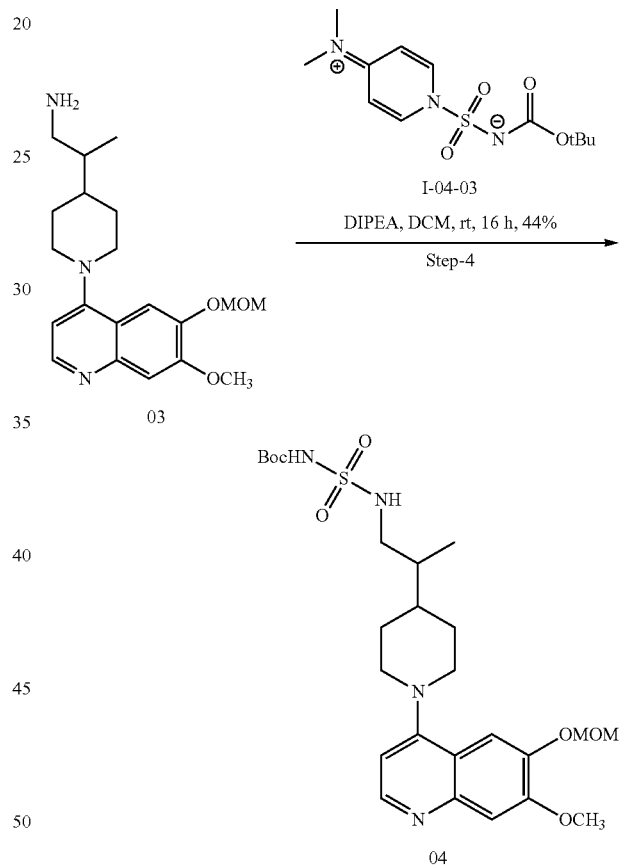

To a stirred solution of 2-(1-(7-methoxy-6-(methoxymethoxy)quinolin-4-yl)piperidin-4-yl)propan-1-amine (03) (450 mg, 1.25 mmol, 1 eq) in DCM (9 mL) was added DIPEA (0.33 mL, 1.87 mmol, 1.5 eq) and (tert-butoxycarbonyl)((4-(dimethyliminio)pyridin-1(4H)-yl) sulfonyl)amide (I-04-03) (452 mg, 1.50 mmol, 1.2 eq). The reaction mixture was stirred at room temperature for 16 h. After completion of reaction, the reaction mixture was quenched with water and extracted with DCM (2×40 mL). The combined organic layers were washed with brine (30 mL), dried over sodium sulfate and concentrated under reduced pressure to afford crude. The crude compound was purified by silica gel (100-200 mesh) column purification [eluted with 3% MeOH in DCM] to afford tert-butyl (N-(2-

(1-(7-methoxy-6-(methoxymethoxy)quinolin-4-yl)piperidin-4-yl)propyl)sulfamoyl)carbamate (04) (300 mg, yield: 44%) as an off-white solid. TLC system MeOH:DCM (5:95), $R_f$ value: 0.5; LCMS (m/z): 539.4 (M+H)$^+$.

Synthesis of N—(N-(2-(1-(6-hydroxy-7-methoxyquinolin-4-yl)piperidin-4-yl)propyl)sulfuricdiamide formate salt (I-09)

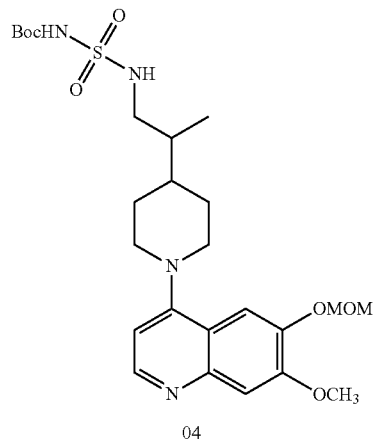

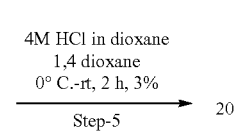

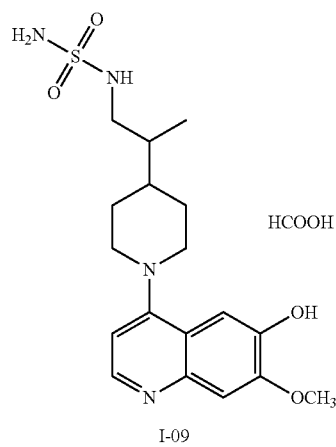

I-09

To a stirred solution of tert-butyl (N-(2-(1-(7-methoxy-6-(methoxymethoxy)quinolin-4-yl)piperidin-4-yl)propyl)sulfamoyl)carbamate (04) (300 mg, 0.55 mmol, 1 eq) in 1,4 Dioxane (1 mL) at 0° C. was added 4M Dioxane.HCl (2 mL) and stirred at room temperature for 2 h. After completion of reaction by TLC, volatiles were evaporated to provide residue. The crude compound was purified by Reverse phase purification [gradient elution with 1-15% (0.1% FA in H$_2$O)+ACN] to afford N—(N-(2-(1-(6-hydroxy-7-methoxyquinolin-4-yl)piperidin-4-yl)propyl)sulfuricdiamide formate salt (I-09) (7 mg, yield: 3%) as an off-white solid. TLC system MeOH:DCM (10:90), $R_f$ value: 0.2; LCMS (m/z): 395.3 (M+H): $^1$HNMR (400 MHz, DMSO-d$_6$) δ 8.40 (d, J=5.2 Hz, 1H), 8.35 (brs, 2H), 7.25 (s, 1H), 7.24 (s, 1H), 6.77 (d, J=5.2 Hz, 1H), 6.50-6.47 (brs, 3H), 3.89 (s, 3H), 3.49-3.47 (m, 2H), 3.05-2.94 (m, 1H), 2.78-2.73 (m, 1H), 2.71-2.67 (m, 2H), 1.75-1.72 (m, 2H), 1.63-1.52 (m, 4H), 0.92 (d, J=6.8 Hz, 3H).

Synthesis of I-10

Synthesis of 4-chloro-7-methoxyquinolin-6-ol (01)

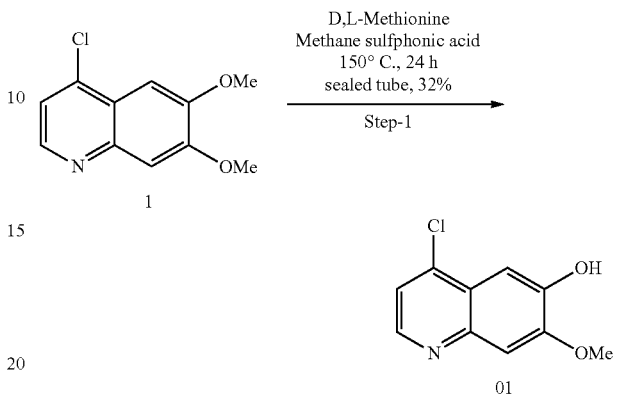

To a stirred solution of 4-chloro-6,7-dimethoxyquinoline (1) (5 g, 22.4 mmol, 1 eq) in Methane sulphonic acid (25 mL) was added D,L-Methionine (8.3 g, 56 mmol, 2.5 eq). The reaction mixture was stirred at 150° C. for 24 h in a sealed tube. After completion of reaction by TLC, the reaction mixture was poured into ice and basified with aqueous NH$_3$ (pH-9) and extracted with EtOAc (3×100 mL). The combined organic layers were dried over sodium sulfate and concentrated under reduced pressure to afford crude. The crude compound was purified by silica gel (100-200 mesh) column [eluted with 2% MeOH in DCM] to afford 4-chloro-7-methoxyquinolin-6-ol (01) (1.5 g, yield: 32%) as yellow solid. TLC system EtOAc:Hexane (60:40), $R_f$ value: 0.4 (long UV); LCMS (m/z): 210.1 (M+H)$^+$; $^1$HNMR (400 MHz, DMSO-d$_6$) δ 10.6-10.1 (br, 1H), 8.54 (d, J=4.8 Hz, 1H), 7.49 (d, J=4.8 Hz, 1H), 7.43 (s, 1H), 7.40 (s, 1H), 3.97 (s, 3H).

Synthesis of 4-chloro-7-methoxy-6-(2-methoxyethoxy)quinoline (02)

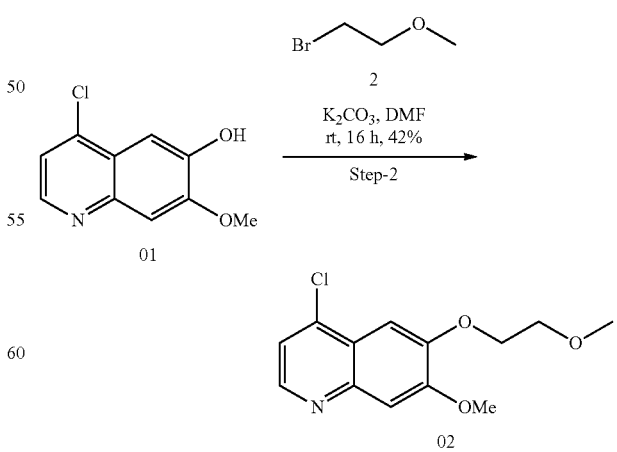

To a stirred solution of 4-chloro-7-methoxyquinolin-6-ol (01) (1.5 g, 7.17 mmol, 1 eq) in DMF (15 mL) at 0° C. was added K$_2$CO$_3$ (1.98 g, 14.3 mmol, 2 eq), 1-bromo-2-methoxyethane (1.98 g, 14.3 mmol, 2 eq), The reaction mixture was stirred at room temperature for 16 h. After completion of reaction by TLC, the reaction mixture was diluted with water and extracted with EtOAc (2×50 mL). The combined organic layers were washed with brine (30 mL), dried over sodium sulfate and concentrated under reduced pressure to afford crude. The crude compound was purified by 100-200 mesh silica gel column by eluting with 2% MeOH in DCM to afford 4-chloro-7-methoxy-6-(2-methoxyethoxy)quinoline (02) (800 mg, yield: 42%) as Gummy solid. TLC system EtOAc:Hexane (60:40), R$_f$ value: 0.4; LCMS (m/z): 268.1 (M+H)$^+$; $^1$HNMR (400 MHz, CDCl$_3$) δ 8.57 (d, J=4.8 Hz, 1H), 7.43 (s, 1H), 7.40 (s, 1H), 7.35 (d, J=4.8 Hz, 1H), 4.34 (t, J=4.8 Hz, 2H), 4.04 (s, 3H), 3.89 (t, J=4.8 Hz, 2H), 3.49 (s, 3H).

Synthesis of 2-(1-(7-methoxy-6-(2-methoxyethoxy)quinolin-4-yl)piperidin-4-yl)propanenitrile (03)

mmol, 0.1 eq), X-Phos (0.28 g, 0.59 mmol, 0.2 eq). The reaction mixture was stirred at 110° C. for 16 h. After completion of reaction by TLC, the reaction mixture was filtered through Celite pad and concentrated under reduced pressure to provide crude. The crude compound was purified by 100-200 mesh silica gel column by eluting with 3% MeOH in DCM to afford 2-(1-(7-methoxy-6-(2-methoxyethoxy)quinolin-4-yl)piperidin-4-yl)propanenitrile (03) (500 mg, yield: 45%) as yellow solid. TLC system MeOH:DCM (10:90), R$_f$ value: 0.5; LCMS (m/z): 370.3 (M+H)$^+$; $^1$HNMR (400 MHz, DMSO-d$_6$) δ 8.49 (d, J=5.2 Hz, 1H), 7.31 (s, 1H), 7.19 (s, 1H), 6.87 (d, J=5.2 Hz, 1H), 4.24-4.22 (m, 2H), 3.92 (s, 3H), 3.76 (t, J=4.8 Hz, 2H), 3.57 (t, J=12.0 Hz, 2H), 3.35 (s, 3H), 2.91-2.90 (m, 1H), 2.77 (t, J=12 Hz, 2H), 2.00-1.89 (m, 2H), 1.67-1.58 (m, 3H), 1.32 (d, J=7.2 Hz, 3H).

Synthesis of 2-(1-(7-methoxy-6-(2-methoxyethoxy)quinolin-4-yl)piperidin-4-yl)propan-1-amine (04)

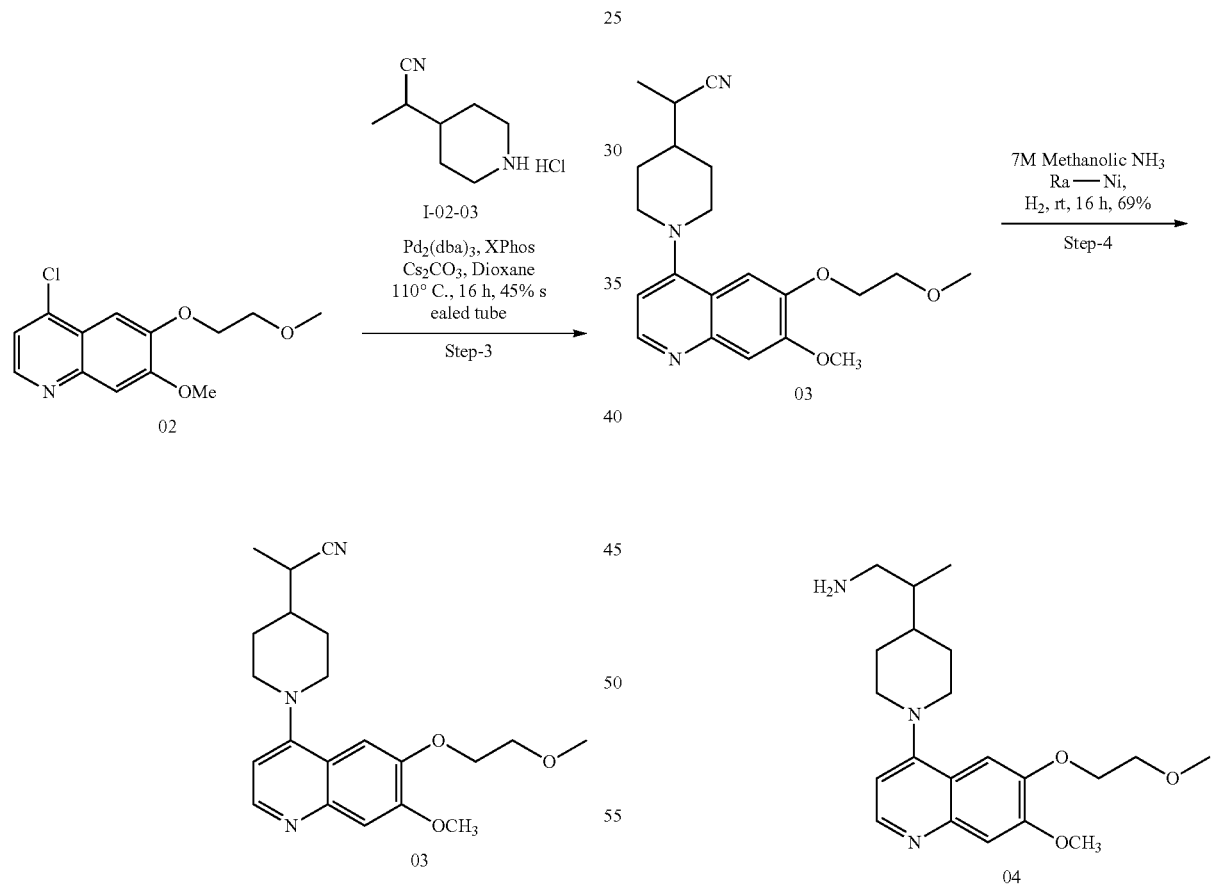

In a sealed tube, to a stirred solution of 4-chloro-7-methoxy-6-(2-methoxyethoxy)quinoline (02) (800 mg, 2.99 mmol, 1 eq) in 1,4 Dioxane (8 mL) was added 2-(piperidin-4-yl)propanenitrile hydro chloride (I-02-03) (490 mg, 3.59 mmol, 1.2 eq) and degassed for 10 mins. Then added Cs$_2$CO$_3$ (2.9 g, 8.98 mmol, 3 eq), Pd$_2$(dba)$_3$ (0.27 g, 0.29

To a stirred solution of 2-(1-(7-methoxy-6-(2-methoxyethoxy)quinolin-4-yl)piperidin-4-yl)propanenitrile (03) (500 mg, 2.03 mmol, 1 eq) in 7M Methanolic.NH$_3$ (5 mL) was added Ra—Ni (1 g). The reaction mixture was stirred at room temperature for 16 h under H$_2$ balloon pressure. After completion of reaction by TLC, reaction mixture was filtered through Celite pad and filtrate evaporated under reduced pressure to afford 2-(1-(7-methoxy-6-(2-methoxyethoxy) quinolin-4-yl)piperidin-4-yl)propan-1-amine (04) (350 mg, yield: 69%) as a gummy compound. TLC system MeOH: DCM (10:90), R$_f$ value: 0.1; LCMS (m/z): 374.4 (M+H)$^+$; $^1$HNMR (400 MHz, DMSO-d$_6$) δ 8.49 (d, J=5.6 Hz, 1H), 7.90 (brs, 2H), 7.35 (s, 1H), 7.23 (s, 1H), 6.92 (d, J=5.2 Hz, 1H), 4.10-4.09 (m, 2H), 3.89 (s, 3H), 3.77-3.68 (m, 4H), 3.35 (s, 3H), 2.89-2.75 (m, 3H), 2.69-2.66 (m, 1H), 1.78-1.75 (m, 3H), 1.57-1.48 (m, 3H), 0.98 (d, J=7.2 Hz, 3H).

Synthesis of tert-butyl (N-(2-(1-(7-methoxy-6-(2-methoxyethoxy)quinolin-4-yl)piperidin-4-yl)propyl) sulfamoyl)carbamate (05)

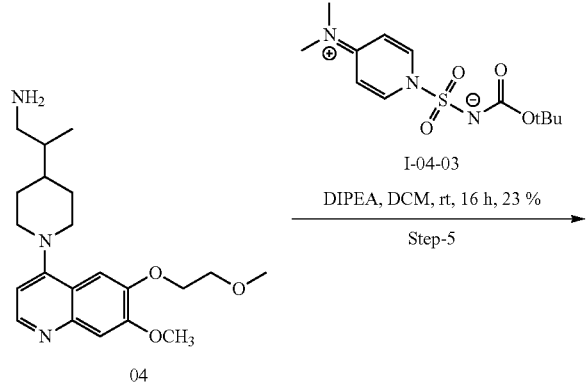

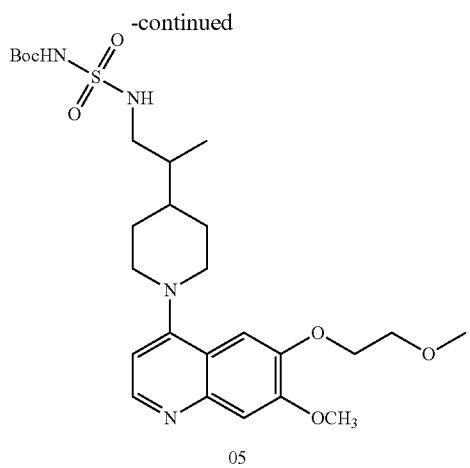

To a stirred solution of 2-(1-(7-methoxy-6-(2-methoxy-ethoxy)quinolin-4-yl)piperidin-4-yl)propan-1-amine (04) (350 mg, 0.93 mmol, 1 eq) in DCM (7 mL) was added DIPEA (0.25 mL, 1.4 mmol, 1.5 eq), (tert-butoxycarbonyl) ((4-(dimethyliminio)pyridin-1(4H)-yl)sulfonyl)amide (I-04-03) (338 mg, 1.12 mmol, 1.2 eq). The reaction mixture was stirred at room temperature for 16 h. After completion of reaction, the reaction mixture was quenched with water and extracted with DCM (2×50 mL). The combined organic layers were washed with brine (50 mL), dried over sodium sulfate and concentrated under reduced pressure to afford crude. The crude compound was purified by Reverse phase [eluted with 35% (0.1% FA in H2O)+ACN] to afford tert-butyl (N-(2-(1-(7-methoxy-6-(2-methoxyethoxy)quinolin-4-yl)piperidin-4-yl)propyl)sulfamoyl)carbamate (05) (120 mg, yield: 23%) as off-white solid. TLC system MeOH: DCM (5:95), R$_f$ value: 0.5; LCMS (m/z): 553.4 (M+H)$^+$ and 453.4 (M+H-Boc)$^+$ Synthesis of N-(2-(1-(7-methoxy-6-(2-methoxy-ethoxy)quinolin-4-yl)piperidin-4-yl)propyl)anino-sulfonamide formate salt (I-10)

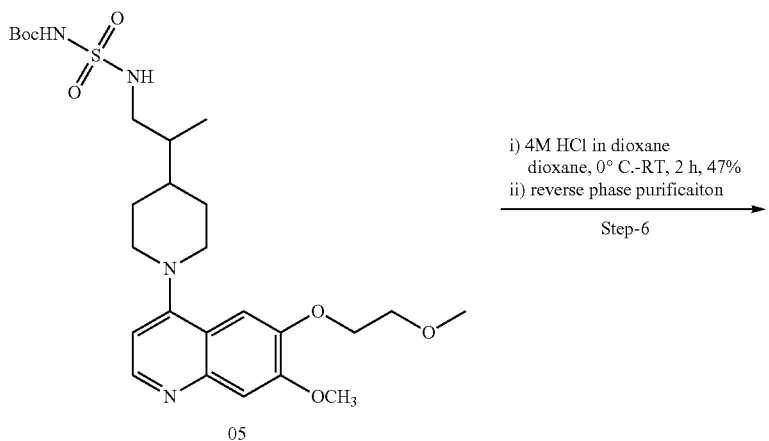

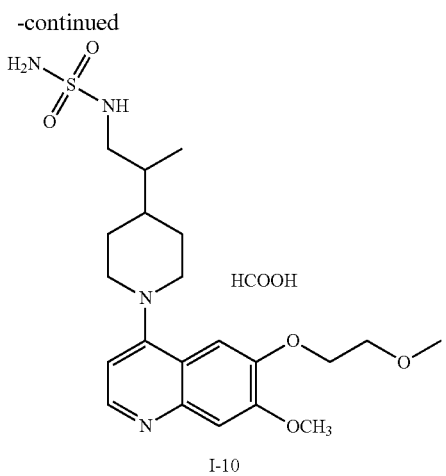

I-10

To a solution of tert-butyl tert-butyl (N-(2-(1-(7-methoxy-6-(2-methoxyethoxy)quinolin-4-yl)piperidin-4-yl)propyl)sulfamoyl)carbamate (05) (120 mg, 0.25 mmol, 1 eq) in dioxane at 0° C. was added 4M Dioxane.HCl (2 mL) and stirred at room temperature for 2 h. After completion of reaction by TLC, volatiles were evaporated. The crude compound was purified by prep HPLC to afford N-(2-(1-(7-methoxy-6-(2-methoxyethoxy)quinolin-4-yl)piperidin-4-yl)propyl)aninosulfonamide formate salt (I-10) (20 mg, yield: 47%) as an off-white solid. TLC system MeOH:DCM (10:90), $R_f$ value: 0.3; LCMS (m/z): 453.3 (M+H), $^1$HNMR (400 MHz, DMSO-$d_6$) δ 8.48 (d, J=5.2 Hz, 1H), 8.14 (formate salt proton), 7.31 (s, 1H), 7.22 (s, 1H), 6.88 (d, J=5.2 Hz, 1H), 6.49-6.47 (m, 3H), 4.24 (t, J=4.8 Hz, 2H), 3.92 (s, 3H), 3.75 (t, J=4.8 Hz, 2H), 3.63-3.61 (m, 2H), 3.34 (s, 3H), 2.99-2.94 (m, 1H), 2.82-2.74 (m, 3H), 1.77-1.75 (m, 2H), 1.64-1.52 (m, 4H), 0.92 (d, J=6.4 Hz, 3H).

Synthesis of I-11

Synthesis of 2-(2-bromoethoxy)tetrahydro-2H-pyran (01)

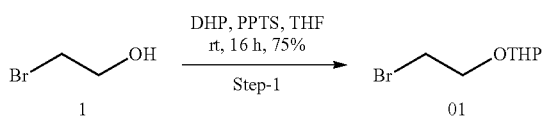

To a stirred solution of 2-bromoethan-1-ol (1) (2 g, 1.61 mmol, 1 eq) in THF (20 mL) was added 3,4 Dihydropyran (1.7 mL, 1.93 mmol, 1.2 eq), p-Toluenesulfonic acid pyridine salt (PPTS) (406 mg, 0.16 mmol, 0.1 eq). The reaction mixture was stirred at room temperature for 16 h. After completion of reaction by TLC, the reaction mixture was poured into water and extracted with EtOAc (2×30 mL). The combined organic layers were washed with brine (30 mL), dried over sodium sulfate and concentrated to afford 2-(2-bromoethoxy)tetrahydro-2H-pyran (01) (2.5 g, yield: 75%) as pale yellow liquid. TLC system EtOAc:Hexane (20:80), $R_f$ value: 0.5; $^1$HNMR (400 MHz, DMSO-$d_6$) δ 4.67 (t, J=3.6 Hz, 1H), 4.05-3.99 (m, 1H), 3.91-3.86 (m, 2H), 3.80-3.74 (m, 1H), 3.55-3.47 (m, 4H), 1.86-1.81 (m, 2H), 1.77-1.69 (m, 2H), impurities were also observed.

Synthesis of 4-chloro-7-methoxy-6-(2-((tetrahydro-2H-pyran-2-yl)oxy)ethoxy)quinoline (02)

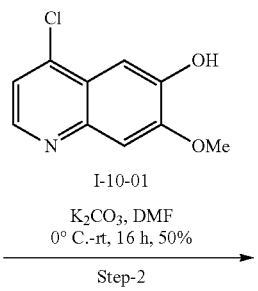

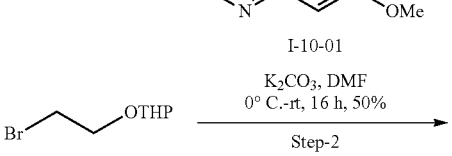

To a stirred solution of 4-chloro-7-methoxyquinolin-6-ol (I-10-01) (1 g, 4.78 mmol, 1 eq) in DMF (10 mL) at 0° C. was added $K_2CO_3$ (1.29 g, 9.56 mmol, 2 eq) and 2-(2-bromoethoxy)tetrahydro-2H-pyran (01) (1.46 g, 7.17 mmol, 1.5 eq). The reaction mixture was stirred at room temperature for 16 h. After completion of reaction by TLC, the reaction mixture was diluted with ice-cold water and extracted with EtOAc (2×40 mL). The combined organic layers were washed with brine (15 mL), dried over sodium sulfate and concentrated under reduced pressure to afford crude. The crude compound was purified by silica gel (100-200 mesh) column chromatography [eluted with 2% MeOH in DCM] to afford 4-chloro-7-methoxy-6-(2-((tetrahydro-2H-pyran-2-yl)oxy)ethoxy)quinoline (02) (800 mg, yield: 50%) as Gummy solid. TLC system EtOAc:Hexane (60:40), $R_f$ value: 0.4; LCMS (m/z): 338.1 (M+H)$^+$.

Synthesis of 2-(1-(7-methoxy-6-(2-((tetrahydro-2H-pyran-2-yl)oxy)ethoxy)quinolin-4-yl)piperidin-4-yl)propanenitrile (03)

Synthesis of 2-(1-(7-methoxy-6-(2-((tetrahydro-2H-pyran-2-yl)oxy)ethoxy)quinolin-4-yl)piperidin-4-yl)propan-1-amine (04)

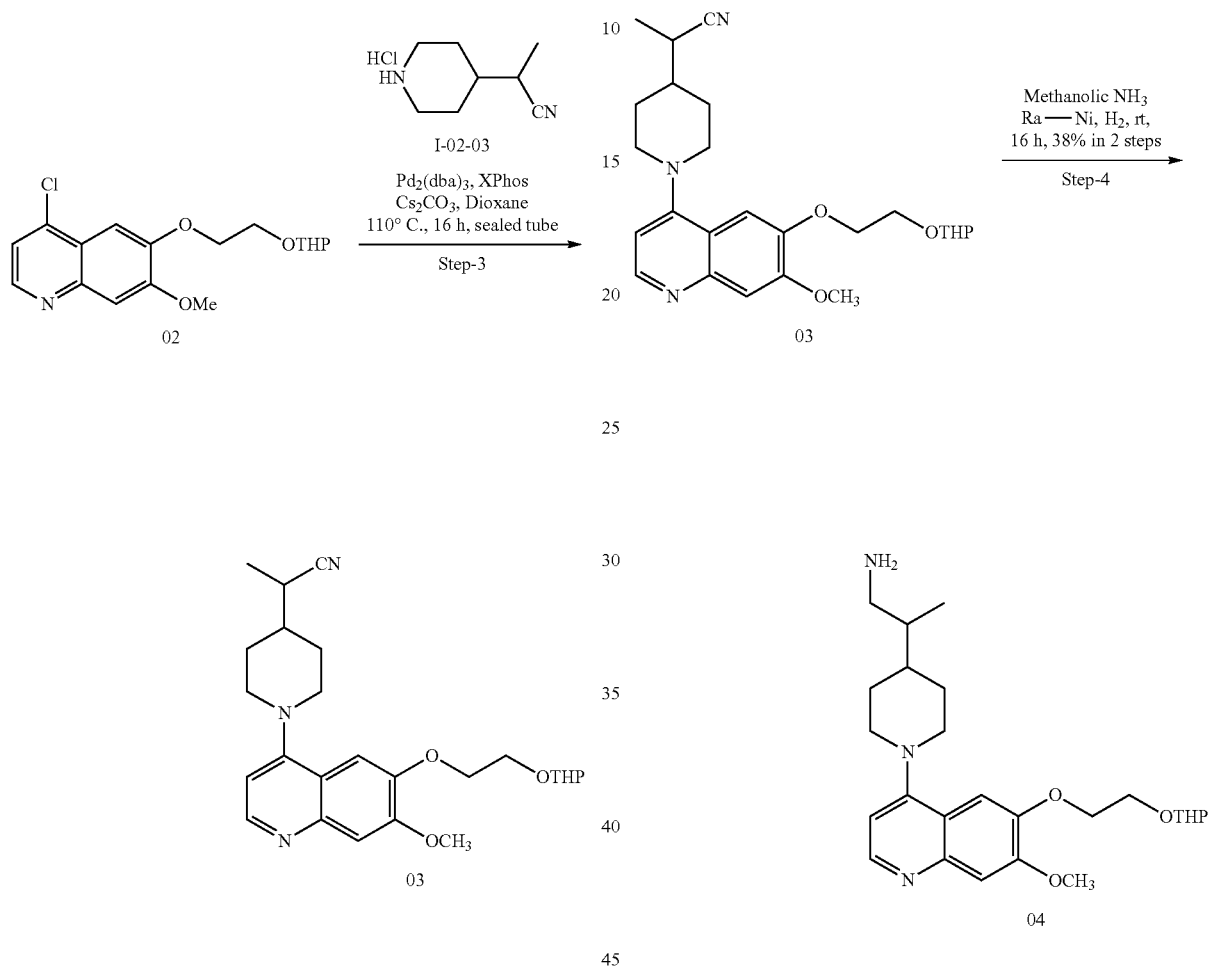

To a stirred solution of 4-chloro-7-methoxy-6-(2-((tetrahydro-2H-pyran-2-yl)oxy)ethoxy)quinoline (02) (800 mg, 2.37 mmol, 1 eq) in 1,4 Dioxane (8 mL) was added 2-(piperidin-4-yl)propanenitrile hydro chloride (I-02-03) (0.39 g, 2.84 mmol, 1.2 eq) and degassed for 10 mins. Then added Cs$_2$CO$_3$ (2.3 g, 7.11 mmol, 3 eq), Pd$_2$(dba)$_3$ (0.22 g, 0.23 mmol, 0.1 eq), X-Phos (0.22 g, 0.47 mmol, 0.2 eq). The reaction mixture was stirred at 110° C. for 16 h in a sealed tube. After completion of reaction by TLC, the reaction mixture was filtered through Celite pad and concentrated to provide crude.

The crude compound was purified by silica gel [100-200 mesh] chromatography [eluted with 3% MeOH in DCM] to afford 2-(1-(7-methoxy-6-(2-((tetrahydro-2H-pyran-2-yl)oxy)ethoxy)quinolin-4-yl)piperidin-4-yl)propanenitrile (03) (600 mg) as yellow solid. TLC system MeOH:DCM (10:90), LCMS (m/z): 440.4 (M+1H)$^+$. Although the purified material was not completely pure, taken forward to next step.

To a stirred solution of 2-(1-(7-methoxy-6-(2-((tetrahydro-2H-pyran-2-yl)oxy)ethoxy)quinolin-4-yl)piperidin-4-yl)propanenitrile (03) (600 mg; 60% purity, 1.36 mmol, 1 eq) in 7M Methanolic.NH$_3$ (6 mL) was added Ra—Ni (1.2 g). The reaction mixture was stirred at room temperature for 16 h under H$_2$ balloon pressure. After completion of reaction by TLC, reaction mixture was filtered through Celite pad and concentrated to afford crude. Crude was trituration's with diethyl ether to afford 2-(1-(7-methoxy-6-(2-((tetrahydro-2H-pyran-2-yl)oxy)ethoxy)quinolin-4-yl)piperidin-4-yl)propan-1-amine (04) (400 mg, yield: 38% over two steps) as a gummy compound. TLC system MeOH:DCM (10:90), R$_f$ value: 0.1; LCMS (m/z): 444.4 (M+H)$^+$; $^1$HNMR (400 MHz, DMSO-d$_6$) δ 8.48 (d, J=4.8 Hz, 1H), 7.30 (s, 1H), 7.22 (s, 1H), 6.84 (d, J=4.8 Hz, 1H), 4.71-4.70 (m, 1H), 4.27-4.25 (m, 2H), 4.02-3.97 (m, 1H), 3.91 (s, 3H), 3.84-3.80 (m, 2H), 3.54-3.42 (m, 4H), 2.74-2.67 (m, 3H), 1.77-1.64 (m, 5H), 1.50-1.43 (m, 8H), 0.93 (d, J=6.4 Hz, 3H).

Synthesis of tert-butyl N-(2-(1-(7-methoxy-6-(2-((tetrahydro-2H-pyran-2-yl)oxy)ethoxy)quinolin-4-yl)piperidin-4-yl)propyl)sulfamoylcarbamate (05)

Synthesis of N-(2-(1-(6-(2-hydroxyethoxy)-7-methoxyquinolin-4-yl)piperidin-4-yl)propyl)aminosulfonamide formate salt (I-11)

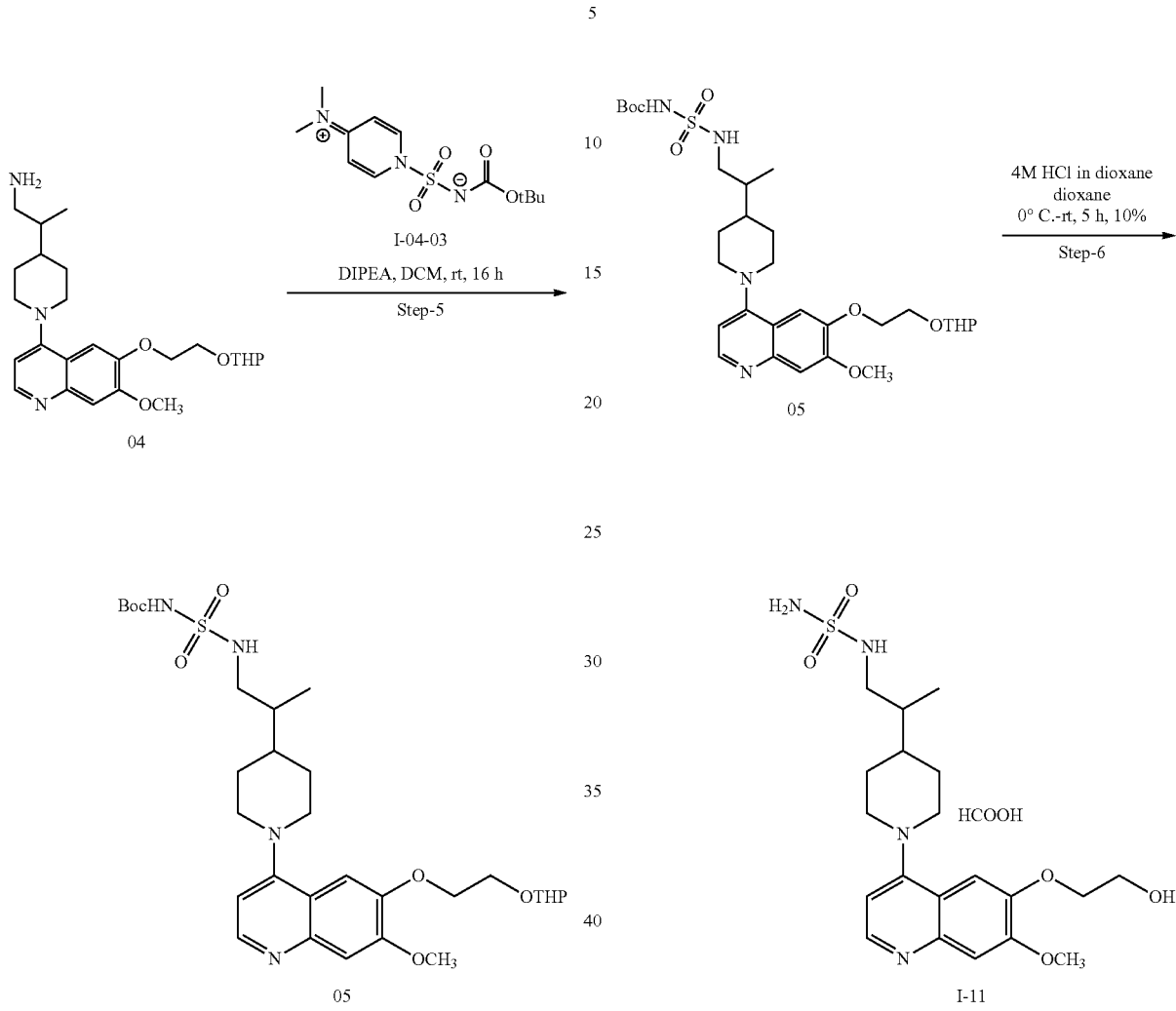

To a stirred solution of 2-(1-(7-methoxy-6-(2-((tetrahydro-2H-pyran-2-yl)oxy)ethoxy)quinolin-4-yl)piperidin-4-yl)propan-1-amine (04) (400 mg, 0.9 mmol, 1.0 eq) in DCM (8 mL) was added DIPEA (0.21 mL, 1.17 mmol, 1.3 eq) and (tert-butoxycarbonyl)((4-(dimethyliminio)pyridin-1(4H)-yl)sulfonyl)amide (I-04-03) (325 mg, 1.08 mmol, 1.2 eq). The reaction mixture was stirred at room temperature for 16 h. After completion of reaction, the reaction mixture was quenched with water and extracted with DCM (2×20 mL). The combined organic layers were washed with brine (10 mL) dried over sodium sulfate and concentrated under reduced pressure to afford crude. The crude compound was purified by Reverse phase column [using 0.1% FA in $H_2O$/ACN as eluent] to afford tert-butyl N-(2-(1-(7-methoxy-6-(2-((tetrahydro-2H-pyran-2-yl)oxy)ethoxy)quinolin-4-yl)piperidin-4-yl)propyl)sulfamoylcarbamate (05) (250 mg) as gummy solid. TLC system MeOH:DCM (5:95), $R_f$ value: 0.5; LCMS (m/z): 623.5 $(M+H)^+$. Although the purified material was not completely pure, taken forward to next step.

To a stirred solution of tert-butyl N-(2-(1-(7-methoxy-6-(2-((tetrahydro-2H-pyran-2-yl)oxy)ethoxy)quinolin-4-yl)piperidin-4-yl)propyl)sulfamoylcarbamate (05) (250 mg, 0.4 mmol, 1 eq) in 1,4 Dioxane at 0° C. was added 4M Dioxane. HCl (2 mL) slowly. The reaction was then allowed to stir at room temperature for 5 h. After completion of reaction by TLC, volatiles were evaporated, the crude compound was purified by Prep HPLC purification to afford N-(2-(1-(6-(2-hydroxyethoxy)-7-methoxyquinolin-4-yl)piperidin-4-yl) propyl)aminosulfonamide format salt (I-11) (38 mg, yield: 10% over two steps) as an off-white solid. TLC system MeOH:DCM (10:90), $R_f$ value: 0.3; LCMS (m/z): 439.3 (M+H—HCOOH), $^1$HNMR (400 MHz, DMSO-$d_6$) δ 8.47 (d, J=4.8 Hz, 1H), 8.15 (format salt proton), 7.30 (s, 1H), 7.20 (s, 1H), 6.84 (d, J=5.2 Hz, 1H), 6.48-6.45 (m, 3H), 4.93 (brs, H), 4.11 (t, J=4.8 Hz, 2H), 3.91 (s, 3H), 3.83-3.81 (m, 2H), 3.53-3.51 (m, 2H), 3.00-2.94 (m, 1H), 2.79-2.67 (m, 3H), 1.77-1.75 (m, 2H), 1.62-1.51 (m, 4H), 0.92 (d, J=6.8 Hz, 3H)

Synthesis of I-12

Synthesis of 4-(2-methoxy-4-nitrophenyl) morpholine (01)

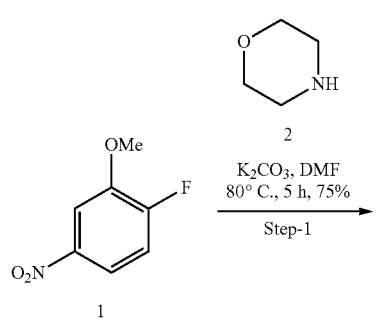

To a stirred solution of 1-fluoro-2-methoxy-4-nitrobenzene (1) (10 g, 58.44 mmol, 1 eq) in DMF (50 mL) was added K$_2$CO$_3$ (16.13 g, 116.8 mmol, 2 eq) and morpholine (2) (10.16 g, 116.8 mmol, 2 eq). The reaction mixture was stirred at 80° C. for 5 h. After completion of reaction by TLC, the reaction mixture was poured into ice cold water, precipitated solid was filtered and dried under vacuum to afford 4-(2-methoxy-4-nitrophenyl) morpholine (01) (8 g, yield: 75%) as yellow solid. TLC system EOAc:Hexane (30:70), R$_f$ value: 0.2; LCMS (m/z): 239.1 (M+H)$^+$; $^1$HNMR (400 MHz, CDCl$_3$) δ 7.87 (dd, J=8.8 Hz, 2.4 Hz, 1H), 7.72 (d, J=2.4 Hz, 1H), 6.89 (d, J=8.8 Hz, 1H), 3.96 (s, 3H), 3.89 (t, J=4.8 Hz, 4H), 3.22 (t, J=4.8 Hz, 4H).

Synthesis of 3-methoxy-4-morpholinoaniline (02)

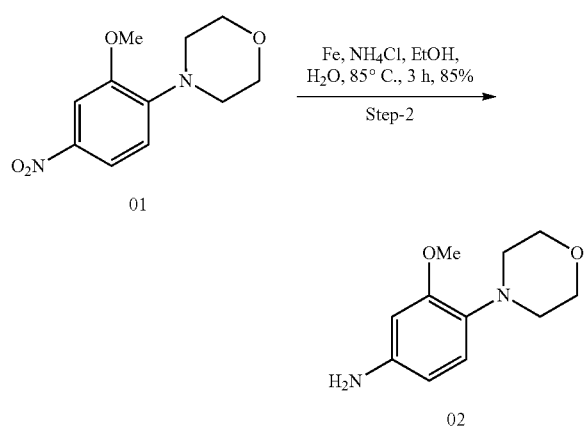

To a stirred solution of 4-(2-methoxy-4-nitrophenyl) morpholine (01) (8 g, 33.5 mmol, 1 eq) in Ethanol:H$_2$O (2:1) (120 mL), was added NH$_4$Cl (8.93 g, 167 mmol, 5 eq), Fe powder (9.32 g, 167 mmol, 5 eq). The reaction mixture was stirred at 85° C. for 3 h. After completion of reaction by TLC, the reaction mixture was filtered through Celite pad and washed with EtOAc (200 mL). The filtrate was washed with brine (50 mL), dried over sodium sulfate and concentrated under reduced pressure to afford 3-methoxy-4-morpholinoaniline (02) (6 g, yield: 85%) as brown solid. TLC system MeOH:DCM (10:90), R$_f$ value: 0.2; LCMS (m/z): 209.2 (M+H)$^+$; $^1$HNMR (400 MHz, DMSO-d$_6$) δ 6.60 (d, J=8.4 Hz, 1H), 6.23 (d, J=2.4 Hz, 1H), 6.07 (dd, J=2.4 Hz, 8.0 Hz, 1H), 4.72 (s, 2H), 3.68 (s, 3H), 3.66 (t, J=4.8 Hz, 4H), 2.77 (t, J=4.8 Hz, 4H).

Synthesis of 7-methoxy-6-morpholinoquinoline-4(1H)-one (03)

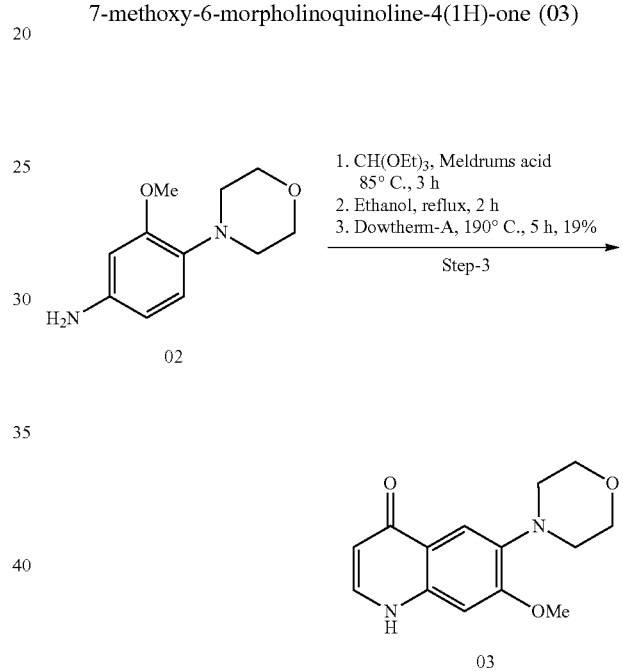

A solution of Meldrum's acid (3.85 g, 3.37 mmol, 1 eq) and Triethyl orthoformate (1.5 mL, 10.1 mmol, 3 eq) was stirred at 85° C. for 3 h. Thus, diluted with ethanol (50 mL) and added 3-methoxy-4-morpholinoaniline (02) (5 g, 3.37 mmol, 1 eq). The resulting mixture was stirred at 85° C. for 3 h. Later, cooled to 0° C., brown color solid precipitated which was filtered and dried under vacuum. To this solid added Dowtherm-A (50 mL) and heated at 190° C. for 5 h. After completion of reaction by TLC, the reaction mixture was poured into hexane (200 mL), precipitated solid was filtered and dried under vacuum to afford crude. Crude compound was purified by silica gel (60-120 mesh) column chromatography [gradient elution with 10-15% MeOH in DCM] to afford 7-methoxy-6-morpholinoquinoline-4(1H)-one (03) (1.2 g, yield: 19%) as brown solid. TLC system MeOH:DCM (20:80), R$_f$ value: 0.2; LCMS (m/z): 261.1 (M+H)$^+$; $^1$HNMR (400 MHz, CDCl$_3$) δ 7.77 (s, 1H), 7.58 (d, J=6.4 Hz, 1H), 6.91 (s, 1H), 6.22 (d, J=7.2 Hz, 1H), 3.88 (s, 3H), 3.86 (t, J=4.4 Hz, 4H), 3.07 (t, J=4.4 Hz, 4H).

Synthesis of 4-(4-chloro-7-methoxyquinolin-6-yl)morpholine (04)

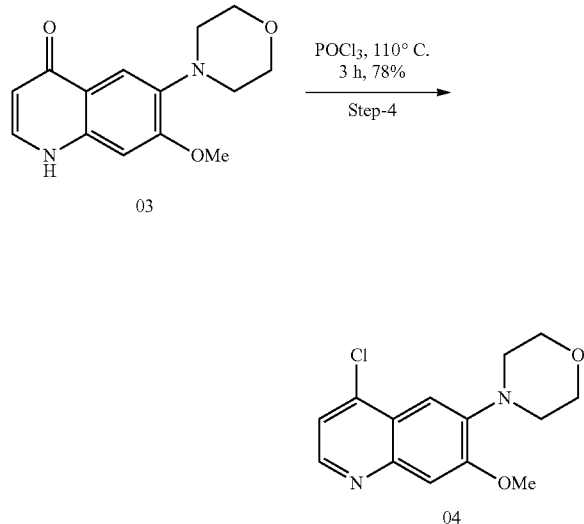

A suspension of 7-methoxy-6-morpholinoquinolin-4 (1H)-one (03) (1.2 g, 4.6 mmol, 1 eq) in POCl₃ (12 mL) was stirred at 110° C. for 3 h. After completion of reaction by TLC, reaction mixture was poured into ice and basified with saturated cold NaHCO₃ solution [pH-8] and extracted with EtOAc (3×60 mL). The combined organic layers were washed with brine (20 mL), dried over sodium sulfate and concentrated under reduced pressure to afford crude. Crude compound was purified by silica gel (60-120 mesh) column chromatography [eluted with 1% MeOH in DCM] to afford 4-(4-chloro-7-methoxyquinolin-6-yl)morpholine (04) (1 g, yield: 78%) as brown solid. TLC system EtOAc:Hexane (70:30), R$_f$ value: 0.6; LCMS (m/z): 279.1 (M+H)⁺; ¹HNMR (400 MHz, CDCl₃) δ 8.57 (d, J=4.8 Hz, 1H), 7.52 (s, 1H), 7.48 (s, 1H), 7.34 (d, J=4.8 Hz, 1H), 4.03 (s, 3H), 3.95 (t, J=4.4 Hz, 4H), 3.24 (t, J=4.4 Hz, 4H).

Synthesis of 2-(1-(7-methoxy-6-morpholinoquinolin-4-yl)piperidin-4-yl)propanenitrile (05)

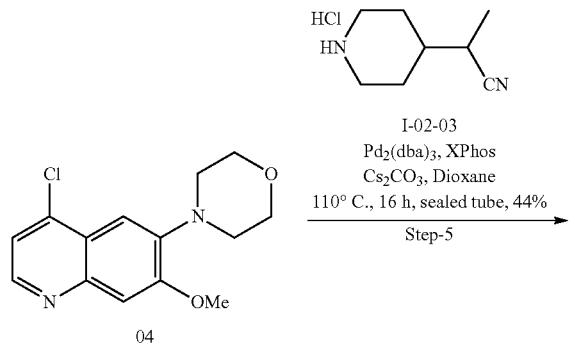

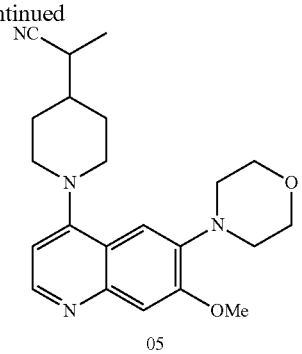

To a stirred solution of 4-(4-chloro-7-methoxyquinolin-6-yl)morpholine (04) (1 g, 3.59 mmol, 1 eq) in 1,4 Dioxane (10 mL) was added 2-(piperidin-4-yl)propanenitrile. HCl (I-02-03) (0.76 g, 4.30 mmol, 1.2 eq), Cs₂CO₃ (3.5 g, 10.7 mmol, 3 eq) and degassed for 10 mins. Later, added X-Phos (0.34 g, 0.71 mmol, 0.2 eq), Pd₂(dba)₃ (0.32 g, 0.35 mmol, 0.1 eq) and the reaction mixture was stirred at 110° C. for 16 h in a sealed tube. After completion of reaction by TLC, the reaction mixture was filtered through Celite pad and concentrated to provide crude. Crude compound was purified by silica gel (60-120 mesh) column chromatography [eluted with 3-4% MeOH in DCM] to afford 2-(1-(7-methoxy-6-morpholinoquinolin-4-yl)piperidin-4-yl)propanenitrile (05) (600 mg, yield: 44%) as brown gummy solid. TLC system MeOH:DCM (5:95), R$_f$ value: 0.3; LCMS (m/z): 381.3 (M+H)⁺; 72% Purity.

Synthesis of 2-(1-(7-methoxy-6-morpholinoquinolin-4-yl)piperidin-4-yl)propan-1-amine (06)

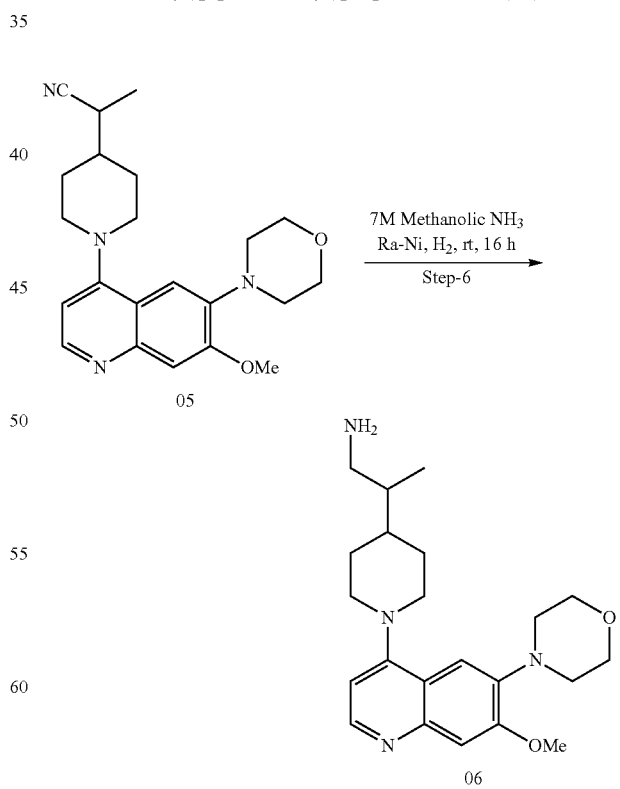

To a stirred solution of 2-(1-(7-methoxy-6-morpholinoquinolin-4-yl)piperidin-4-yl)propanenitrile (05) (600 mg, 1.57 mmol, 1 eq) in 7M Methanolic.NH$_3$ (6 mL) was added Raney-Ni (1.2 g). The reaction mixture was stirred at room temperature for 16 h under H$_2$ balloon pressure. After completion of reaction by TLC, reaction mixture was filtered through Celite pad and concentrated to afford 2-(1-(7-methoxy-6-morpholinoquinolin-4-yl)piperidin-4-yl)propan-1-amine (06) (420 mg) as a gummy compound. TLC system MeOH:DCM (10:90), R$_f$ value: 0.1; LCMS (m/z): 385.3 (M+H)$^+$; 70% purity.

Synthesis of tert-butyl (N-(2-(1-(7-methoxy-6-morpholinoquinolin-4-yl)piperidin-4-yl)propyl)sulfamoyl)carbamate (07)

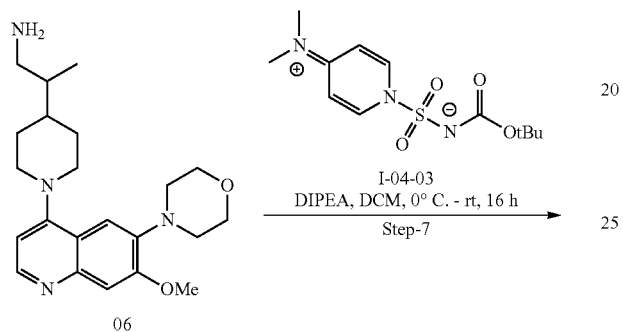

Synthesis of N—(N-(2-(1-(7-methoxy-6-morpholinoquinolin-4-yl)piperidin-4-yl)propyl)sulfuricdiamide (I-12)

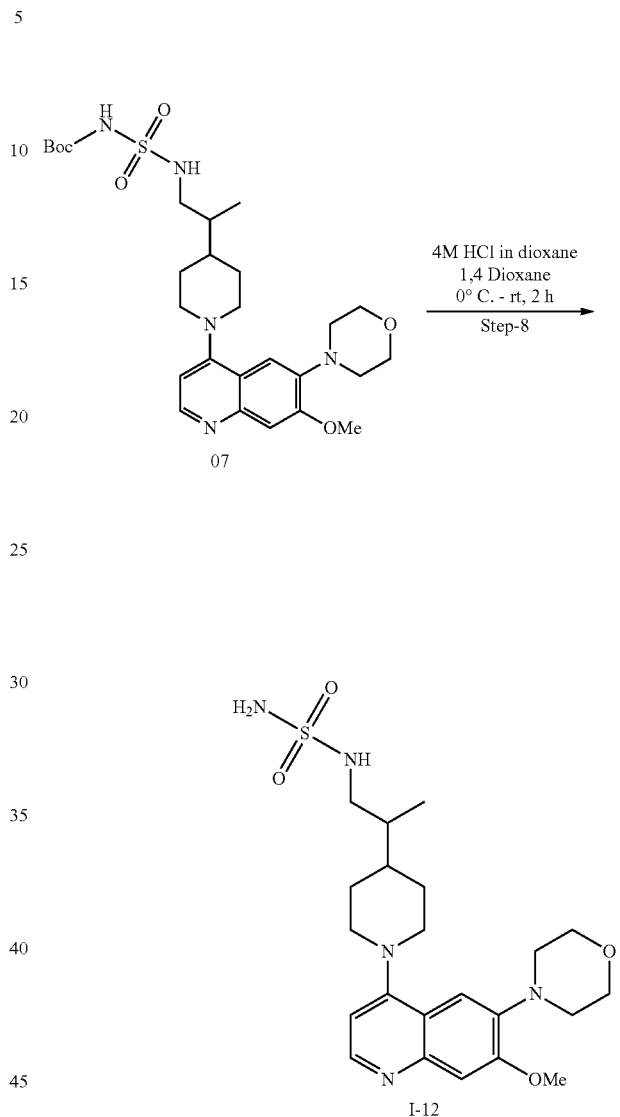

To a stirred solution of 2-(1-(7-methoxy-6-morpholinoquinolin-4-yl)piperidin-4-yl)propan-1-amine (06) (400 mg, 1.0 mmol, 1 eq) in DCM (8 mL) at 0° C. was added DIPEA (0.3 mL, 1.50 mmol, 1.5 eq), and (tert-butoxycarbonyl)((4-(dimethyliminio)pyridin-1(4H)-yl)sulfonyl)amide (I-04-03) (362 mg, 1.20 mmol, 1.2 eq). The reaction mixture was stirred at room temperature for 16 h. After completion of reaction, the reaction mixture was quenched with water and extracted with DCM (2×30 mL). The combined organic layers were washed with brine (10 mL), dried over sodium sulfate and concentrated under reduced pressure to afford crude. Crude compound was purified by silica gel (60-120 mesh) column chromatography [eluted at 5% MeOH in DCM] to afford tert-butyl (N-(2-(1-(7-methoxy-6-morpholinoquinolin-4-yl)piperidin-4-yl)propyl)sulfamoyl)carbamate (07) (400 mg) as gummy solid. TLC system MeOH:DCM (5:95), R$_f$ value: 0.5; LCMS (m/z): 564.4 (M+H)$^+$; 50% purity. The material was taken forward to next step without further enriching the purity.

To a stirred solution of tert-butyl (N-(2-(1-(7-methoxy-6-morpholinoquinolin-4-yl)piperidin-4-yl)propyl)sulfamoyl) carbamate (07) (400 mg, 50% purity) in 1,4 Dioxane cooled to 0° C. added 4M Dioxane.HCl (2 mL) and stirred at room temperature for 2 h. After completion of reaction by TLC, volatiles were evaporated and the obtained crude compound was purified by prep HPLC [FA method] to afford N—(N-(2-(1-(7-methoxy-6-morpholinoquinolin-4-yl)piperidin-4-yl)propyl)sulfuricdiamide (I-12) (45 mg, yield: 3% over four steps) as pale yellow solid. TLC system MeOH:DCM (10:90), R$_f$ value: 0.3; LCMS (m/z): 464.3 (M+H); $^1$HNMR (400 MHz, DMSO-d$_6$) δ 8.47 (d, J=6.8 Hz, 1H), 7.34 (s, 1H), 7.20 (s, 1H), 7.03 (d, J=6.8 Hz, 1H), 6.51-6.48 (m, 3H), 4.09-4.06 (m, 2H), 3.98 (s, 3H), 3.79-3.77 (m, 4H), 3.37-3.27 (m, 2H), 3.17-3.15 (m, 4H), 2.97-2.91 (m, 1H), 2.80-2.75 (m, 1H), 1.81-1.44 (m, 6H), 0.89 (d, J=6.8 Hz, 3H)

Synthesis of I-13

Synthesis of tert-butyl 4-(cyanomethylene)piperidine-1-carboxylate (01)

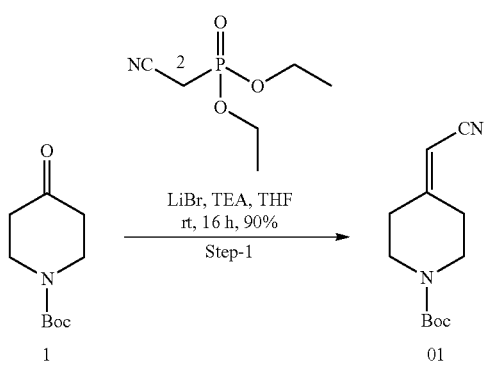 [SMILES: CC(C)(C)OC(=O)N1CCC(=O)CC1 ; CCOP(=O)(CC#N)OCC ; CC(C)(C)OC(=O)N1CCC(=CC#N)CC1]

To a stirred solution of tert-butyl 4-oxopiperidine-1-carboxylate (1) (2 g, 10.05 mmol, 1 eq) in THF (20 mL) at 0° was added diethyl (cyanomethyl)phosphonate (2) (2.66 g, 15.07 mmol, 1.5 eq), LiBr (1 g, 12.06 mmol, 1.2 eq) and TEA (2.8 mL, 20.1 mmol, 2 eq). The reaction mixture was allowed to stir at room temperature for 16 h. After completion of reaction by TLC, the reaction mixture was diluted with water and extracted with EtOAc (3×30 mL). The combined organic layers were washed with brine (30 mL) dried over sodium sulfate and concentrated. The crude was purified by silica column chromatography by eluting with 20% EtOAc in Hexane to afford tert-butyl 4-(cyanomethylene)piperidine-1-carboxylate (01) as a white solid (2 g, yield: 90%). TLC system: EtOAc/hexane (30:70; Ninhydrin stain), $R_f$ value: ~0.6; $^1$H NMR (400 MHz, CDCl$_3$) δ 5.19 (s, 1H), 3.54-3.48 (m, 4H), 2.56 (t, J=5.6 Hz, 2H), 2.32 (t, J=5.6 Hz, 2H), 1.47 (s, 9H).

Synthesis of tert-butyl 4-(cyanomethyl)piperidine-1-carboxylate (02)

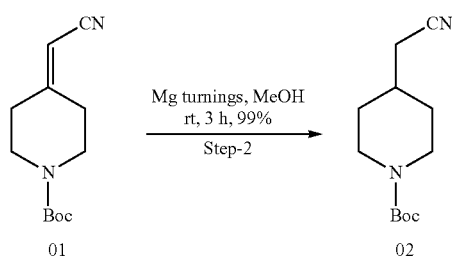 [SMILES: CC(C)(C)OC(=O)N1CCC(=CC#N)CC1 ; CC(C)(C)OC(=O)N1CCC(CC#N)CC1]

To a stirred solution of tert-butyl 4-(cyanomethylene)piperidine-1-carboxylate (01) (2 g, 8.9 mmol, 1 eq) in dry methanol (100 mL) was added Mg turnings (8.57 g, 35.7, 40 eq). The reaction mixture was stirred at room temperature for 3 h. After completion of reaction by TLC, the reaction mixture was quenched with 6N HCl, evaporated and extracted with EtOAc (2×50 mL). The combined organic layers were washed with brine (50 mL) dried over sodium sulfate and concentrated under reduced pressure to afford tert-butyl 4-(1-cyanoethyl)piperidine-1-carboxylate (02) (2 g, yield: 99%) as gummy liquid. TLC system: EtoAc: Hexane (20:80; Ninhydrin stain), $R_f$ value: ~0.5; $^1$H NMR (400 MHz, CDCl$_3$) δ 4.16-4.12 (m, 2H), 2.74-2.68 (m, 2H), 2.31 (d, J=6.4 Hz, 2H), 1.86-1.81 (m, 1H), 1.79-1.77 (m, 2H), 1.43 (s, 9H), 1.31-1.21 (m, 2H),

Synthesis of tert-butyl 4-(1-cyanopropyl)piperidine-1-carboxylate (03)

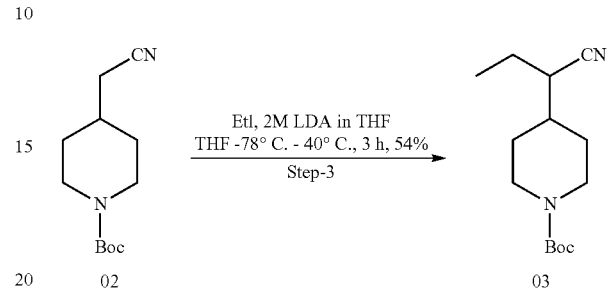

To a solution of tert-butyl 4-(1-cyanoethyl)piperidine-1-carboxylate (02) (2 g, 8.92 mmol, 1 eq) in dry THF (15 mL) cooled to −78° C. and added LDA (2M in THF) (4.46 mL, 8.92 mmol, 1 eq) stirred for 30 mins. Then added Ethyl Iodide in THF (0.66 mL, 8.92 mmol, 1 eq), stirred at −40° C. for 2.5 h. After completion of reaction by TLC, the reaction mixture was quenched with NH$_4$Cl solution and extracted with EtOAc (2×30 mL). The combined organic layers were washed with brine (10 mL) dried over sodium sulfate and concentrated under reduced pressure to afford tert-butyl 4-(1-cyanopropyl)piperidine-1-carboxylate (03) (1.2 g, yield: 54%) as liquid. TLC system: EtoAc:Hexane (20:80; Ninhydrin stain), $R_f$ value: 0.6; $^1$H NMR (400 MHz, CDCl$_3$) δ 4.19-4.17 (m, 2H), 2.68-2.66 (m, 2H), 2.37 (q, J=6.8 Hz, 1H), 1.86-1.81 (m, 1H), 1.70-1.62 (m, 4H), 1.45 (s, 9H), 1.38-1.32 (m, 2H), 1.21 (t, J=7.2 Hz, 3H),

Synthesis of 2-(piperidin-4-yl)butanenitrile. HCl (04)

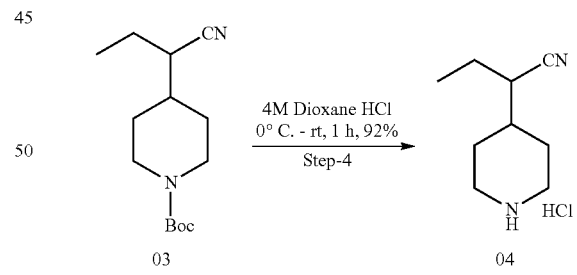

A solution of tert-butyl 4-(1-cyanopropyl)piperidine-1-carboxylate (03) (1.2 g, 5 mmol, 1 eq) in 4M Dioxane.HCl (12 mL) was stirred at room temperature for 1 h, After completion of reaction by TLC, the reaction mixture was concentrated under reduced pressure to afford 2-(piperidin-4-yl)propanenitrile hydrochloride (04) (0.86 g, yield: 92%) as white solid. TLC system EtoAc (100%, Ninhydrin stain), $R_f$ value: 0.1; $^1$HNMR (400 MHz, DMSO-d$_6$) δ 9.01-8.71 (br, 2H), 3.28-3.25 (m, 2H), 2.89-2.75 (m, 3H), 1.90-1.80 (m, 3H), 1.61-1.55 (m, 2H), 1.55-1.46 (m, 2H), 0.99 (t, J=7.2 Hz, 3H).

Synthesis of 2-(1-(6,7-dimethoxyquinolin-4-yl)piperidin-4-yl)butanenitrile (05)

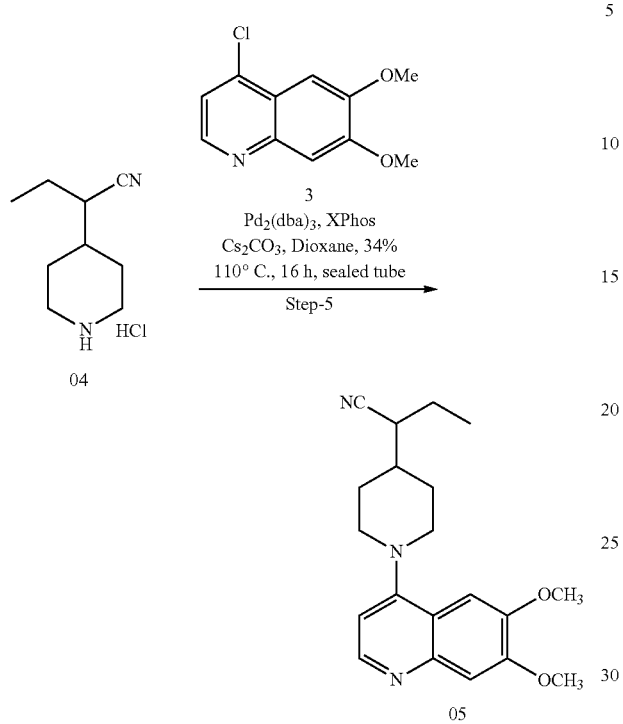

To a stirred solution of 4-chloro-6,7-dimethoxyquinoline (3) (1 g, 4.46 mmol, 1 eq) in 1,4 Dioxane (10 mL) was added 2-(piperidin-4-yl)propanenitrile hydrochloride (04) (0.84 g, 4.46 mmol, 1 eq) degassed for 10 mins, added Cs$_2$CO$_3$ (4.34 g, 13.3 mmol, 3 eq), Pd$_2$(dba)$_3$ (0.4 g, 0.44 mmol, 0.1 eq), X-Phos (0.42 g, 0.89 mmol, 0.2 eq). The reaction mixture was stirred at 110° C. for 16 h in a sealed tube. After completion of reaction by TLC, the reaction mixture was filtered through Celite pad and concentrated to provide crude. The crude compound was trituration's with Diethyl ether to afford 2-(1-(6,7-dimethoxyquinolin-4-yl)piperidin-4-yl)butanenitrile (05) (0.5 g, yield: 34%) as pale yellow solid. TLC system MeOH:DCM (10:90), R$_f$ value: 0.5; LCMS (m/z): 340.3 (M+H)$^+$.

Synthesis of 2-(1-(6,7-dimethoxyquinolin-4-yl)piperidin-4-yl)butan-1-amine (06)

To a stirred solution of 2-(1-(6,7-dimethoxyquinolin-4-yl)piperidin-4-yl)propanenitrile (05 (500 mg, 1.47 mmol, 1 eq), in 7M methanolic.NH$_3$ (5 mL) was added Ra—Ni (1 g). The reaction mixture was stirred at room temperature for 16 h under H$_2$ balloon pressure. After completion of reaction by TLC, reaction mixture was filtered through Celite pad and concentrated to afford 2-(1-(6,7-dimethoxyquinolin-4-yl)piperidin-4-yl)butan-1-amine (06) (400 mg, yield: 79%) as off-white solid. TLC system MeOH:DCM (10:90), R$_f$ value: 0.1; LCMS (m/z): 344.3 (M+H)$^+$.

Synthesis of tert-butyl (N-(2-(1-(6,7-dimethoxyquinolin-4-yl)piperidin-4-yl)butyl)sulfamoyl)carbamate (07)

To a stirred solution of 2-(1-(6,7-dimethoxyquinolin-4-yl)piperidin-4-yl)butan-1-amine (06) (400 mg, 1.16 mmol, 1.0 eq) in DCM (8 mL) was added DIPEA (0.31 mL, 1.74 mmol, 1.5 eq), (tert-butoxycarbonyl)((4-(dimethyliminio)pyridin-1(4H)-yl)sulfonyl)amide (I-04-03) (459 mg, 1.52 mmol, 1.3 eq). The reaction mixture was stirred at RT for 16 h. After completion of reaction, the reaction mixture was diluted with water and extracted with DCM (2×20 mL). The combined organic layers were washed with brine (10 mL) dried over sodium sulfate and concentrated under reduced pressure to afford crude. The crude compound was purified by prep HPLC to afford tert-butyl (N-(2-(1-(6,7-dimethoxyquinolin-4-yl)piperidin-4-yl)butyl)sulfamoyl)carbamate (07) (100 mg, yield: 16%) as off-white solid. TLC system MeOH:DCM (5:95), $R_f$ value: 0.5; LCMS (m/z): 523.6 (M+H)$^+$; $^1$HNMR (400 MHz, DMSO-$d_6$) δ 8.47 (d, J=4.8 Hz, 1H), 8.14 (s, 1H), 7.45 (t, 1H), 7.29 (s, 1H), 7.16 (s, 1H), 6.84 (d, J=4.8 Hz, 1H), 3.90 (s, 6H), 3.54-3.52 (m, 2H), 2.98-2.86 (m, 2H), 2.74-2.71 (m, 2H), 1.75-1.71 (m, 2H), 1.62-1.55 (m, 4H), 1.43 (s, 9H), 1.35-1.26 (m, 2H), 0.88 (t, J=6.8 Hz, 3H).

Synthesis of N-(2-(1-(6,7-dimethoxyquinolin-4-yl)piperidin-4-yl)butyl)sulfuricdiamide (I-13)

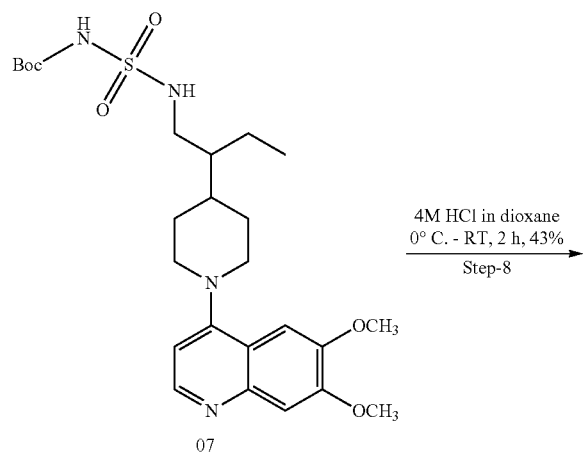

07

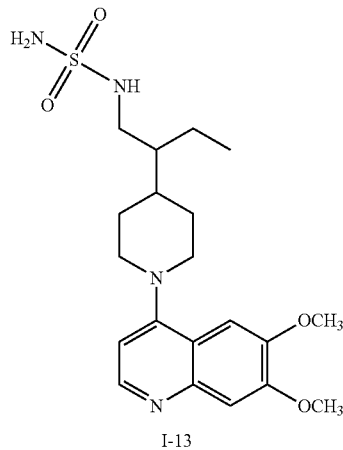

I-13

A solution of tert-butyl (N-(2-(1-(6,7-dimethoxyquinolin-4-yl)piperidin-4-yl)butyl)sulfamoyl)carbamate (07) (100 mg, 0.19 mmol, 1 eq), in 4M Dioxane.HCl (2 mL) was stirred at room temperature for 2 h. After completion of reaction by TLC, reaction mixture was concentrated and diluted with Ethyl acetate (10 mL) and washed with aqueous NaHCO$_3$ solution and brine (10 mL) dried over sodium sulfate and concentrated, to afford N-(2-(1-(6,7-dimethoxyquinolin-4-yl)piperidin-4-yl)butyl)sulfuricdiamide (I-13) (35 mg, yield: 43%) as an off-white solid. TLC system MeOH:DCM (10:90), $R_f$ value: 0.3; LCMS (m/z): 423.3 (M+H)$^+$; $^1$HNMR (400 MHz, DMSO-$d_6$) δ 8.47 (d, J=4.8 Hz, 1H), 7.29 (s, 1H), 7.17 (s, 1H), 6.84 (d, J=4.8 Hz, 1H), 6.47 (s, 2H), 6.38 (t, J=5.6 Hz, 1H), 3.90 (s, 6H), 3.54-3.52 (m, 2H), 2.97-2.84 (m, 2H), 2.71 (t, J=10.8 Hz, 2H), 1.78-1.75 (m, 2H), 1.63-1.47 (m, 3H), 1.38-1.29 (m, 3H), 0.90 (t, J=7.2 Hz, 3H).

Synthesis of I-14

Synthesis of tert-butyl 4-(2-cyanopropan-2-yl)piperidine-1-carboxylate (01)

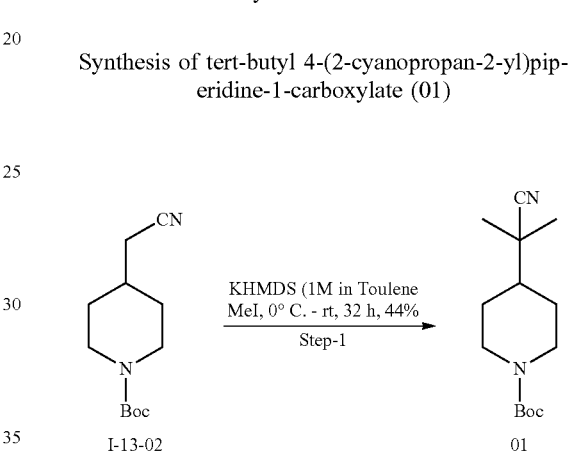

To a stirred solution of tert-butyl 4-(cyanomethyl)piperidine-1-carboxylate (I-13-02) (1 g, 4.2 mmol, 1 eq) in THF (10 mL) at 0° C. was added KHMDS (1M in Toluene) (21 mL, 21 mmol, 5 eq) stirred at 0° C. for 10 mins. Then added Iodomethane (0.59 mL, 8.4 mmol, 2 eq) in THF (2 mL). The reaction mixture was allowed to stir at room temperature for 16 h. After completion of reaction by TLC, the reaction mixture was diluted with water and extracted with EtOAc (3×30 mL). The combined organic layers were washed with brine (30 mL), dried over sodium sulfate and concentrated to afford Crude 1 g (Mono methyl compound). Crude (Mono methyl compound) (1 g, 4.2 mmol, 1 eq) in THF (10 mL) at 0° C. was added KHMDS (1M in Toluene) (21 mL, 21 mmol, 5 eq) stirred at 0° C. for 10 mins followed by addition of Iodomethane (2 mL) (0.59 mL, 8.4 mmol, 2 eq) in THF. The reaction mixture was allowed to stir at room temperature for 16 h. After completion of reaction by TLC, the reaction mixture was diluted with water and extracted with EtOAc (3×30 mL). The combined organic layers were washed with brine (30 mL), dried over sodium sulfate and concentrated to afford crude. Crude was purified by silica column chromatography by eluting with 10% EtOAc in Hexane to afford tert-butyl 4-(2-cyanopropan-2-yl)piperidine-1-carboxylate (01) as gummy liquid (500 mg, yield: 44%). TLC system: EtOAc/hexane (20:80; Ninhydrin stain), $R_f$ value: ~0.5; $^1$H NMR (400 MHz, CDCl$_3$) δ 4.23 (brs, 2H), 2.68-2.63 (m, 2H), 1.81-1.78 (m, 2H), 1.51-1.48 (m, 1H), 1.45 (s, 9H), 1.36-1.30 (m, 8H).

Synthesis of 2-methyl-2-(piperidin-4-yl)propanenitrile hydrochloride (02)

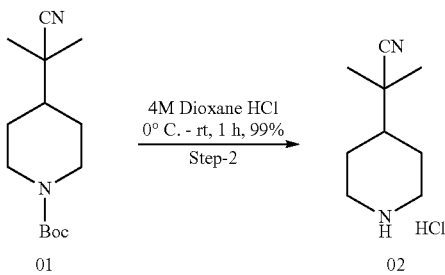 [SMILES: CC(C)(C)OC(=O)N1CCC(C(C)(C)C#N)CC1 ; CC(C)(C#N)C1CCNCC1 ; Cl]

A solution of 4-(2-cyanopropan-2-yl)piperidine-1-carboxylate (01) (500 mg, 1.98 mmol, 1 eq) in 4M Dioxane.HCl (5 mL) was stirred at room temperature for 1 h, After completion of reaction by TLC, the reaction mixture was concentrated under reduced pressure to afford 2-methyl-2-(piperidin-4-yl)propanenitrile hydrochloride (02) (410 mg, yield: 99%) as white solid. TLC system EtoAc (100%, Ninhydrin stain), $R_f$ value: 0.1; $^1$HNMR (400 MHz, DMSO-$d_6$) δ 8.88 (brs, 1H), 8.43 (brs, 1H), 3.38-3.35 (m, 2H), 2.85-2.81 (m, 2H), 1.94-1.91 (m, 2H), 1.71-1.63 (m, 1H), 1.53-1.43 (m, 2H), 1.33 (s, 6H).

Synthesis of 2-(1-(6,7-dimethoxyquinolin-4-yl)piperidin-4-yl)-2-methylpropanenitrile (03)

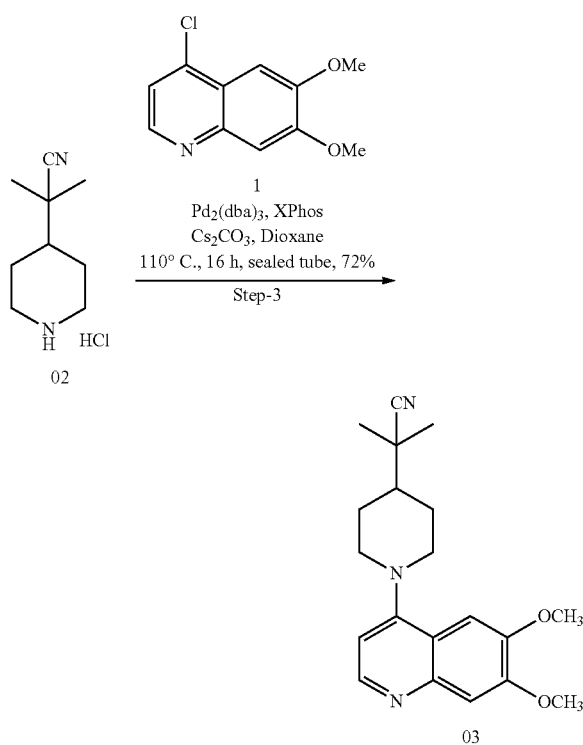

To a stirred solution of 2-methyl-2-(piperidin-4-yl)propanenitrile HCl (02) (408 mg, 2.24 mmol, 1 eq) in 1,4 Dioxane (10 mL) was added 4-chloro-6,7-dimethoxyquinoline (1) (500 mg, 2.24 mmol, 1 eq) degassed for 10 mins. Then added $Cs_2CO_3$ (2.18 g, 6.73 mmol, 3 eq), $Pd_2(dba)_3$ (205 mg, 0.22 mmol, 0.1 eq), X-Phos (213 mg, 0.44 mmol, 0.2 eq). The reaction mixture was stirred at 110° C. for 16 h in a sealed tube. After completion of reaction by TLC, the reaction mixture was filtered through Celite pad and concentrated to provide crude. The crude compound was purified by silica gel chromatography [eluted with 3% MeOH in DCM] to afford 2-(1-(6,7-dimethoxyquinolin-4-yl)piperidin-4-yl)-2-methylpropanenitrile (03) (0.55 g, yield: 72%) as pale yellow solid. TLC system MeOH:DCM (10:90), $R_f$ value: 0.5; LCMS (m/z): 340.4 (M+H)$^+$; $^1$HNMR (400 MHz, DMSO-$d_6$) δ 8.49 (d, J=4.8 Hz, 1H), 7.31 (s, 1H), 7.15 (s, 1H), 6.87 (d, J=4.8 Hz, 1H), 3.91 and 3.90 (2s, 6H), 3.62-3.59 (m, 2H), 2.75-2.72 (m, 2H), 1.99-1.96 (m, 2H), 1.67-1.62 (m, 3H), 1.37 (s, 6H).

Synthesis of 2-(1-(6,7-dimethoxyquinolin-4-yl)piperidin-4-yl)-2-methylpropan-1-amine (04)

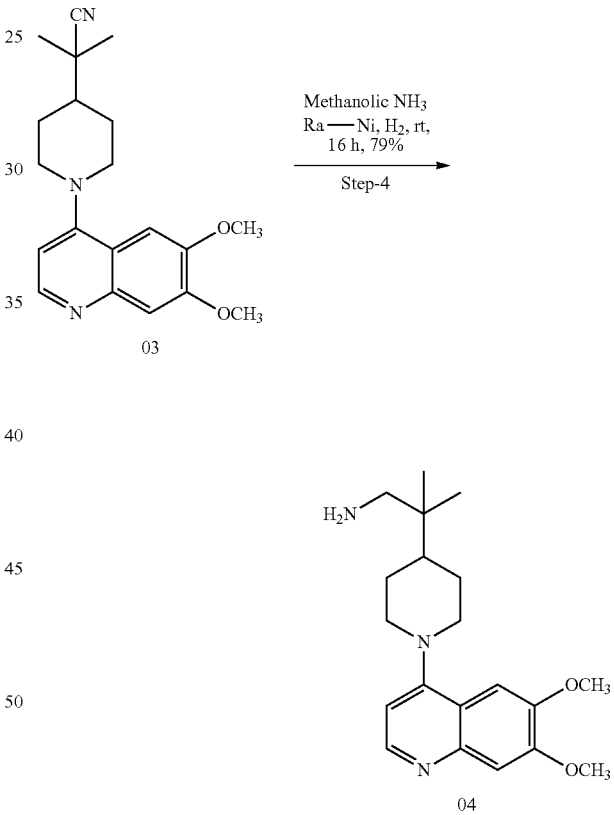

To a stirred solution of 2-(1-(6,7-dimethoxyquinolin-4-yl)piperidin-4-yl)-2-methylpropanenitrile (03) (550 mg, 1.47 mmol, 1 eq) in 7M methanolic.$NH_3$ (5 mL) was added Ra—Ni (1 g). The reaction mixture was stirred at room temperature for 16 h under $H_2$ balloon pressure. After completion of reaction by TLC, reaction mixture was filtered through Celite pad and concentrated to afford 2-(1-(6,7-dimethoxyquinolin-4-yl)piperidin-4-yl)-2-methylpropan-1-amine (04) (400 mg, yield: 79%) as off-white solid. TLC system MeOH:DCM (10:90), $R_f$ value: 0.1; LCMS (m/z): 344.3 (M+H)$^+$; 68% purity. Taken forward to next step.

Synthesis of tert-butyl (N-(2-(1-(6,7-dimethoxyquinolin-4-yl)piperidin-4-yl)-2-methylpropyl)sulfamoyl)carbamate (05)

Synthesis of N-(2-(1-(6,7-dimethoxyquinolin-4-yl)piperidin-4-yl)-2-methylpropyl)sulfuricdiamide hydro chloride salt (I-14)

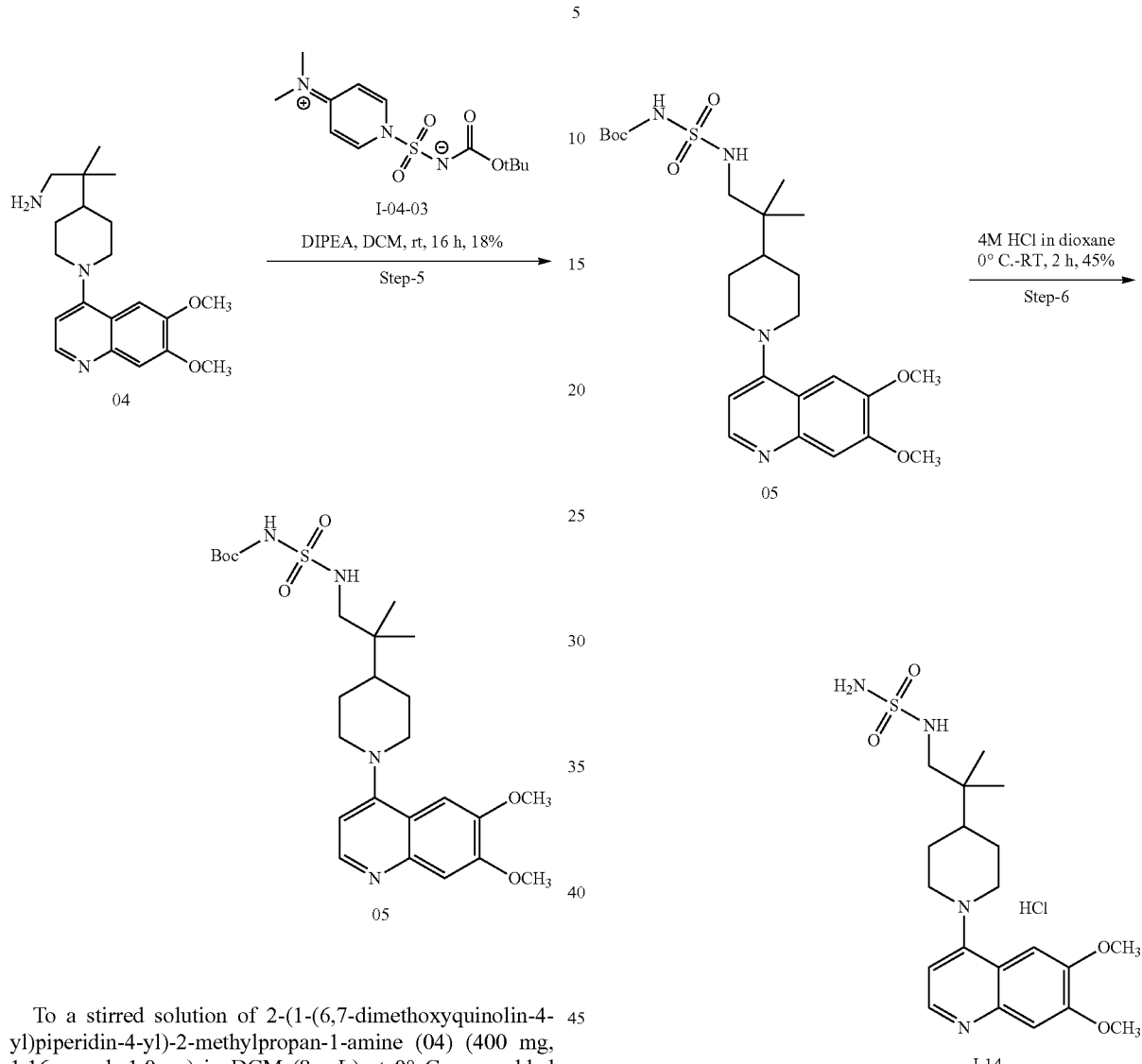

To a stirred solution of 2-(1-(6,7-dimethoxyquinolin-4-yl)piperidin-4-yl)-2-methylpropan-1-amine (04) (400 mg, 1.16 mmol, 1.0 eq) in DCM (8 mL) at 0° C. was added DIPEA (0.31 mL, 1.74 mmol, 1.5 eq) and (tert-butoxycarbonyl)((4-(dimethyliminio)pyridin-1(4H)-yl)sulfonyl)amide (I-04-03) (456 mg, 1.51 mmol, 1.3 eq). The reaction mixture was stirred at RT for 16 h. After completion of reaction, the reaction mixture was diluted with water and extracted with DCM (2×20 mL). The combined organic layers were washed with brine (10 mL), dried over sodium sulfate and concentrated under reduced pressure to provide crude. The crude compound was purified by prep HPLC to afford tert-butyl N-(2-(1-(6,7-dimethoxyquinolin-4-yl)piperidin-4-yl)-2-methylpropyl)sulfamoylcarbamate (05) (110 mg, yield: 18%) as off-white solid. TLC system MeOH:DCM (5:95), $R_f$ value: 0.5; LCMS (m/z): 523.4 (M+H)$^+$; $^1$HNMR (400 MHz, DMSO-d$_6$) δ 10.81 (s, 1H), 8.51 (d, J=7.2 Hz, 1H), 7.51 (t, J=6.8 Hz, 1H), 7.33 (s, 1H), 7.25 (s, 1H), 7.10 (d, J=7.2 Hz, 1H), 4.15-4.12 (m, 2H), 3.98 and 3.96 (2s, 6H), 3.26-3.23 (m, 2H), 2.81-2.79 (m, 2H), 1.83-1.80 (m, 2H), 1.70-1.64 (m, 1H), 1.51-1.46 (m, 2H), 1.43 (s, 9H), 0.85 (s, 6H).

A solution of tert-butyl N-(2-(1-(6,7-dimethoxyquinolin-4-yl)piperidin-4-yl)-2-methylpropyl)sulfamoylcarbamate (05) (100 mg, 0.19 mmol, 1 eq), in 4M Dioxane.HCl (2 mL) was stirred at room temperature for 2 h. After completion of reaction by TLC, reaction mixture was concentrated followed by diethyl ether trituration afforded N-(2-(1-(6,7-dimethoxyquinolin-4-yl)piperidin-4-yl)-2-methylpropyl)sulfuricdiamide hydro chloride salt (I-14) (40 mg, yield: 45%) as an off-white solid. TLC system MeOH:DCM (10:90), $R_f$ value: 0.3; LCMS (m/z): 423.3 (M+H)$^+$; $^1$HNMR (400 MHz, DMSO-d$_6$) δ 14.35 (s, 1H), 8.50 (d, J=6.8 Hz, 1H), 7.42 (s, 1H), 7.24 (s, 1H), 7.10 (d, J=6.8 Hz, 1H), 6.46-6.41 (m, 3H), 4.15-4.12 (m, 2H), 3.97 and 3.96 (2 s, 6H), 3.30-3.24 (m, 2H), 2.77-2.75 (m, 2H), 1.86-1.83 (m, 2H), 1.69-1.63 (m, 1H), 1.50-1.47 (m, 2H), 0.85 (s, 6H).

Synthesis of I-15

Synthesis of N-(2-(1-(6,7-dimethoxyquinolin-4-yl)piperidin-4-yl)propyl)Methyaminosulfonamide (I-15)

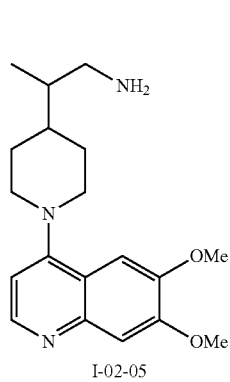
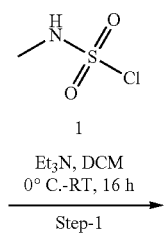
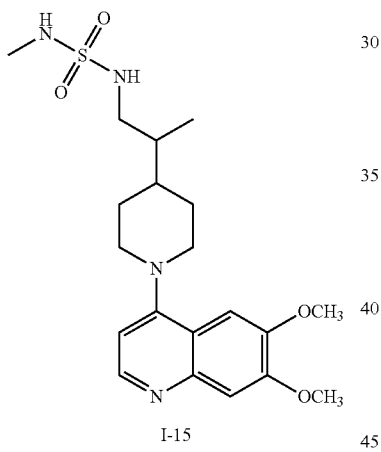

To a stirred solution of 2-(1-(6,7-dimethoxyquinolin-4-yl)piperidin-4-yl)propan-1-amine (I-02-05) (500 mg, 1.51 mmol, 1 eq) in DCM (20 mL) was added TEA (0.43 mL, 3.03 mmol, 2 eq) at 0° C. followed by methylsulfamoyl chloride (1) (294 mg, 2.27 mmol, 1.5 eq). The reaction mixture was stirred at room temperature for 16 h. After completion of reaction by TLC, reaction mixture was concentrated and purified by reverse phase Grace purification [eluted at 30% of 0.1% FA in H$_2$O/ACN] to afford N-(2-(1-(6,7-dimethoxyquinolin-4-yl)piperidin-4-yl)propyl) Methyaminosulfonamide (I-15) (50 mg, yield: 8%) as an off-white solid. TLC system MeOH:DCM (10:90), R$_f$ value: 0.6; LCMS (m/z): 423.3 (M+H)$^+$; $^1$HNMR (400 MHz, DMSO-d$_6$) δ 8.50 (d, J=6.0 Hz, 1H), 7.35 (s, 1H), 7.21 (s, 1H), 7.03 (d, J=6.0 Hz, 1H), 6.85 (t, J=6.0 Hz, 1H), 6.66 (q, J=5.2 Hz, 1H), 3.95 and 3.94 (2s, 6H), 3.93-3.91 (m, 2H), 3.14-3.05 (m, 2H), 2.90-2.84 (m, 1H), 2.72-2.66 (m, 1H), 2.43 (d, J=5.2 Hz, 3H), 1.82-1.78 (m, 2H), 1.68-1.48 (m, 4H), 0.91 (d, J=6.8 Hz, 3H).

Synthesis of I-16

Synthesis of 2-(1-(6,7-dimethoxyquinolin-4-yl)piperidin-4-yl)propanal (01)

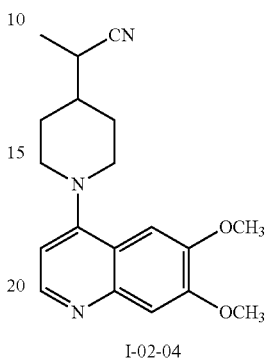
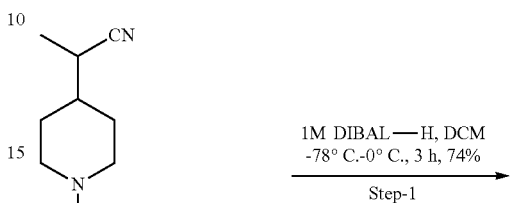
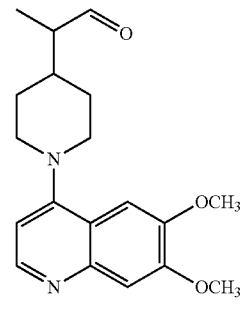

To a stirred solution of 2-(1-(6,7-dimethoxyquinolin-4-yl)piperidin-4-yl)propanenitrile (I-02-04) (800 mg, 2.46 mmol, 1 eq) in DCM (8 mL) at −78° C. was added DIBAL-H (1M in Hexane) (4.92 mL, 4.92 mmol, 2 eq). The reaction mixture was allowed to stir at 0° C. for 3 h. After completion of reaction by TLC, the reaction mixture was quenched with sat. NH$_4$Cl solution and extracted with DCM (3×30 mL). The combined organic layers were washed with brine (15 mL) dried over sodium sulfate and concentrated. The crude was purified by silica column chromatography by eluting with 5% MeOH in DCM to afford 2-(1-(6,7-dimethoxyquinolin-4-yl)piperidin-4-yl)propanal (01) as a gummy liquid (600 mg, yield: 74%). TLC system: MeOH/DCM (10:90), R$_f$ value: ~0.5; LCMS (m/z): 329.4 (M+H)$^+$; $^1$H NMR (400 MHz, CDCl$_3$) δ 9.74 (s, 1H), 8.50 (d, J=5.6 Hz, 1H), 7.57 (s, 1H), 7.17 (s, 1H), 6.81 (d, J=5.6 Hz, 1H), 4.06 and 4.04 (2s, 6H), 3.74-3.71 (m, 2H), 2.96-2.91 (m, 2H), 2.41-2.40 (m, 1H), 1.98-1.68 (m, 5H), 1.19 (d, J=6.8 Hz, 3H).

113
Synthesis of N-(2-(1-(6,7-dimethoxyquinolin-4-yl)piperidin-4-yl)propyl)cyclopropanamine (02)

114
Synthesis of tert-butyl N-cyclopropyl-N-(2-(1-(6,7-dimethoxyquinolin-4-yl)piperidin-4-yl)propyl)sulfamoylcarbamate (03)

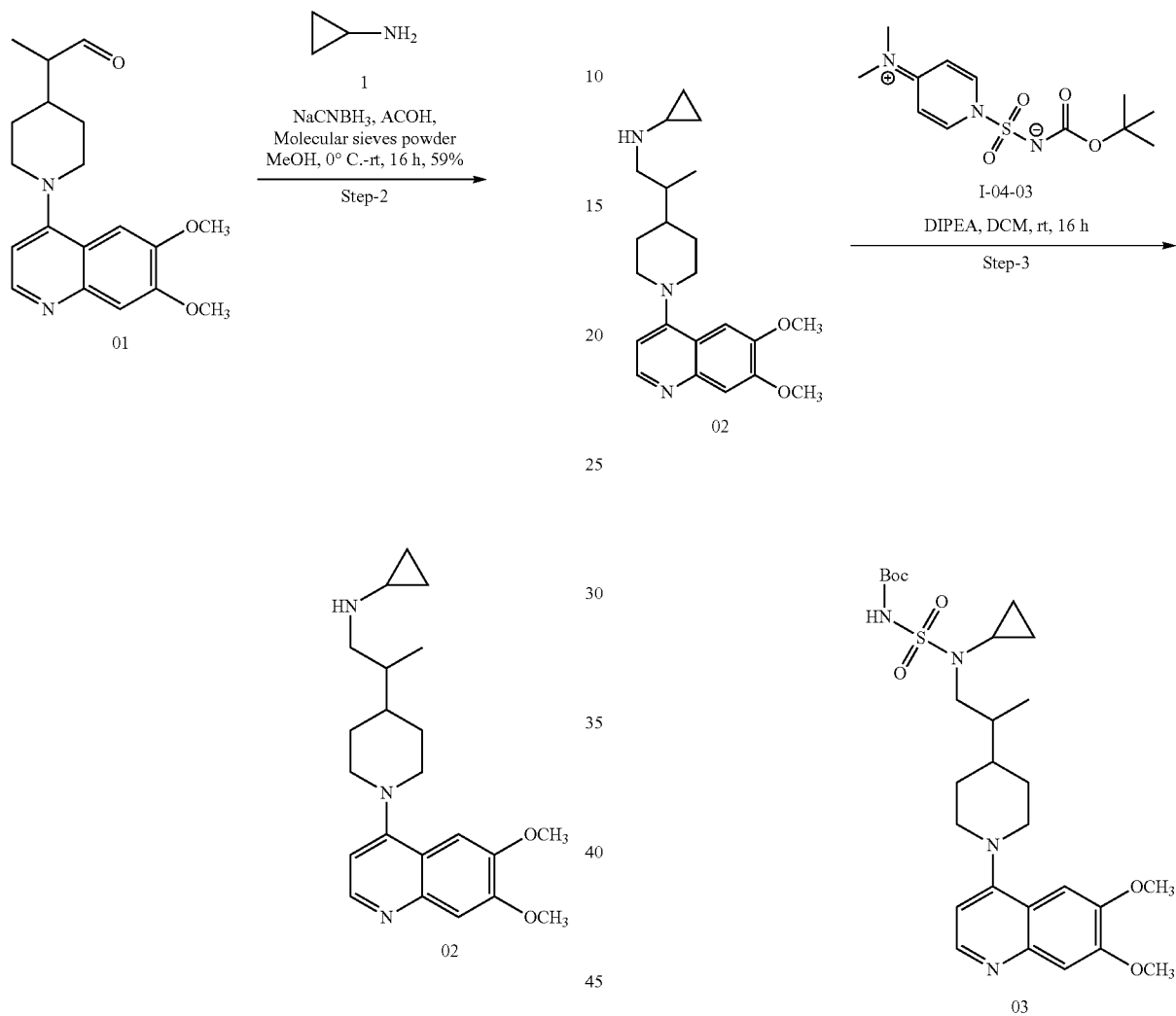

To a stirred solution of 2-(1-(6,7-dimethoxyquinolin-4-yl)piperidin-4-yl)propanal (01) (600 mg, 1.82 mmol, 1 eq) in methanol (6 mL) cooled to 0° C. and added cyclopropanamine (1) (125 mg, 2.19 mmol, 1.2 eq), Molecular sieves powder (600 mg), AcOH (Catalytic). The reaction mixture was stirred at room temperature for 0.5 h, then added NaCNBH₃ (114 mg, 1.82 mmol, 1 eq) and stirred at room temperature for 16 h. After completion of reaction by TLC, the reaction mixture was quenched with cold water and extracted with 10% MeOH+DCM (2×30 mL). The combined organic layers were washed with brine (20 mL) dried over sodium sulfate and concentrated under reduced pressure to afford crude. Crude compound was triturated with diethyl ether to afford N-(2-(1-(6,7-dimethoxyquinolin-4-yl)piperidin-4-yl)propyl)cyclopropanamine (02) (400 mg, yield: 59%) as gummy solid. TLC system: MeOH/DCM (10:90), R$_f$ value: ~0.3; LCMS (m/z): 370.3 (M+H)⁺.

To a stirred solution of N-(2-(1-(6,7-dimethoxyquinolin-4-yl)piperidin-4-yl)propyl)cyclopropanamine (02) (400 mg, 1.08 mmol, 1 eq) in DCM (8 mL) was added DIPEA (0.29 mL, 1.62 mmol, 1.5 eq), (tert-butoxycarbonyl)((4-(dimethyliminio)pyridin-1(4H)-yl)sulfonyl)amide (I-04-03) (422 mg, 1.4 mmol, 1.3 eq). The reaction mixture was stirred at room temperature for 16 h. After completion of reaction by TLC, the reaction mixture was quenched with water and extracted with DCM (2×20 mL). The combined organic layers were washed with brine (10 mL) dried over sodium sulfate and concentrated under reduced pressure to provide crude which was purified by prep-HPLC to afford tert-butyl N-cyclopropyl-N-(2-(1-(6,7-dimethoxyquinolin-4-yl)piperidin-4-yl)propyl)sulfamoylcarbamate (03) (100 mg, yield: 16%) as off-white solid. TLC system MeOH:DCM (5:95), R$_f$ value: 0.5; LCMS (m/z): 549.4 (M+H)⁺, De-boc m/z was also observed.

115
Synthesis of N-cyclopropyl-N-(2-(1-(6,7-dimethoxyquinolin-4-yl)piperidin-4-yl)propyl)aminosulfonamide formate salt (I-16)

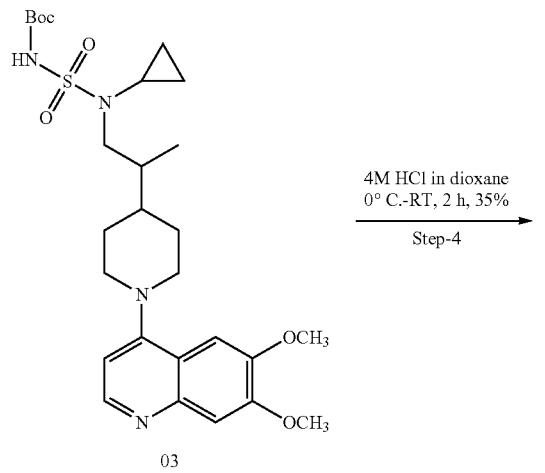

A solution of tert-butyl N-cyclopropyl-N-(2-(1-(6,7-dimethoxyquinolin-4-yl)piperidin-4-yl)propyl)sulfamoylcarbamate (03) (200 mg, 0.36 mmol, 1 eq) in 4M Dioxane.HCl (2 mL) was stirred at room temperature for 2 h. After completion of reaction by TLC, the reaction mixture was concentrated under reduced pressure to afford crude. Crude was purified by prep HPLC to afford N-cyclopropyl-N-(2-(1-(6,7-dimethoxyquinolin-4-yl)piperidin-4-yl)propyl)aminosulfonamide formate salt (I-16) (55 mg, yield: 35%) as white solid. TLC system MeOH:DCM (10:90), $R_f$ value: 0.3; LCMS (m/z): 449.3 (M+H-HCOOH)$^+$; $^1$HNMR (400 MHz, DMSO-d$_6$) δ 8.47 (d, J=5.2 Hz, 1H), 8.14 (s, 1H), 7.29 (s, 1H), 7.17 (s, 1H), 6.85 (d, J=5.2 Hz, 1H), 6.80 (s, 2H), 3.91 and 3.90 (2s, 6H), 3.55-3.52 (m, 2H), 3.19-3.15 (m, 1H), 2.88-2.83 (m, 1H), 2.74-2.67 (m, 2H), 2.28-2.25 (m, 1H), 1.95-1.92 (m, 1H), 1.77-1.67 (m, 3H), 1.55-1.52 (m, 2H), 0.88 (d, J=6.8 Hz, 3H), 0.76-0.66 (m, 4H)

116
Synthesis of I-17

Synthesis of tert-butyl 5,6-dihydro-[3,4'-bipyridine]-1(2H)-carboxylate (01)

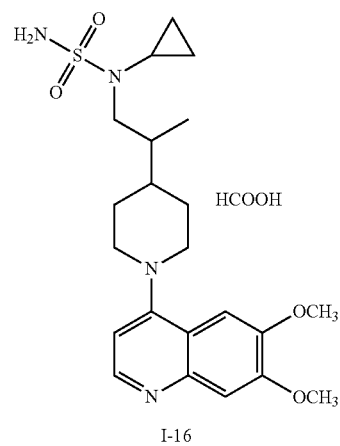

To a stirred solution of 4-bromopyridine hydrochloride (1) (2 g, 10.3 mmol, 1 eq) and tert-butyl 3-(4,4,5,5-tetramethyl-1,3,2-dioxaborolan-2-yl)-5,6-dihydropyridine-1 (2H)-carboxylate (2) (3.2 g, 10.3 mmol, 1 eq) in DME:H$_2$O (2:1) 30 mL was added sodium carbonate (5.4 g, 51.5 mmol, 5 eq) and Pd(PPh$_3$)$_4$ (238 mg, 0.20 mmol, 0.02 eq) and degassed for 15 mins. The reaction mixture was stirred at 100° C. for 16 h in a sealed tube. After completion of reaction by TLC, the reaction mixture was filtered through Celite pad and filtrate was concentrated to provide crude. The crude was purified by silica gel (60-120 mesh) column [eluted at 20% EtOAc in Hexane] to afford tert-butyl 5,6-dihydro-[3,4'-bipyridine]-1(2H)-carboxylate (01) (2.2 g, yield: 84%) as a pale yellow solid. TLC system EtOAc:Hexane (50:50), $R_f$ value: 0.2, LCMS (m/z): 261.2 (M+H)$^+$; $^1$HNMR (400 MHz, DMSO-d$_6$) δ 8.55 (d, J=5.2 Hz, 2H), 7.25 (d, J=6.0 Hz, 2H), 6.48-6.46 (m, 1H), 4.26 (brs, 2H), 3.56 (t, J=5.6 Hz, 2H), 2.35 (brs, 2H), 1.49 (s, 9H).

Synthesis of tert-butyl [3,4'-bipiperidine]-1-carboxylate (02)

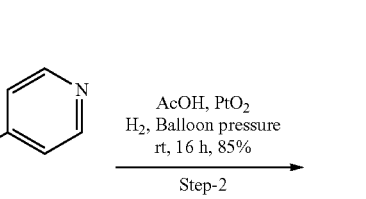

-continued

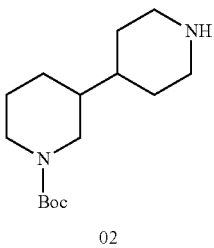

02

To a stirred solution of tert-butyl 5,6-dihydro-[3,4'-bipyridine]-1(2H)-carboxylate (01) (1 g, 3.84 mmol, 1 eq) in acetic acid (20 mL) was added PtO₂ (300 mg). The reaction mixture was stirred at room temperature for 16 h under H₂ balloon pressure. After completion of reaction by TLC, the reaction mixture was filtered through Celite pad and filtrate was concentrated to afford tert-butyl [3,4'-bipiperidine]-1-carboxylate (02) (850 mg, yield: 85%) as a pale-yellow solid. TLC system MeOH:DCM (10:90), R$_f$ value: 0.1; ¹HNMR (400 MHz, DMSO-d₆) δ 3.81-3.72 (br, 2H), 3.17-3.14 (m, 2H), 2.79-2.62 (m, 4H), 1.74-1.70 (m, 4H), 1.61-1.57 (m, 1H), 1.38 (s, 9H), 1.29-1.23 (m, 6H).

Synthesis of tert-butyl 1'-(6,7-dimethoxyquinolin-4-yl)-[3,4'-bipiperidine]-1-carboxylate (03)

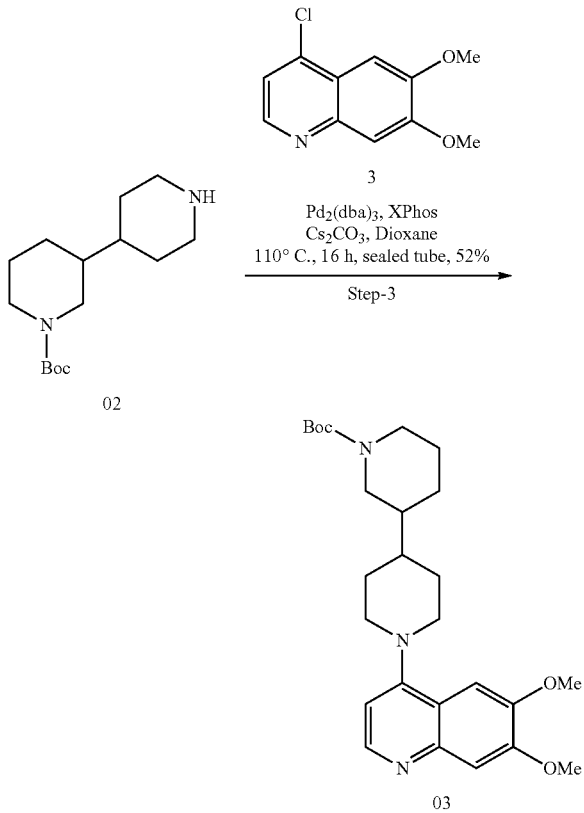

To a stirred solution of 4-chloro-6,7-dimethoxyquinoline (3) (500 mg, 2.24 mmol, 1 eq) in 1,4 Dioxane (5 mL) was added tert-butyl [3,4'-bipiperidine]-1-carboxylate (02) (720 mg, 2.68 mmol, 1.2 eq) and degassed for 10 mins. Then added Cs₂CO₃ (2.1 g, 6.72 mmol, 3 eq), Pd₂(dba)₃ (0.20 g, 0.22 mmol, 0.1 eq), X-Phos (0.21 g, 0.44 mmol, 0.2 eq). The reaction mixture was stirred at 110° C. for 16 h in a sealed tube. After completion of reaction by TLC, the reaction mixture was filtered through Celite pad and concentrated to provide crude. Crude compound was purified by silica gel (60-120 mesh) column [eluted at 5% MeOH in DCM] to afford tert-1'-(6, butyl 7-dimethoxyquinolin-4-yl)-[3,4'-bipiperidine]-1-carboxylate (03) (520 mg, yield: 52%) as a brown gummy liquid. TLC system MeOH:DCM (10:90), R$_f$ value: 0.3; LCMS (m/z): 456.3 (M+H)⁺; ¹HNMR (400 MHz, CDCl₃) δ 8.55 (d, J=5.2 Hz, 1H), 7.46 (s, 1H), 7.22 (s, 1H), 6.78 (d, J=5.2 Hz, 1H), 4.03 (s, 3H), 4.01 (s, 3H), 3.98-3.93 (m, 2H), 3.63-3.60 (m, 2H), 2.79-2.74 (m, 4H), 2.04-1.85 (m, 6H), 1.47 (s, 9H), 1.45-1.38 (m, 4H), aliphatic region was not clear in the NMR spectrum.

Synthesis of 4-([3,4'-bipiperidin]-1'-yl)-6,7-dimethoxyquinoline hydrochloride (04)

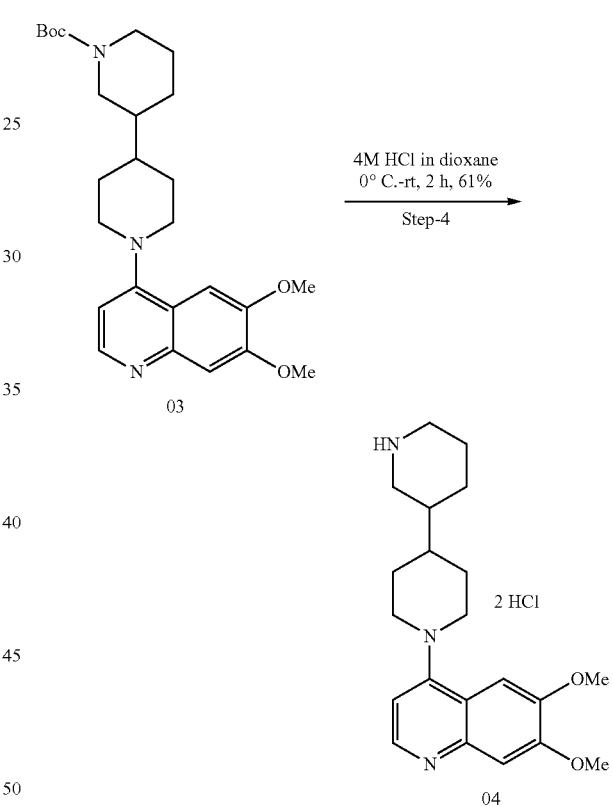

A solution of tert-1'-(6, butyl 7-dimethoxyquinolin-4-yl)-[3,4'-bipiperidine]-1-carboxylate (03) (520 mg, 1.14 mmol, 1 eq) in 4M Dioxane.HCl (6 mL) was stirred at 0° C. for 15 min and allowed to reach room temperature, further stirred for 2 h. After completion of reaction by TLC, volatiles were evaporated. Crude was triturated with diethyl ether to afford 4-([3,4'-bipiperidin]-1'-yl)-6,7-dimethoxyquinoline hydrochloride (04) (250 mg, yield: 61%) as an off white solid. TLC system MeOH:DCM (10:90), R$_f$ value: 0.1; LCMS (m/z): 356.3 (M+H)⁺; ¹HNMR (400 MHz, DMSO-d₆) δ 14.9 (s, 1H), 9.24-9.22 (m, 1H), 9.00-8.97 (m, 1H), 8.53 (d, J=6.4 Hz, 1H), 7.56 (s, 1H), 7.22 (s, 1H), 7.11 (d, J=6.4 Hz, 1H), 4.09-4.07 (m, 2H), 3.97 (s, 6H), 3.27-3.18 (m, 4H), 2.65-2.55 (m, 2H), 1.89-1.83 (m, 4H), 1.68-1.60 (m, 3H), 1.56-1.48 (m, 3H).

119

Synthesis of tert-butyl ((1'-(6,7-dimethoxyquinolin-4-yl)-[3,4'-bipiperidin]-1-yl)sulfonyl)carbamate (05)

120

Synthesis of 6,7-dimethoxy-4-(1-(aminosulfonyl)-[3,4'-bipiperidin]-1'-yl)quinoline formate salt (I-17)

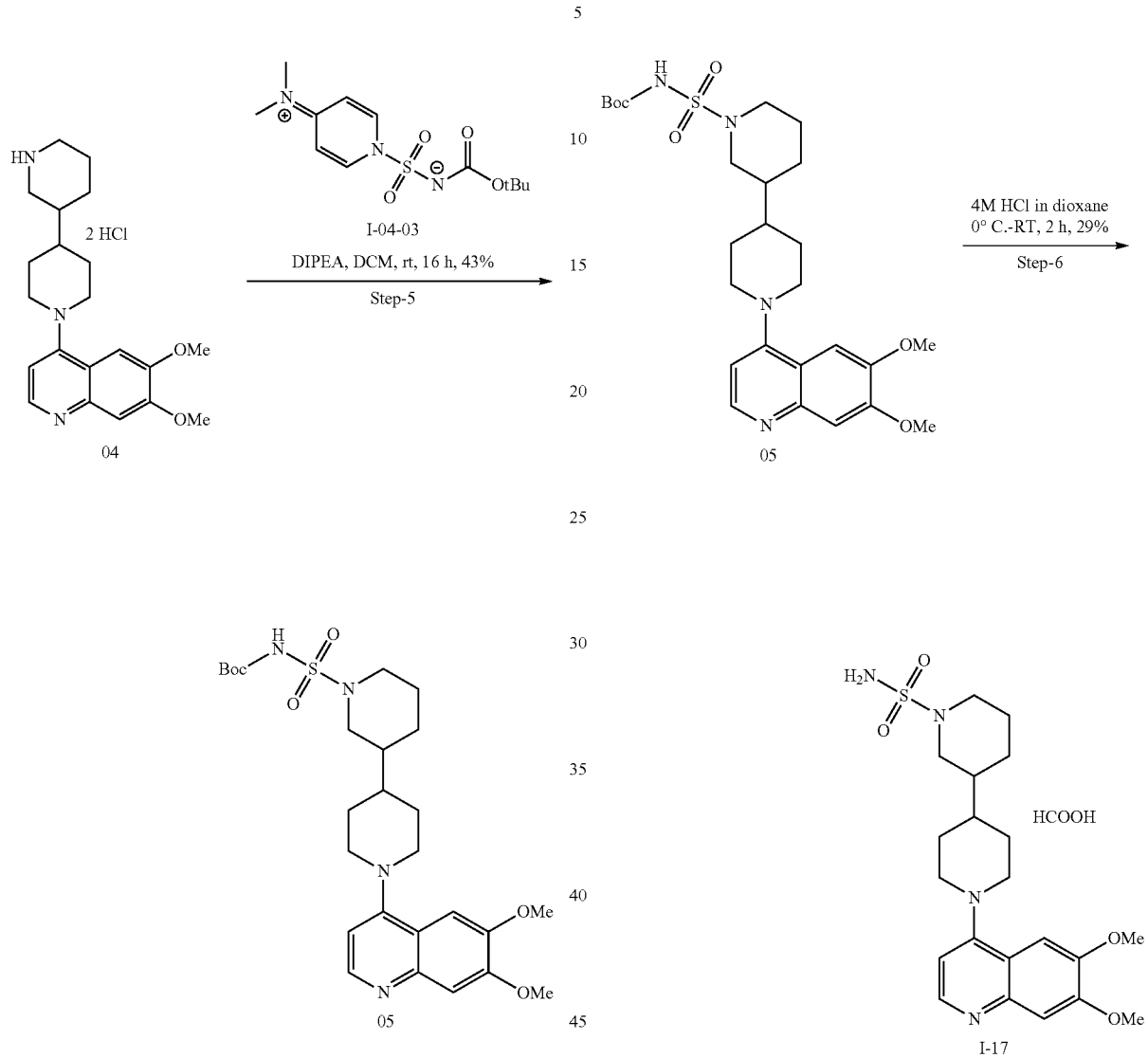

To a stirred solution of 4-([3,4'-bipiperidin]-1'-yl)-6,7-dimethoxyquinoline hydrochloride (04) (250 mg, 0.54 mmol, 1 eq) in DCM (5 mL) was added DIPEA (0.18 mL, 0.82 mmol, 1.5 eq) and (tert-butoxycarbonyl)((4-(dimethyliminio)pyridin-(4H)-yl)sulfonyl)amide (I-04-03) (275 mg, 0.71 mmol, 1.3 eq). The reaction mixture was stirred at room temperature for 16 h. After completion of reaction, the reaction mixture was quenched with water and extracted with DCM (2×20 mL). The combined organic layers were washed with brine (20 mL) dried over sodium sulfate and concentrated under reduced pressure to afford crude. The crude compound was purified by Reverse phase C18 column [eluted using 0.1% FA in H2O/ACN] to afford tert-butyl ((1'-(6,7-dimethoxyquinolin-4-yl)-[3,4'-bipiperidin]-1-yl)sulfonyl)carbamate (05) (150 mg, yield: 43%) as an off white solid. TLC system MeOH:DCM (5:95), $R_f$ value: 0.5; LCMS (m/z): 535.3 (M+H)$^+$.

A solution of tert-butyl ((1'-(6,7-dimethoxyquinolin-4-yl)-[3,4'-bipiperidin]-1-yl)sulfonyl)carbamate (05) (150 mg, 0.28 mmol, 1 eq) in 4M Dioxane.HCl (2 mL) was stirred at 0° C. for 15 min and allowed to reach room temperature, continued for 2 h. After completion of reaction by TLC, volatiles were evaporated. Crude compound was purified by Prep HPLC purification to afford 6,7-dimethoxy-4-(1-(aminosulfonyl)-[3,4'-bipiperidin]-1'-yl)quinoline as formate salt (I-17) (35 mg, yield: 29%) as a white solid. TLC system MeOH:DCM (10:90), $R_f$ value: 0.2; LCMS (m/z): 435.3 (M+H-HCOOH)$^+$; $^1$HNMR (400 MHz, DMSO-d$_6$) δ 8.48 (d, J=5.2 Hz, 1H), 8.13 (formate salt proton), 7.30 (s, 1H), 7.17 (s, 1H), 6.86 (d, J=5.2 Hz, 1H), 6.68 (s, 2H), 3.91 (s, 6H), 3.57-3.54 (m, 2H), 3.50-3.47 (m, 2H), 3.39-3.37 (br, 1H), 2.75-2.71 (m, 2H), 2.36 (t, J=10.8 Hz, 1H), 1.90-1.75 (m, 4H), 1.56-1.47 (m, 5H), 1.11-1.08 (m, 1H).

121
Synthesis of I-18

Synthesis of Ethyl 1-(6,7-dimethoxyquinolin-4-yl)piperidine-4-carboxylate (01)

122
Synthesis of 1-(6,7-dimethoxyquinolin-4-yl)piperidine-4-carboxylic acid (02)

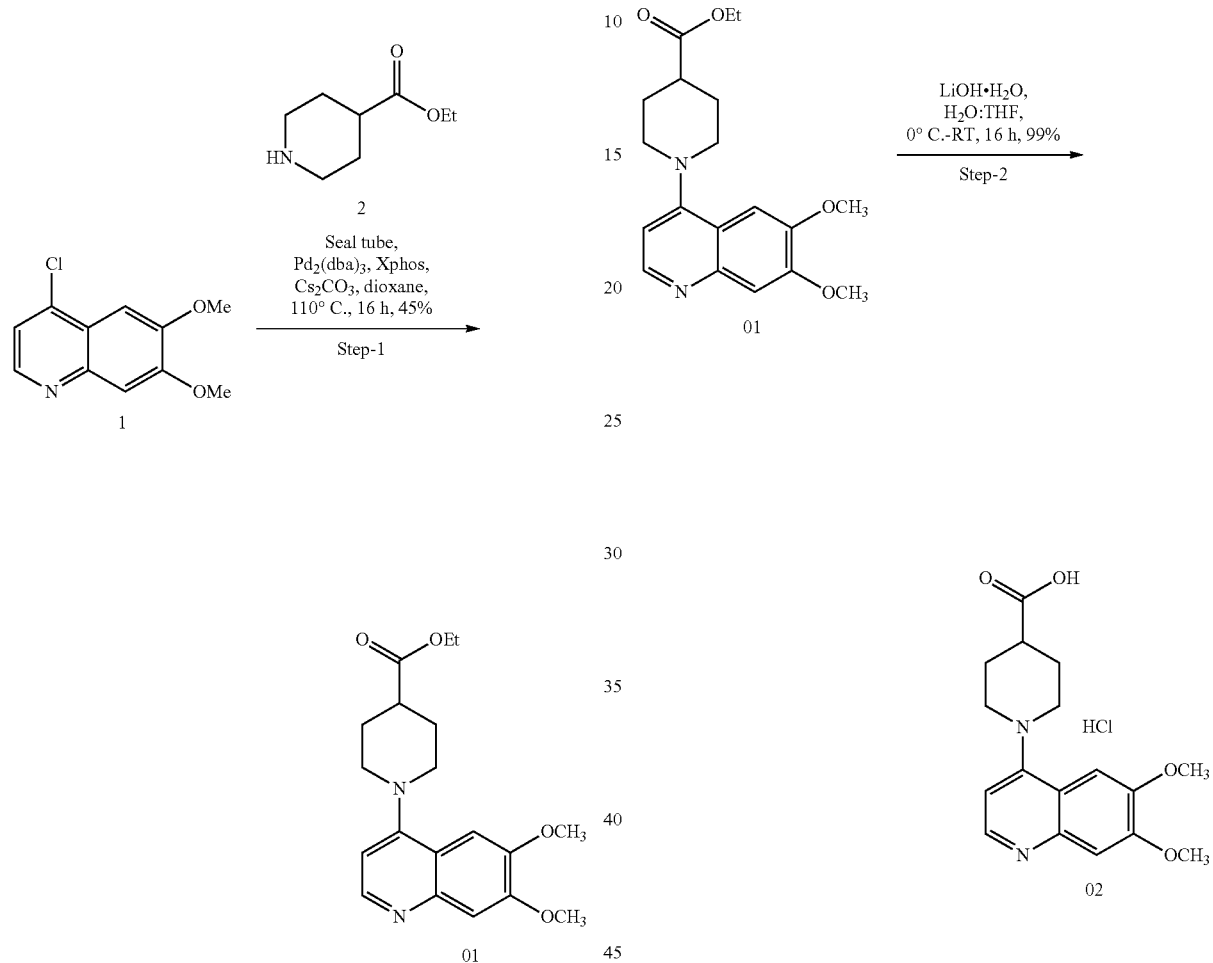

To a stirred solution of 4-chloro-6,7-dimethoxyquinoline (1) (1 g, 4.46 mmol, 1 eq) in 1,4 Dioxane (20 mL) was added ethyl piperidine-4-carboxylate (2) (0.84 g, 5.35 mmol, 1.2 eq) degassed for 10 mins, added $Cs_2CO_3$ (4.34 g, 13.3 mmol, 3 eq), $Pd_2(dba)_3$ (0.40 g, 0.44 mmol, 0.1 eq), X-Phos (0.42 mg, 0.89 mmol, 0.2 eq). The reaction mixture was stirred at 110° C. for 16 h in a sealed tube. After completion of reaction by TLC, the reaction mixture was filtered through Celite pad, washed with ethyl acetate and concentrated to provide crude. The crude compound was purified by 100-200 mesh silica gel column by eluting with 3% MeOH in DCM to afford Ethyl 1-(6,7-dimethoxyquinolin-4-yl)piperidine-4-carboxylate (01) (650 mg, yield: 45%) as white solid. TLC system MeOH:DCM (10:90), $R_f$ value: 0.5; LCMS (m/z): 345.4 (M+H)⁺;

To a stirred solution of ethyl 1-(6,7-dimethoxyquinolin-4-yl)piperidine-4-carboxylate (01) (650 mg, 1.53 mmol, 1 eq), in $THF:H_2O$ (2:1) (10 mL), was added LiOH.$H_2O$ (193 mg, 4.59 mmol, 1 eq), at 0° C. The reaction mixture was stirred at room temperature for 16 h. After completion of reaction by TLC, reaction mixture was concentrated and washed with diethyl ether (50 mL). The aqueous layer was adjust to pH-7 by using 2 N aq HCl and concentrated under reduced pressure to afford 1-(6,7-dimethoxyquinolin-4-yl)piperidine-4-carboxylic acid (02) (590 mg, yield: 99%) as off-white solid. TLC system MeOH:DCM (20:80), $R_f$ value: 0.1; LCMS (m/z): 317.4 (M+H)⁺; ¹HNMR (400 MHz, DMSO-$d_6$) δ 15.38 (s, 1H), 12.45 (s, 1H), 8.53 (d, J=6.8 Hz, 1H), 7.69 (s, 1H), 7.21 (s, 1H), 7.12 (d, J=6.8 Hz, 1H), 3.99-3.98 (m, 2H), 3.97 and 3.96 (2s, 6H), 2.71-2.67 (m, 1H), 2.09-2.05 (m, 2H), 1.89-1.84 (m, 2H), 2 protons were merged with solvent peaks.

123
Synthesis of N-(1-cyanocyclopropyl)-1-(6,7-dimethoxyquinolin-4-yl)piperidine-4-carboxamide (I-18)

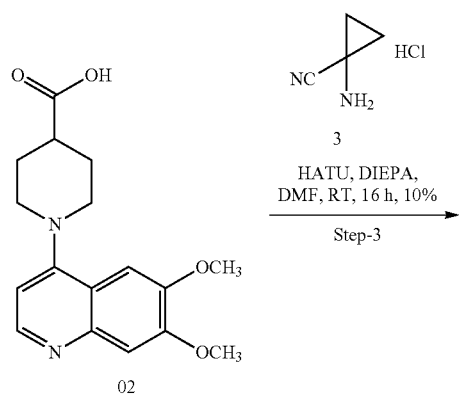

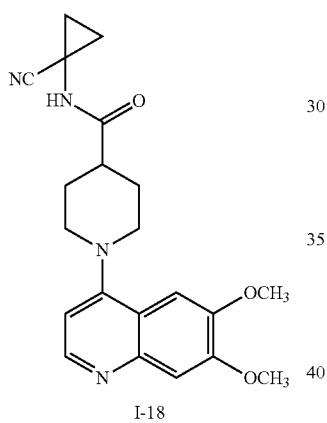

124
Synthesis of I-19

N-(2-(1-(6,7-dimethoxyquinolin-4-yl)piperidin-4-yl)propyl)methanesulfonamide

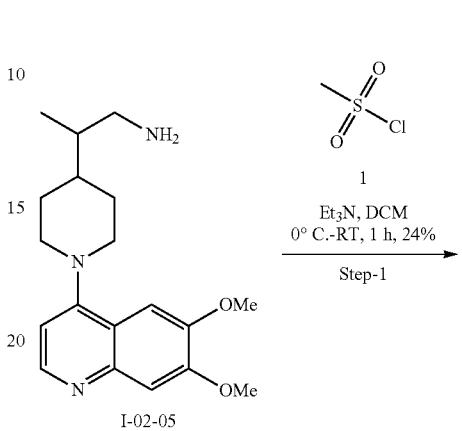

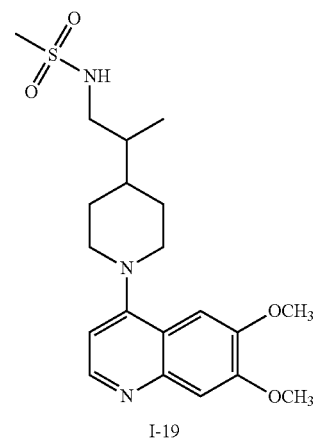

To a stirred solution of 1-(6,7-dimethoxyquinolin-4-yl)piperidine-4-carboxylic acid (02) (300 mg, 0.94 mmol, 1.0 eq) in DMF (3 mL) was added 1-aminocyclopropane-1-carbonitrile hydrogen chloride (3) (110 mg, 0.94 mmol, 1.5 eq), HATU (536 mg, 1.41 mmol, 1.5 eq), DIPEA (0.78 mL, 4.7 mmol, 1.5 eq), The reaction mixture was stirred at RT for 16 h. After completion of reaction, the reaction mixture was diluted with water and extracted with Ethyl acetate (2×50 mL). The combined organic layers were washed with brine (20 mL) dried over sodium sulfate and concentrated under reduced pressure to afford crude. The crude compound was purified by Reverse phase grace purification [gradient elution with 40% H$_2$O/ACN] to afford N-(1-cyanocyclopropyl)-1-(6,7-dimethoxyquinolin-4-yl)piperidine-4-carboxamide (I-18) (36 mg, yield: 10%) as off-white solid. TLC system MeOH:DCM (10:90), R$_f$ value: 0.4; LCMS (m/z): 381.2 (M+H)$^+$; $^1$HNMR (400 MHz, DMSO-d$_6$) δ 8.82 (s, 1H), 8.49 (d, J=5.2 Hz, 1H), 7.30 (s, 1H), 7.16 (s, 1H), 6.88 (d, J=5.2 Hz, 1H), 3.92 and 3.91 (2s, 6H), 3.55-3.52 (m, 2H), 2.78-2.76 (m, 2H), 2.35-2.33 (m, 1H), 1.88-1.85 (m, 4H), 1.50-1.47 (m, 2H), 1.14-1.11 (m, 2H).

To a stirred solution of 2-(1-(6,7-dimethoxyquinolin-4-yl)piperidin-4-yl)propan-1-amine (I-02-05) (200 mg, 0.607 mmol, 1 eq) in DCM (4 mL) was added TEA (0.12 mL, 0.911 mmol, 1.5 eq), methane sulfonyl chloride (1) (0.05 mL, 0.72 mmol, 1.5 eq) at 0° C. The reaction mixture was stirred at room temperature for 1 h. After completion of reaction by TLC, reaction mixture was diluted with water and extracted with DCM. The organic layer was washed with brine, dried over sodium sulphate and concentrated to provide crude. The crude was purified by 100-200 mesh silica gel column by eluting with 2% MeOH+DCM to afford N-(2-(1-(6,7-dimethoxyquinolin-4-yl)piperidin-4-yl)propyl)methanesulfonamide (I-19) (60 mg, yield: 24%) as off-white solid. TLC system MeOH:DCM (10:90), R$_f$ value: 0.6; LCMS (m/z): 408.3 (M+H)$^+$; $^1$HNMR (400 MHz, DMSO-d$_6$) δ 8.48 (d, J=5.2 Hz, 1H), 7.29 (s, 1H), 7.17 (s, 1H), 6.97 (t, J=6.0 Hz, 1H), 6.86 (d, J=4.8 Hz, 1H), 3.91 (s, 6H), 3.57-3.54 (m, 2H), 3.06-3.00 (m, 1H), 2.90 (s, 3H), 2.85-2.82 (m, 1H), 2.76-12.71 (m, 2H), 1.81-1.76 (m, 2H), 1.59-1.55 (m, 4H), 0.93 (d, J=6.8 Hz, 3H).

Synthesis of I-20

Synthesis of tert-butyl 4-(6,7-dimethoxyquinolin-4-yl)piperazine-1-carboxylate (01)

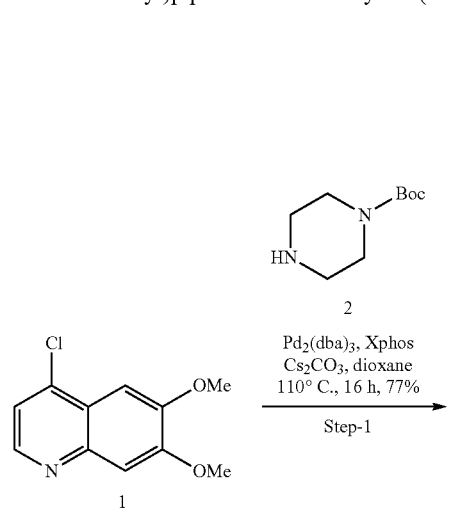

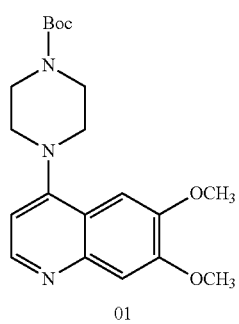

To a stirred solution of 4-chloro-6,7-dimethoxyquinoline (1) (1 g, 4.48 mmol, 1 eq), in 1,4 Dioxane (10 mL) was added tert-butyl piperazine-1-carboxylate (2) (1 g, 5.38 mmol, 1.2 eq) and degassed for 10 min. Later, added $Cs_2CO_3$ (2.91 g, 8.96 mmol, 2 eq), $Pd_2(dba)_3$ (0.41 g, 0.44 mmol, 0.1 eq), X-Phos (0.42 mg, 0.89 mmol, 0.2 eq). The reaction mixture was stirred at 110° C. for 16 h in a sealed tube. After completion of reaction by TLC, the reaction mixture was filtered through Celite pad and filtrate was concentrated to provide crude. The crude compound was purified by silica gel (100-200 mesh) chromatography [eluted with 3% MeOH+DCM] to afford tert-butyl 4-(6,7-dimethoxyquinolin-4-yl)piperazine-1-carboxylate (01) (1.3 g, yield: 77%) as white solid. TLC system MeOH:DCM (10:90), $R_f$ value: 0.5; LCMS (m/z): 374.2 $(M+H)^+$; $^1$HNMR (400 MHz, $CDCl_3$) δ 8.59 (d, J=5.2 Hz, 1H), 7.40 (s, 1H), 7.26 (s, 1H), 6.79 (d, J=5.2 Hz, 1H), 4.03 and 4.01 (2s, 6H), 3.70 (t, J=4.8 Hz, 4H), 3.15 (t, J=4.8 Hz, 4H), 1.51 (s, 9H).

Synthesis of 6,7-dimethoxy-4-(piperazin-1-yl)quinoline (02)

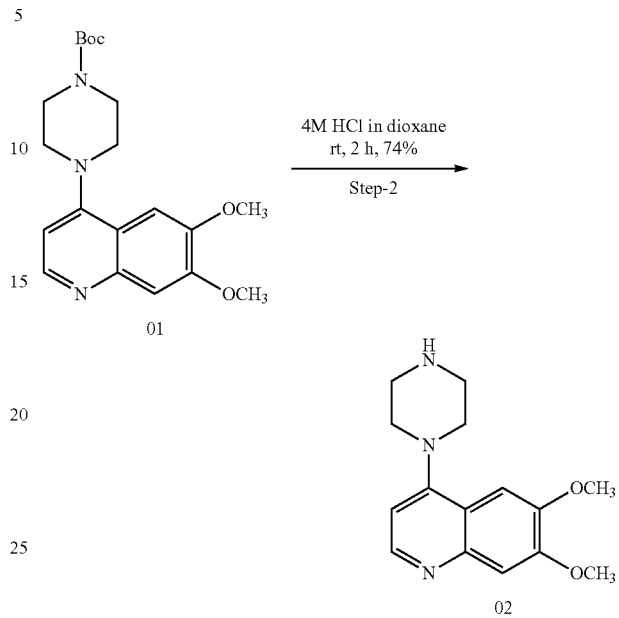

A solution of tert-butyl 4-(6,7-dimethoxyquinolin-4-yl)piperazine-1-carboxylate (01) (1.3 g, 5 mmol, 1 eq) in 4M Dioxane. HCl (13 mL) was stirred at room temperature for 2 h. After completion of reaction by TLC, the reaction mixture was evaporated under reduced pressure to afford Crude. Crude compound was basified with Saturated $NaHCO_3$ solution and extracted with 10% MeOH+DCM (2×50 mL). The combined organic layers were washed with brine (20 mL), dried over sodium sulfate and concentrated to afford 6,7-dimethoxy-4-(piperazin-1-yl)quinoline (02) (0.65 g, yield: 74%) as brown solid. TLC system MeOH:DCM (10:90), $R_f$ value: 0.2; LCMS (m/z): 274.4 $(M+H)^+$.

Synthesis of tert-butyl (2-hydroxypropyl)carbamate (03)

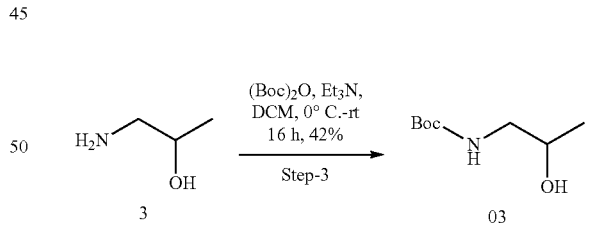

To a stirred solution of I-aminopropan-2-ol (3) (5 g, 66.7 mmol, 1.0 eq) in DCM (50 mL) at 0° C. was added triethylamine (9.2 mL, 66.7 mmol, 1 eq) followed by drop-wise addition of $(Boc)_2O$ (14.3 mL, 66.7 mmol, 1 eq) under nitrogen flush. The reaction was stirred at room temperature for 16 h. After completion of reaction by TLC, the reaction mixture was diluted with ice cold water and extracted with DCM (2×100 mL). The combined organic layer was washed with water (50 mL), brine solution (50 mL), dried over sodium sulfate and concentrated under reduced pressure to provide crude. The crude compound was purified by silica gel (100-200 mesh) chromatography [gradient elution with 20-25% Ethyl acetate/Hexane] to afford tert-butyl (2-hydroxypropyl)carbamate (03) as a yellow liquid (5 g, 42%). TLC system: EtOAc/hexane (50:50; Ninhydrin stain), $R_f$ value: ~0.4; $^1$HNMR (400 MHz, DMSO-$d_6$) δ 6.64 (brs, 1H), 4.55 (d, J=4.8 Hz, 1H), 3.60-3.55 (m, 1H), 2.90-2.81 (m, 2H), 1.37 (s, 9H), 0.98 (d, J=6.4 Hz, 3H).

Synthesis of tert-butyl (2-oxopropyl)carbamate (04)

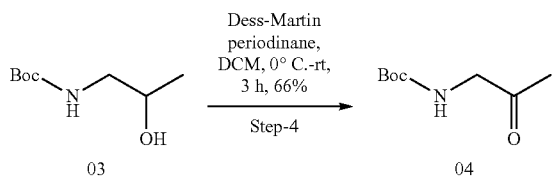

To a stirred solution of tert-butyl (2-hydroxypropyl)carbamate (03) (1.5 g, 5.71 mmol, 1 eq) in dry DCM (15 mL) at 0° C. was added Dess-Martin periodinane (4.8 g, 6.85 mmol, 1.2 eq). The reaction mixture was stirred at room temperature for 3 h. After completion of reaction by TLC, the reaction mixture was diluted with water and extracted with EtOAc (2×50 mL). The combined organic layers were washed with brine (30 mL), dried over sodium sulfate and concentrated to provide crude. The crude compound was purified by silica gel (100-200 mesh) chromatography [gradient elution with 5-10% Ethyl acetate/Hexane] to afford tert-butyl (2-oxopropyl)carbamate (04) (1 g, yield: 66%) as colorless liquid. TLC system: EtoAc:Hexane (50:50; Ninhydrin stain), $R_f$ value: ~0.6; $^1$H NMR (400 MHz, CDCl$_3$) δ 5.25 (brs, 1H), 4.03 (d, J=4.8 Hz, 2H), 2.18 (s, 3H), 1.46 (s, 9H), Synthesis of tert-butyl (2-(4-(6,7-dimethoxyquinolin-4-yl)piperazin-1-yl)propyl)carbamate (05)

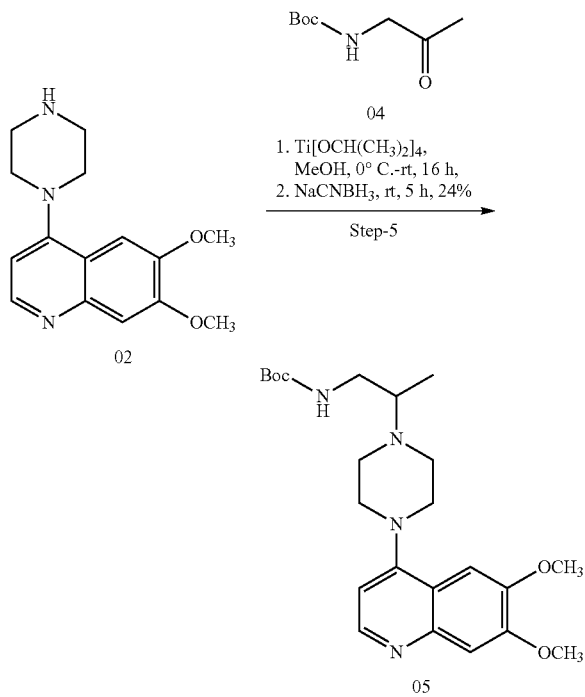

To a stirred solution of 6,7-dimethoxy-4-(piperazin-1-yl)quinoline (02) (650 mg, 2.38 mmol, 1 eq) in methanol (8 mL) was added tert-butyl (2-oxopropyl)carbamate (04) (0.41 g, 2.38 mmol, 1 eq) and Titanium isopropoxide (0.69 mL, 4.76 mmol, 2 eq). The reaction mixture was stirred at room temperature for 16 h. Later, reaction mixture was cooled to 0° C., added NaCNBH$_3$ (224 mg, 3.57 mmol, 1.5 eq) and stirred at room temperature for 5 h. After completion of reaction by TLC, reaction mixture was quenched with water and extracted with 10% MeOH+DCM (2×50 mL). The combined organic layers were washed with brine (20 mL), dried over sodium sulfate and concentrated. The crude compound was purified by silica gel (100-200 mesh) column chromatography [eluted with 5% MeOH+DCM] to afford tert-butyl (2-(4-(6,7-dimethoxyquinolin-4-yl)piperazin-1-yl)propyl)carbamate (05) (0.2 g, yield: 20%) as brown solid. TLC system MeOH:DCM (10:90), $R_f$ value: 0.5; LCMS (m/z): 431.3 (M+H)$^+$; $^1$HNMR (400 MHz, DMSO-$d_6$) δ 8.49 (d, J=4.8 Hz, 1H), 7.33 (s, 1H), 7.20 (s, 1H), 6.84 (d, J=4.8 Hz, 1H), 6.61-6.59 (m, 1H), 3.90 (s, 6H), 3.72-3.67 (m, 1H), 3.16-3.11 (m, 4H), 2.82-2.67 (m, 6H), 1.39 (s, 9H), 0.98 (d, J=6.4 Hz, 3H).

Synthesis of 2-(4-(6,7-dimethoxyquinolin-4-yl)piperazin-1-yl)propan-1-amine hydro chloride (06)

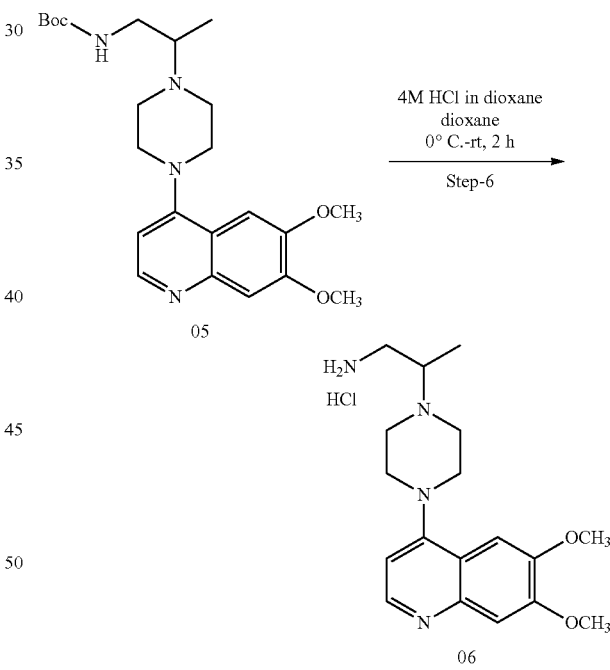

To a stirred solution of tert-butyl (2-(4-(6,7-dimethoxyquinolin-4-yl)piperazin-1-yl)propyl)carbamate (05) (200 mg, 0.46 mmol, 1 eq) in dioxane at 0° C. was added 4M Dioxane.HCl (4 mL) and stirred at room temperature for 2 h, After completion of reaction by TLC, the reaction mixture was concentrated under reduced pressure to afford 2-(4-(6,7-dimethoxyquinolin-4-yl)piperazin-1-yl)propan-1-amine hydrochloride (06) (0.17 g) as brown solid. TLC system MeOH:DCM (10:90), $R_f$ value: 0.1; LCMS (m/z): 331.3 (M+H)$^+$ not as a molecular ion peak. 274.2 was major ion peak which is a fragment of desired product. Both LCMS and 1H NMR spectrum were not supportive in identification of product; however, the material was taken forward to next step and confirmed at that stage.

Synthesis of tert-butyl (N-(2-(4-(6,7-dimethoxyquinolin-4-yl)piperazin-1-yl)propyl)sulfamoyl)carbamate (07)

Synthesis of N-(2-(4-(6,7-dimethoxyquinolin-4-yl)piperazin-1-yl)propyl)aminosulfonamide formate salt (I-20)

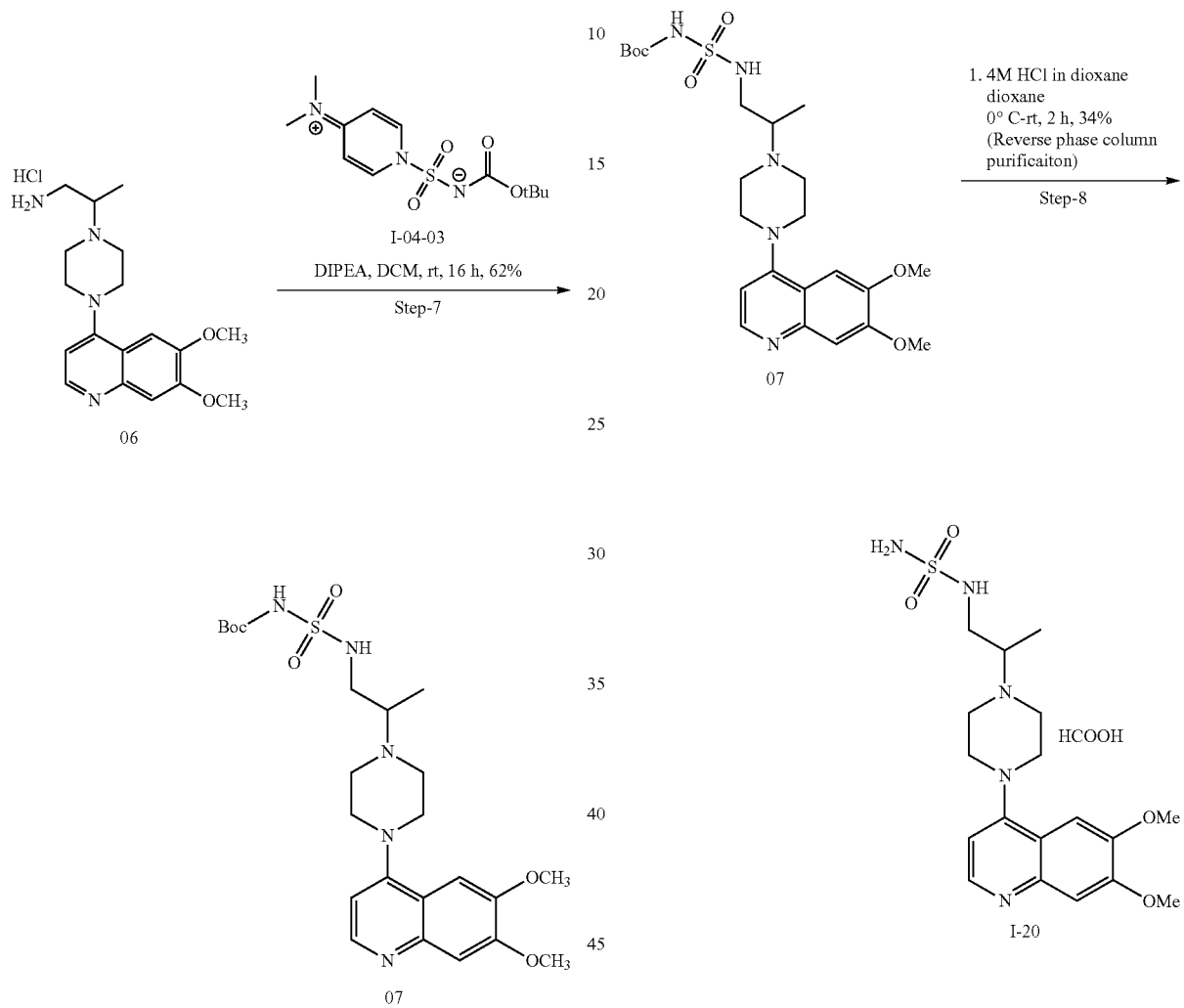

To a stirred solution of 2-(4-(6,7-dimethoxyquinolin-4-yl)piperazin-1-yl)propan-1-amine hydro chloride (06) (170 mg, 0.46 mmol, 1.0 eq) in DCM (4 mL) was added DIPEA (0.25 mL, 1.38 mmol, 3 eq) and (tert-butoxycarbonyl)((4-(dimethyliminio)pyridin-1(4H)-yl)sulfonyl)amide (I-04-03) (181 mg, 0.60 mmol, 1.3 eq). The reaction mixture was stirred at room temperature for 16 h. After completion of reaction, the reaction mixture was diluted with water and extracted with DCM (2×20 mL). The combined organic layers were washed with brine (10 mL) dried over sodium sulfate and concentrated under reduced pressure to afford crude. The crude compound was purified by prep HPLC to afford tert-butyl (N-(2-(4-(6,7-dimethoxyquinolin-4-yl)piperazin-1-yl)propyl)sulfamoyl)carbamate (07) (150 mg, 62% over two steps) as off-white solid. TLC system MeOH:DCM (5:95), $R_f$ value: 0.5; LCMS (m/z): 508.3 (M−H)⁺.

To a stirred solution of tert-butyl (N-(2-(4-(6,7-dimethoxyquinolin-4-yl)piperazin-1-yl)propyl)sulfamoyl)carbamate (07) (150 mg, 0.29 mmol, 1 eq) in dioxane at 0° C. was added 4M Dioxane.HCl (1 mL) and stirred at room temperature for 2 h. After completion of reaction by TLC, reaction mixture was concentrated to afford Crude. Crude compound was purified by Reverse phase purification [gradient elution with 0-20% (0.1% FA in $H_2O$)+ACN] to afford N-(2-(4-(6,7-dimethoxyquinolin-4-yl)piperazin-1-yl)propyl)aminosulfonamide format salt (I-20) (42 mg, yield: 34%) as a white solid. TLC system MeOH:DCM (20:80), $R_f$ value: 0.1; LCMS (m/z): 410.3 (M+H)⁺; ¹HNMR (400 MHz, DMSO-d₆) δ 8.50 (d, J=4.8 Hz, 1H), 8.14 (format salt proton), 7.32 (s, 1H), 7.21 (s, 1H), 6.88 (d, J=4.8 Hz, 1H), 6.59 (brs, 2H), 6.09 (brs, 1H), 3.91 (s, 6H), 3.20-3.17 (m, 4H), 3.10-3.05 (m, 1H), 2.87-2.77 (m, 6H), 1.05 (d, J=5.6 Hz, 3H).

Synthesis of I-21

Synthesis of (R)-tert-butyl 4-(6,7-dimethoxyquinolin-4-yl)-2-methylpiperazine-1-carboxylate (01)

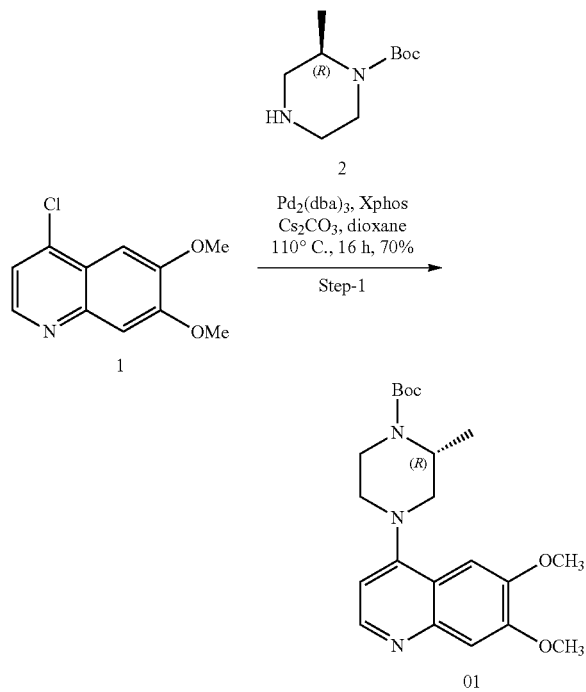

To a stirred solution of 4-chloro-6,7-dimethoxyquinoline (1) (1 g, 4.48 mmol, 1 eq) in 1,4 Dioxane (10 mL) was added (R)-tert-butyl 2-methylpiperazine-1-carboxylate (2) (1.0 g, 5.38 mmol, 1.2 eq) and degassed for 10 mins. Then added $Cs_2CO_3$ (4.2 g, 13.4 mmol, 3 eq), $Pd_2(dba)_3$ (0.41 g, 0.44 mmol, 0.1 eq), X-Phos (0.42 g, 0.89 mmol, 0.2 eq). The reaction mixture was stirred at 110° C. for 16 h in a sealed tube. After completion of reaction by TLC, the reaction mixture was filtered through Celite pad and concentrated to provide crude. The crude compound was purified by silica gel (100-200 mesh) chromatography [eluted with 3% MeOH in DCM] to afford (R)-tert-butyl 4-(6,7-dimethoxyquinolin-4-yl)-2-methylpiperazine-1-carboxylate (01) (1.2 g, yield: 70%) as off white solid. TLC system MeOH:DCM (10:90), $R_f$ value: 0.4; LCMS (m/z): 388.3 $(M+H)^+$;

Synthesis of (R)-6,7-dimethoxy-4-(3-methylpiperazin-1-yl)quinoline hydro chloride (02)

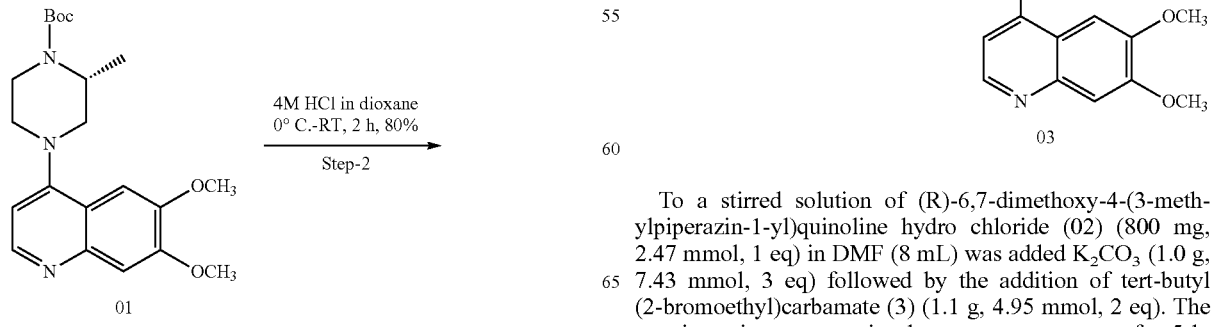

A solution of (R)-tert-butyl 4-(6,7-dimethoxyquinolin-4-yl)-2-methylpiperazine-1-carboxylate (01) (1.2 g, 3.10 mmol, 1 eq) in 4M Dioxane.HCl (15 mL) was stirred at 0° C. to room temperature for 2 h. After completion of reaction by TLC, volatiles were evaporated and the obtained crude was triturated with diethyl ether to afford (R)-6,7-dimethoxy-4-(3-methylpiperazin-1-yl)quinoline hydro chloride (02) (800 mg, yield: 80%) as an off-white solid. TLC system MeOH:DCM (10:90), $R_f$ value: 0.1; LCMS (m/z): 288.2 $(M+H-HCl)^+$; peak shape was not good. $^1$HNMR (400 MHz, DMSO-$d_6$) δ 9.65-9.62 (brs, 2H), 8.69 (d, J=6.4 Hz, 1H), 7.53 (s, 1H), 7.31 (d, J=6.4 Hz, 1H), 7.25 (s, 1H), 4.08-4.04 (m, 2H), 4.01 (s, 3H), 3.99 (s, 3H), 3.96-3.92 (m, 1H), 3.66-3.63 (m, 2H), 1.35 (d, J=6.4 Hz, 3H), 2 protons might merged with DMSO-$d_6$ peaks in the spectrum.

Synthesis of (R)-tert-butyl (2-(4-(6,7-dimethoxyquinolin-4-yl)-2-methylpiperazin-1-yl)ethyl)carbamate (03)

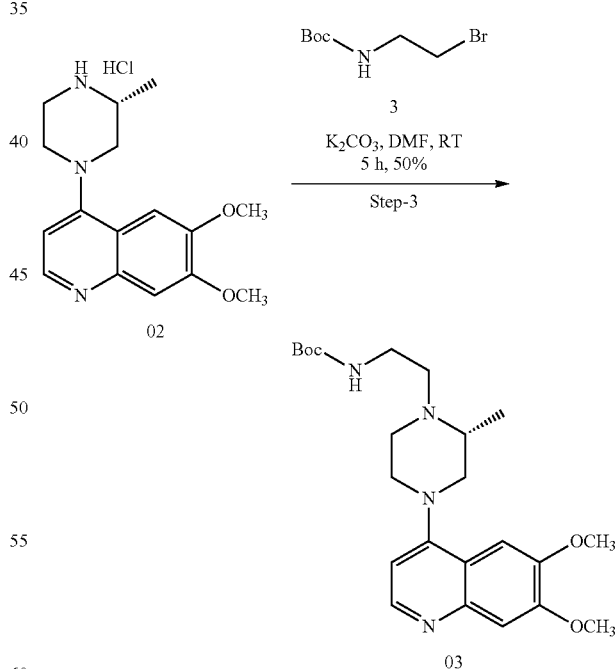

To a stirred solution of (R)-6,7-dimethoxy-4-(3-methylpiperazin-1-yl)quinoline hydro chloride (02) (800 mg, 2.47 mmol, 1 eq) in DMF (8 mL) was added $K_2CO_3$ (1.0 g, 7.43 mmol, 3 eq) followed by the addition of tert-butyl (2-bromoethyl)carbamate (3) (1.1 g, 4.95 mmol, 2 eq). The reaction mixture was stirred at room temperature for 5 h.

After completion of reaction, the reaction mixture was quenched with water and extracted with EtOAc (2×40 mL). The combined organic layers were washed with brine (20 mL), dried over sodium sulfate and concentrated under reduced pressure to afford crude. The crude compound was purified by silica gel (100-200 mesh) chromatography [gradient elution with 0-4% MeOH in DCM] to afford (R)-tert-butyl (2-(4-(6,7-dimethoxyquinolin-4-yl)-2-methylpiperazin-1-yl)ethyl)carbamate (03) (500 mg, yield: 50%) as an off-white solid. TLC system MeOH:DCM (10:90), $R_f$ value: 0.4; LCMS (m/z): 431.4 (M+H)$^+$; $^1$HNMR (400 MHz, CDCl$_3$) δ 8.57 (d, J=4.8 Hz, 1H), 7.40 (s, 1H), 7.28 (s, 1H), 6.79 (d, J=5.2 Hz, 1H), 4.93 (brs, 1H) 4.03 (s, 3H), 4.00 (s, 3H), 3.32-3.19 (m, 4H), 3.17-3.15 (m, 1H), 2.97-2.84 (m, 3H), 2.66-2.61 (m, 1H), 2.47-2.40 (m, 2H), 1.47 (s, 9H), 1.21 (d, J=6 Hz, 3H). Aliphatic protons are not clean as there is traces of compd-3 remained even after purification.

Synthesis of (R)-2-(4-(6,7-dimethoxyquinolin-4-yl)-2-methylpiperazin-1-yl)ethanamine hydro chloride (04)

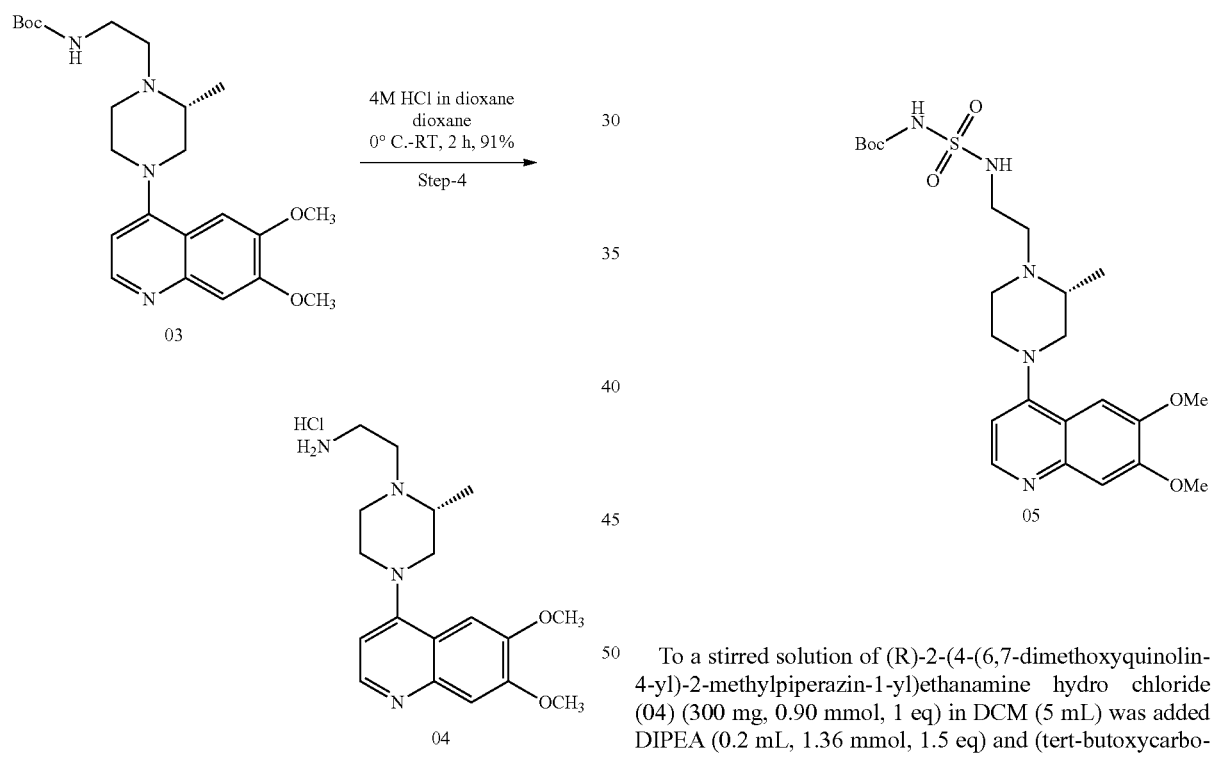

To a stirred solution of (R)-tert-butyl (2-(4-(6,7-dimethoxyquinolin-4-yl)-2-methylpiperazin-1-yl)ethyl)carbamate (03) (500 mg, 1.16 mmol, 1 eq) in 1,4 Dioxane at 0° C. was added 4M Dioxane.HCl (5 mL) and stirred at room temperature for 2 h. After completion of reaction by TLC, volatiles were evaporated and crude was triturated with diethyl ether to afford (R)-2-(4-(6,7-dimethoxyquinolin-4-yl)-2-methylpiperazin-1-yl)ethanamine hydro chloride (04) (350 mg, yield: 91%) as an off-white solid. TLC system MeOH:DCM (10:90), $R_f$ value: 0.1; LCMS (m/z): 331.3 (M+H-HCl)$^+$;

Synthesis of (R)-tert-butyl N-(2-(4-(6,7-dimethoxy-quinolin-4-yl)-2-methylpiperazin-1-yl)ethyl)sulfamoylcarbamate (05)

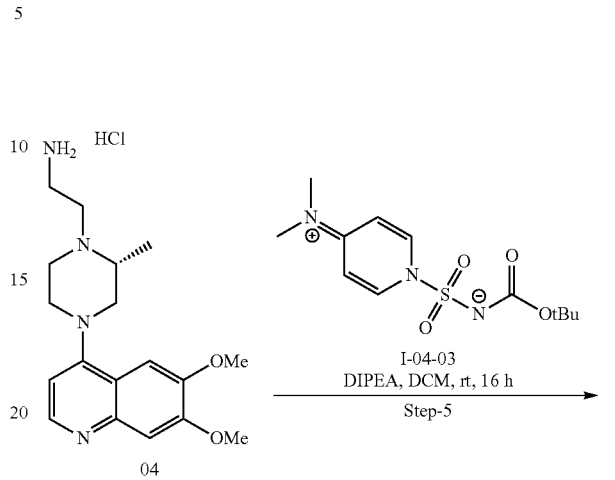

To a stirred solution of (R)-2-(4-(6,7-dimethoxyquinolin-4-yl)-2-methylpiperazin-1-yl)ethanamine hydro chloride (04) (300 mg, 0.90 mmol, 1 eq) in DCM (5 mL) was added DIPEA (0.2 mL, 1.36 mmol, 1.5 eq) and (tert-butoxycarbonyl)((4-(dimethyliminio)pyridin-1(4H)-yl)sulfonyl)amide (I-04-03) (355 mg, 1.18 mmol, 1.3 eq). The reaction mixture was stirred at room temperature for 16 h. After completion of reaction, the reaction mixture was quenched with water and extracted with DCM (2×20 mL). The combined organic layers were washed with brine (10 mL) dried over sodium sulfate and concentrated under reduced pressure to afford crude. The crude compound was purified by reverse phase column [gradient elution with 10-40% water/ACN] to afford (R)-tert-butyl N-(2-(4-(6,7-dimethoxyquinolin-4-yl)-2-methylpiperazin-1-yl)ethyl)sulfamoylcarbamate (05) (108 mg) as off-white solid. TLC system MeOH:DCM (5:95), $R_f$ value: 0.5; LCMS (m/z): 510.3 (M+H)$^+$; 60% purity.

135

Synthesis of (R)—N-(2-(4-(6,7-dimethoxyquinolin-4-yl)-2-methylpiperazin-1-yl)ethyl)aminosulfonamide formate salt (I-21)

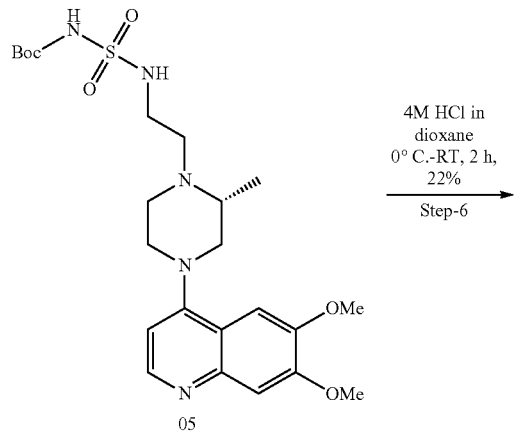

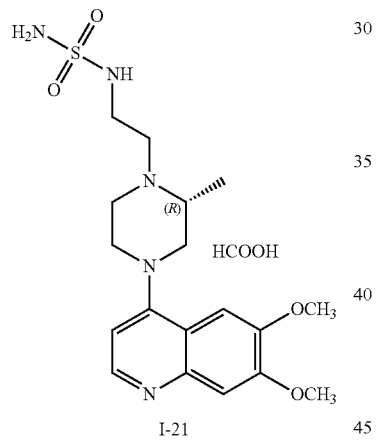

A solution of (R)-tert-butyl N-(2-(4-(6,7-dimethoxyquinolin-4-yl)-2-methylpiperazin-1-yl)ethyl)sulfamoylcarbamate (05) (100 mg, 0.19 mmol, 1 eq) in 4M Dioxane.HCl (3 mL) was stirred from 0° C. to room temperature for 2 h. After completion of reaction by TLC, volatiles were evaporated and given diethyl ether washings. The crude compound was purified by reverse phase column [gradient elution with 0-30% (0.1% FA in H$_2$O)/ACN] to afford (R)—N-(2-(4-(6,7-dimethoxyquinolin-4-yl)-2-methylpiperazin-1-yl)ethyl) aminosulfonamide formate salt (I-21) (20 mg, yield: 22%) as an off-white solid. TLC system MeOH:DCM (10:90), R$_f$ value: 0.1; LCMS (m/z): 410.3 (M+H)$^+$; $^1$HNMR (400 MHz, DMSO-d$_6$) δ 8.50 (d, J=4.8 Hz, 1H), 8.14 (formate salt proton), 7.32 (s, 1H), 7.22 (s, 1H), 6.88-6.87 (m, 1H), 6.58 (brs, 2H), 6.33 (brs, 1H), 3.91 (s, 6H), 3.22-3.19 (m, 2H), 3.09-3.01 (m, 4H), 2.88-2.82 (m, 3H), 2.68-2.66 (m, 1H), 2.57-2.52 (m, 1H), 1.17 (brs, 3H).

136

Synthesis of I-22

Synthesis of ethyl 1-(1-(6,7-dimethoxyquinolin-4-yl) piperidin-4-yl) cyclopropane-1-carboxylate (01)

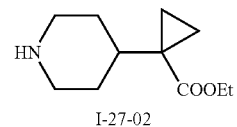

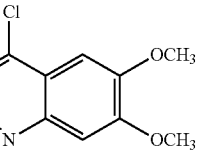

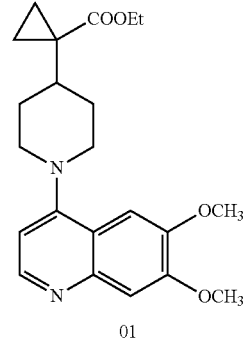

To a stirred solution of 4-chloro-6,7-dimethoxyquinoline (1) (2.5 g, 11.18 mmol, 1 eq) in 1,4 Dioxane (25 mL) were added ethyl 1-(piperidin-4-yl)cyclopropane-1-carboxylate (I-27-02) (2.6 g, 13.41 mmol, 1.2 eq) and Cs$_2$CO$_3$ (18 g, 55.9 mmol, 5 eq). The reaction mixture was degassed for 10 min. Then added Pd$_2$(dba)$_3$ (511 mg, 0.55 mmol, 0.05 eq) and X-phos (798 mg, 1.67 mmol, 0.15 eq) and stirred at 110° C. for 16 h in a sealed tube. After completion of reaction by TLC, the reaction mixture was filtered through Celite pad and concentrated to provide crude. The crude compound was purified by silica gel (100-200 mesh) column chromatography [eluted with EtOAc] to afford ethyl 1-(1-(6,7-dimethoxyquinolin-4-yl) piperidin-4-yl) cyclopropane-1-carboxylate (01) (1.48 g, yield: 80%) as a brown gummy solid. TLC system: EtOAc (100), R$_f$ value: 0.2; LCMS (m/z): 385.3 (M+H)$^+$. 74% purity.

Synthesis of (1-(1-(6,7-dimethoxyquinolin-4-yl) piperidin-4-yl) cyclopropyl) methanol (02)

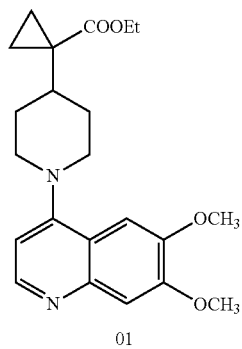

01

LAH (1M THF), THF
-78 C.-0° C., 2 h
─────────────→
Step-2

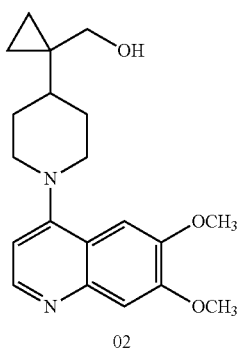

02

To a stirred solution of ethyl 1-(1-(6,7-dimethoxyquinolin-4-yl)piperidin-4-yl)cyclopropane-1-carboxylate (01) (1.4 g, 3.64 mmol, 1 eq) in THF (14 mL) at −78° C. was added LAH (1.0 M in THF) (18.2 mL, 18.21 mmol, 5 eq). The reaction mixture was stirred at 0° C. for 2 h. After completion of reaction by TLC, the reaction mixture was quenched with NH$_4$Cl and extracted with EtOAc (2×50 mL). The combined organic layers were washed with brine (30 mL), dried over sodium sulfate and concentrated under reduced pressure to afford (1-(1-(6,7-dimethoxyquinolin-4-yl) piperidin-4-yl) cyclopropyl) methanol (02) (1.2 g) as a black solid. TLC system MeOH:DCM (10:90), R$_f$ value: 0.3; LCMS (m/z): 343.3 (M+H)$^+$; 44% purity.

Synthesis of 4-(4-(1-(azidomethyl) cyclopropyl) piperidin-1-yl)-6,7-dimethoxyquinoline (03)

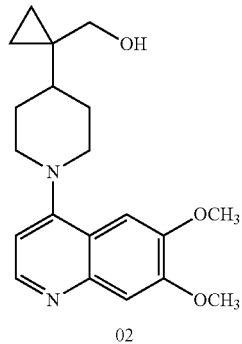

02

DPPA, DBU,
THF, rt, 48 h
─────────────→
Step-3

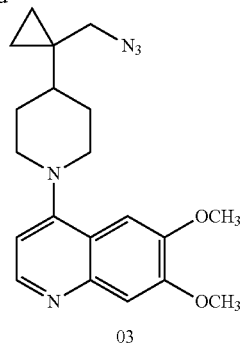

03

To a stirred solution of (1-(1-(6,7-dimethoxyquinolin-4-yl)piperidin-4-yl)cyclopropyl)methanol (02) (1.2 g, 44% purity, 3.50 mmol, 1 eq) in THF (12 mL) was added DBU (2.6 mL, 17.51 mmol, 5 eq), diphenyl phosphoryl azide (3.0 mL, 14.03 mmol, 4 eq). The reaction mixture was stirred at room temperature for 48 h. After completion of reaction, the reaction mixture was quenched with aq. NaHCO$_3$ solution and extracted with EtOAc (2×70 mL). The combined organic layers were washed with brine (30 mL), dried over sodium sulfate and concentrated under reduced pressure to afford crude. The crude was purified by silica gel column chromatography [eluted with 3% MeOH in DCM)] to afford 4-(4-(1-(azidomethyl) cyclopropyl) piperidin-1-yl)-6,7-dimethoxyquinoline (03) (400 mg) as colorless gummy solid. TLC system MeOH:DCM (10:90), R$_f$ value: 0.7; LCMS (m/z): 368.3 (M+H)$^+$; 56% purity.

Synthesis of (1-(1-(6,7-dimethoxyquinolin-4-yl) piperidin-4-yl) cyclopropyl) methanamine (04)

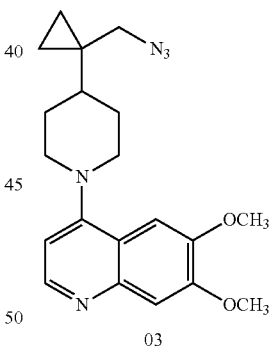

03

10% Pd/C, MeOH
H$_2$ balloon pressure,
rt, 16 h, 16% in
3 steps
─────────────→
Step-4

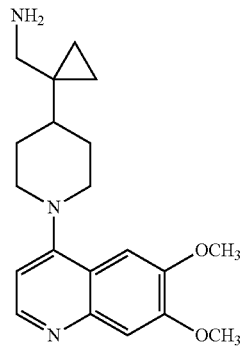

04

To a stirred solution of 4-(4-(1-(azidomethyl)cyclopropyl) piperidin-1-yl)-6,7-dimethoxyquinoline (03) (400 mg, 56% purity, 1.08 mmol, 1 eq) in MeOH (8 mL) was added 10% Pd/C (160 mg) The reaction mixture was stirred at room temperature for 16 h under $H_2$ balloon pressure. After completion of reaction by TLC, the reaction mixture was filtered through Celite pad and filtrate was concentrated under reduced pressure to afford (1-(1-(6,7-dimethoxyquinolin-4-yl) piperidin-4-yl) cyclopropyl) methanamine (04) (200 mg, yield: 16% over three steps) as a gummy liquid. TLC system MeOH:DCM (10:90), $R_{f\ value}$: 0.1; LCMS (m/z): 342.3 $(M+H)^+$.

Synthesis of tert-butyl (N-((1-(1-(6,7-dimethoxyquinolin-4-yl) piperidin-4-yl) cyclopropyl) methyl) sulfamoyl) carbamate (05)

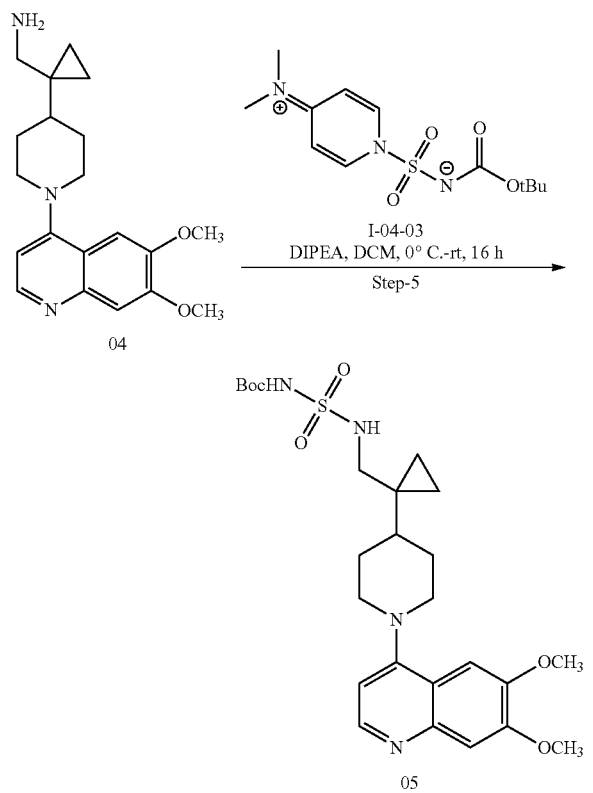

To a stirred solution of (1-(1-(6,7-dimethoxyquinolin-4-yl)piperidin-4-yl)cyclopropyl)methanamine (04) (200 mg, 0.58 mmol, 1 eq) in DCM (2 mL) at 0° C. was added DIPEA (0.15 mL, 0.87 mmol, 1.5 eq) and (tert-butoxycarbonyl)((4-(dimethyliminio)pyridin-1(4H)-yl)sulfonyl)amide (I-04-03) (208 g, 0.69 mmol, 1.2 eq). The reaction mixture was stirred at room temperature for 16 h. After completion of reaction by TLC, reaction mixture was quenched with water and extracted with DCM (2×30 mL). The combined organic layers were washed with brine (10 mL), dried over sodium sulfate and concentrated under reduced pressure to get crude compound. The crude compound was purified by silica gel (100-200 mesh) column chromatography [eluted with 3% MeOH in DCM) to afford tert-butyl (N-((1-(1-(6,7-dimethoxyquinolin-4-yl) piperidin-4-yl) cyclopropyl) methyl) sulfamoyl) carbamate (05) (180 mg). TLC system MeOH: DCM (10:90), $R_f$ value: 0.6; LCMS (m/z): 521.4 $(M+H)^+$; 57% purity.

Synthesis of N—(N-((1-(1-(6,7-dimethoxyquinolin-4-yl)piperidin-4-yl)cyclopropyl)methyl)sulfamoyl) acetamide format salt (I-22)

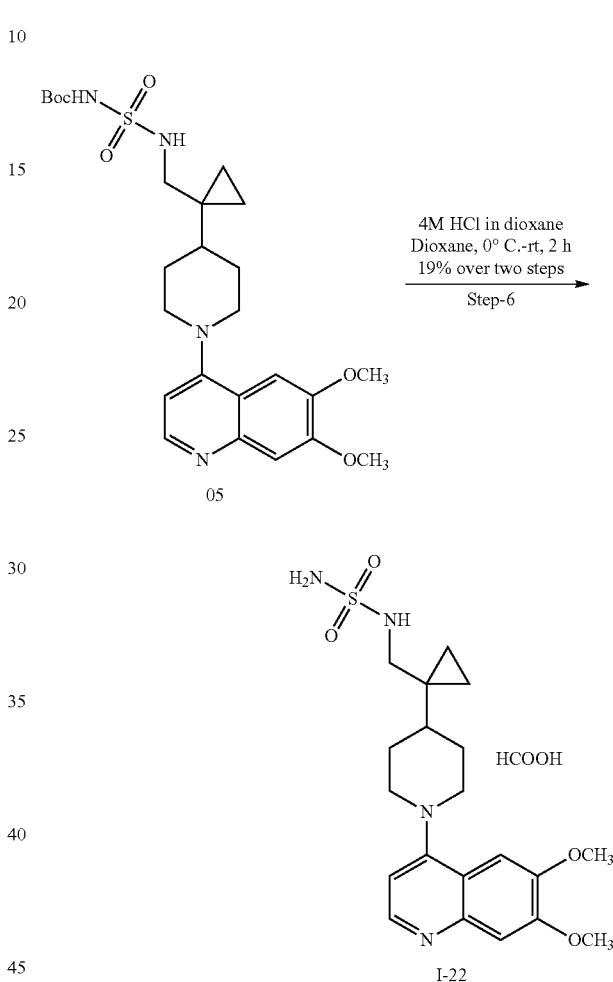

To a stirred solution of tert-butyl (N-((1-(1-(6,7-dimethoxyquinolin-4-yl)piperidin-4-yl)cyclopropyl)methyl)sulfamoyl)carbamate (05) (180 mg, 57% purity; 0.34 mmol, 1 eq) in 1,4 Dioxane (0.5 mL) at 0° C. was added 4M HCl in Dioxane (2 mL). The reaction mixture was stirred at room temperature for 2 h. After completion of reaction by TLC, volatiles were evaporated, the crude compound was purified by reverse phase column chromatography [gradient elution with 1-16% (0.1% FA in water+ACN) to afford N—(N-((1-(1-(6,7-dimethoxyquinolin-4-yl)piperidin-4-yl)cyclopropyl) methyl)sulfamoyl) acetamide format salt (I-22) (45 mg, yield: 19% over two steps) as a white solid. TLC system MeOH:DCM (10:90), $R_f$ value: 0.3; LCMS (m/z): 421.3 $(M+H)^+$; $^1$HNMR (400 MHz, DMSO-$d_6$) δ 8.47 (d, J=4.8 Hz, 1H), 8.19 (format salt proton), 7.29 (s, 1H), 7.18 (s, 1H), 6.83 (d, J=5.2 Hz, 1H), 6.48-6.45 (m, 3H), 3.90 (s, 6H), 3.54-3.41 (m, 2H), 2.89 (d, J=6.4 Hz, 2H), 2.68 (t, J=11.2 Hz, 2H), 1.77-1.74 (m, 2H), 1.64-1.56 (m, 2H), 1.52-1.49 (m, 1H), 0.41 (s, 4H).

Synthesis of I-23

Synthesis of tert-butyl (1-(6,7-dimethoxyquinolin-4-yl) piperidin-4-yl) carbamate (01)

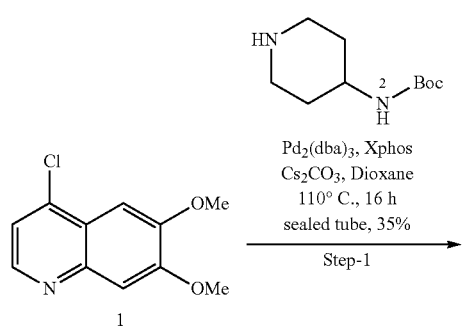

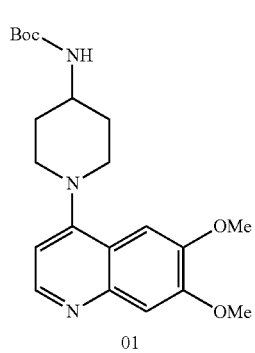

To a stirred solution of 4-chloro-6,7-dimethoxyquinoline (1) (1 g, 4.49 mmol, 1 eq) in 1,4 Dioxane (10 mL) was added tert-butyl piperidin-4-ylcarbamate (2) (1.07 g, 5.38 mmol, 1.2 eq) and degassed for 10 mins. Then added $Cs_2CO_3$ (4.37 g, 13.4 mmol, 3 eq), $Pd_2(dba)_3$ (0.41 g, 0.449 mmol, 0.1 eq), X-Phos (0.44 g, 0.89 mmol, 0.2 eq). The reaction mixture was stirred at 110° C. for 16 h in a sealed tube. After completion of reaction by TLC, the reaction mixture was filtered through Celite pad and filtrate was concentrated to afford crude. The crude compound was purified by silica gel (100-200) column chromatography [eluted with 3% MeOH in DCM] to afford tert-butyl (1-(6,7-dimethoxyquinolin-4-yl) piperidin-4-yl) carbamate (01) (0.6 g, yield: 35%) as yellow solid. TLC system MeOH:DCM (10:90), $R_f$ value: 0.3; LCMS (m/z): 388.3 (M+H)$^+$. $^1$HNMR (400 MHz, DMSO-$d_6$) δ 8.48 (d, J=5.2 Hz, 1H), 7.36 (s, 1H), 7.14 (s, 1H), 6.94-6.93 (m, 1H), 6.72 (d, J=5.2 Hz, 1H), 3.90 (s, 6H), 3.46-3.43 (m, 2H), 2.87-2.80 (m, 2H), 2.38-2.32 (m, 1H), 1.96-1.93 (m, 2H), 1.74-1.71 (m, 2H), 1.40 (s, 9H).

Synthesis of 1-(6,7-dimethoxyquinolin-4-yl)piperidin-4-amine.HCl (02)

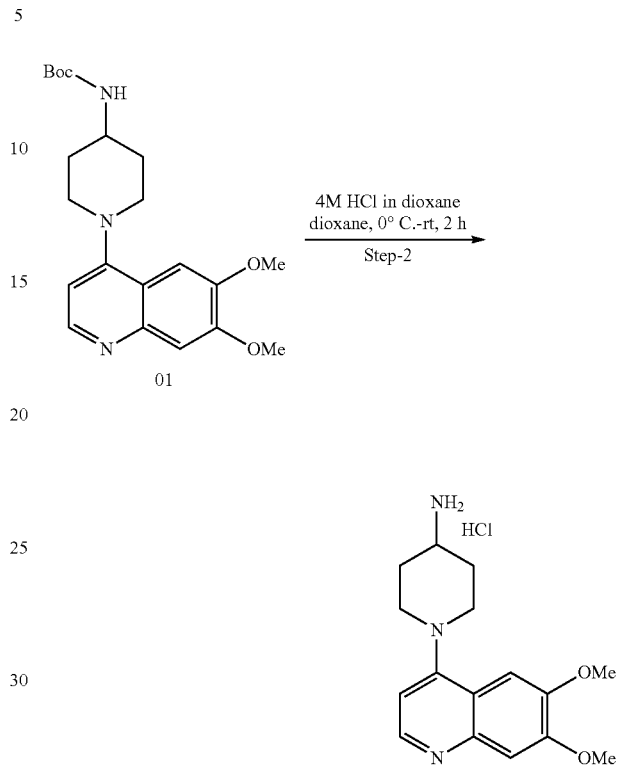

To a solution of tert-butyl (1-(6,7-dimethoxyquinolin-4-yl) piperidin-4-yl) carbamate (01) (600 mg, 0.645 mmol, 1 eq) in 1,4 Dioxane (2 mL) at 0° C. was added 4M HCl in dioxane (6 mL) and stirred at room temperature for 2 h. After completion of reaction by TLC, volatiles were evaporated and the obtained crude was purified by trituration's with diethyl ether to afford 1-(6,7-dimethoxyquinolin-4-yl)piperidin-4-amine hydrogen chloride (02) (400 mg) as white solid. TLC system MeOH:DCM (10:90), $R_f$ value: 0.1; LCMS (m/z): 288.2 (M+H)$^+$; 63% purity.

Synthesis of tert-butyl (N-(1-(6,7-dimethoxyquinolin-4-yl)piperidin-4-yl)sulfamoyl)carbamate (03)

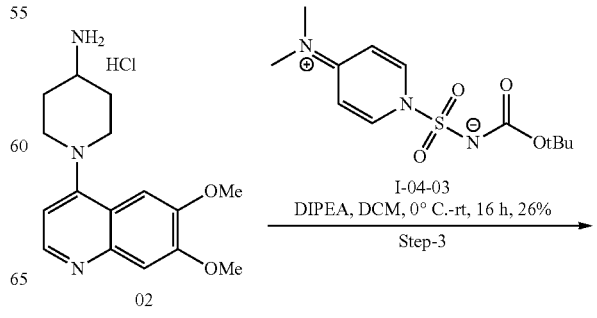

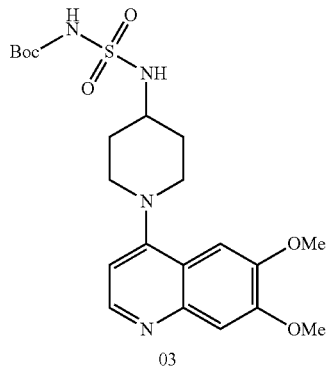

03

To a stirred solution of 1-(6,7-dimethoxyquinolin-4-yl) piperidin-4-amine hydrogen chloride (02) (400 mg, 1.23 mmol, 1.0 eq) in DCM (10 mL) at 0° C. was added DIPEA (0.34 mL, 1.84 mmol, 1.5 eq) and (tert-butoxycarbonyl)((4-(dimethyliminio)pyridin-1(4H)-yl)sulfonyl)amide (I-04-03) (444 mg, 1.47 mmol, 1.2 eq). The reaction mixture was stirred at room temperature for 16 h. After completion of reaction by TLC, the reaction mixture was diluted with water and extracted with DCM (2×25 mL). The combined organic layers were washed with brine (10 mL), dried over sodium sulfate and concentrated under reduced pressure to afford crude. The crude compound was purified by reverse phase grace purification [gradient elution with 0-50% of (0.05% FA in H₂O)/ACN] to afford tert-butyl (N-(1-(6,7-dimethoxyquinolin-4-yl)piperidin-4-yl)sulfamoyl)carbamate (03) (150 mg, yield: 26%) as an yellow solid. TLC system MeOH:DCM (10:90), R$_f$ value: 0.4; LCMS (m/z): 467.3 (M+H)⁺.

Synthesis of N—(N-(1-(6,7-dimethoxyquinolin-4-yl)piperidin-4-yl)sulfuricdiamide formate salt (I-23)

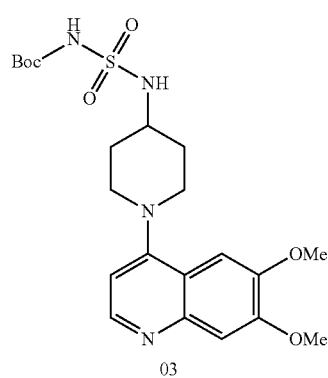

03

4M HCl in dioxane
dioxane
0° C.-rt, 2 h, 42%
Step-4

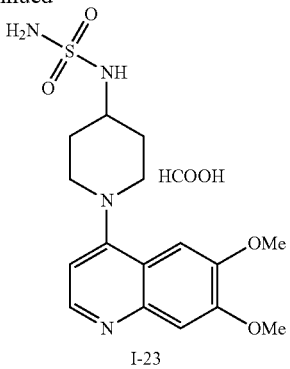

I-23

To a solution of tert-butyl (N-(1-(6,7-dimethoxyquinolin-4-yl)piperidin-4-yl)sulfamoyl)carbamate (03) (150 mg, 0.32 mmol, 1 eq) in 1,4 Dioxane (1 mL) at 0° C. was added 4M Dioxane in HCl (2 mL) and stirred at room temperature for 2 h. After completion of reaction by TLC, volatiles were evaporated and the obtained crude compound was purified by reverse phase grace column [with a gradient elution of 10-50% of (0.01% FA in H₂O)/ACN] to afford N—(N-(1-(6,7-dimethoxyquinolin-4-yl)piperidin-4-yl)sulfuricdiamide formate salt (I-23) (49 mg, yield: 42%) as white solid. TLC system MeOH:DCM (10:90), R$_f$ value: 0.2; LCMS (m/z): 367.2 (M+H)⁺, ¹HNMR (400 MHz, DMSO-d₆) δ 8.49 (d, J=5.2 Hz, 1H), 8.14 (formate salt proton), 7.33 (s, 1H), 7.15 (s, 1H), 6.91 (d, J=5.2 Hz, 1H), 6.70 (d, J=7.2 Hz, 1H), 6.57 (s, 2H), 3.92 (s, 6H), 3.55-3.52 (m, 2H), 3.36-3.31 (m, 1H), 2.96-2.92 (m, 2H), 2.12-2.09 (m, 2H), 1.79-1.72 (m, 2H).

Synthesis of I-24

Synthesis of 8-(6,7-dimethoxyquinolin-4-yl)-1,4-dioxa-8-azaspiro [4.5] decane (01)

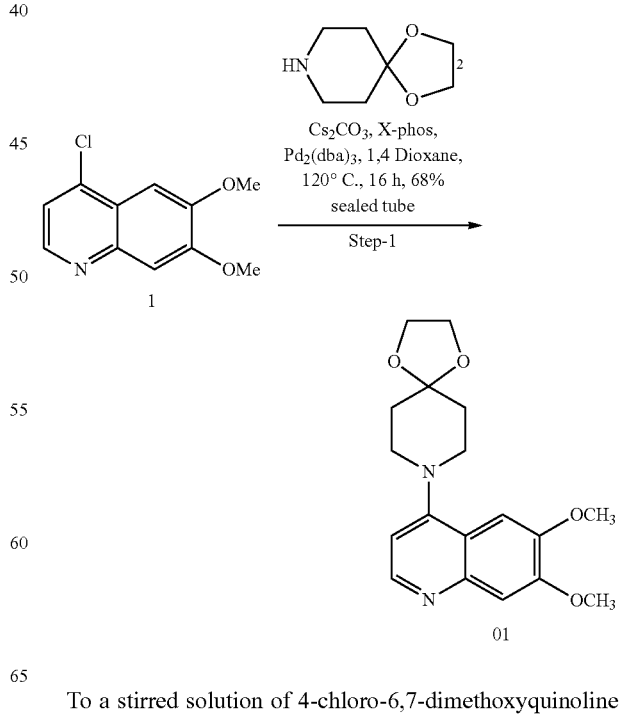

To a stirred solution of 4-chloro-6,7-dimethoxyquinoline (1) (2 g, 8.92 mmol, 1 eq) in 1,4 Dioxane (20 mL) was added 1,4-dioxa-8-azaspiro[4.5]decane (2) (1.5 g, 10.7 mmol, 1.2 eq), Cs$_2$CO$_3$ (8.7 g, 26.7 mmol, 3 eq) and degassed for 10 mins. Later, added X-Phos (850 mg, 1.78 mmol, 0.2 eq), Pd$_2$(dba)$_3$ (816 mg, 0.89 mmol, 0.1 eq). The resulting mixture was stirred at 120° C. for 16 h in a sealed tube. After completion of reaction by TLC, the reaction mixture was filtered through Celite pad, washed with ethyl acetate and concentrated to provide crude. The crude compound was purified by silica gel (100-200 mesh) column chromatography [eluted with 5% MeOH in DCM] to afford 8-(6,7-dimethoxyquinolin-4-yl)-1,4-dioxa-8-azaspiro [4.5] decane (01) (2 g, yield: 68%) as a brown color solid. TLC system: MeOH:DCM (10:90), R$_f$ value: 0.3; LCMS (m/z): 331.3 (M+H)$^+$; $^1$HNMR (400 MHz, CDCl$_3$) δ 8.55 (d, J=5.2 Hz, 1H), 7.43 (s, 1H), 7.24 (s, 1H), 6.81 (d, J=5.2 Hz, 1H), 4.04-4.01 (m, 4H), 3.99 (s, 3H), 3.98 (s, 3H), 3.31 (t, J=5.2 Hz, 4H), 2.01 (t, J=5.6 Hz, 4H).

Synthesis of 1-(6,7-dimethoxyquinolin-4-yl) piperidin-4-one (02)

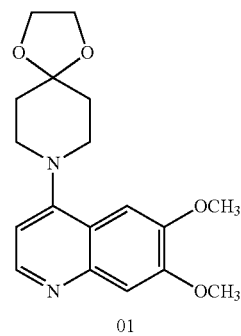

Methanol, 3N aq HCl,
70° C., 16 h, 70%
Step-2

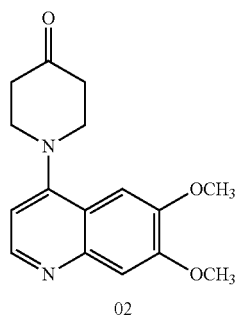

To a stirred solution of 8-(6,7-dimethoxyquinolin-4-yl)-1,4-dioxa-8-azaspiro [4.5]decane (01) (2 g, 6.06 mmol, 1 eq) in methanol (20 mL) was added 3N aq.HCl (10 mL). The reaction mixture was stirred at 70° C. for 16 h. After completion of reaction by TLC, reaction mixture was basified with saturated aq. NaHCO$_3$ solution and extracted with EtOAc (3×60 mL). The combined organic layer was washed with brine (50 mL), dried over sodium sulfate and concentrated to afford crude. The crude compound was purified by silica gel (100-200 mesh) column chromatography [eluted with 5% MeOH in DCM] to afford 1-(6,7-dimethoxyquinolin-4-yl) piperidin-4-one (02) (1.2 g, yield: 70%) as a yellow color solid. TLC system MeOH:DCM (10:90), R$_f$ value: 0.5; LCMS (m/z): 287.3 (M+H)$^+$; $^1$HNMR (400 MHz, DMSO-de) δ 8.51 (d, J=4.8 Hz, 1H), 7.34 (s, 1H), 7.29 (s, 1H), 6.93 (d, J=4.8 Hz, 1H), 3.94 (s, 3H), 3.91 (s, 3H), 3.46 (t, J=6.0 Hz, 4H), 2.0 (t, J=6.0 Hz, 4H).

Synthesis of N-cyclopropyl-1-(6,7-dimethoxyquinolin-4-yl) piperidin-4-amine (03)

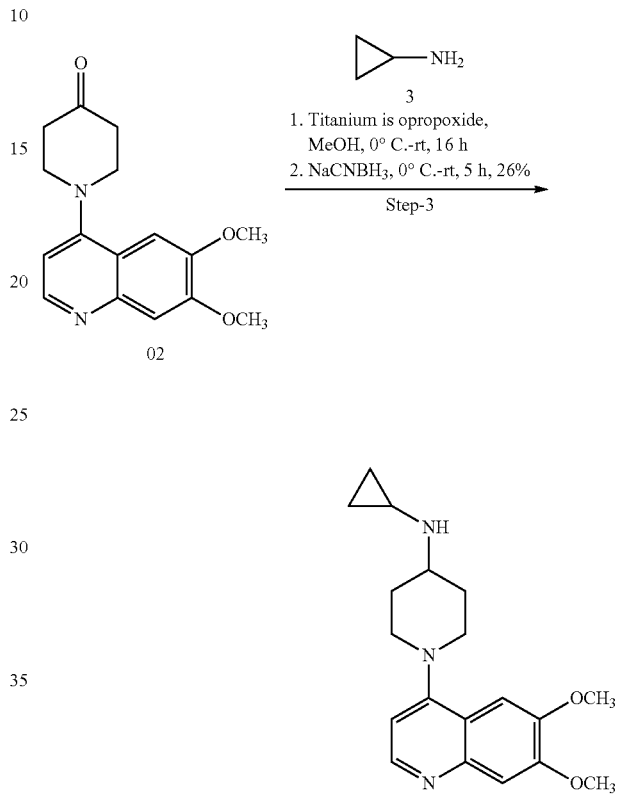

To a stirred solution of 1-(6,7-dimethoxyquinolin-4-yl) piperidin-4-one (02) (1.2 g, 4.19 mmol, 1 eq) in methanol (12 mL) at 0° C. was added cyclopropyl amine (3) (0.4 mL, 6.29 mmol, 1.5 eq) and titaniumisopropoxide (2.5 mL, 8.39 mmol, 2 eq). The reaction mixture was stirred at room temperature for 16 h. After 16 h, at 0° C. was added sodium cyanoborohydride (394 mg, 6.29 mmol, 1.5 eq) and continued stirring at room temperature for 5 h. After completion of reaction by TLC, reaction mixture was diluted with ice cold water and extracted with EtOAc (2×100 mL). The combined organic layer was washed with brine (80 mL), dried over sodium sulfate and concentrated to afford crude. The crude compound was purified by silica gel (100-200 mesh) column chromatography [eluted with 8% MeOH in DCM] to afford N-cyclopropyl-1-(6,7-dimethoxyquinolin-4-yl)piperidin-4-amine (03) (350 mg, yield: 26%) as pale yellow gummy material. TLC system MeOH:DCM (10:90), R$_f$ value: 0.3; LCMS (m/z): 328.3 (M+H)$^+$; $^1$HNMR (400 MHz, DMSO-d$_6$) δ 8.47 (d, J=4.8 Hz, 1H), 7.29 (s, 1H), 7.16 (s, 1H), 6.85 (d, J=5.2 Hz, 1H), 3.90 (s, 6H), 3.46-3.43 (m, 2H), 2.84-2.74 (m, 3H), 2.17-2.15 (m, 1H), 2.07-2.04 (m, 2H), 1.65-1.56 (m, 2H), 0.43-0.39 (m, 2H), 0.27-0.24 (m, 2H). NH proton was not clearly evident in the spectrum.

147

Synthesis of tert-butyl (N-cyclopropyl-N-(1-(6,7-dimethoxyquinolin-4-yl)piperidin-4-yl)sulfamoyl) carbamate (04)

148

Synthesis of N—(N-cyclopropyl-N-(1-(6,7-dimethoxyquinolin-4-yl)piperidin-4-yl)sulfuricdiamide formate salt (I-24)

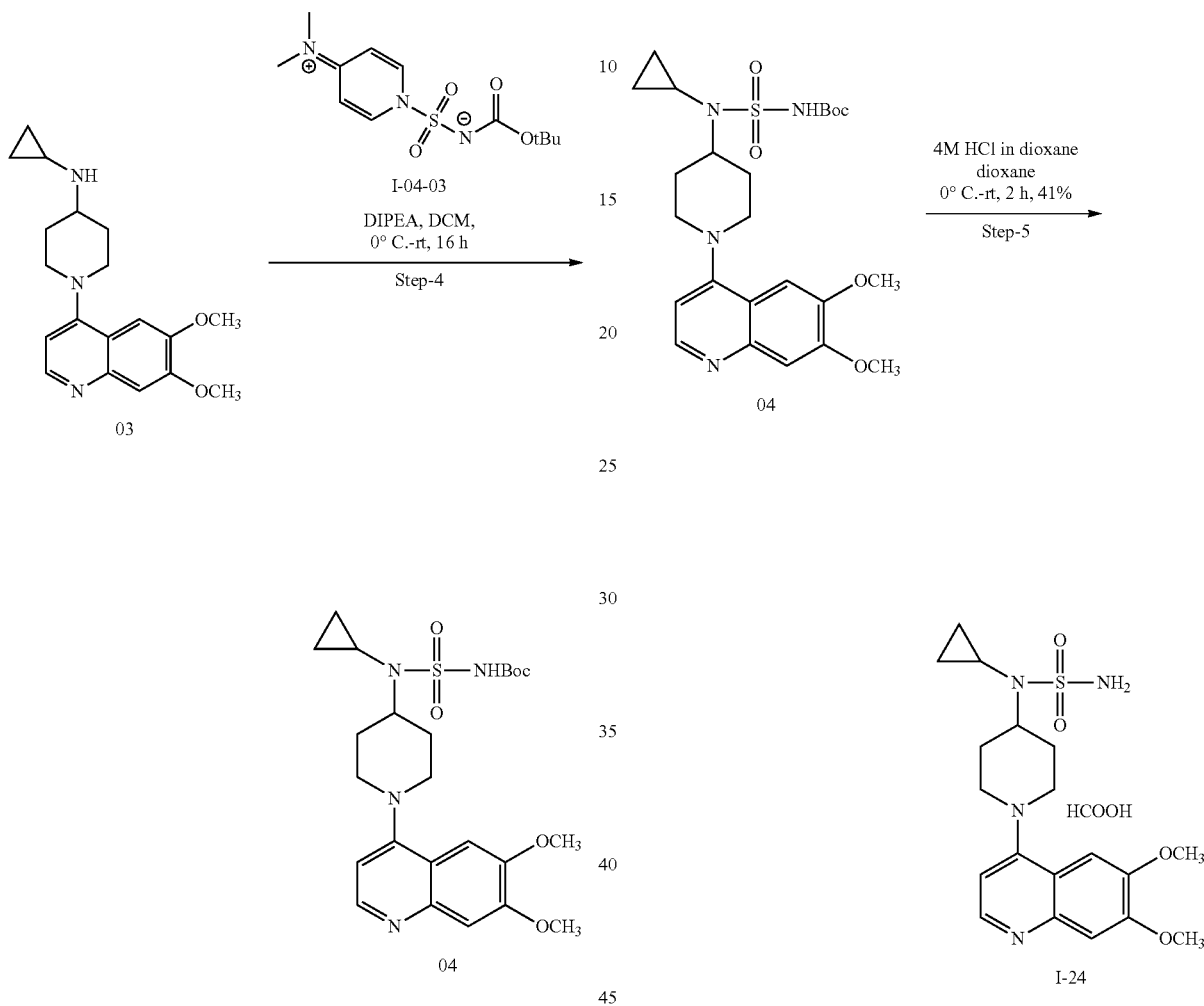

To a stirred solution of N-cyclopropyl-1-(6,7-dimethoxyquinazolin-4-yl)piperidin-4-amine (03) (350 mg, 1.07 mmol, 1.0 eq) in DCM (5 mL) at 0° C. was added DIPEA (0.2 mL, 1.60 mmol, 1.5 eq) and (tert-butoxycarbonyl)((4-(dimethyliminio)pyridin-1(4H)-yl)sulfonyl)amide (I-04-03) (386 mg, 1.28 mmol, 1.2 eq). The reaction mixture was stirred at room temperature for 16 h. After completion of reaction, the reaction mixture was diluted with water and extracted with DCM (2×30 mL). The combined organic layers were washed with brine (20 mL), dried over sodium sulfate and concentrated under reduced pressure to afford crude. The crude compound was purified by silica gel (100-200 mesh) column chromatography [eluted with 5% MeOH in DCM] to afford tert-butyl (N-cyclopropyl-N-(1-(6,7-dimethoxyquinolin-4-yl)piperidin-4-yl)sulfamoyl)carbamate (04) (200 mg) as an off white solid. TLC system MeOH:DCM (5:95), $R_f$ value: 0.5; LCMS (m/z): 507.3 (M+H)$^+$.

To a stirred solution of tert-butyl (N-cyclopropyl-N-(1-(6,7-dimethoxyquinolin-4-yl) piperidin-4-yl) sulfamoyl) carbamate (04) (200 mg, 0.39 mmol, 1 eq) in 1,4 Dioxane at 0° C. was added 4M Dioxane.HCl (2 mL) drop-wise. The reaction mixture was stirred at room temperature for 2 h. After completion of reaction by TLC, reaction mixture was evaporated under reduced pressure to afford crude. The crude was purified by prep-HPLC to afford N—(N-cyclopropyl-N-(1-(6,7-dimethoxyquinolin-4-yl)piperidin-4-yl) sulfuricdiamide formate salt (I-24) (55 mg, yield: 41%) as an off-white solid. TLC system MeOH:DCM (10:90), $R_f$ value: 0.1; LCMS (m/z): 407.2 (M+H)$^+$; $^1$HNMR (400 MHz, DMSO-d$_6$) δ 8.53 (brs, 1H), 8.15 (formate salt proton), 7.33 (br, 1H), 7.19 (br, 1H), 6.95 (br, 1H), 6.90 (s, 2H), 3.94 (s, 3H), 3.92 (s, 3H), 3.85-3.79 (m, 1H), 3.71-3.68 (m, 2H), 2.91 (t, J=12 Hz, 2H), 2.35-2.34 (m, 1H), 2.23-2.15 (m, 2H), 2.00-1.97 (m, 2H), 0.81-0.74 (m, 4H).

Synthesis of I-25

Synthesis of 2-(1-(6,7-dimethoxyquinolin-4-yl)piperidin-4-yl)butanenitrile (01)

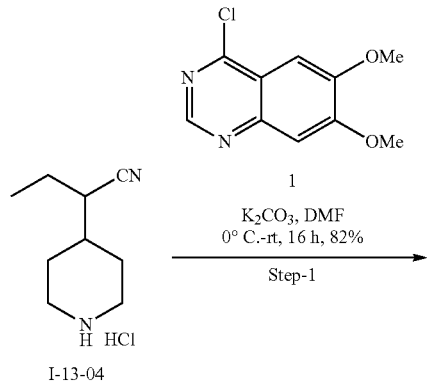

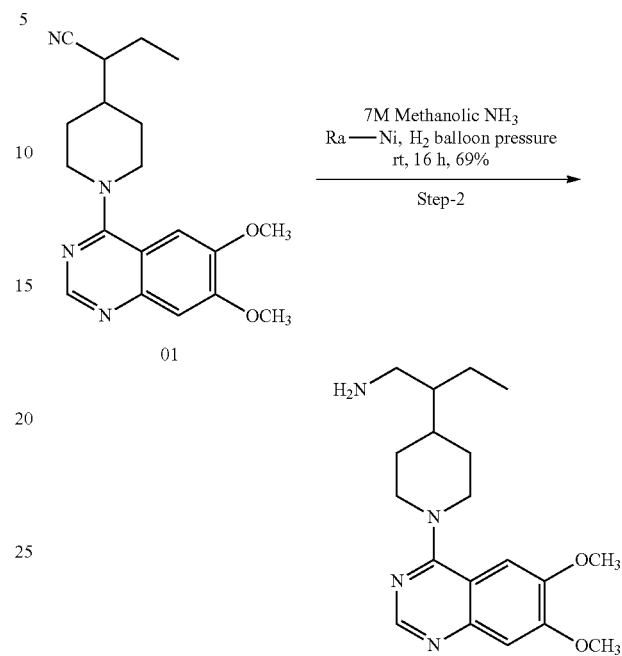

Synthesis of 2-(1-(6,7-dimethoxyquinazolin-4-yl)piperidin-4-yl)butan-1-amine (02)

To a stirred solution of 4-chloro-6,7-dimethoxyquinazoline (1) (400 mg, 1.78 mmol, 1.0 eq) in DMF (4 mL) at 0° C. was added $K_2CO_3$ (0.98 g, 7.14 mmol, 4 eq) and 2-(piperidin-4-yl)butanenitrile hydrogen chloride (I-13-04) (402 mg, 2.14 mmol, 1.2 eq). The reaction mixture was stirred at room temperature for 16 h. After completion of reaction by TLC, the reaction mixture was quenched with ice water and extracted with EtOAc (2×50 mL). The combined organic layers were washed with brine (50 mL) dried over sodium sulfate and concentrated under reduced pressure to afford crude. The crude compound was purified by silica gel column chromatography [eluted at 53% EtOAc in hexane] to afford 2-(1-(6,7-dimethoxyquinazolin-4-yl)piperidin-4-yl)butanenitrile (01) (500 mg, yield: 82%) as a colorless liquid. TLC system 80% EtOAc:Hexane (80:20), $R_f$ value: 0.5; LCMS (m/z): 341.3 (M+H)$^+$; $^1$HNMR (400 MHz, CDCl$_3$) δ 8.67 (s, 1H), 7.25 (s, 1H), 7.09 (s, 1H), 4.25-4.19 (m, 2H), 4.03 (s, 3H), 4.00 (s, 3H), 3.07-3.00 (m, 2H), 2.50-2.48 (m, 1H), 2.05-2.04 (m, 1H), 1.89-1.82 (m, 2H), 1.77-1.68 (m, 4H), 1.15 (t, J=7.2 Hz, 3H).

To a stirred solution of 2-(1-(6,7-dimethoxyquinazolin-4-yl)piperidin-4-yl)butanenitrile (01) (500 mg, 1.64 mmol, 1 eq) in 7M Methanolic.NH$_3$ (10 mL) was added Raney-Ni (1.0 g). The reaction mixture was stirred at room temperature for 16 h under H$_2$ balloon pressure. After completion of reaction by TLC, reaction mixture was filtered through Celite pad and concentrated to afford 2-(1-(6,7-dimethoxyquinazolin-4-yl)piperidin-4-yl)butan-1-amine (02) (350 mg, yield: 69%) as an off-white solid. TLC system MeOH:DCM (10:90), $R_f$ value: 0.1; LCMS (m/z): 345.4 (M+H)$^+$; $^1$HNMR (400 MHz, DMSO-d$_6$) δ 8.52 (s, 1H), 8.01-7.95 (br, 2H), 7.20 (s, 1H), 7.11 (s, 1H), 4.23-4.20 (m, 2H), 3.93 (s, 3H), 3.91 (s, 3H), 3.05-2.99 (m, 2H), 2.88-2.83 (m, 1H), 2.74-2.73 (m, 1H), 1.76-1.68 (m, 3H), 1.53-1.44 (m, 4H), 1.35-1.33 (m, 1H), 0.89 (d, J=7.2 Hz, 3H).

Synthesis of tert-butyl (N-(2-(1-(6,7-dimethoxyquinazolin-4-yl)piperidin-4-yl)butyl)sulfamoyl)carbamate (03)

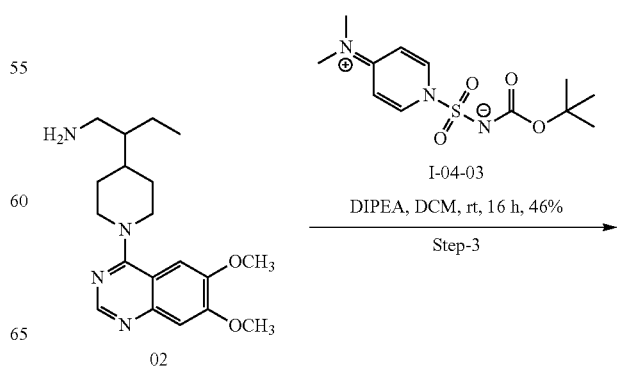

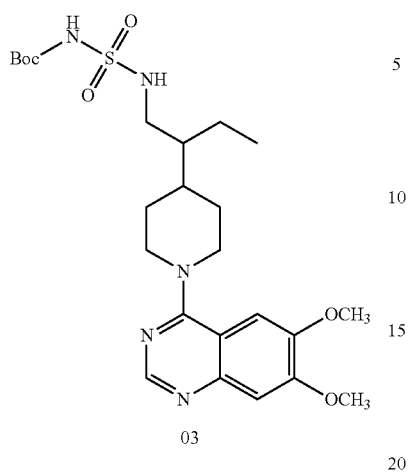

03

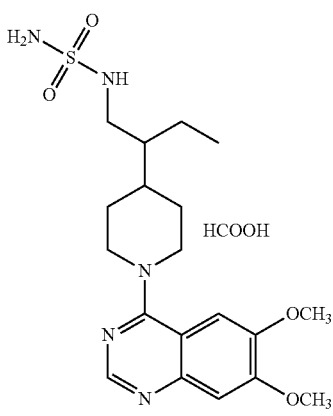

I-25

To a stirred solution of 2-(1-(6,7-dimethoxyquinazolin-4-yl)piperidin-4-yl)butan-1-amine (02) (350 mg, 1.02 mmol, 1 eq) in DCM (7 mL) was added DIPEA (0.26 mL, 1.53 mmol, 1.5 eq), (tert-butoxycarbonyl)((4-(dimethyliminio)pyridin-1(4H)-yl)sulfonyl)amide (I-04-03) (367 mg, 1.22 mmol, 1.2 eq). The reaction mixture was stirred at room temperature for 16 h. After completion of reaction, the reaction mixture was quenched with water and extracted with DCM (2×30 mL). The combined organic layers were washed with brine (30 mL), dried over sodium sulfate and concentrated under reduced pressure to afford crude. The crude compound was purified by silica gel (100-200 mesh) column chromatography [eluded with 3% MeOH in DCM] to afford tert-butyl (N-(2-(1-(6,7-dimethoxyquinazolin-4-yl)piperidin-4-yl)butyl)sulfamoyl)carbamate (03) (250 mg, yield: 46%) as off-white solid. TLC system MeOH:DCM (10:90), $R_f$ value: 0.4; LCMS (m/z): 524.4 (M+H)$^+$.

Synthesis of N—(N-(2-(1-(6,7-dimethoxyquinazolin-4-yl)piperidin-4-yl)butyl)sulfuricdiamide formate salt (I-25)

A solution of tert-butyl (N-(2-(1-(7-methoxyquinazolin-4-yl)piperidin-4-yl)butyl)sulfamoyl)carbamate (03) (250 mg, 0.48 mmol, 1 eq) in 4M HCl in Dioxane (2.5 mL) at 0° C. was stirred for 15 min later at room temperature for 2 h. After completion of reaction by TLC, volatiles were evaporated and rude compound was purified by reverse phase column chromatography [eluting with 23% (0.1% FA in water+ACN)] to afford N—(N-(2-(1-(6,7-dimethoxyquinazolin-4-yl)piperidin-4-yl)butyl)sulfuricdiamide formate salt (I-25) (30 mg, yield: 27%) as an off-white solid. TLC system MeOH:DCM (10:90), $R_f$ value: 0.3; LCMS (m/z): 424.3 (M+H)$^+$; $^1$HNMR (400 MHz, DMSO-d$_6$) δ 8.51 (s, 1H), 8.16 (formate salt proton), 7.19 (s, 1H), 7.12 (s, 1H), 6.46 (s, 2H), 6.38 (t, J=6.4 Hz, 1H), 4.22-4.19 (m, 2H), 3.92 (s, 3H), 3.90 (s, 3H), 3.02-2.93 (m, 2H), 2.90-2.82 (m, 2H), 1.74-1.71 (m, 3H), 1.49-1.27 (m, 5H), 0.88 (t, J=7.2 Hz, 3H).

Synthesis of I-26

Synthesis of 2-(1-(6,7-dimethoxyquinazolin-4-yl)piperidin-4-yl)-2-methylpropanenitrile (01)

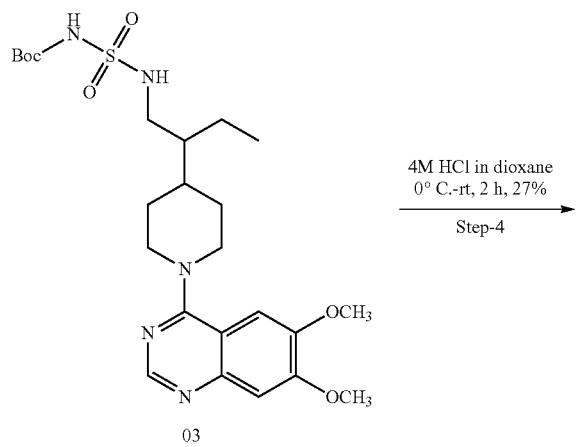

03

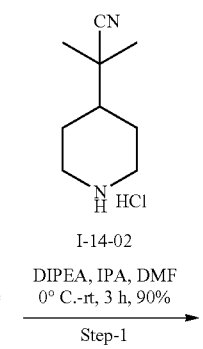

I-14-02

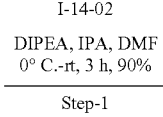

1

4M HCl in dioxane
0° C.-rt, 2 h, 27%
Step-4

DIPEA, IPA, DMF
0° C.-rt, 3 h, 90%
Step-1

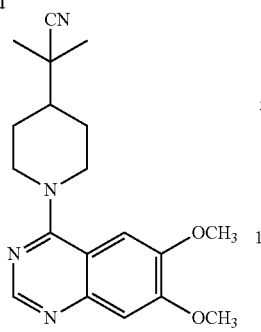

To a stirred solution of 4-chloro-6,7-dimethoxyquinazoline (1) (300 mg, 1.33 mmol, 1 eq) in IPA (3 mL) at 0° C. was added DIPEA (0.6 mL, 3.34 mmol, 2.5 eq), 2-methyl-2-(piperidin-4-yl)propanenitrile HCl (I-14-02) (247 mg, 1.60 mmol, 1.2 eq) and catalytic amount of DMF. The reaction mixture was stirred at room temperature for 3 h. After completion of reaction by TLC, the reaction mixture was diluted with ice cold water and extracted with EtOAC (2×50 mL). The combined organic layers were washed with brine (30 mL), dried over sodium sulfate and concentrated to afford crude. Crude was purified by silica gel (100-200) column purification [eluted at 4% MeOH in DCM] to afford 2-(1-(6,7-dimethoxyquinazolin-4-yl)piperidin-4-yl)-2-methylpropanenitrile (01) (0.45 g, yield: 90%) as off white solid. TLC system MeOH:DCM (10:90), $R_f$ value: 0.4; LCMS (m/z): 341.2 (M+H)$^+$.

Synthesis of 2-(1-(6,7-dimethoxyquinazolin-4-yl)piperidin-4-yl)-2-methylpropan-1-amine (02)

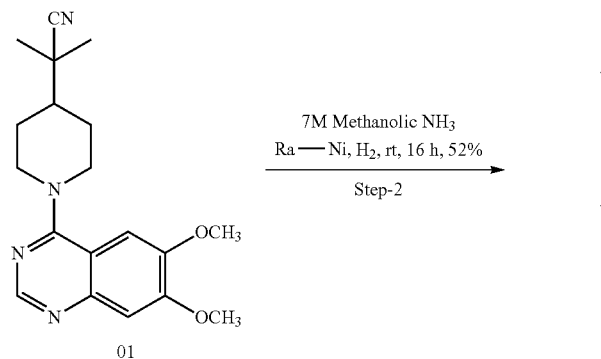

To a stirred solution of 2-(1-(6,7-dimethoxyquinazolin-4-yl)piperidin-4-yl)-2-methylpropanenitrile (01) (450 mg, 1.32 mmol, 1 eq) in 7N Methanolic.NH$_3$ (5 mL) was added Ra—Ni (1 g). The reaction mixture was stirred at room temperature for 16 h under H$_2$ balloon pressure. After completion of reaction by TLC, reaction mixture was filtered through Celite pad and concentrated to afford 2-(1-(6,7-dimethoxyquinazolin-4-yl)piperidin-4-yl)-2-methylpropan-1-amine (02) (240 mg, yield: 52%) as an off-white solid. TLC system MeOH:DCM (10:90), $R_f$ value: 0.1; $^1$HNMR (400 MHz, DMSO-d$_6$) δ 8.52 (s, 1H), 7.83 (brs, 2H), 7.20 (s, 1H), 7.13 (s, 1H), 4.25-4.22 (m, 2H), 3.92 (s, 3H), 3.91 (s, 3H), 2.99 (t, J=12 Hz, 2H), 2.73 (s, 2H), 1.75-1.73 (m, 2H), 1.55-1.44 (m, 3H), 0.93 (s, 6H).

Synthesis of tert-butyl (N-(2-(1-(6,7-dimethoxyquinazolin-4-yl)piperidin-4-yl)-2-methylpropyl)sulfamoyl)carbamate (03)

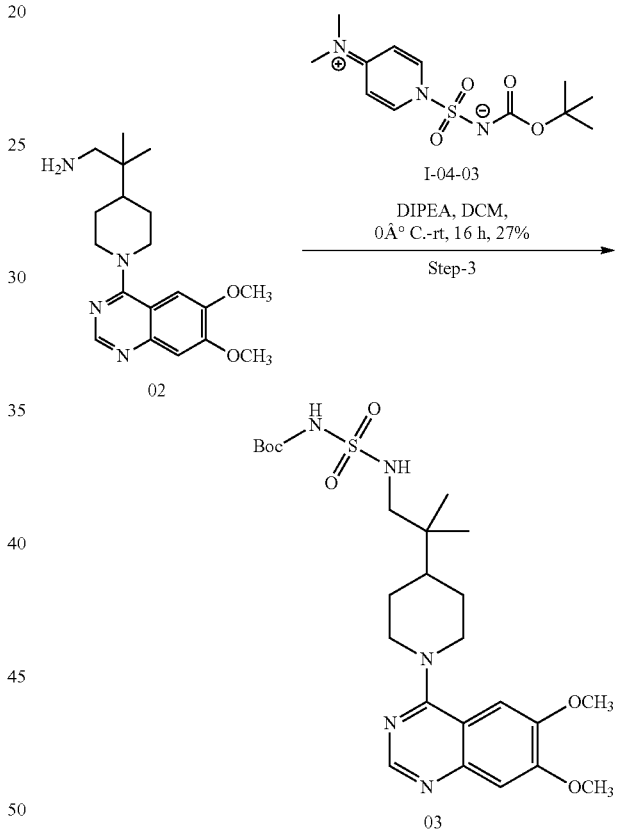

To a stirred solution of 2-(1-(6,7-dimethoxyquinazolin-4-yl)piperidin-4-yl)-2-methylpropan-1-amine (02) (240 mg, 0.69 mmol, 1.0 eq) in DCM (5 mL) at 0° C. was added DIPEA (0.18 mL, 1.04 mmol, 1.5 eq) and (tert-butoxycarbonyl)((4-(dimethyliminio)pyridin-1(4H)-yl)sulfonyl) amide (I-04-03) (252 mg, 0.83 mmol, 1.2 eq). The reaction mixture was stirred at room temperature for 16 h. After completion of reaction, the reaction mixture was diluted with water and extracted with DCM (2×20 mL). The combined organic layers were washed with brine (10 mL), dried over sodium sulfate and concentrated under reduced pressure to afford crude. Crude was purified by silica gel (100-200) column purification [eluting with 5% MeOH in DCM] to afford tert-butyl (N-(2-(1-(6,7-dimethoxyquinazolin-4-yl)piperidin-4-yl)-2-methylpropyl)sulfamoyl)carbamate (03) (180 mg, yield: 27%) as a white solid. TLC system MeOH:DCM (5:95), R$_f$ value: 0.5; LCMS (m/z): 524.3 (M+H)$^+$; $^1$HNMR (400 MHz, DMSO-d$_6$) δ 10.79 (brs, 1H), 8.51 (s, 1H), 7.43 (brs, 1H), 7.19 (s, 1H), 7.12 (s, 1H), 4.24-4.21 (m, 2H), 3.92 (s, 3H), 3.90 (s, 3H), 2.97 (t, J=12 Hz, 2H), 2.78 (d, J=6.8 Hz, 2H), 1.75-1.72 (m, 2H), 1.57-1.54 (m, 1H), 1.43 (s, 9H), 1.42-1.41 (m, 2H), 0.84 (s, 6H).

Synthesis of N-(2-(1-(6,7-dimethoxyquinazolin-4-yl)piperidin-4-yl)-2-methylpropyl)sulfuricdiamide formate salt (I-26)

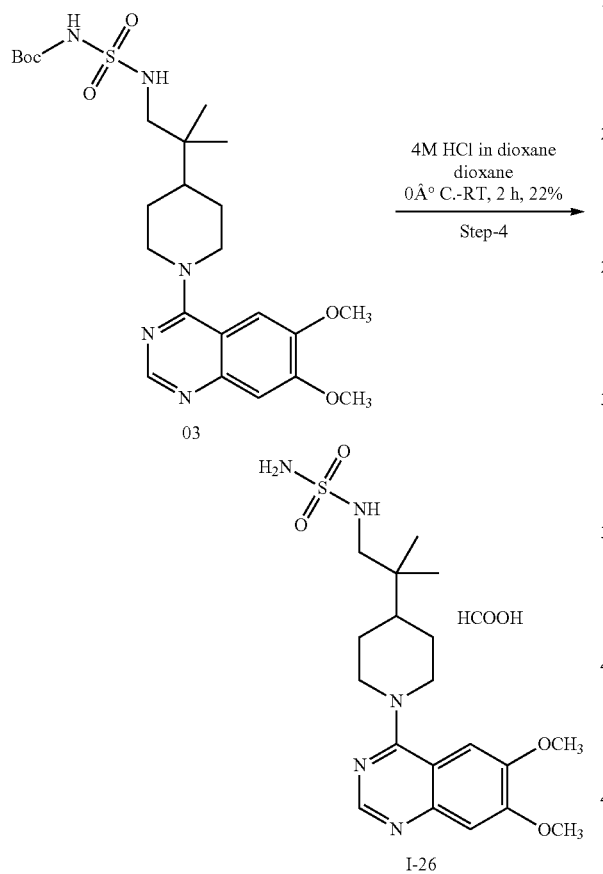

To a stirred solution of tert-butyl (N-(2-(1-(6,7-dimethoxyquinazolin-4-yl)piperidin-4-yl)-2-methylpropyl)sulfamoyl)carbamate (03) (180 mg, 0.34 mmol, 1 eq) in 1,4 Dioxane (1 mL) at 0° C. was added 4M Dioxane.HCl (3 mL) drop-wise. The reaction was allowed to stirred at room temperature for 2 h. After completion of reaction by TLC, reaction mixture was concentrated to afford crude. The crude was purified by prep-HPLC to afford N-(2-(1-(6,7-dimethoxyquinazolin-4-yl)piperidin-4-yl)-2-methylpropyl)sulfuricdiamide formate salt (I-26) (33 mg, yield: 22%) as an off-white solid. TLC system MeOH:DCM (10:90), R$_f$ value: 0.5; LCMS (m/z): 424.3 (M+H)$^+$; $^1$HNMR (400 MHz, DMSO-d$_6$) δ 8.51 (s, 1H), 8.13 (formate salt proton), 7.19 (s, 1H), 7.12 (s, 1H), 6.45 (s, 2H), 6.38 (t, J=6.8 Hz, 1H), 4.25-4.22 (m, 2H), 3.92 (s, 3H), 3.91 (s, 3H), 2.98 (t, J=12 Hz, 2H), 2.75 (t, J=6.8 Hz, 2H), 1.78-1.75 (m, 2H), 1.56-1.53 (m, 1H), 1.44-1.38 (m, 2H), 0.84 (s, 6H).

Synthesis of I-27

Synthesis of ethyl 1-(pyridin-4-yl) cyclopropane-1-carboxylate (01)

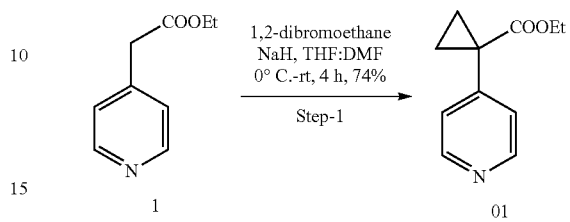

To a stirred solution of ethyl 2-(pyridin-4-yl)acetate (1) (10 g, 60.56 mmol, 1 eq) in THF:DMF (1:1) (200 mL) cooled to 0° C., added NaH (60%) (12.1 g, 303 mmol, 5 eq) and stirred for 30 min at 0° C. Later, added 1,2-dibromoethane (15.7 mL, 181.68 mmol, 3 eq), allowed to reach room temperature and continued stirring for 3.5 h. After completion of reaction by TLC, the reaction mixture was quenched with ice cold water and extracted with EtOAc (2×200 mL). The combined organic layers were washed with brine (80 mL), dried over sodium sulfate and concentrated under reduced pressure to afford crude. The crude compound was purified by silica gel (100-200 mesh) column chromatography [eluted with DCM] to afford ethyl 1-(pyridin-4-yl) cyclopropane-1-carboxylate (01) (8.5 g, yield: 74%) as a brown solid. TLC system: EOAc:Hexane (30:70), R$_f$ value: 0.4; LCMS (m/z): 192.2 (M+H)$^+$; $^1$HNMR (400 MHz, CDCl$_3$) δ 8.54 (dd, J=4.4 Hz, 1.6 Hz, 2H), 7.25 (dd, J=4.4 Hz, 1.6 Hz, 2H), 4.12 (q, J=7.2 Hz, 2H), 1.66-1.63 (m, 2H), 1.21-1.18 (m, 5H).

Synthesis of ethyl 1-(piperidin-4-yl) cyclopropane-1-carboxylate (02)

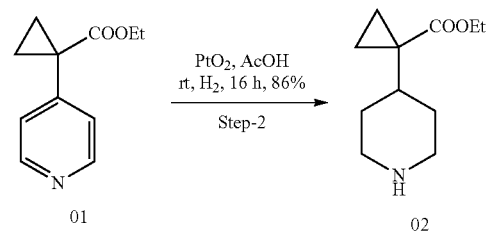 [SMILES: CCOC(=O)C1(c2ccncc2)CC1 ; CCOC(=O)C1(C2CCNCC2)CC1]

To a stirred solution of ethyl 1-(pyridin-4-yl) cyclopropane-1-carboxylate (01) (8.5 g, 44.5 mmol, 1 eq) in AcOH (85 mL) was added PtO$_2$ (2 g) and stirred at room temperature for 16 h under H$_2$ balloon pressure. After completion of reaction by TLC, the reaction mixture was filtered through Celite pad, washed with DCM and concentrated under reduced pressure to afford ethyl 1-(piperidin-4-yl) cyclopropane-1-carboxylate (02) (7.5 g, yield: 86%) as a black color liquid. TLC system: MeOH:DCM (10:90), R$_f$ value: 0.1; $^1$HNMR (400 MHz, CDCl$_3$) δ 4.11 (q, J=7.2 Hz, 2H), 3.43-3.40 (m, 2H), 2.81-2.78 (m, 2H), 1.78-1.77 (m, 4H), 1.27-1.18 (m, 6H), 0.78-0.76 (m, 2H).

Synthesis of ethyl 1-(1-(6,7-dimethoxyquinazolin-4-yl) piperidin-4-yl) cyclopropane-1-carboxylate (03)

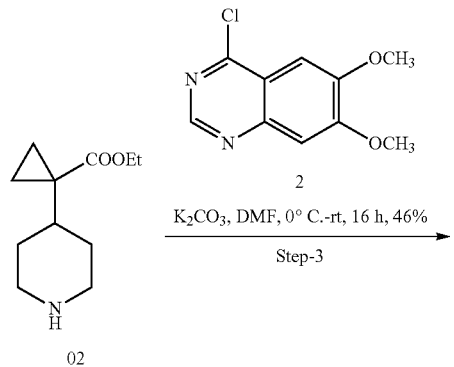

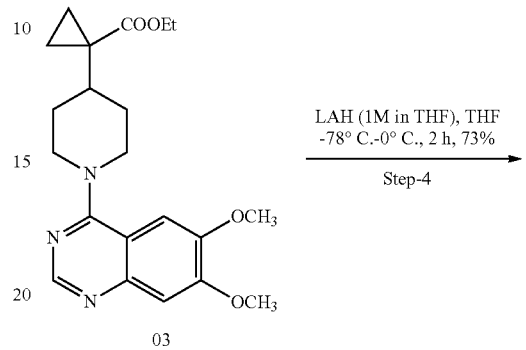

Synthesis of (1-(1-(6,7-dimethoxyquinazolin-4-yl) piperidin-4-yl) cyclopropyl) methanol (04)

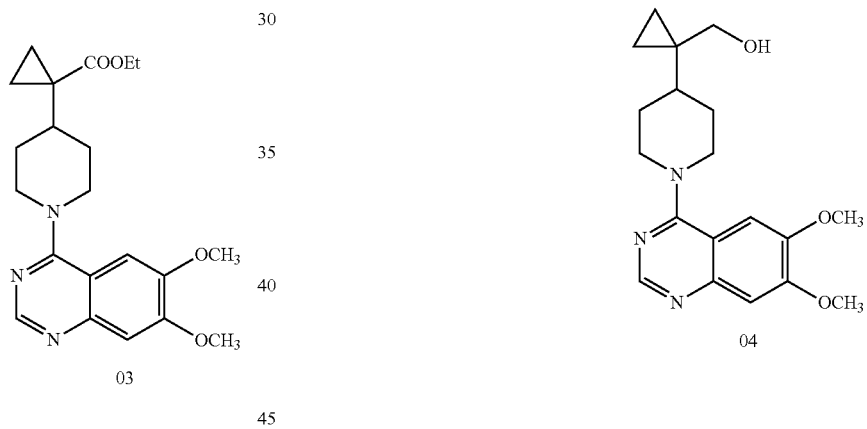

To a stirred solution of 4-chloro-6,7-dimethoxyquinazoline (2) (2.5 g, 11.16 mmol, 1 eq) in DMF (25 mL) cooled to 0° C., added ethyl 1-(piperidin-4-yl) cyclopropane-1-carboxylate (02) (3.28 g, 16.74 mmol, 1.5 eq) and $K_2CO_3$ (7.7 g, 55.8 mmol, 5 eq). The reaction mixture was stirred at room temperature for 16 h. After completion of reaction by TLC, the reaction mixture was poured into ice cold water, precipitated solid was filtered and dried under vacuum to afford ethyl 1-(1-(6,7-dimethoxyquinazolin-4-yl) piperidin-4-yl) cyclopropane-1-carboxylate (03) (2 g, yield: 46%) as off-white solid. TLC system: MeOH:DCM (10:90), $R_f$ value: 0.4; LCMS (m/z): 386.3 (M+H)$^+$; $^1$HNMR (400 MHz, DMSO-$d_6$) δ 8.51 (s, 1H), 7.20 (s, 1H), 7.10 (s, 1H), 4.22-4.19 (m, 2H), 4.03 (q, J=7.2 Hz, 2H), 3.92 (s, 3H), 3.90 (s, 3H), 2.99-2.97 (m, 2H), 1.73-1.71 (m, 5H), 1.14 (t, J=7.2 Hz, 3H), 1.06-1.03 (m, 2H), 0.87-0.85 (m, 2H).

To a stirred solution of ethyl 1-(1-(6,7-dimethoxyquinazolin-4-yl) piperidin-4-yl) cyclopropane-1-carboxylate (03) (2 g, 5.19 mmol, 1 eq) in THF (20 mL) at −78° C. was added 1.0 M LAH in THF (10.3 mL, 10.3 mmol, 2 eq). The reaction mixture was stirred while allowing from −78° C. to 0° C. for 2 h. After completion of reaction by TLC, the reaction mixture was quenched with saturated $NH_4Cl$ solution and extracted with EtOAc (2×80 mL). The combined organic layer was washed with brine (30 mL), dried over sodium sulfate and concentrated under reduced pressure to afford (1-(1-(6,7-dimethoxyquinazolin-4-yl) piperidin-4-yl) cyclopropyl) methanol (04) (1.3 g yield: 73%) as colorless liquid. TLC system MeOH:DCM (10:90), $R_f$ value: 0.3; LCMS (m/z): 344.3 (M+H)$^+$. $^1$HNMR (400 MHz, DMSO-$d_6$) δ 8.50 (s, 1H), 7.19 (s, 1H), 7.11 (s, 1H), 4.41 (t, J=5.6 Hz, 1H), 4.23-4.20 (m, 2H), 3.92 (s, 3H), 3.90 (s, 3H), 3.31-3.30 (m, 2H), 2.96-2.90 (m, 2H), 1.75-1.72 (m, 2H), 1.59-1.52 (m, 2H), 1.48-1.44 (m, 1H), 0.33 (m, 4H).

Synthesis of 4-(4-(1-(azidomethyl) cyclopropyl) piperidin-1-yl)-6,7-dimethoxyquinazoline (05)

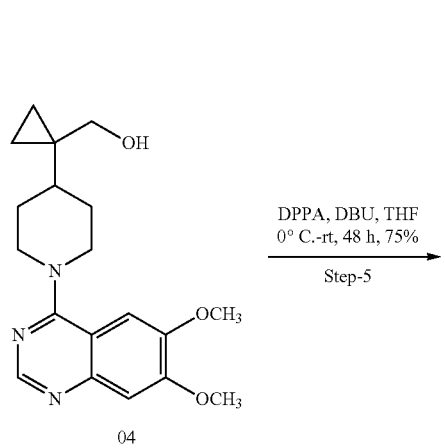

Synthesis of (1-(1-(6,7-dimethoxyquinazolin-4-yl) piperidin-4-yl) cyclopropyl) methanamine (06)

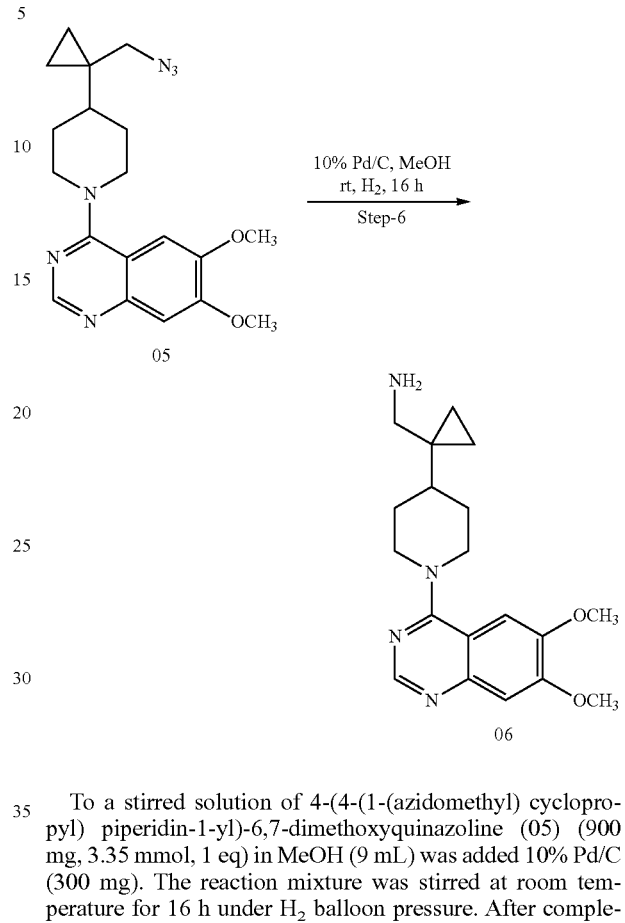

To a stirred solution of (1-(1-(6,7-dimethoxyquinazolin-4-yl) piperidin-4-yl) cyclopropyl) methanol (04) (1.3 g, 3.70 mmol, 1 eq) in THF (13 mL) cooled to 0° C., added DBU (2.2 mL, 14.8 mmol, 4 eq), DPPA (2.54 mL, 11.1 mmol, 3 eq). The reaction mixture was stirred at room temperature for 48 h. After completion of reaction, the reaction mixture was quenched with aq. NaHCO$_3$ solution and extracted with EtOAc (2×70 mL). The combined organic layer was washed with brine (30 mL), dried over sodium sulfate and concentrated under reduced pressure to afford crude. The crude compound was purified by silica gel (100-200 mesh) column chromatography [eluted with 2% MeOH in DCM] to afford 4-(4-(1-(azidomethyl) cyclopropyl) piperidin-1-yl)-6,7-dimethoxyquinazoline (05) (900 mg, yield: 75%) as colorless gummy liquid. TLC system MeOH:DCM (10:90), R$_f$ value: 0.7; LCMS (m/z): 369.3 (M+H). $^1$HNMR (400 MHz, CDCl$_3$) δ 8.65 (s, 1H), 7.23 (s, 1H), 7.10 (s, 1H), 4.27-4.24 (m, 2H), 4.02 (s, 3H), 4.00 (s, 3H), 3.24 (s, 2H), 3.03-2.96 (m, 2H), 1.86-1.83 (m, 2H), 1.71-1.67 (m, 2H), 1.46-1.42 (m, 1H), 0.57-0.50 (m, 4H).

To a stirred solution of 4-(4-(1-(azidomethyl) cyclopropyl) piperidin-1-yl)-6,7-dimethoxyquinazoline (05) (900 mg, 3.35 mmol, 1 eq) in MeOH (9 mL) was added 10% Pd/C (300 mg). The reaction mixture was stirred at room temperature for 16 h under H$_2$ balloon pressure. After completion of reaction by TLC, the reaction mixture was filtered through Celite pad, washed with methanol and concentrated under reduced pressure to afford (1-(1-(6,7-dimethoxyquinazolin-4-yl) piperidin-4-yl) cyclopropyl) methanamine (06) (500 mg) as a gummy liquid. TLC system MeOH:DCM (10:90), R$_f$ value: 0.1; LCMS (m/z): 343.3 (M+H)$^+$.

Synthesis of tert-butyl (N-((1-(1-(6,7-dimethoxyquinazolin-4-yl) piperidin-4-yl) cyclopropyl) methyl) sulfamoyl) carbamate (07)

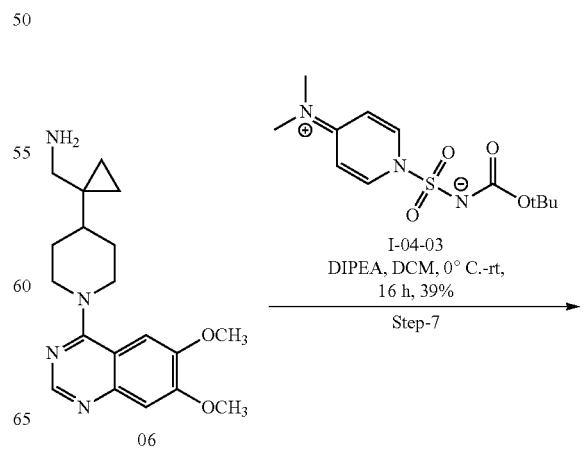

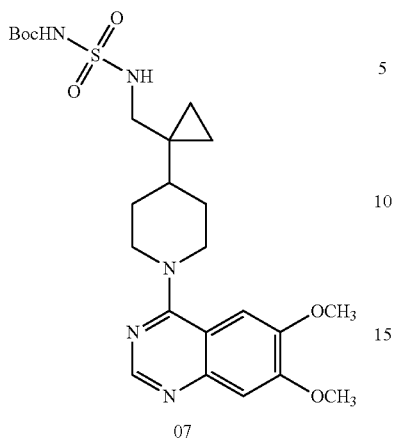

07

To a stirred solution of (1-(1-(6,7-dimethoxyquinazolin-4-yl)piperidin-4-yl)cyclopropyl)methanamine (06) (300 mg, 0.87 mmol, 1 eq) in DCM (6 mL) at 0° C. was added DIPEA (0.24 mL, 1.31 mmol, 1.5 eq) and (tert-butoxycarbonyl)((4-(dimethyliminio)pyridin-1(4H)-yl)sulfonyl)amide (I-04-03) (314 mg, 1.04 mmol, 1.2 eq). The reaction mixture was stirred at room temperature for 16 h. After completion of reaction by TLC, reaction mixture was quenched with water and extracted with DCM (2×30 mL). The combined organic layer was washed with brine (30 mL), dried over sodium sulfate and concentrated under reduced pressure to get crude compound. The crude compound was purified by using silica gel (100-200 mesh) column chromatography [eluted with 5% MeOH in DCM) to afford tert-butyl (N-((1-(1-(6,7-dimethoxyquinazolin-4-yl)piperidin-4-yl)cyclopropyl)methyl)sulfamoyl) carbamate (07) (180 mg, yield: 39%). TLC system MeOH:DCM (10:90), R$_f$ value: 0.5; LCMS (m/z): 522.3 (M+H)$^+$.

Synthesis of N—(N-((1-(1-(6,7-dimethoxyquinazolin-4-yl)piperidin-4-yl)cyclopropyl)methyl)sulfuricdiamide formate salt (I-27)

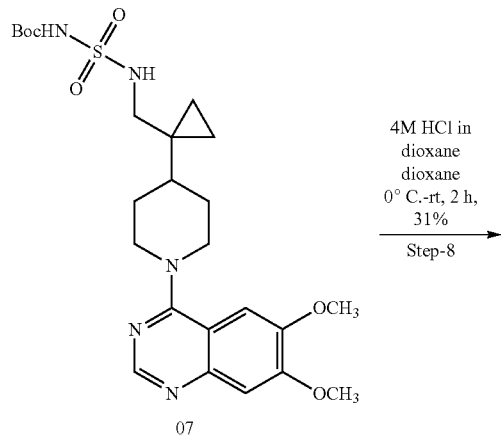

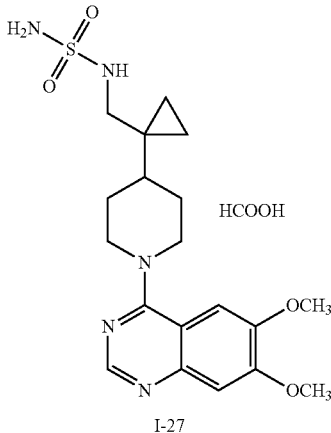

I-27

To a stirred solution of tert-butyl (N-((1-(1-(6,7-dimethoxyquinazolin-4-yl)piperidin-4-yl)cyclopropyl)methyl)sulfamoyl)carbamate (07) (180 mg, 0.34 mmol, 1 eq) in 1,4 Dioxane (0.5 mL) at 0° C. was added 4M HCl in Dioxane (2 mL). The reaction mixture was stirred at room temperature for 2 h. After completion of reaction by TLC, volatiles were evaporated and the obtained material was purified by reverse phase column chromatography [eluted with 20% (0.1% FA in water+ACN) to afford N—(N-((1-(1-(6,7-dimethoxyquinazolin-4-yl)piperidin-4-yl)cyclopropyl)methyl)sulfuricdiamide formate salt (I-27) (45 mg, yield: 31%) as a white solid. TLC system MeOH:DCM (10:90), R$_f$ value: 0.3; LCMS (m/z): 422.3 (M+H)$^+$; $^1$HNMR (400 MHz, DMSO-d$_6$) δ 8.50 (s, 1H), 8.26 (formate salt proton), 7.19 (s, 1H), 7.11 (s, 1H), 6.49-6.46 (m, 3H), 4.22-4.19 (m, 2H), 3.92 (s, 3H), 3.91 (s, 3H), 2.96-2.90 (m, 2H), 2.86-2.85 (m, 2H), 1.74-1.72 (m, 2H), 1.60-1.45 (m, 3H), 0.39-0.37 (m, 4H).

Synthesis of I-28

Synthesis of 4-chloro-7-methoxyquinazolin-6-ol (01)

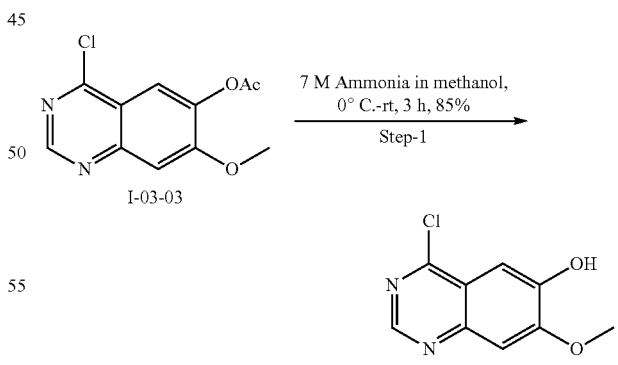

To a stirred solution of 4-chloro-7-methoxyquinazolin-6-yl acetate (I-03-03) (700 mg, 2.77 mmol, 1 eq) in methanol (2 mL) at 0° C. was added 7 M Ammonia in methanol (7 mL). The reaction mixture was stirred at room temperature for 3 h. After completion of reaction by TLC, the reaction mixture was evaporated under reduced pressure to afford crude material which was purified by trituration with pentane to afford 4-chloro-7-methoxyquinazolin-6-ol (01) (500 mg, yield: 85%) as an off white solid. TLC system: EtOAc, $R_f$ value: 0.5; LCMS (m/z): 211.1 (M+H)$^+$; $^1$HNMR (400 MHz, DMSO-d$_6$) 10.79-10.76 (br, 1H), 8.82 (s, 1H), 7.43 (s, 1H), 7.41 (s, 1H), 4.02 (s, 3H).

Synthesis of 4-chloro-7-methoxy-6-(methoxymethoxy)quinazoline (02)

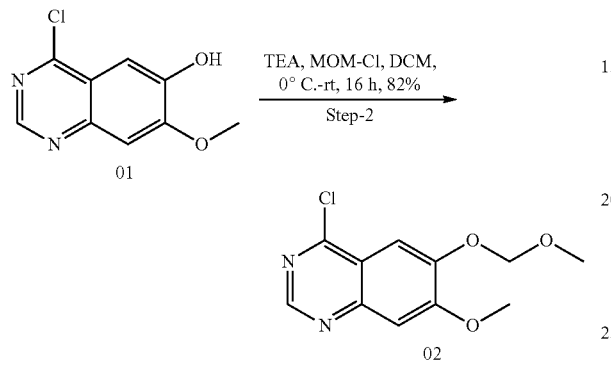

To a stirred solution of 4-chloro-7-methoxyquinazolin-6-ol (01) (500 mg, 2.38 mmol, 1 eq) in DCM (5 mL) at 0° C. was added TEA (1.6 mL, 11.9 mmol, 5 eq) and MOM-Cl (0.7 mL, 9.52 mmol, 4 eq). The reaction mixture was stirred at room temperature for 16 h. After completion of reaction by TLC, reaction mixture was diluted with water and extracted with DCM (2×30 mL). The combined organic layers was washed with brine (30 mL), dried over sodium sulfate and concentrated under reduced pressure to afford crude material which was purified by trituration with pentane to afford 4-chloro-7-methoxy-6-(methoxymethoxy)quinazoline (02) (500 mg, yield: 82%) as an off white solid. TLC system: EtOAc, $R_f$ value: 0.7; $^1$HNMR (400 MHz, CDCl$_3$) δ 8.88 (s, 1H), 7.78 (s, 1H), 7.37 (s, 1H), 5.43 (s, 2H), 4.08 (s, 3H), 3.58 (s, 3H).

Synthesis of tert-butyl 4-(1-cyanoethyl)piperidine-1-carboxylate (03)

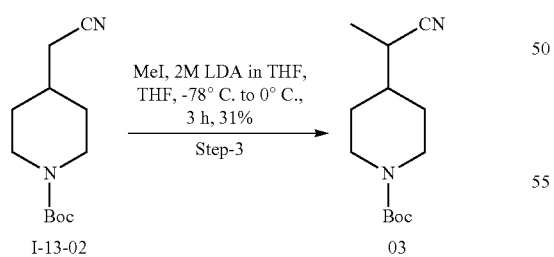

To a stirred solution of tert-butyl 4-(cyanomethyl)piperidine-1-carboxylate (I-13-02) (6 g, 26.7 mmol, 1 eq) in dry THF (30 mL) at −78° C. was added LDA (2M in THF) (20 mL, 40.0 mmol, 1.5 eq) drop wise. The reaction was stirred for 30 min at −78° C. and added methyl iodide (1.6 mL, 32.1 mmol, 1.2 eq) in THF (5 mL). Later, the reaction mixture was stirred at 0° C. for 2.5 h. After completion of reaction by TLC, the reaction mixture was quenched with saturated NH$_4$Cl solution and extracted with EtOAc (2×100 mL). The combined organic layers were washed with brine (50 mL), dried over sodium sulfate and concentrated under reduced pressure to afford crude. The crude compound was purified by silica gel (100-200 mesh) column chromatography [eluted with 7% EtOAc in hexane] to afford tert-butyl 4-(1-cyanoethyl)piperidine-1-carboxylate (03) (2 g, yield: 31%) as an gummy solid. TLC system EtOAc:Hexane (20:80; Ninhydrin stain), $R_f$ value: 0.5; $^1$HNMR (400 MHz, CDCl$_3$) δ 4.19-4.13 (m, 2H), 2.71-2.65 (m, 2H), 2.56-2.49 (m, 1H), 1.87-1.83 (m, 1H), 1.73-1.70 (m, 1H), 1.61-1.59 (m, 1H), 1.46 (s, 9H), 1.31 (d, J=4.0 Hz, 3H), 1.29-1.26 (m, 2H).

Synthesis of tert-butyl 4-(1-aminopropan-2-yl)piperidine-1-carboxylate (04)

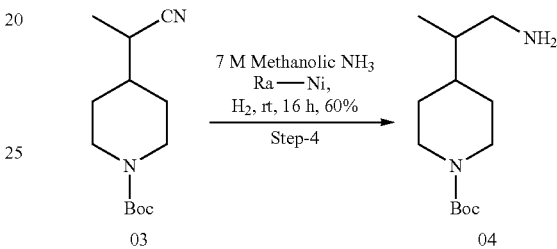

To a stirred solution of tert-butyl 4-(1-cyanoethyl)piperidine-1-carboxylate (03) (2 g, 8.36 mmol, 1 eq) in 7 M Methanolic ammonia (10 mL) was added Raney-Ni (4 g). The reaction mixture was stirred at room temperature for 16 h under H$_2$ balloon pressure. After completion of reaction by TLC, The reaction mixture was filtered through Celite pad and the filtrate was concentrated under reduced pressure to afford tert-butyl 4-(1-aminopropan-2-yl)piperidine-1-carboxylate (04) (1.2 g, yield: 60%) as colorless gummy liquid. TLC system EtOAc (Ninhydrin stain), $R_f$ value: 0.1; $^1$HNMR (400 MHz, DMSO-d$_6$) δ 3.97-3.94 (m, 2H), 2.61-2.50 (m, 3H), 2.38-2.34 (m, 1H), 1.54-1.49 (m, 2H), 1.45-1.43 (m, 1H), 1.38 (s, 9H), 1.28-1.22 (m, 1H), 1.13-1.02 (m, 2H), 0.80 (d, J=6.8 Hz, 3H). NH$_2$ protons were not clearly evident in the spectrum.

Synthesis of tert-butyl 4-(1-((N-(tert-butoxycarbonyl)sulfamoyl)amino)propan-2-yl)piperidine-1-carboxylate (05)

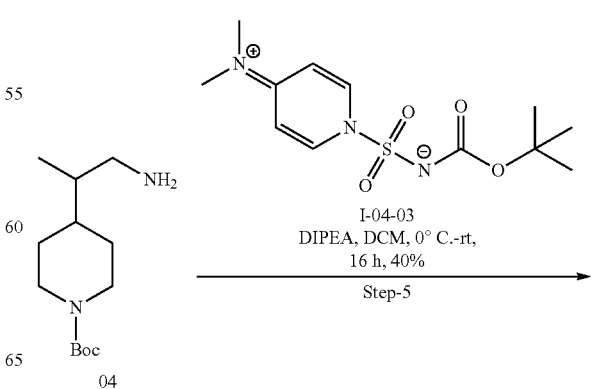

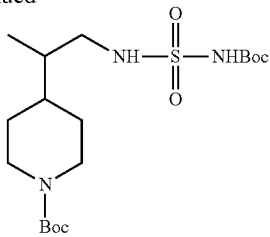

05

To a stirred solution of tert-butyl 4-(1-aminopropan-2-yl)piperidine-1-carboxylate (04) (1.2 g, 4.95 mmol, 1 eq) in DCM (12 mL) at 0° C. was added DIPEA (1.3 mL, 7.43 mmol, 1.5 eq) and (tert-butoxycarbonyl)((4-(dimethyliminio)pyridin-1(4H)-yl)sulfonyl)amide (I-04-03) (1.79 g, 5.95 mmol, 1.2 eq). The reaction mixture was stirred at room temperature for 16 h. After completion of reaction by TLC, the reaction mixture was quenched with water and extracted with DCM (2×50 mL). The combined organic layers were washed with brine (20 mL), dried over sodium sulfate and concentrated under reduced pressure to afford crude. The crude compound was purified by silica gel (100-200 mesh) column chromatography [eluted with 25% EtOAc in hexane] to afford tert-butyl 4-(1-((N-(tert-butoxycarbonyl)sulfamoyl) amino)propan-2-yl)piperidine-1-carboxylate (05) (800 mg, yield: 40%) as colorless gummy liquid. TLC system MeOH:DCM (5:95: Ninhydrin stain), $R_f$ value: 0.4; $^1$HNMR (400 MHz, DMSO-$d_6$) δ 10.75 (s, 1H), 7.53 (t, J=5.6 Hz, 1H), 3.97-3.94 (m, 2H), 2.89-2.86 (m, 1H), 2.73-2.70 (m, 2H), 2.68-2.65 (m, 1H), 1.58-1.48 (m, 4H), 1.42 (s, 9H), 1.38 (s, 9H), 1.08-0.96 (m, 2H), 0.79 (d, J=6.8 Hz, 3H).

Synthesis of N—(N-(2-(piperidin-4-yl)propyl)sulfiricdiamide hydro chloride (06)

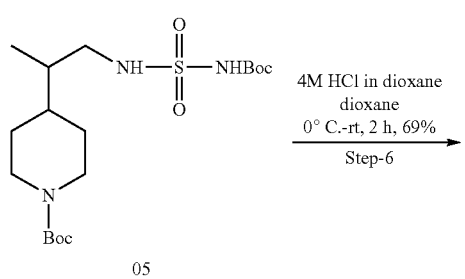

To a stirred solution of tert-butyl 4-(1-((N-(tert-butoxycarbonyl)sulfamoyl)amino)propan-2-yl)piperidine-1-carboxylate (05) (800 mg, 1.90 mmol, 1 eq) in 1,4 Dioxane (2 mL) at 0° C. was added 4M Dioxane.HCl (4 mL) drop-wise. The reaction mixture was allowed to stir at room tempera- ture for 2 h. After completion of reaction by TLC, reaction mixture was concentrated under reduced pressure to afford N—(N-(2-(piperidin-4-yl)propyl)sulfiricdiamide hydro chloride (06) (340 mg, yield: 69%) as gummy liquid. TLC system MeOH:DCM (10:90; Ninhydrin stain), $R_f$ value: 0.1; $^1$HNMR (400 MHz, DMSO-$d_6$) δ 8.87 (brs, 1H), 8.61 (brs, 1H), 6.51-6.47 (br, 3H), 3.26-3.23 (m, 2H), 2.87-2.70 (m, 4H), 1.69-1.66 (m, 2H), 1.55-1.37 (m, 4H), 0.81 (d, J=6.8 Hz, 3H).

Synthesis of N—(N-(2-(1-(7-methoxy-6-(methoxymethoxy)quinazolin-4-yl)piperidin-4-yl)propyl)sulfuricdiamide (I-28)

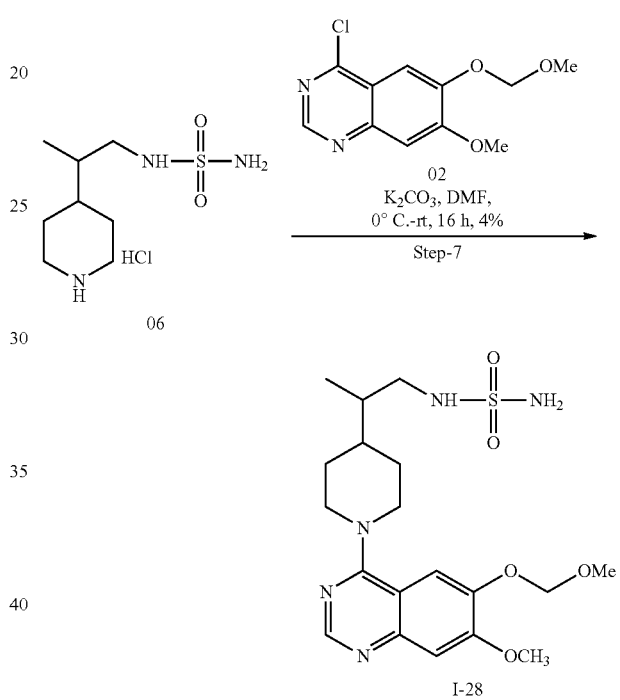

To a stirred solution of 4-chloro-7-methoxy-6-(methoxymethoxy)quinazoline (02) (250 mg, 0.98 mmol, 1 eq) in DMF (2.5 mL) at 0° C. was added K$_2$CO$_3$ (407 mg, 2.95 mmol, 3 eq) and N—(N-(2-(piperidin-4-yl)propyl)sulfiricdiamide hydro chloride (06) (327 mg, 1.27 mmol, 1.3 eq). The reaction mixture was stirred at room temperature for 16 h. After completion of reaction, the reaction mixture was quenched with ice cold water and extracted with EtOAc (2×60 mL). The combined organic layers were washed with brine (20 mL), dried over sodium sulfate and concentrated under reduced pressure to afford crude. The crude compound was purified by reverse phase column [gradient elution with 1-19% water in ACN] to afford N—(N-(2-(1-(7-methoxy-6-(methoxymethoxy)quinazolin-4-yl)piperidin-4-yl)propyl)sulfuricdiamide (I-28) (23 mg, yield: 5%) as an off white solid. TLC system: MeOH:DCM (10:90), $R_f$ value: 0.4; LCMS (m/z): 440.3 (M+H)$^+$; $^1$HNMR (400 MHz, DMSO-$d_6$) δ 8.51 (s, 1H), 7.44 (s, 1H), 7.22 (s, 1H), 6.46-6.44 (m, 3H), 5.31 (s, 2H), 4.22-4.19 (m, 2H), 3.94 (s, 3H), 3.43 (s, 3H), 3.03-2.90 (m, 3H), 2.76-2.73 (m, 1H), 1.72-1.58 (m, 4H), 1.51-1.35 (m, 2H), 0.87 (d, J=6.8 Hz, 3H).

Synthesis of I-29

Synthesis of tert-butyl (1-(6,7-dimethoxyquinazolin-4-yl) piperidin-4-yl) carbamate (01)

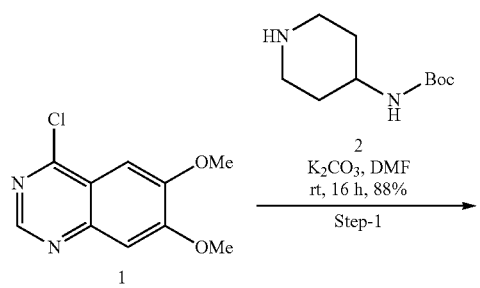

Synthesis of 1-(6,7-dimethoxyquinazolin-4-yl) piperidin-4-amine hydrogen chloride (02)

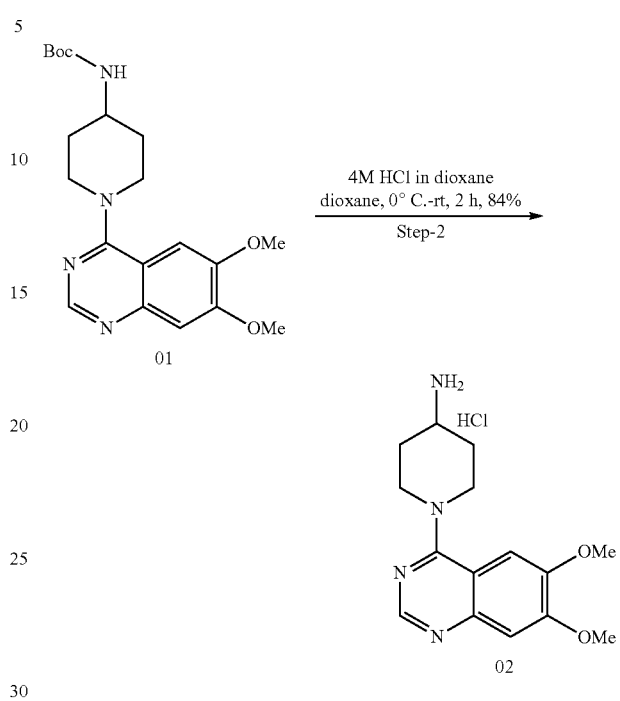

To a stirred solution of tert-butyl (1-(6,7-dimethoxyquinazolin-4-yl) piperidin-4-yl) carbamate (01) (1.0 g, 2.58 mmol, 1 eq) in 1,4 Dioxane (2 mL) at 0° C. was added 4M HCl in Dioxane (10 mL) and stirred at room temperature for 2 h. After completion of reaction by TLC, volatiles were evaporated and the obtained crude was purified by trituration with diethyl ether to afford 1-(6,7-dimethoxyquinazolin-4-yl) piperidin-4-amine hydrogen chloride (02) (700 mg, yield: 84%) as white solid. TLC system MeOH:DCM (10:90), $R_f$ value: 0.1; LCMS (m/z): 289.2 (M+H)$^+$; $^1$HNMR (400 MHz, DMSO-d$_6$) δ 8.80 (s, 1H), 8.39 (brs, 3H), 7.39 (s, 1H), 7.29 (s, 1H), 4.69-4.65 (m, 2H), 3.98 (s, 3H), 3.96 (s, 3H), 3.62-3.56 (m, 3H), 2.19-2.16 (m, 2H), 1.79-1.70 (m, 2H).

To a stirred solution of 4-chloro-6,7-dimethoxyquinazoline (1) (1 g, 4.64 mmol, 1 eq) in DMF (10 mL) was added K$_2$CO$_3$ (1.92 g, 13.92 mmol, 3 eq) and tert-butyl piperidin-4-yl carbamate (2) (1 g, 5.35 mmol, 1.2 eq) at 0° C. The reaction mixture was stirred at room temperature for 16 h. After completion of reaction by TLC, the reaction mixture was diluted with water and extracted with Ethyl acetate (2×70 mL). The combined organic layers were washed with brine (50 mL) dried over sodium sulfate and concentrated under reduced pressure to afford crude. The crude purified by trituration with diethyl ether to afford tert-butyl (1-(6,7-dimethoxyquinazolin-4-yl) piperidin-4-yl) carbamate (01) (1.45 g, yield: 88%) as white solid. TLC system MeOH:DCM (5:95), $R_f$ value: 0.25; LCMS (m/z): 389.3 (M+H)$^+$; $^1$HNMR (400 MHz, DMSO-d$_6$) δ 8.52 (s, 1H), 7.20 (s, 1H), 7.08 (s, 1H), 6.92 (d, J=7.6 Hz, 1H), 4.11-4.07 (m, 2H), 3.93 (s, 3H), 3.91 (s, 3H), 3.57-3.75 (m, 1H), 3.15 (t, J=11.6 Hz, 2H), 1.91-1.89 (m, 2H), 1.64-1.54 (m, 2H), 1.40 (s, 9H).

Synthesis of tert-butyl (N-(1-(6,7-dimethoxyquinazolin-4-yl) piperidin-4-yl) sulfamoyl) carbamate (03)

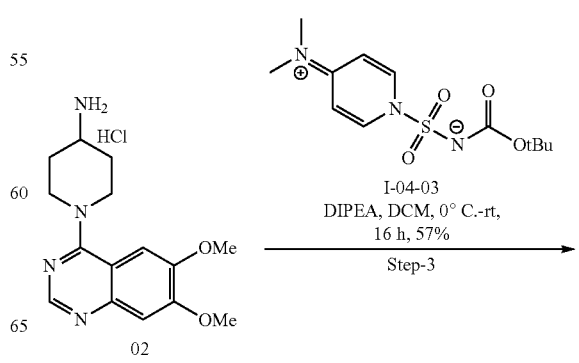

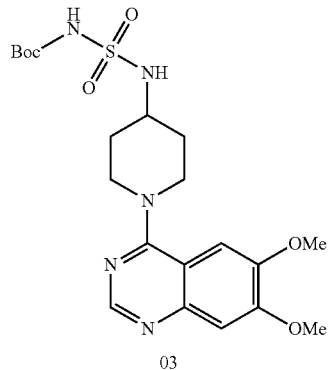

03

To a stirred solution 1-(6,7-dimethoxyquinazolin-4-yl) piperidin-4-amine hydrogen chloride (02) (500 mg, 1.54 mmol, 1.0 eq) in DCM (10 mL) at 0° C. was added DIPEA (0.43 mL, 2.31 mmol, 1.5 eq) and (tert-butoxycarbonyl)((4-(dimethyliminio)pyridin-1(4H)-yl)sulfonyl)amide (I-04-03) (560 mg, 1.85 mmol, 1.2 eq) and stirred at room temperature for 16 h. After completion of reaction by TLC, the reaction mixture was diluted with water and extracted with DCM (2×30 mL). The combined organic layers were washed with brine (30 mL), dried over sodium sulfate and concentrated under reduced pressure to afford crude. The crude compound was purified by silica gel (100-200 mesh) column chromatography [eluted with 3% MeOH+DCM] to afford tert-butyl (N-(1-(6,7-dimethoxyquinazolin-4-yl) piperidin-4-yl) sulfamoyl) carbamate (03) (410 mg, yield: 57%) as yellow solid. TLC system MeOH:DCM (10:90), R$_f$ value: 0.4; LCMS (m/z): 468.3 (M+H)$^+$.

Synthesis of N—(N-(1-(6,7-dimethoxyquinazolin-4-yl)piperidin-4-yl)sulfuricdiamide formate salt (I-29)

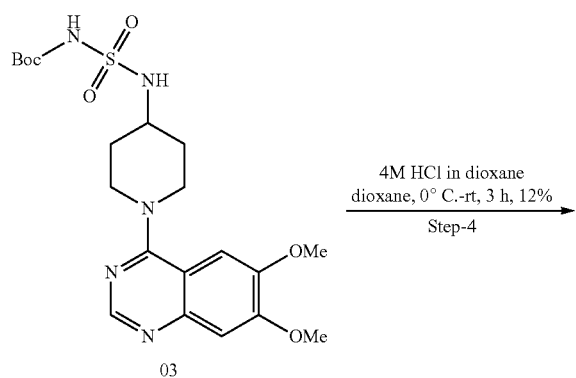

03

4M HCl in dioxane
dioxane, 0° C.-rt, 3 h, 12%
Step-4

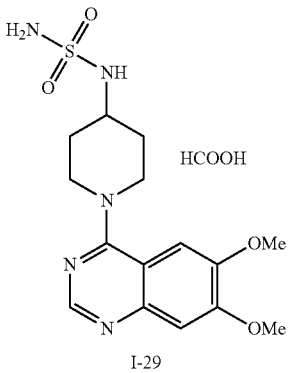

I-29

To a stirred solution of tert-butyl (N-(1-(6,7-dimethoxyquinazolin-4-yl) piperidin-4-yl) sulfamoyl) carbamate (03) (400 mg, 1.08 mmol, 1 eq) in 1,4 Dioxane (2 mL) at 0° C. was added 4M HCl in Dioxane (4 mL) and stirred at room temperature for 3 h. After completion of reaction by TLC, volatiles were evaporated and the obtained crude was purified by prep HPLC [FA method] to afford N—(N-(1-(6,7-dimethoxyquinazolin-4-yl)piperidin-4-yl)sulfuricdiamide formate salt (I-29) (44 mg, yield: 12%) as white solid. TLC system MeOH:DCM (10:90), R$_f$ value: 0.2; LCMS (m/z): 368.3 (M+H)$^+$, $^1$HNMR (400 MHz, DMSO-d$_6$) δ 8.52 (s, 1H), 8.14 (formate salt proton), 7.21 (s, 1H), 7.09 (s, 1H), 6.68 (d, J=7.2 Hz, 2H), 6.55 (s, 1H), 4.10-4.07 (m, 2H), 3.93 (s, 3H) 3.91 (s, 3H), 3.42-3.40 (m, 1H), 3.20-3.14 (m, 2H), 2.05-2.03 (m, 2H), 1.68-1.63 (m, 2H).

Synthesis of I-30

Synthesis of piperidin-4-one hydrochloride (01)

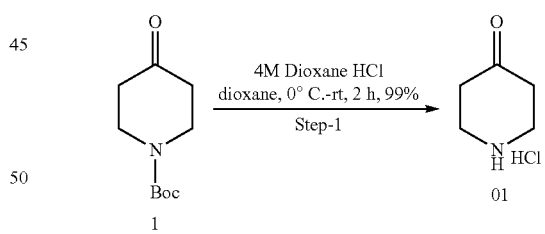

To a solution of tert-butyl 4-oxopiperidine-1-carboxylate (1) (1.0 g, 5.02 mmol, 1 eq) in 1,4 Dioxane (2 mL) at 0° C. was added 4M HCl in Dioxane (10 mL) and stirred at room temperature for 2 h. After completion of reaction by TLC, volatiles were evaporated and the obtained crude was purified by trituration with diethyl ether to afford piperidin-4-one hydrochloride (01) (500 mg, yield: 99%) as white solid. TLC system MeOH:DCM (10:90), R$_f$ value: 0.1; $^1$HNMR (400 MHz, DMSO-d$_6$) δ 9.45 (brs, 2H), 3.39 (t, J=6.4 Hz, 4H), 2.58 (t, J=6.4 Hz, 4H).

Synthesis of 1-(6,7-dimethoxyquinazolin-4-yl) piperidin-4-one (02)

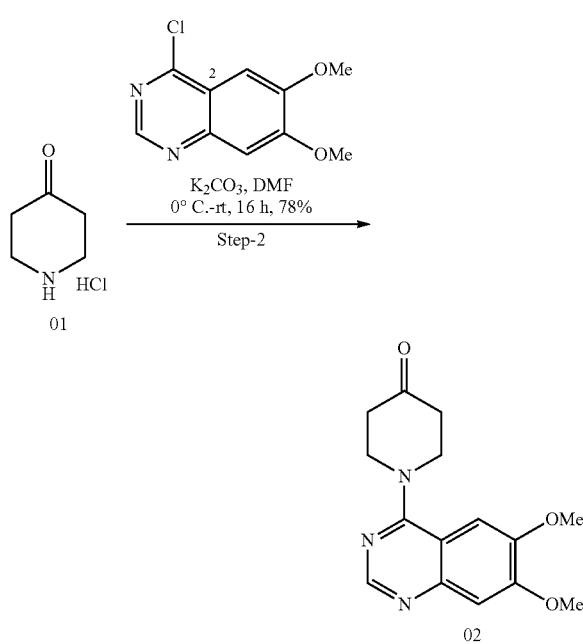

To a stirred solution of piperidin-4-one hydrochloride (01) (500 mg, 2.23 mmol, 1 eq) in DMF (5 mL) at 0° C. was added K$_2$CO$_3$ (923 mg, 6.69 mmol, 3 eq) and 4-chloro-6,7-dimethoxyquinazoline (2) (360 mg, 2.67 mmol, 1.2 eq). The reaction mixture was stirred at room temperature for 16 h. After completion of reaction by TLC, the reaction mixture was diluted with water and extracted with Ethyl acetate (2×30 mL). The combined organic layers were washed with brine (30 mL), dried over sodium sulfate and concentrated under reduced pressure to afford crude. The crude was purified by trituration with diethyl ether to afford 1-(6,7-dimethoxyquinazolin-4-yl) piperidin-4-one (02) (500 mg, yield: 78%) as yellow solid. TLC system MeOH:DCM (5:95), R$_f$ value: 0.25; LCMS (m/z): 288.3 (M+H)$^+$; $^1$HNMR (400 MHz, DMSO-d$_6$) δ 8.57 (s, 1H), 7.24 (s, 1H), 7.23 (s, 1H), 3.96 (t, J=6.0 Hz, 4H), 3.94 (s, 3H), 3.93 (s, 3H), 2.60 (t, J=6.0 Hz, 4H).

Synthesis of N-cyclopropyl-1-(6,7-dimethoxyquinazolin-4-yl) piperidin-4-amine (03)

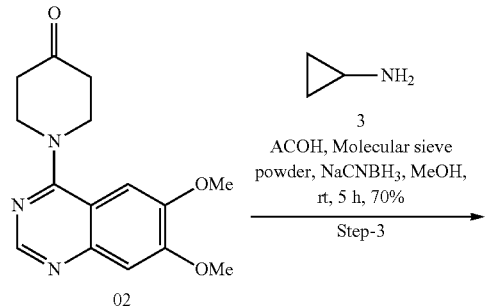

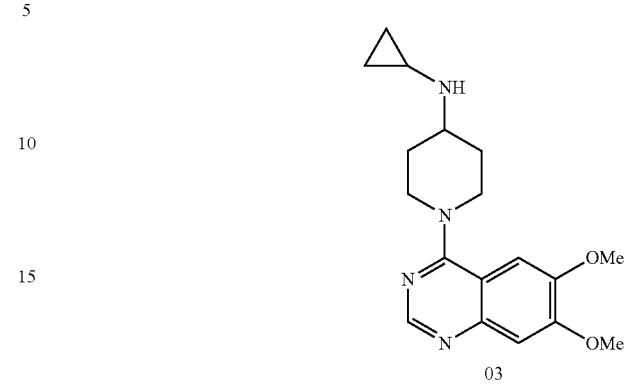

To a stirred solution of 1-(6,7-dimethoxyquinazolin-4-yl) piperidin-4-one (02) (500 mg, 1.74 mmol, 1.0 eq) in MeOH (10 mL) was added cyclopropanamine (3) (100 mg, 1.74 mmol, 1 eq), molecular sieves (1 g) and acetic acid (Catalytic). The reaction mixture was stirred at room temperature for 30 min, then added NaCNBH$_3$ (164 mg, 2.61 mmol, 1.5 eq). The reaction mixture was stirred at room temperature for 5 h. After completion of reaction, the reaction mixture was filtered through Celite pad, washed with 5% MeOH+DCM. The filtrate was dried over sodium sulfate and concentrated under reduced pressure to afford crude. The crude was purified by trituration with diethyl ether to afford N-cyclopropyl-1-(6,7-dimethoxyquinazolin-4-yl) piperidin-4-amine (03) (400 mg, yield: 70%) as yellow gummy. TLC system MeOH:DCM (5:95), R$_f$ value: 0.2; LCMS (m/z): 329.3 (M+H)$^+$.

Synthesis of tert-butyl (N-cyclopropyl-N-(1-(6,7-dimethoxyquinazolin-4-yl) piperidin-4-yl) sulfamoyl) (04)

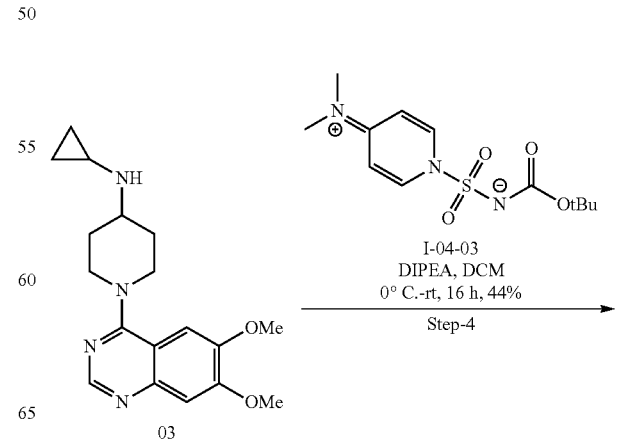

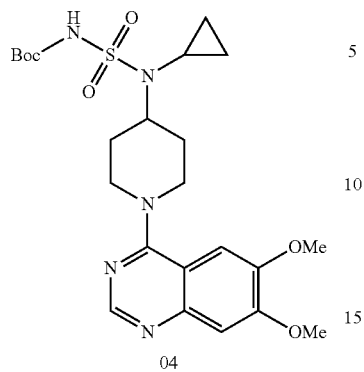

04

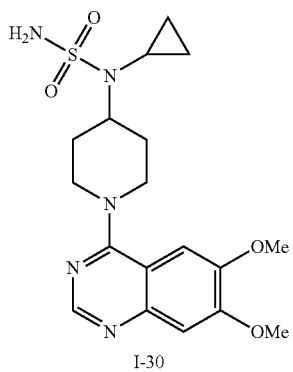

I-30

To a stirred solution N-cyclopropyl-1-(6,7-dimethoxyquinazolin-4-yl) piperidin-4-amine (03) (600 mg, 1.82 mmol, 1.0 eq) in DCM (12 mL) at 0° C. was added DIPEA (0.49 mL, 2.74 mmol, 1.5 eq) and (tert-butoxycarbonyl)((4-(dimethyliminio)pyridin-1(4H)-yl)sulfonyl)amide (I-04-03) (660 mg, 2.19 mmol, 1.2 eq). The reaction mixture was stirred at room temperature for 16 h. After completion of reaction by TLC, the reaction mixture was diluted with water and extracted with Ethyl acetate (2×40 mL). The combined organic layers was washed with brine solution (20 mL), dried over sodium sulfate and concentrated under reduced pressure to afford crude. The crude compound was purified by silica gel (100-200 mesh) column purification [gradient elution with 0-4% MeOH+DCM] to afford tert-butyl (N-cyclopropyl-N-(1-(6,7-dimethoxyquinazolin-4-yl) piperidin-4-yl)sulfamoyl) carbamate (04) (410 mg, yield: 44%) as an white solid. TLC system MeOH:DCM (10:90), R$_f$ value: 0.4; LCMS (m/z): 508.3 (M+H)$^+$, $^1$HNMR (400 MHz, DMSO-d$_6$) δ 11.13 (s, 1H), 8.54 (s, 1H), 7.22 (s, 1H), 7.13 (s, 1H), 4.29-4.26 (m, 2H), 4.06-4.03 (m, 1H), 3.93 (s, 3H), 3.92 (s, 3H), 3.10-3.04 (m, 2H), 2.43-2.42 (m, 1H), 2.12-2.08 (m, 2H), 1.90-1.87 (m, 2H), 1.44 (s, 9H), 0.85-0.83 (m, 2H), 0.76-0.74 (m, 2H).

Synthesis of N—(N-cyclopropyl-N-(1-(6,7-dimethoxyquinazolin-4-yl)piperidin-4-yl)sulfuricdiamide (I-30)

To a stirred solution of tert-butyl (N-cyclopropyl-N-(1-(6,7-dimethoxyquinazolin-4-yl) piperidin-4-yl)sulfamoyl) carbamate (04) (200 mg, 0.39 mmol, 1 eq) in 1,4 Dioxane (2 mL) cooled to 0° C., added 4M HCl in Dioxane (4 mL) and stirred at room temperature for 2 h. After completion of reaction by TLC, volatiles were evaporated and the obtained crude was purified by prep HPLC (FA method) to afford N—(N-cyclopropyl-N-(1-(6,7-dimethoxyquinazolin-4-yl) piperidin-4-yl)sulfuricdiamide (I-30) (49 mg, yield: 28%) as white solid. TLC system MeOH:DCM (10:90), R$_f$ value: 0.2; LCMS (m/z): 408.3 (M+H)$^+$, $^1$HNMR (400 MHz, DMSO-d$_6$) δ 8.54 (s, 1H), 7.21 (s, 1H), 7.13 (s, 1H), 6.88 (s, 2H), 4.29-4.26 (m, 2H), 3.93 (s, 3H), 3.92 (s, 3H), 3.89-3.86 (m, 1H), 3.07 (t, J=12.4 Hz, 2H), 2.32-2.30 (m, 1H), 2.09-2.03 (m, 2H), 1.95-1.92 (m, 2H), 0.76-0.70 (m, 4H).

Synthesis of I-31

Synthesis of 1-(4-(6,7-dimethoxyquinolin-4-yl)piperazin-1-yl)cyclopropanecarbonitrile (01)

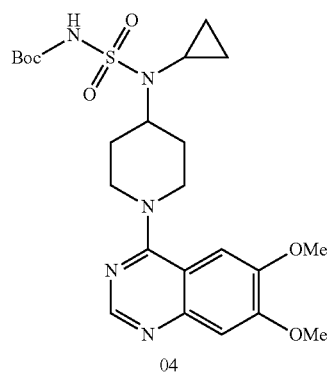

04

4M HCl in Dioxane
dioxane, 0° C.-rt, 2 h
28%
Step-5

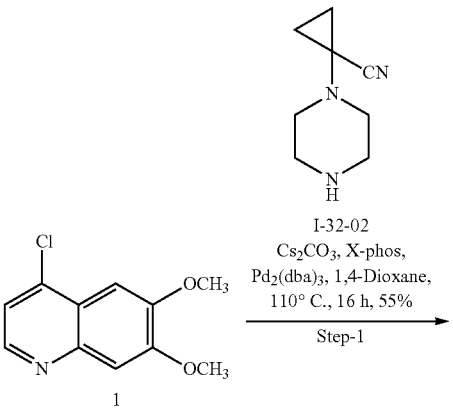

1

I-32-02
Cs$_2$CO$_3$, X-phos,
Pd$_2$(dba)$_3$, 1,4-Dioxane,
110° C., 16 h, 55%
Step-1

-continued

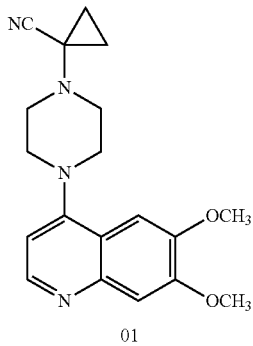

In a sealed tube, to a stirred solution of 4-chloro-6,7-dimethoxyquinoline (1) (600 mg, 2.67 mmol, 1.0 eq) and 1-(piperazin-1-yl)cyclopropanecarbonitrile (I-32-02) (485 mg, 3.21 mmol, 1.2 eq) in 1,4-Dioxane (6 mL) was added $Cs_2CO_3$ (2.6 g, 8.03 mmol, 3.0 eq) and X-Phos (255 mg, 0.53 mmol, 0.2 eq) degassed for 20 minutes. Later added $Pd_2(dba)_3$ (245 mg, 0.26 mmol, 0.1 eq) and heated to 110° C., stirred for 16 h. After completion of reaction by TLC, reaction mixture filtered through Celite bed, washed with 10% MeOH:DCM and concentrated to get crude. The crude compound was purified by silica gel (60-120 mesh) column [with a gradient elution of 0-2% of MeOH in DCM] to afford 1-(4-(6,7-dimethoxyquinolin-4-yl)piperazin-1-yl)cyclopropanecarbonitrile (01) (500 mg, yield: 55%) as brown color gummy liquid. TLC system MeOH:DCM (10:90), $R_f$ value: 0.4; LCMS (m/z): 339.3 (M+H)$^+$; $^1$HNMR (400 MHz, CDCl$_3$) δ 8.57 (d, J=5.2 Hz, 1H), 7.40 (s, 1H), 7.28 (s, 1H), 6.77 (d, J=4.8 Hz, 1H), 4.04 and 4.03 (2s, 6H), 3.18 (brs, 4H), 3.02 (t, J=4.8 Hz, 4H), 1.31-1.28 (m, 2H), 1.14-1.11 (m, 2H).

Synthesis of (1-(4-(6,7-dimethoxyquinolin-4-yl)piperazin-1-yl)cyclopropyl)methanamine (02)

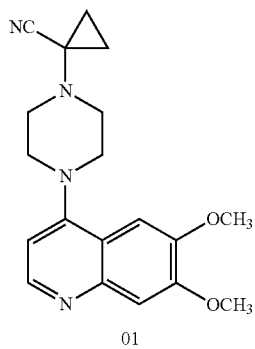

Methanolic NH$_3$
Ra—Ni,
RT, 16 h, 69%
Step-2

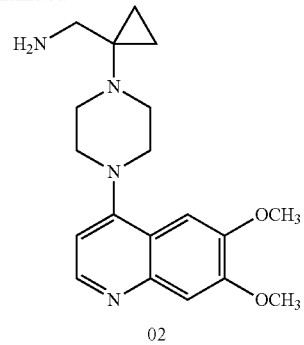

To a stirred solution of 1-(4-(6,7-dimethoxyquinolin-4-yl)piperazin-1-yl)cyclopropanecarbonitrile (01) (500 mg, 1.47 mmol, 1.0 eq) in 7 M Methanolic ammonia (5 mL) was added Ra—Ni (250 mg). The reaction mixture was stirred at room temperature for 16 h under hydrogen bladder pressure. After completion of reaction by TLC, the reaction mixture filtered through Celite bed, washed with 10% MeOH:DCM and filtrate was evaporated under reduced pressure to afford (1-(4-(6,7-dimethoxyquinolin-4-yl)piperazin-1-yl)cyclopropyl)methanamine (02) (300 mg, yield: 59%) as brown color liquid. TLC system MeOH:DCM (10:90), $R_f$ value: 0.1; LCMS (m/z): 343.2 (M+H)$^+$.

Synthesis of tert-butyl N-((1-(4-(6,7-dimethoxyquinolin-4-yl)piperazin-1-yl)cyclopropyl)methyl)sulfamoylcarbamate (03)

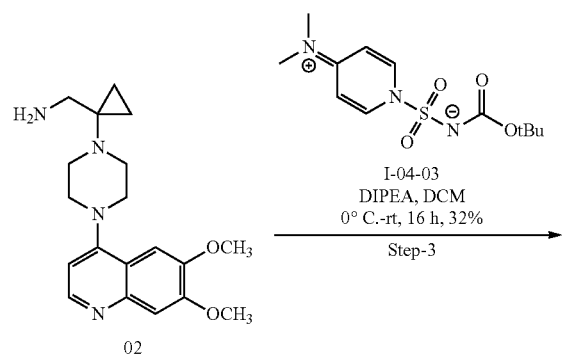

I-04-03
DIPEA, DCM
0° C.-rt, 16 h, 32%
Step-3

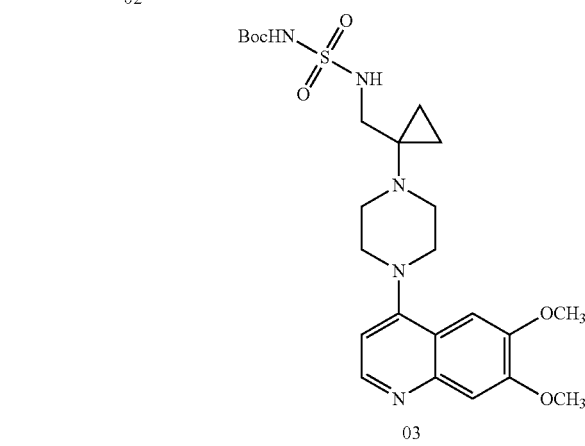

To a stirred solution of (1-(4-(6,7-dimethoxyquinolin-4-yl)piperazin-1-yl)cyclopropyl)methanamine (02) (300 mg, 0.87 mmol, 1.0 eq) in DCM (5 mL) at 0° C. was added DIPEA (0.23 mL, 1.31 mmol, 1.5 eq) and (tert-butoxycarbonyl)((4-(dimethyliminio)pyridin-1(4H)-yl)sulfonyl)amide (I-04-03) (358 mg, 1.05 mmol, 1.2 eq). The reaction mixture was stirred at room temperature for 16 h. After completion of reaction by TLC, reaction mixture was diluted with water and extracted with DCM (2×40 mL). Combined organic layer was dried under $Na_2SO_4$ and concentrated to get crude. The crude was purified by grace reverse phase column chromatography [with a gradient elution of 0-20% of ACN in 0.1% of FA in water] to afford tert-butyl N-((1-(4-(6,7-dimethoxyquinolin-4-yl)piperazin-1-yl)cyclopropyl)methyl)sulfamoylcarbamate (03) (150 mg, yield: 32%) as yellow color gummy liquid. TLC system MeOH:DCM (10:90), $R_f$ value: 0.5; LCMS (m/z): 522.3 $(M+H)^+$.

Synthesis of N-((1-(4-(6,7-dimethoxyquinolin-4-yl)piperazin-1-yl)cyclopropyl)methyl)sulfuricdiamide (I-31 as TFA salt)

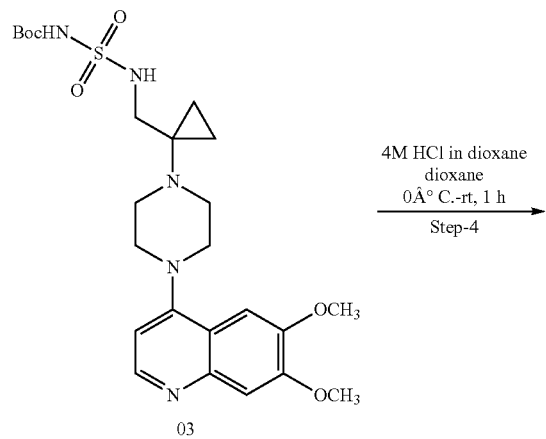

To a stirred solution of tert-butyl N-((1-(4-(6,7-dimethoxyquinolin-4-yl)piperazin-1-yl)cyclopropyl)methyl)sulfamoylcarbamate (03) (150 mg, 0.28 mmol, 1.0 eq) in 1,4-dioxane (1 mL) at 0° C. was added 4M HCl in Dioxane (1.5 mL) and stirred at RT for 1 h. After completion of reaction, the reaction mixture was evaporated under reduced pressure to get crude. The crude material was purified by prep-HPLC [using TFA buffer] to afford N-((1-(4-(6,7-dimethoxyquinolin-4-yl)piperazin-1-yl)cyclopropyl)methyl)sulfuricdiamide as TFA salt (I-31) (1 mg, yield: 9%) as off white solid. TLC system MeOH:DCM (10:90), $R_f$ value: 0.2; LCMS (m/z): 422.3 $(M+H)^+$; $^1$HNMR (400 MHz, DMSO) δ 8.58 (d, J=6.4 Hz, 1H), 7.37 (s, 1H), 7.26 (s, 1H), 7.15 (d, J=6.8 Hz, 1H), 6.59-6.54 (br, 3H), 3.98 and 3.97 (2s, 6H), 3.69-3.62 (br, 4H), 3.15-3.05 (br, 6H), 0.76-0.68 (brs, 4H).

Synthesis of I-32

Synthesis of 1-(4-benzylpiperazin-1-yl)cyclopropanecarbonitrile (01)

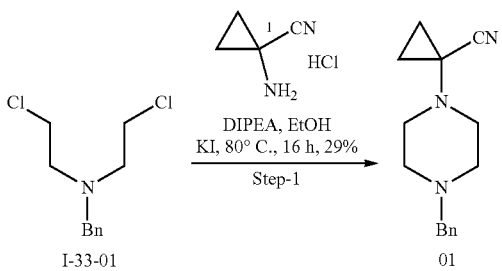 [SMILES: ClCCN(CCCl)Cc1ccccc1 ; N#CC1(N)CC1 ; Cl ; N#CC1(N2CCN(Cc3ccccc3)CC2)CC1]

To a stirred solution of N-benzyl-2-chloro-N-(2-chloroethyl)ethan-1-amine (I-33-01) (5 g, 21.5 mmol, 1 eq) in ethanol (100 mL) was added DIPEA (50 mL, 10 Vol), 1-aminocyclopropanecarbonitrile hydrogen chloride (1) (2.8 g, 23.7 mmol, 1.1 eq) and KI (536 mg, 3.23 mmol, 0.15 eq). The reaction mixture was stirred at 80° C. for 16 h. After completion of reaction by TLC, diluted with water (50 mL) and extracted with ethyl acetate (3×80 mL). Combined organic layer was washed with brine solution (50 mL), dried over $Na_2SO_4$ and concentrated to get crude. The crude compound was purified by silica gel (60-120 mesh) column [with a gradient elution of 0-10% of EtOAc in Hexane] to afford 1-(4-benzylpiperazin-1-yl)cyclopropanecarbonitrile (01) (1.5 g, yield: 29%) as pale yellow gummy liquid. TLC system EtOAc:Hexane (50:50), $R_{f\ value}$: 0.6; LCMS (m/z): 242.2 $(M+H)^+$; $^1$HNMR (400 MHz, $CDCl_3$) δ 7.34-7.22 (m, 4H), 7.28-7.24 (m, 1H), 3.46 (s, 2H), 2.74 (t, J=4.8 Hz, 4H), 2.44 (brs, 4H), 1.24-1.16 (m, 2H), 1.02-0.99 (m, 2H).

Synthesis of 1-(piperazin-1-yl)cyclopropanecarbonitrile (02)

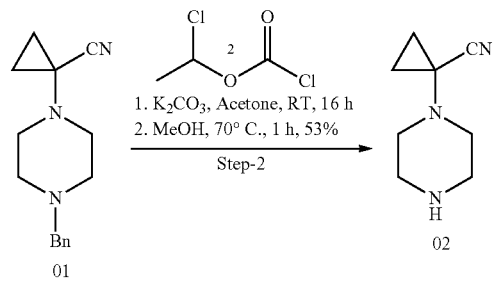

To a stirred solution of 1-(4-benzylpiperazin-1-yl)cyclopropanecarbonitrile (01) (1.5 g, 6.22 mmol, 1.0 eq) in acetone (15 mL) was added $K_2CO_3$ (2.5 g, 18.6 mmol, 3 eq) and 1-chloro ethyl chloro formate (2) (1 mL, 9.33 mmol, 1.5 eq). The reaction mixture was stirred at RT for 16 h. After completion of reaction by TLC, reaction mixture was evaporated, diluted with MeOH (15 mL) and stirred at 70° C. for 1 h. After 1 h, volatiles were evaporated and acidified with 2 N HCl and washed with DCM (2×25 mL). Aqueous layer was neutralized with 4 M NaOH and extracted with DCM (2×50 mL). Combined organic layer was washed with brine solution, dried over Na$_2$SO$_4$ and concentrated to afford 1-(piperazin-1-yl)cyclopropanecarbonitrile (02) (500 mg, yield: 53%) as brown color liquid. TLC system MeOH: DCM (10:90), R$_f$ value: 0.1; $^1$HNMR (400 MHz, CDCl$_3$) δ 2.91 (brs, 4H), 2.76 (t, J=4.8 Hz, 4H), 1.27-1.25 (m, 2H), 0.93-0.91 (m, 2H)

Synthesis of 1-(4-(6,7-dimethoxyquinazolin-4-yl)piperazin-1-yl)cyclopropanecarbonitrile (03)

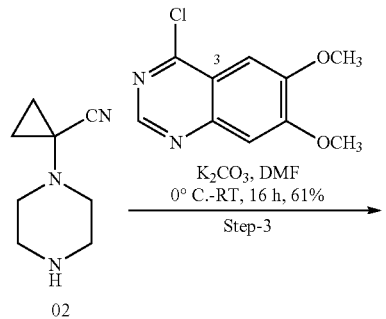

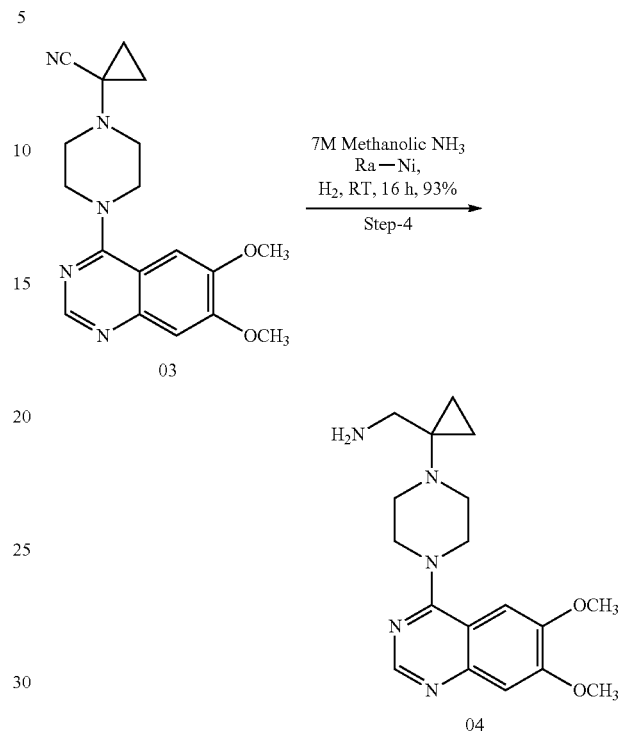

To a stirred solution of 4-chloro-6,7-dimethoxyquinazoline (3) (500 mg, 2.23 mmol, 1 eq) in DMF (5 mL) at 0° C. was added K$_2$CO$_3$ (924 mg, 6.69 mmol, 3.0 eq), 1-(piperazin-1-yl)cyclopropanecarbonitrile (02) (438 mg, 2.90 mmol, 1.3 eq) and was stirred at room temperature for 16 h. After completion of reaction by TLC, the reaction mixture was diluted with ice cold water water and extracted with EtOAc (2×25 mL). Combined organic layer was washed with brine solution, dried over Na$_2$SO$_4$ and concentrated to get crude. The crude compound was purified by silica gel (60-120 mesh) column [with a gradient elution of 0-1% of MeOH in DCM] to afford 1-(4-(6,7-dimethoxyquinazolin-4-yl)piperazin-1-yl)cyclopropanecarbonitrile (03) (350 mg, yield: 61%) as pale green solid. TLC system EtOAc:Hexane (30:70), R$_f$ value: 0.1; $^1$HNMR (400 MHz, DMSO-d$_6$) δ 8.57 (s, 1H), 7.24 (s, 1H), 7.13 (s, 1H), 3.93 (s, 6H), 3.60 (brs, 4H), 2.83 (t, J=4.8 Hz, 4H), 1.30-1.27 (m, 2H), 1.14-1.09 (m, 2H).

Synthesis of (1-(4-(6,7-dimethoxyquinazolin-4-yl)piperazin-1-yl)cyclopropyl)methanamine (04)

To a stirred solution of 1-(4-(6,7-dimethoxyquinazolin-4-yl)piperazin-1-yl)cyclopropanecarbonitrile (03) (350 mg, 1.03 mmol, 1.0 eq) in 7 M Methanolic ammonia (5 mL) was added Ra—Ni (150 mg) and stirred at room temperature for 16 h under hydrogen bladder pressure. After completion of reaction, the reaction mixture was filtered through Celite bed and washed with 10% MeOH in DCM. Filtrate was concentrated to afford (1-(4-(6,7-dimethoxyquinazolin-4-yl)piperazin-1-yl)cyclopropyl)methanamine (04) (330 mg, yield: 93%) as brown color liquid. TLC system MeOH: DCM (10:90), R$_f$ value: 0.1; LCMS (m/z): 344.3 (M+H)$^+$ Synthesis of tert-butyl N-((1-(4-(6,7-dimethoxyquinazolin-4-yl)piperazin-1-yl)cyclopropyl)methyl)sulfamoylcarbamate (05)

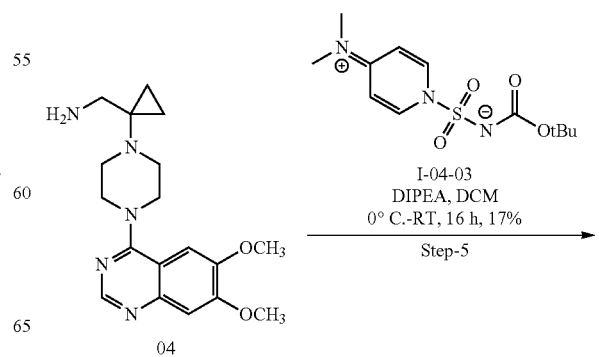

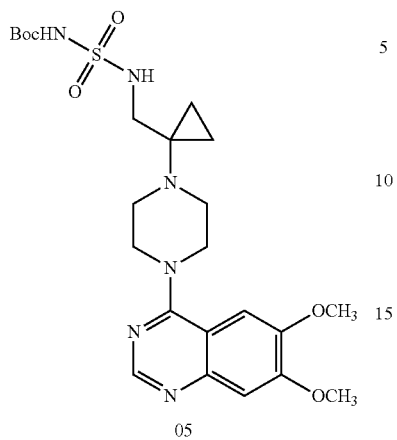

05

To a stirred solution of (1-(4-(6,7-dimethoxyquinazolin-4-yl)piperazin-1-yl)cyclopropyl)methanamine (04) (330 mg, 0.96 mmol, 1.0 eq) in DCM (5 mL) at 0° C. was added DIPEA (0.25 mL, 1.44 mmol, 1.5 eq) and (tert-butoxycarbonyl)((4-(dimethyliminio)pyridin-1(4H)-yl)sulfonyl)amide (I-04-03) (347 mg, 1.15 mmol, 1.2 eq). The reaction mixture was stirred at room temperature for 16 h. After completion of reaction by TLC, diluted with water and extracted with DCM (2×30 mL) Combined organic layer was washed with brine solution, dried over $Na_2SO_4$ and concentrated to get crude. The crude compound was purified by reverse phase column [with a gradient elution of 0-30% of ACN in $H_2O$] to afford tert-butyl N-((1-(4-(6,7-dimethoxyquinazolin-4-yl)piperazin-1-yl)cyclopropyl)methyl)sulfamoylcarbamate (05) (50 mg, yield: 17%) as white solid. TLC system MeOH:DCM (10:90), $R_f$ value: 0.5; LCMS (m/z): 523.4 (M+H)$^+$.

Synthesis of N-((1-(4-(6,7-dimethoxyquinazolin-4-yl)piperazin-1-yl)cyclopropyl)methyl)sulfuricdiamide (I-32)

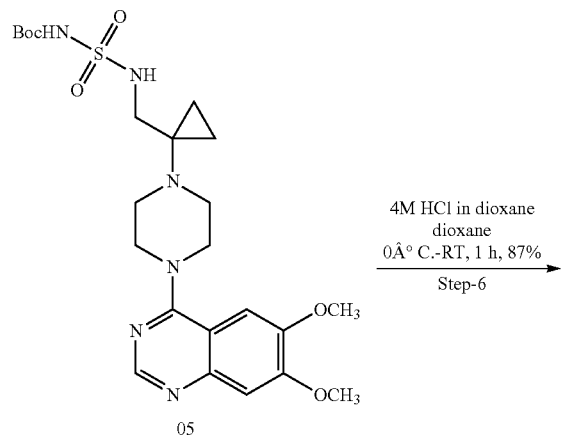

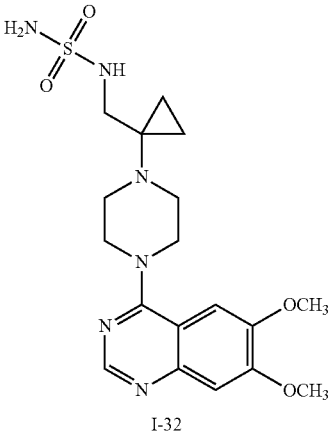

I-32

To a stirred solution of tert-butyl N-((1-(4-(6,7-dimethoxyquinazolin-4-yl)piperazin-1-yl)cyclopropyl)methyl)sulfamoylcarbamate (05) (50 mg, 0.09 mmol, 1.0 eq) in 1,4-dioxane (0.5 mL) at 0° C. was added 4M HCl in Dioxane (1 mL) and stirred at room temperature for 1 h. After completion of reaction by TLC, volatiles were evaporated and obtained crude was purified by grace reverse phase column chromatography [with a gradient elution of 0-30% of ACN in $H_2O$] to afford N-((1-(4-(6,7-dimethoxyquinazolin-4-yl)piperazin-1-yl)cyclopropyl)methyl)sulfuricdiamide (I-32) (35 mg, yield: 87%) as off-white solid. TLC system MeOH:DCM (10:90), $R_f$ value: 0.1; LCMS (m/z): 423.2 (M+H)$^+$; $^1$HNMR (400 MHz, DMSO-d$_6$) δ 8.52 (s, 1H), 7.21 (s, 1H), 7.14 (s, 1H), 6.46 (s, 2H), 6.39 (d, J=6.4 Hz, 1H), 3.92 and 3.01 (2s, 6H), 3.52 (brs, 4H), 3.07 (d, J=6.4 Hz, 2H), 2.92 (t, J=4.8 Hz, 4H), 0.66-0.64 (m, 2H), 0.54-0.52 (m, 2H).

Synthesis of I-33

Synthesis of N-benzyl-2-chloro-N-(2-chloroethyl)ethan-1-amine (01)

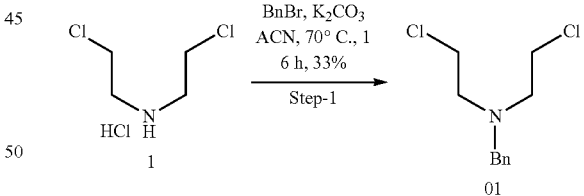

To a stirred solution of bis(2-chloroethyl)amine hydrochloride (1) (50 g, 281 mmol, 1 eq) in ACN (500 mL) was added $K_2CO_3$ (38 g, 281 mmol, 1 eq), BnBr (33 mL, 281 mmol, 1 eq) and stirred at 70° C. for 16 h. After completion of reaction by TLC, diluted with water (200 mL) and extracted with ethyl acetate (2×200 mL). Combined organic layer was dried over $Na_2SO_4$ and concentrated to get crude. The crude compound was purified by silica gel (60-120 mesh) column by eluting in hexane to afford N-benzyl-2-chloro-N-(2-chloroethyl)ethan-1-amine (01) (20 g, yield: 33%) as colorless liquid. TLC system hexane, $R_f$ value: 0.8; $^1$HNMR (400 MHz, CDCl$_3$) δ 7.34-7.32 (m, 4H), 7.30-7.27 (m, 1H), 3.74 (s, 2H), 3.50 (t, J=7.2 Hz, 4H), 2.93 (t, J=7.2 Hz, 4H).

Synthesis of ethyl 1-(4-benzylpiperazin-1-yl)cyclopropane-1-carboxylate (02)

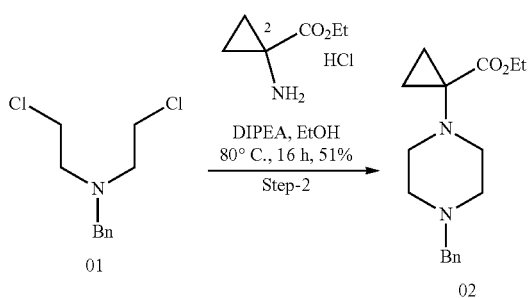 [SMILES: ClCCN(CCCl)Cc1ccccc1 ; CCOC(=O)C1(N)CC1 ; Cl ; CCOC(=O)C1(N2CCN(Cc3ccccc3)CC2)CC1]

To a stirred solution of N-benzyl-2-chloro-N-(2-chloroethyl)ethan-1-amine (01) (8 g, 34.4 mmol, 1 eq), in ethanol (160 mL) at room temperature was added DIPEA (80 mL, 10 Vol) and followed by the addition of ethyl 1-aminocyclopropane-1-carboxylate hydrogen chloride (2) (6.2 g, 37.9 mmol, 1.1 eq). The reaction mixture was stirred at 80° C. for 16 h. After completion of reaction by TLC, diluted with water (100 mL) and extracted with ethyl acetate (2×70 mL). Combined organic layer was dried over $Na_2SO_4$ and concentrated to get crude. The crude compound was purified by silica gel (60-120 mesh) column [with a gradient elution of 0-10% EtOAc in Hexane] to afford ethyl 1-(4-benzylpiperazin-1-yl)cyclopropane-1-carboxylate (02) (5.1 g, yield: 51%) as colorless liquid. TLC system EtOAc:Hexane (30:70), $R_f$ value: 0.4; $^1$HNMR (400 MHz, $CDCl_3$) δ 7.34-7.28 (m, 4H), 7.25-7.22 (m, 1H), 4.13 (q, J=7.2 Hz, 2H), 3.49 (s, 2H), 2.96 (brs, 4H), 2.35 (brs, 4H), 1.28-1.23 (m, 5H), 0.91-0.89 (m, 2H).

Synthesis of ethyl 1-(piperazin-1-yl)cyclopropane-1-carboxylate (03)

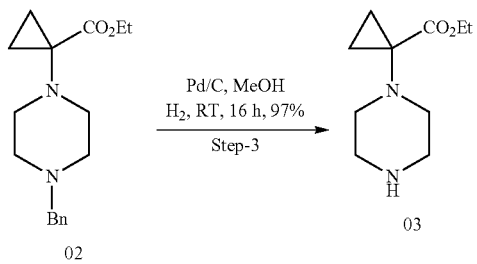 [SMILES: CCOC(=O)C1(N2CCN(Cc3ccccc3)CC2)CC1 ; CCOC(=O)C1(N2CCNCC2)CC1]

To a stirred solution of ethyl 1-(4-benzylpiperazin-1-yl)cyclopropane-1-carboxylate (02) (5.1 g, 17.7 mmol, 1.0 eq) in MeOH (50 mL) at room temperature was added 10% Pd/C (2 g). The reaction mixture was stirred for 16 h under hydrogen bladder pressure at RT. After completion of reaction, the reaction mixture was filtered through Celite bed and washed with ethyl acetate (2×50 mL). The filtrate was concentrated and dried to afford ethyl 1-(piperazin-1-yl)cyclopropane-1-carboxylate (03) (3.6 g, yield: 97%) as colorless liquid. TLC system EtOAc:Hexane (30:70), $R_f$ value: 0.1; LCMS (m/z): 199.2 (M+H)$^+$; $^1$HNMR (400 MHz, DMSO-$d_6$) δ 4.13 (q, J=7.2 Hz, 2H), 2.97 (brs, 4H), 2.86-2.81 (m, 4H), 2.70 (brs, 1H), 1.29-1.20 (m, 5H), 0.93-0.91 (m, 2H).

Synthesis of tert-butyl 4-(1-(ethoxycarbonyl)cyclopropyl)piperazine-1-carboxylate (04)

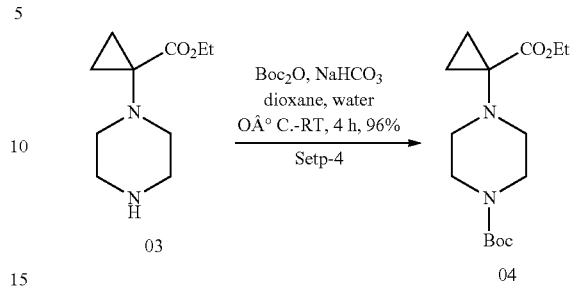

To a stirred solution of ethyl 1-(piperazin-1-yl)cyclopropane-1-carboxylate (03) (3.6 g, 18.8 mmol, 1.0 eq) in dioxane (90 mL) and water (45 mL) at 0° C. was added $NaHCO_3$ (4.2 g, 54.5 mmol, 3.0 eq) followed by addition of Boc-anhydride (3.7 mL, 18.8 mmol, 1.0 eq). The resulting reaction mixture was stirred at RT for 4 h. After completion of reaction, the reaction mixture was diluted with water and extracted with EtOAc (2×80 mL). Combined organic layer was dried over $Na_2SO_4$ and concentrated to get crude. The crude compound was purified by silica gel (60-120 mesh) column [with a gradient elution of 0-10% EtOAc in Hexane] to afford tert-butyl 4-(1-(ethoxycarbonyl)cyclopropyl)piperazine-1-carboxylate (04) (5 g, yield: 96%) as colorless liquid. TLC system EtOAc:Hexane (30:70), $R_f$ value: 0.1; $^1$HNMR (400 MHz, $CDCl_3$) δ 4.11 (q, J=7.2 Hz, 2H), 3.35-3.25 (br, 4H), 2.91-2.87 (brs, 4H), 1.46 (s, 9H), 1.29-1.27 (m, 2H), 1.25 (t, J=7.2 Hz, 3H), 0.95-0.92 (m, 2H).

Synthesis of tert-butyl 4-(1-(hydroxymethyl)cyclopropyl)piperazine-1-carboxylate (05)

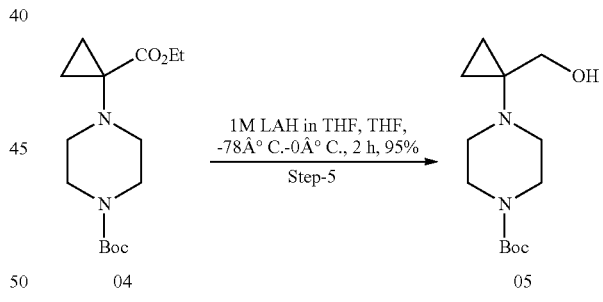

To a stirred solution of tert-butyl 4-(1-(ethoxycarbonyl)cyclopropyl)piperazine-1-carboxylate (04) (5 g, 16.7 mmol, 1.0 eq) in THF (50 mL) at −78° C., was added LAH (1.0 M in THF) (50 mL, 50.3 mmol, 3.0 eq). The reaction mixture was allowed to reach 0° C. and stirred for 2 h. After completion of reaction by TLC, quenched with saturated $NH_4Cl$ solution and filtered through Celite bed. The filtrate was extracted with EtOAc (3×60 mL), dried over $Na_2SO_4$ and concentrated under reduced pressure to afford tert-butyl 4-(1-(hydroxymethyl)cyclopropyl)piperazine-1-carboxylate (05) (4 g, yield: 95%) as off-white solid. TLC system EtOAc:Hexane (50:50), $R_f$ value: 0.4; LCMS (m/z): 257.2 (M+H)$^+$; $^1$HNMR (400 MHz, $CDCl_3$) δ 3.57 (d, J=3.6 Hz, 2H), 3.35 (t, J=5.2 Hz, 4H), 2.68 (t, J=5.2 Hz, 4H), 1.45 (s, 9H), 0.72-0.69 (m, 2H), 0.55-0.53 (m, 2H).

Synthesis of tert-butyl 4-(1-(bromomethyl)cyclopropyl)piperazine-1-carboxylate (06)

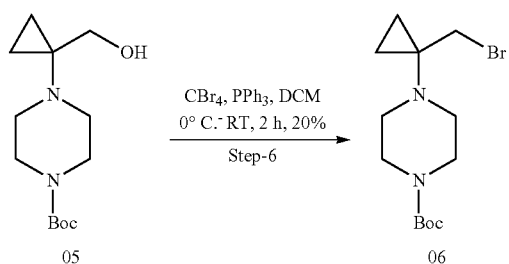 [SMILES: CC(C)(C)OC(=O)N1CCN(C2(CO)CC2)CC1 ; CC(C)(C)OC(=O)N1CCN(C2(CBr)CC2)CC1]

To a stirred solution of tert-butyl 4-(1-(hydroxymethyl)cyclopropyl)piperazine-1-carboxylate (05) (4 g, 15.6 mmol, 1.0 eq) in DCM (50 mL) at 0° C. was added PPh$_3$ (5.3 g, 20.3 mmol, 1.3 eq) and CBr$_4$ (6.7 g, 20.3 mmol, 1.3 eq) and stirred at room temperature for 2 h. After completion of reaction, diluted with water and extracted with DCM (3×50 mL). Combined organic layer was washed with brine solution, dried over Na$_2$SO$_4$ and concentrated to get crude. The crude compound was purified by silica gel (60-120 mesh) column [with a gradient elution of 0-2% EtOAc in Hexane] to afford tert-butyl 4-(1-(bromomethyl)cyclopropyl)piperazine-1-carboxylate (06) (1 g, yield: 20%) as colorless liquid. TLC system EtOAc:Hexane (30:70), R$_f$ value: 0.8; $^1$HNMR (400 MHz, CDCl$_3$) δ 3.55 (s, 2H), 3.35-3.31 (m, 4H), 2.79 (t, J=5.2 Hz, 4H), 1.46 (s, 9H), 0.95-0.92 (m, 2H), 0.79-0.75 (m, 2H).

Synthesis of tert-butyl 4-(1-(azidomethyl)cyclopropyl)piperazine-1-carboxylate (07)

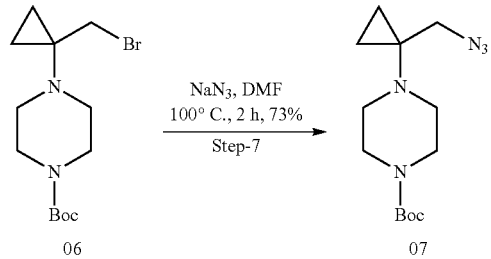 [SMILES: CC(C)(C)OC(=O)N1CCN(C2(CBr)CC2)CC1 ; CC(C)(C)OC(=O)N1CCN(C2(CN=[N+]=[N-])CC2)CC1]

To a stirred solution of tert-butyl 4-(1-(bromomethyl)cyclopropyl)piperazine-1-carboxylate (06) (1 g, 3.13 mmol, 1.0 eq) in DMF (10 mL) was added NaN$_3$ (0.244 g, 3.75 mmol, 1.2 eq) and stirred at 100° C. for 2 h. After completion of reaction, the reaction mixture was diluted with water and extracted with EtOAc (2×50 mL). Combined organic layer was washed with brine solution, dried over Na$_2$SO$_4$ and concentrated under reduced pressure to get crude. The crude compound was purified by silica gel (60-120 mesh) column [with a gradient elution of 0-5% EtOAc in Hexane] to afford tert-butyl 4-(1-(azidomethyl)cyclopropyl)piperazine-1-carboxylate (07) (650 mg, yield: 73%) as colorless liquid. TLC system EtOAc:Hexane (10:90), R$_f$ value: 0.4; $^1$HNMR (400 MHz, CDCl$_3$) δ 3.34 (t, J=5.2 Hz, 4H), 3.28 (s, 2H), 2.70 (t, J=5.2 Hz, 4H), 1.46 (s, 9H), 0.73-0.71 (m, 2H), 0.63-0.61 (m, 2H).

Synthesis of tert-butyl 4-(1-(aminomethyl)cyclopropyl)piperazine-1-carboxylate (08)

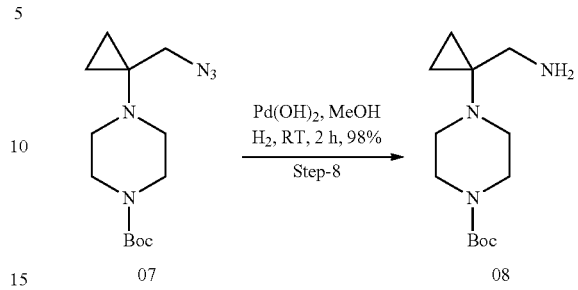

To a stirred solution of tert-butyl 4-(1-(azidomethyl)cyclopropyl)piperazine-1-carboxylate (07) (650 mg, 2.31 mmol, 1.0 eq) in MeOH (6 mL) was added Pd(OH)$_2$ (120 mg) and stirred at room temperature for 2 h under hydrogen bladder pressure. After completion of reaction, the reaction mixture was filtered through a Celite bed and washed with ethyl acetate (2×50 mL). Filtrate was evaporated under reduced pressure to afford tert-butyl 4-(1-(aminomethyl)cyclopropyl)piperazine-1-carboxylate (08) (640 mg, yield: 98%) as brown color liquid. TLC system MeOH:DCM (10:90), R$_f$ value: 0.1; $^1$HNMR (400 MHz, DMSO-d$_6$) δ 3.22-3.20 (m, 4H), 3.17 (s, 2H), 2.66 (s, 2H), 2.60 (t, J=5.2 Hz, 4H), 1.39 (s, 9H), 0.53-0.51 (m, 2H), 0.47-0.45 (m, 2H).

Synthesis of tert-butyl 4-(1-(((N-(tert-butoxycarbonyl)sulfamoyl)amino)methyl)cyclopropyl)piperazine-1-carboxylate (09)

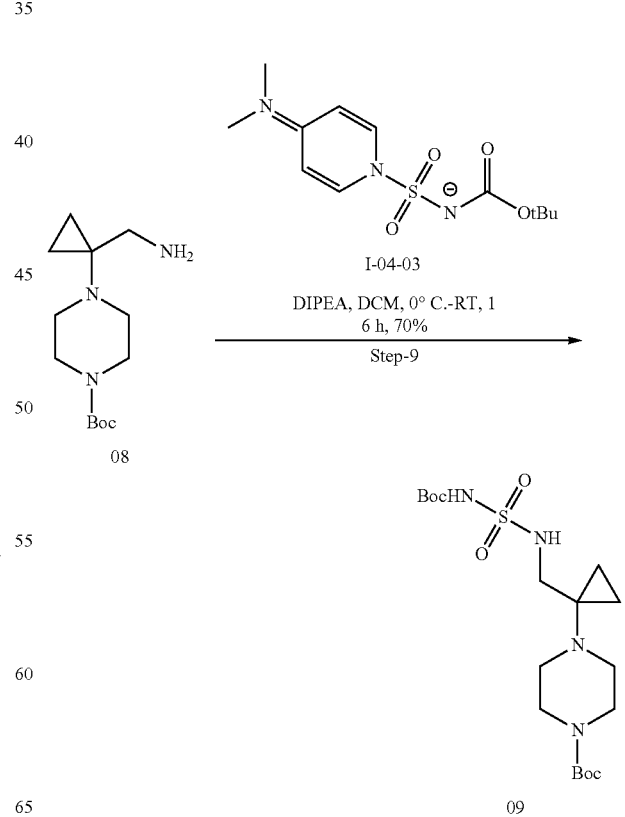

To a stirred solution of tert-butyl 4-(1-(aminomethyl) cyclopropyl)piperazine-1-carboxylate (08) (640 mg, 2.50 mmol, 1.0 eq) in DCM (10 mL) at 0° C. was added DIPEA (0.6 mL, 3.76 mmol, 1.5 eq) and (tert-butoxycarbonyl)((4-(dimethyliminio)pyridin-1(4H)-yl)sulfonyl)amide (I-04-03) (1 g, 3.01 mmol, 1.2 eq) and stirred at room temperature for 16 h. After completion of reaction by TLC, diluted with water and extracted with DCM (3×25 mL). Combined organic layer was washed with brine solution, dried over $Na_2SO_4$ and concentrated under reduced pressure to get crude. The crude compound was purified by silica gel (60-120 mesh) column [with a gradient elution of 10-25% EtOAc in Hexane] to afford tert-butyl 4-(1-(((N-(tert-butoxycarbonyl)sulfamoyl)amino)methyl)cyclopropyl)piperazine-1-carboxylate (09) (700 mg, yield: 70%) as white solid. TLC system EtOAc:Hexane (50:50), $R_f$ value: 0.3; $^1$HNMR (400 MHz, $CDCl_3$) δ 5.31-5.29 (m, 1H), 3.37-3.35 (m, 4H), 3.03 (d, J=5.2 Hz, 2H), 2.58 (t, J=5.2 Hz, 4H), 1.49 (s, 9H), 1.45 (s, 9H), 0.80-0.77 (m, 2H), 0.57-0.54 (m, 2H).

Synthesis of 4-(1-((sulfamoylamino)methyl)cyclopropyl)piperazine (10)

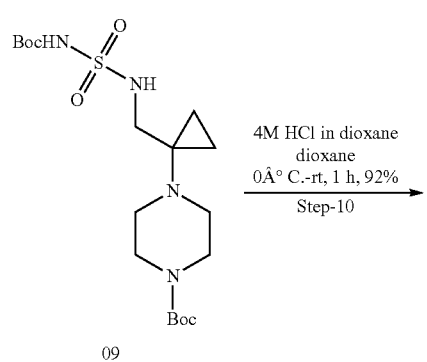

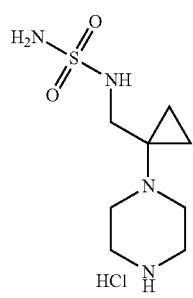

To a stirred solution of tert-butyl 4-(1-(((N-(tert-butoxycarbonyl)sulfamoyl)amino) methyl)cyclopropyl)piperazine-1-carboxylate (09) (700 mg, 1.61 mmol, 1.0 eq) in dioxane (5 mL) at 0° C. was added 4M HCl in Dioxane (5 mL) and stirred at room temperature for 1 h. After completion of reaction, volatiles were evaporated under reduced pressure and triturated with diethyl ether (2×5 mL) to afford 4-(1-((sulfamoylamino)methyl)cyclopropyl)piperazine hydrochloride (10) (350 mg, yield: 92%) as off-white solid. TLC system MeOH:DCM (10:90), $R_f$ value: 0.1; $^1$HNMR (400 MHz, DMSO-$d_6$) δ 8.76-8.73 (br, 2H), 6.63-6.51 (m, 3H), 3.32 (s, 2H), 3.09-2.95 (br, 8H), 0.69-0.60 (br, 4H). NMR was not clean however the material was taken forward to next step.

Synthesis of N-((1-(4-(7-methoxy-6-(methoxymethoxy)quinazolin-4-yl)piperazin-1-yl) cyclopropyl)methyl)sulfuricdiamide (I-33)

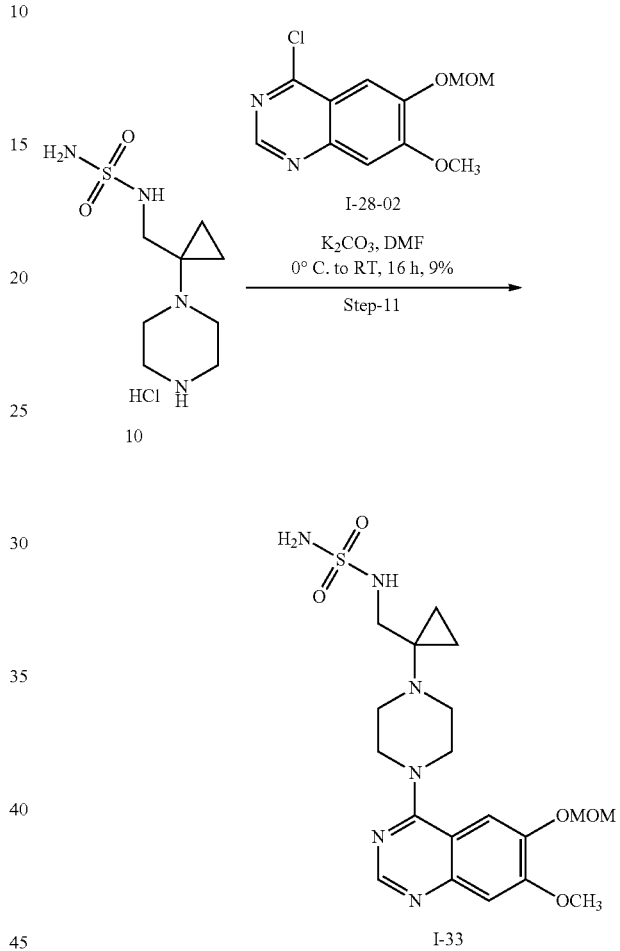

To a stirred solution of 4-chloro-7-methoxy-6-(methoxymethoxy)quinazoline (I-28-02) (150 mg, 0.59 mmol, 1.0 eq) in DMF (3 mL) at 0° C. was added $K_2CO_3$ (244 mg, 1.77 mmol, 3 eq) and 4-(11-((sulfamoylamino) methyl)cyclopropyl)piperazine hydrochloride (10) (207 mg, 0.76 mmol, 1.3 eq). The reaction mixture was stirred at room temperature for 16 h. After completion of reaction, diluted with ice cold water and extracted with EtOAc (2×10 mL). Combined organic layer was washed with brine solution, dried over $Na_2SO_4$ and concentrated to get crude. The crude was purified by giving trituration with 2% MeOH in ACN to afford N-((1-(4-(7-methoxy-6-(methoxymethoxy)quinazolin-4-yl)piperazin-1-yl)cyclopropyl)methyl)sulfuricdiamide (I-33) (25 mg, yield: 9%) as off white solid. TLC system MeOH:DCM (10:90), $R_f$ value: 0.4; LCMS (m/z): 453.3 (M+H)$^+$; $^1$HNMR (400 MHz, DMSO-d) δ 8.52 (s, 1H), 7.44 (s, 1H), 7.24 (s, 1H), 6.45 (s, 2H), 6.37 (t, J=5.2 Hz, 1H), 5.31 (s, 2H), 3.94 (s, 3H), 3.52 (brs, 4H), 3.44 (s, 3H), 3.06 (d, J=5.2 Hz, 2H), 2.90 (t, J=4.8 Hz, 4H), 0.65-0.64 (m, 2H), 0.53-0.52 (m, 2H).

Synthesis of I-34

Synthesis of 4-chloro-6-(fluoromethoxy)-7-methoxyquinazoline (01)

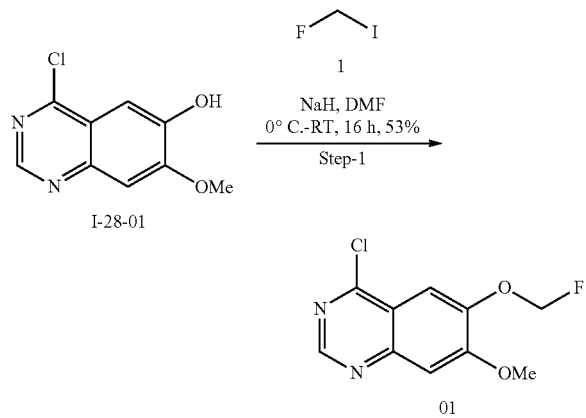

To a stirred solution of 4-chloro-7-methoxyquinazolin-6-ol (I-28-01) (500 mg, 2.38 mmol, 1.0 eq) in DMF (5 mL) at 0° C. was added NaH (60%) (86 mg, 3.57 mmol, 1.5 eq) and 2 M fluoroiodomethane in ACN (1) (1.4 mL, 2.85 mmol, 1.2 eq). The reaction mixture was stirred at RT for 16 h. After completion of reaction by TLC, diluted with water and extracted with EtOAc (2×25 mL). Organic layer was dried over $Na_2SO_4$ and concentrated to provide crude. The crude compound was purified by silica gel column (60-120 mesh) chromatography [with a gradient elution of 0-1% of MeOH in DCM] to afford 4-chloro-6-(fluoromethoxy)-7-methoxyquinazoline (01) (310 mg, yield: 53%) as off-white solid. TLC system EtOAc:Hexane (50:50), $R_f$ value: 0.3; LCMS (m/z): 243.0 (M+H)⁺; ¹HNMR (400 MHz, CDCl₃) δ 8.93 (s, 1H), 7.81 (s, 1H), 7.41 (s, 1H), 5.87 (d, J=53.2 Hz, 2H), 4.08 (s, 3H).

Synthesis of N-((1-(4-(6-(fluoromethoxy)-7-methoxyquinazolin-4-yl)piperazin-1-yl)cyclopropyl)methyl)sulfuricdiamide (I-34)

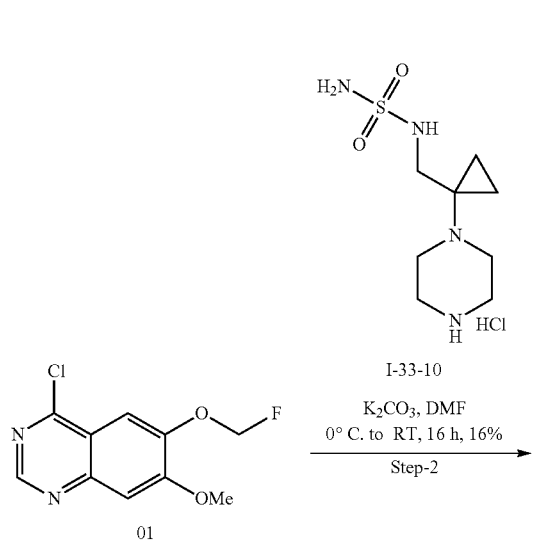

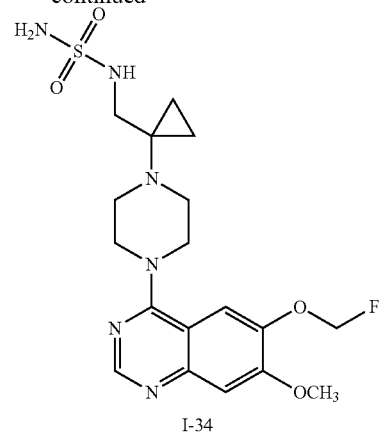

To a stirred solution of 4-chloro-6-(fluoromethoxy)-7-methoxyquinazoline (01) (150 mg, 0.61 mmol, 1.0 eq) in DMF (3 mL) at 0° C. was added $K_2CO_3$ (256 mg, 1.85 mmol, 3 eq) and 4-(1-((sulfamoylamino)methyl)cyclopropyl)piperazine hydro chloride (I-33-10) (217 mg, 0.79 mmol, 1.3 eq). The reaction mixture was stirred at room temperature for 16 h. After completion of reaction by TLC, diluted with ice cold water and extracted with EtOAc (2×10 mL). Organic layer was dried over $Na_2SO_4$ and concentrated to provide crude. The crude compound was purified by trituration with 2% methanol in ACN to afford N-((1-(4-(6-(fluoromethoxy)-7-methoxyquinazolin-4-yl)piperazin-1-yl)cyclopropyl)methyl)sulfuricdiamide (I-34) (45 mg, yield: 16%) as off white solid. TLC system MeOH:DCM (10:90), $R_f$ value: 0.4; LCMS (m/z): 441.3 (M+H); ¹HNMR (400 MHz, DMSO-d₆) δ 8.55 (s, 1H), 7.50 (s, 1H), 7.30 (s, 1H), 6.45 (s, 2H), 6.37 (t, J=6.4 Hz, 1H), 6.00 (d, J=54 Hz, 2H), 3.96 (s, 3H), 3.56 (brs, 4H), 3.06 (d, J=6.4 Hz, 2H), 2.90 (t, J=4.4 Hz, 4H), 0.66-0.64 (m, 2H), 0.54-0.52 (m, 2H).

Synthesis of I-35

Synthesis of tert-butyl 4-(1-(ethoxycarbonyl)cyclopropyl)piperidine-1-carboxylate (01)

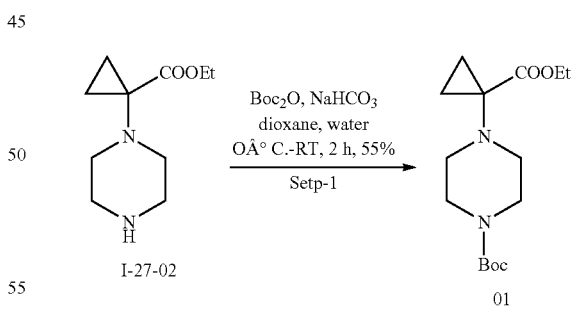

To a stirred solution of ethyl 1-(piperidin-4-yl) cyclopropane-1-carboxylate (I-27-02) (4 g, 20.3 mmol, 1 eq) in 1,4-Dioxane & water (2:1) cooled to 0° C., added NaHCO₃ (5.1 g, 60.8 mmol, 3.0 eq) and (Boc₂)O (4.65 mL, 20.3 mmol, 1.0 eq). The reaction mixture was stirred at room temperature for 2 h. After completion of reaction by TLC, the reaction mixture was diluted with water and extracted with EtOAc (2×80 mL). The combined organic layer was washed with brine solution (30 mL), dried over sodium sulfate and concentrated under reduced pressure to afford crude. The crude compound was purified by silica gel (60-120 mesh) column chromatography [eluting with 5% EtOAc in Hexane] to afford tert-butyl 4-(1-(ethoxycarbonyl)cyclopropyl) piperidine-1-carboxylate (01) (3.3 g, yield: 55%) as colorless gummy liquid. TLC system: EtOAc in Hexane (30:70), $R_{f\ value}$: 0.8; Direct mass (m/z): 242.0 $(M+H-tBu)^+$.

Synthesis of tert-butyl 4-(1-(hydroxymethyl)cyclopropyl)piperidine-1-carboxylate (02)

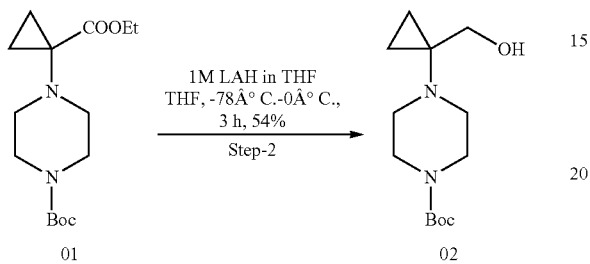

To a stirred solution of tert-butyl 4-(1-(ethoxycarbonyl)cyclopropyl)piperidine-1-carboxylate (01) (3.3 g, 11.1 mmol, 1 eq) in THF (35 mL) at −78° C. was added 1.0 M LAH in THF (33 mL, 33.3 mmol, 3 eq). The reaction mixture was allowed to reach 0° C. in 3 h. After completion of reaction by TLC, the reaction mixture was quenched with saturated NH$_4$Cl solution, extracted with EtOAc (3×80 mL). The combined organic layer was washed with brine solution (50 mL) dried over sodium sulfate and concentrated under reduced pressure to provide crude. The crude compound was purified by silica gel (60-120 mesh) column chromatography [with a gradient elution of 0-30% EtOAc in Hexane] to afford tert-butyl 4-(1-(hydroxymethyl)cyclopropyl)piperidine-1-carboxylate (02) (1.5 g, yield: 54%) as colorless gummy liquid TLC system: EtOAc in Hexane (50:50), $R_f$ value: 0.3; $^1$HNMR (400 MHz, CDCl$_3$) δ 4.19-4.17 (m, 2H), 3.62 (brs, 2H), 2.63-2.56 (m, 2H), 1.64-1.58 (m, 4H), 1.45 (s, 9H), 1.38-1.36 (m, 1H), 0.43-0.36 (m, 4H).

Synthesis tert-butyl 4-(1-(azidomethyl)cyclopropyl)piperidine-1-carboxylate (03)

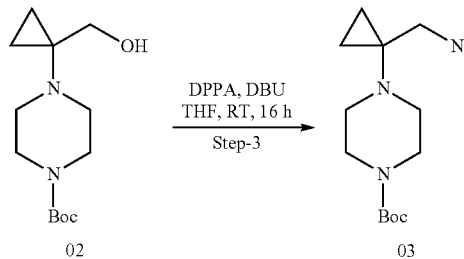

To a stirred solution of tert-butyl 4-(1-(hydroxymethyl)cyclopropyl)piperidine-1-carboxylate (02) (1.4 g, 5.49 mmol, 1 eq) in THF (14 mL) cooled to 0° C., added DBU (6.6 mL, 43.9 mmol, 8 eq), and DPPA (5.9 mL, 27.4 mmol, 5 eq). The reaction mixture was stirred at room temperature for 16 h. After completion of reaction, the reaction mixture was diluted with water and extracted with EtOAc (2×70 mL). The combined organic layer was washed with brine solution (40 mL) dried over sodium sulfate and concentrated under reduced pressure to provide crude. The crude compound was purified by silica gel (60-120 mesh) column chromatography [eluting with 5% EtOAc in Hexane] to afford tert-butyl 4-(1-(azidomethyl)cyclopropyl)piperidine-1-carboxylate (03) (1.9 g) as colorless liquid. TLC system: EtOAc in Hexane (50:50), $R_{f\ value}$: 0.8; Direct mass (m/z): 225.1 $(M+H-tBu)^+$.

Synthesis tert-butyl 4-(1-(aminomethyl)cyclopropyl)piperidine-1-carboxylate (04)

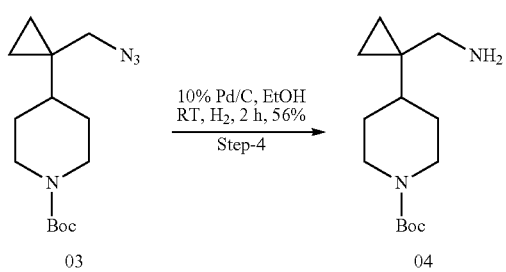 [SMILES: CC(C)(C)OC(=O)N1CCC(C2(CN=[N+]=[N-])CC2)CC1 ; "10% Pd/C, EtOHRT, H2, 2 h, 56%" ; "Step-4" ; CC(C)(C)OC(=O)N1CCC(C2(CN)CC2)CC1]

To a stirred solution of tert-butyl 4-(1-(azidomethyl)cyclopropyl)piperidine-1-carboxylate (03) (1.9 g, 6.78 mmol, 1 eq) in MeOH (20 mL) was added 10% Pd/C (500 mg) and stirred at room temperature for 2 h under H$_2$ balloon pressure. After completion of reaction by TLC, the reaction mixture was filtered through Celite pad and washed with ethanol. Collected filtrate was concentrated under reduced pressure to provide crude. The crude compound was purified by silica gel (60-120 mesh) column chromatography [with a gradient elution of 0-10% MeOH in DCM] to afford tert-butyl 4-(1-(aminomethyl)cyclopropyl)piperidine-1-carboxylate (04) (950 mg, yield: 56%) as a colorless gummy liquid. TLC system: EtOAc in Hexane (50:50), $R_{f\ value}$: 0.1; Direct mass (m/z): 255.2 $(M+H)^+$.

Synthesis of tert-butyl 4-(1-(((N-(tert-butoxycarbonyl)sulfamoyl)amino)methyl)cyclopropyl)piperidine-1-carboxylate (05)

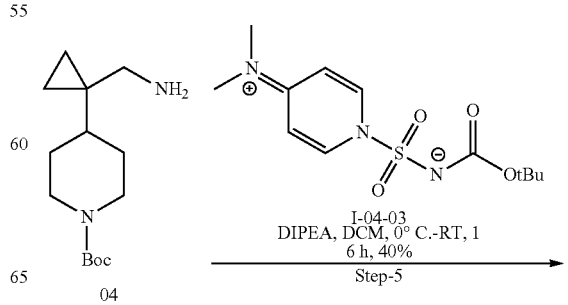

-continued

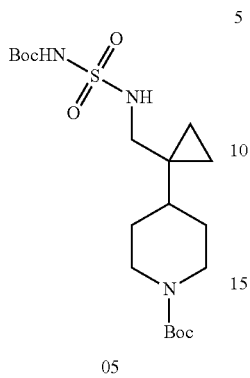

05

To a stirred solution of tert-butyl 4-(1-(aminomethyl) cyclopropyl)piperidine-1-carboxylate (04) (900 mg, 3.54 mmol, 1 eq) in DCM (9 mL) at 0° C. was added DIPEA (0.95 mL, 5.31 mmol, 1.5 eq), (tert-butoxycarbonyl)((4-(dimethyliminio)pyridin-1(4H)-yl)sulfonyl)amide (I-04-03) (1.27 g, 4.25 mmol, 1.2 eq). The reaction mixture was stirred at room temperature for 16 h, After completion of reaction by TLC, reaction mixture was diluted with water and extracted with DCM (2×50 mL). The combined organic layer was washed with brine solution (20 mL) dried over sodium sulfate and concentrated under reduced pressure to get crude compound. The crude compound was purified by silica gel (60-120 mesh) column chromatography [with a gradient elution of 10-30% EtOAc in Hexane] to afford tert-butyl 4-(1-(((N-(tert-butoxycarbonyl)sulfamoyl)amino) methyl)cyclopropyl)piperidine-1-carboxylate (05) (600 mg, yield: 40%) as white solid. TLC system: EtOAc in Hexane (50:50), $R_f$ value: 0.7; $^1$HNMR (400 MHz, CDCl$_3$) δ 6.96 (s, 1H), 4.99 (t, J=6.0 Hz, 1H), 4.15 (brs, 2H), 2.90 (brs, 2H), 2.63-6.57 (m, 2H), 1.49 (s, 9H), 1.45 (s, 9H), 1.37-1.20 (m, 5H), 0.50-0.48 (m, 2H), 0.40-0.37 (m, 2H).

Synthesis of 4-(1-((sulfamoylamino)methyl)cyclo-propyl)piperidine hydrochloride (06)

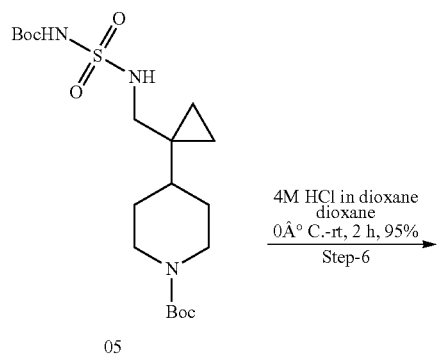

-continued

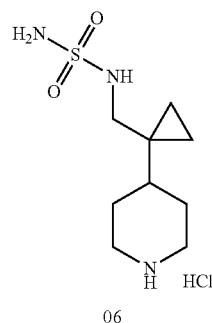

06

To a stirred solution of tert-butyl 4-(1-(((N-(tert-butoxycarbonyl)sulfamoyl)amino)methyl)cyclopropyl)piperidine-1-carboxylate (05) (600 mg, 1.43 mmol, 1 eq) in 1,4 Dioxane (6 mL) at 0° C. was added 4M Dioxane.HCl (2 mL) slowly drop-wise and stirred at room temperature for 2 h. After completion of reaction by TLC, reaction mixture was concentrated and triturated with n-pentane & diethyl ether to afford 4-(1-((sulfamoylamino)methyl)cyclopropyl)piperidine hydrochloride (06) (300 mg, yield: 95%) as an off-white gummy solid. TLC system EtOAc (100; Ninhydrin stain), $R_f$ value: 0.1; $^1$HNMR (400 MHz, DMSO-d$_6$) δ 8.81-8.74 (m, 1H), 8.37-8.35 (m, 1H), 6.54-6.45 (brs, 3H), 3.27-3.24 (m, 2H), 2.79-2.67 (m, 4H), 1.72-1.69 (m, 2H), 1.59-1.42 (m, 2H), 1.24-1.21 (m, 1H), 0.39-0.29 (m, 4H).

Synthesis of N-((1-(1-(7-methoxy-6-(methoxymethoxy)quinazolin-4-yl)piperidin-4-yl) cyclopropyl)methyl)sulfuricdiamide (I-35)

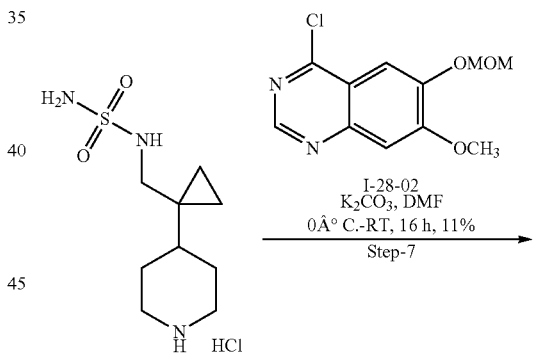

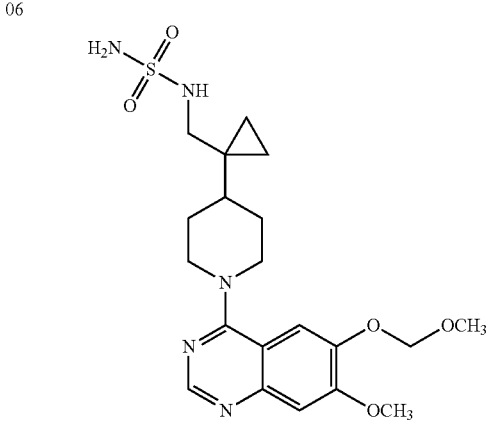

I-35

To a stirred solution of 4-chloro-7-methoxy-6-(methoxymethoxy)quinazoline (I-28-02) (150 mg, 0.59 mmol, 1 eq) in DMF (1.5 mL) at 0° C. was added K₂CO₃ (244 mg, 1.77 mmol, 3 eq) and 4-(1-((sulfamoylamino)methyl)cyclopropyl)piperidine hydrochloride (06) (193 mg, 0.88 mmol, 1.5 eq) and stirred at room temperature for 16 h. After completion of reaction, the reaction mixture was diluted with ice cold water and extracted with EtOAc (2×50 mL). The combined organic layer was washed with brine solution (30 mL) dried over sodium sulfate and concentrated under reduced pressure to afford crude. The crude compound was purified by reverse phase (2-times) column [with a gradient elution of 10-50% ACN in 0.1% FA in water] provided I-35 with 86% purity. Obtained compound was further purified by Prep-HPLC to afford N-((1-(1-(7-methoxy-6-(methoxymethoxy)quinazolin-4-yl)piperidin-4-yl)cyclopropyl)methyl)sulfuricdiamide (I-35) (30 mg, yield: 11%) as white solid. TLC system: EtOAc, R$_f$ value: 0.2; LCMS (m/z): 452.3 (M+H)⁺; ¹HNMR (400 MHz, DMSO-d₆) δ 8.50 (s, 1H), 7.43 (s, 1H), 7.22 (s, 1H), 6.43 (brs, 3H), 5.30 (s, 2H), 4.21 (d, J=8.4 Hz, 2H), 3.94 (s, 3H), 3.44 (s, 3H), 2.97-2.91 (m, 2H), 2.85 (s, 2H), 1.73-1.70 (m, 2H), 1.60-1.57 (m, 1H), 1.47-1.42 (m, 2H), 0.39-0.36 (m, 4H).

Synthesis of I-36

Synthesis of tert-butyl 4-(1-amino-2-methylpropan-2-yl)piperidine-1-carboxylate (01)

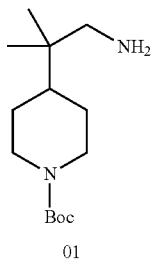

To a stirred solution of tert-butyl 4-(2-cyanopropan-2-yl)piperidine-1-carboxylate (I-14-01) (1.5 g, 5.95 mmol, 1.0 eq) in 7 M Methanolic ammonia (15 mL) was added Ra—Ni (500 mg) and stirred at room temperature for 16 h under hydrogen bladder pressure. After completion of reaction, the reaction mixture was filtered through Celite bed and washed with 10% MeOH:DCM. Filtrate was evaporated under reduced pressure to afford tert-butyl 4-(1-amino-2-methylpropan-2-yl)piperidine-1-carboxylate (01) (1.4 g, yield: 93%) as brown color liquid. TLC system MeOH:DCM (10:90), R$_f$ value: 0.1; ¹HNMR (400 MHz, DMSO-d₆) δ 4.01-3.98 (m, 2H), 2.62-2.57 (brs, 2H), 2.27-2.24 (m, 2H), 1.57-1.53 (m, 2H), 1.38 (s, 10H), 1.05-1.02 (m, 2H), 0.76 (s, 6H).

Synthesis of tert-butyl 4-(1-((N-(tert-butoxycarbonyl)sulfamoyl)amino)-2-methylpropan-2-yl)piperidine-1-carboxylate (02)

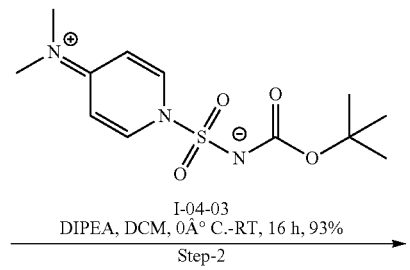

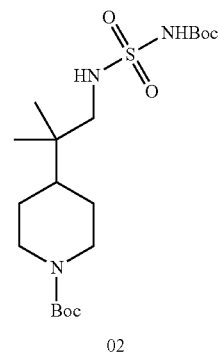

To a stirred solution of tert-butyl 4-(1-amino-2-methylpropan-2-yl)piperidine-1-carboxylate (01) (1.4 g, 5.46 mmol, 1.0 eq) in DCM (15 mL) at 0° C. was added DIPEA (1.5 mL, 8.20 mmol, 1.5 eq) and (tert-butoxycarbonyl)((4-(dimethyliminio)pyridin-1(4H)-yl)sulfonyl)amide (I-04-03) (1.97 g, 6.56 mmol, 1.2 eq) and stirred at room temperature for 16 h. After completion of reaction by TLC, diluted with water and extracted with DCM (3×50 mL). Combined organic layer was washed with brine solution, dried over Na₂SO₄ and concentrated to get crude. The crude was purified by silica gel (60-120 mesh) column chromatography [with a gradient elution of 20-30% EtOAc in Hexane] to afford tert-butyl 4-(1-((N-(tert-butoxycarbonyl)sulfamoyl)amino)-2-methylpropan-2-yl)piperidine-1-carboxylate (02) (2.1 g, yield: 93%) as colorless gummy liquid. TLC system EtOAc:Hexane (50:50), R$_f$ value: 0.4; ¹HNMR (400 MHz, DMSO-d₆) δ 10.76 (s, 1H), 7.39 (t, J=6.8 Hz, 1H), 4.00-3.96 (m, 2H), 2.72 (d, J=6.8 Hz, 2H), 2.63-2.55 (m, 2H), 1.58-1.55 (m, 2H), 1.42 (s, 9H), 1.37-1.35 (m, 10H), 1.04-0.97 (m, 2H), 0.77 (s, 6H).

Synthesis of 4-(2-methyl-1-(sulfamoylamino)propan-2-yl)piperidine hydrochloride (03)

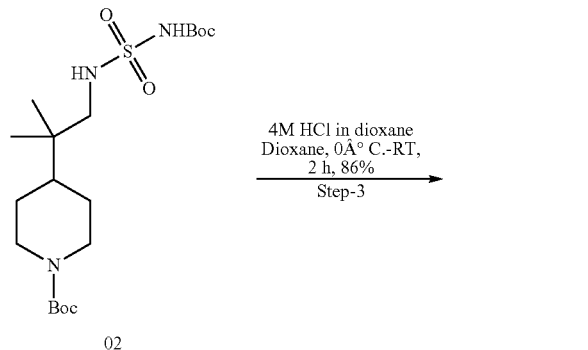

To a stirred solution of tert-butyl 4-(1-((N-(tert-butoxycarbonyl)sulfamoyl)amino)-2-methylpropan-2-yl)piperidine-1-carboxylate (02) (1.5 g, 3.44 mmol, 1.0 eq) in 1,4-dioxane (1 mL) at 0° C. was added 4M HCl in Dioxane (1 mL) and stirred at room temperature for 2 h. After completion of reaction by TLC, volatiles were evaporated to afford 4-(2-methyl-1-(sulfamoylamino)propan-2-yl)piperidine (03) (700 mg, yield: 86%) as colorless gummy liquid. TLC system MeOH:DCM (10:90), $R_f$ value: 0.1; $^1$HNMR (400 MHz, DMSO-d$_6$) δ 8.96 (s, 1H), 8.69 (s, 1H), 6.48-6.39 (m, 3H), 3.27-3.24 (m, 2H), 2.79-2.74 (m, 2H), 2.70 (d, J=6.0 Hz, 2H), 1.75-1.68 (m, 2H), 1.50-1.41 (m, 3H), 0.78 (s, 6H).

Synthesis of N-(2-(1-(7-methoxy-6-(methoxymethoxy)quinazolin-4-yl)piperidin-4-yl)-2-methylpropyl)sulfuricdiamide (I-36)

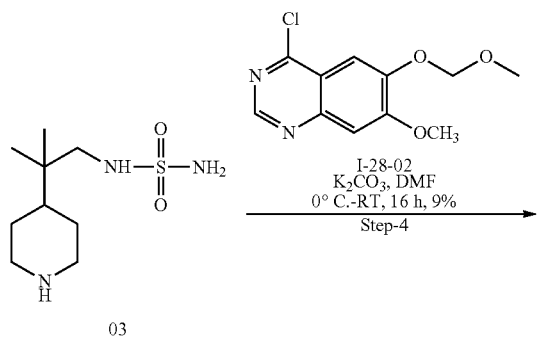

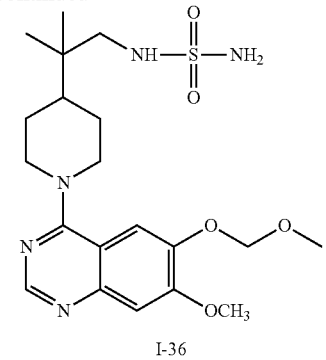

To a stirred solution of 4-chloro-7-methoxy-6-(methoxymethoxy)quinazoline (I-28-02) (250 mg, 0.98 mmol, 1.0 eq) in DMF (5 mL) at 0° C. was added K$_2$CO$_3$ (407 mg, 2.95 mmol, 3.0 eq) followed by addition of 4-(2-methyl-1-(sulfamoylamino)propan-2-yl)piperidine (03) (300 mg, 1.27 mmol, 1.3 eq). The resulting mixture was stirred at room temperature for 16 h. After completion of reaction by TLC, reaction mixture was diluted with ice cold water and stirred for 30 min. Precipitated solid was filtered, washed with diethyl ether and dried under vacuum to afford N-(2-(1-(7-methoxy-6-(methoxymethoxy)quinazolin-4-yl)piperidin-4-yl)-2-methylpropyl)sulfuricdiamide (I-36) (42 mg, yield: 9%) as an off-white solid. TLC system MeOH:DCM (10:90), $R_f$ value: 0.5; LCMS (m/z): 454.3 (M+H)$^+$; $^1$HNMR (400 MHz, DMSO-d) δ 8.50 (s, 1H), 7.44 (s, 1H), 7.22 (s, 1H), 7.44 (s, 2H), 6.36 (s, 1H), 5.31 (s, 2H), 4.25-4.22 (m, 2H), 3.94 (s, 3H), 3.44 (s, 3H), 2.97 (t, J=11.6 Hz, 2H), 2.75 (s, 2H), 1.77-1.74 (m, 2H), 1.57-1.54 (m, 1H), 1.42-1.38 (m, 2H), 0.83 (s, 6H).

Synthesis of I-37

Synthesis of 4-(1-(azidomethyl)cyclopropyl)piperidine hydrochloride (01)

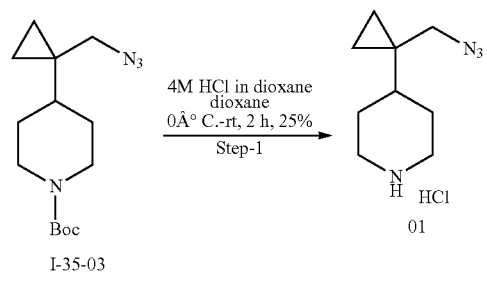

To a stirred solution of tert-butyl 4-(1-(azidomethyl)cyclopropyl)piperidine-1-carboxylate (I-35-03) (1.7 g (crude), 6.07 mmol, 1 eq) in 1,4 Dioxane (17 mL) at 0° C. was added 4M Dioxane.HCl (17 mL) slowly drop-wise and stirred at room temperature for 2 h. After completion of reaction by TLC, reaction mixture was concentrated and triturated with diethyl ether to afford tert-butyl 4-(1-(azidomethyl)cyclopropyl)piperidine hydrochloride (01) (400 mg, yield: 25%) as an off-white gummy solid. TLC system EtOAc in Hexane (50:50, Ninhydrin stain), $R_f$ value: 0.1; Direct mass (m/z): 181.2 (M+H)$^+$, $^1$HNMR (400 MHz,

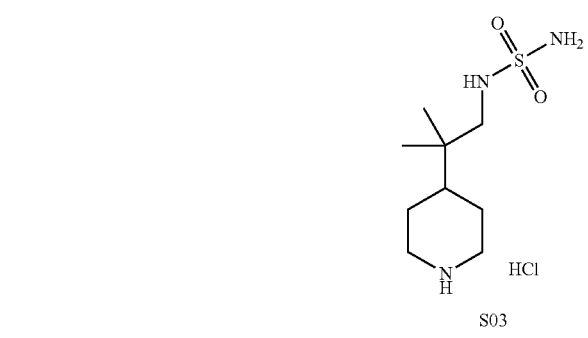

DMSO-d$_6$) δ 8.92-8.57 (br, 2H), 3.27-3.24 (m, 4H), 2.80-2.73 (m, 2H), 1.75-1.71 (m, 2H), 1.60-1.48 (m, 2H), 1.37-1.30 (m, 1H), 0.49-0.45 (m, 4H).

Synthesis of 4-chloro-6-(fluoromethoxy)-7-methoxyquinoline (02)

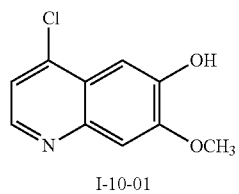
I-10-01

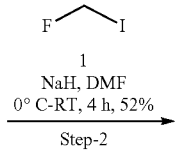
1
NaH, DMF
0° C-RT, 4 h, 52%
Step-2

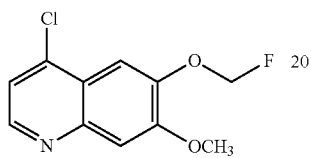
02

To a stirred solution of 4-chloro-7-methoxyquinolin-6-ol (I-10-01) (500 mg, 2.39 mmol, 1 eq) in DMF (5 mL) at 0° C. was added NaH (83 mg, 3.58 mmol, 1.5 eq) and stirred for 15 min. Later added fluoroiodomethane (ca. 2 mol/L in Acetonitrile) (1.4 mL, 2.85 mmol, 1.2 eq) drop-wise for 10 min at 0° C. The reaction mixture was stirred at room temperature for 4 h. After completion of reaction by TLC, reaction mixture was quenched with cold water and extracted with EtOAc (2×80 mL). The combined organic layer was washed with brine solution (30 mL) dried over sodium sulfate and concentrated under reduced pressure to provide crude. The crude compound was purified by silica gel (60-120 mesh) column chromatography [eluting with 30% EtOAc in Hexane] to afford 4-chloro-6-(fluoromethoxy)-7-methoxyquinoline (02) (300 mg, yield: 52%) as an off-white solid, TLC system: EtOAc (100), R$_f$ value: 0.3; LCMS (m/z): 242 (M+H)$^+$, $^1$HNMR (400 MHz, CDCl$_3$) δ 8.65 (d, J=4.8 Hz, 1H), 7.82 (s, 1H), 7.50 (s, 1H), 7.39 (d, J=4.8 Hz, 1H), 5.91 (d, J=53.6 Hz, 2H), 4.05 (s, 3H).

Synthesis 4-(4-(1-(azidomethyl)cyclopropyl)piperidin-1-yl)-6-(fluoromethoxy)-7-methoxyquinoline (03)

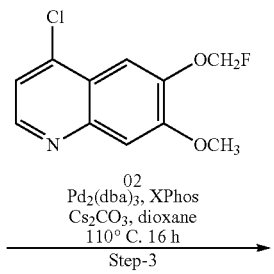
01

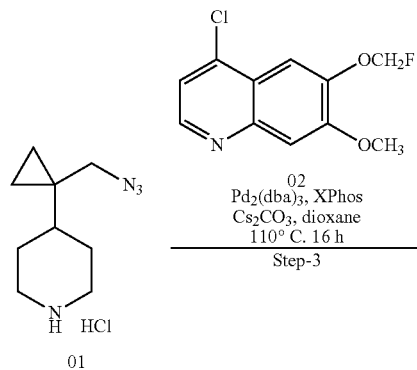
02
Pd$_2$(dba)$_3$, XPhos
Cs$_2$CO$_3$, dioxane
110° C. 16 h
Step-3

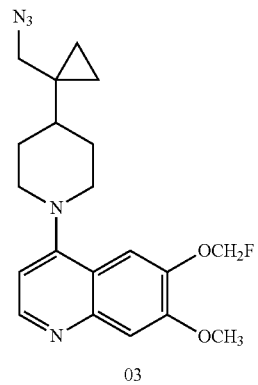
03

To a stirred, degassed solution of 4-chloro-6-(fluoromethoxy)-7-methoxyquinoline (02) (300 mg, 1.24 mmol, 1.0 eq) and 4-(1-(azidomethyl)cyclopropyl)piperidine hydrochloride (01) (322 mg, 1.49 mmol, 1.2 eq) in 1,4-Dioxane (3 mL) was added Cs$_2$CO$_3$ (1.2 g, 3.73 mmol, 3.0 eq) and X-Phos (114 mg, 0.24 mmol, 0.2 eq) and Pd$_2$(dba)$_3$ (114 mg, 0.12 mmol, 0.1 eq). The reaction mixture was stirred at 110° C. for 16 h. After completion of reaction by TLC, the reaction mixture was quenched with cold water, extracted with EtOAc (2×80 mL). The combined organic layer was washed with brine solution (50 mL) dried over sodium sulfate and concentrated under reduced pressure to afford 4-(4-(1-(azidomethyl)cyclopropyl)piperidin-1-yl)-6-(fluoromethoxy)-7-methoxyquinoline (03) (480 mg, 78% purity) as brown color gummy solid. TLC system MeOH: DCM (10:90), R$_f$ value: 0.4; LCMS (m/z): 386.3 (M+H)$^+$. The material was taken forward to next step without purification.

Synthesis (1-(1-(6-(fluoromethoxy)-7-methoxyquinolin-4-yl)piperidin-4-yl)cyclopropyl)methanamine (04)

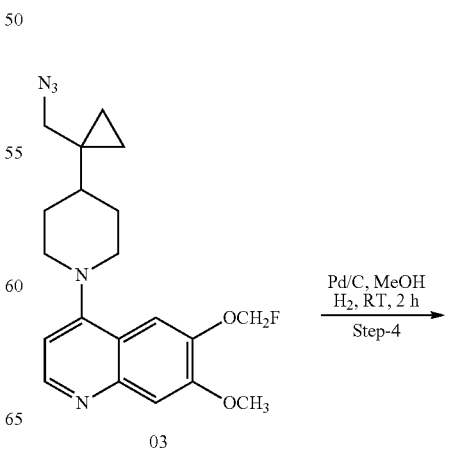
03
Pd/C, MeOH
H$_2$, RT, 2 h
Step-4

-continued

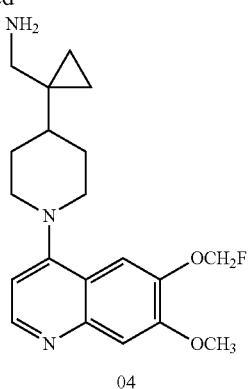

04

To a stirred solution of 4-(4-(1-(azidomethyl)cyclopropyl)piperidin-1-yl)-6-(fluoromethoxy)-7-methoxyquinoline (03) (480 mg, 1.24 mmol, 1 eq) in MeOH (5 mL) was added 10% Pd/C (100 mg) and stirred at room temperature for 2 h under H$_2$ balloon pressure. After completion of reaction by TLC, the reaction mixture was filtered through Celite pad and concentrated under reduced pressure to afford (1-(1-(6-(fluoromethoxy)-7-methoxyquinolin-4-yl)piperidin-4-yl)cyclopropyl)methanamine (04) (480 mg, 45% purity) as brown gummy solid. TLC system: MeOH:DCM (10:90), R$_f$ value: 0.1; LCMS (m/z): 360.2 (M+H)$^+$. The material was taken forward to next step without purification.

Synthesis of tert-butyl (N-((1-(1-(6-(fluoromethoxy)-7-methoxyquinolin-4-yl)piperidin-4-yl)cyclopropyl)methyl)sulfamyl)carbamate (05)

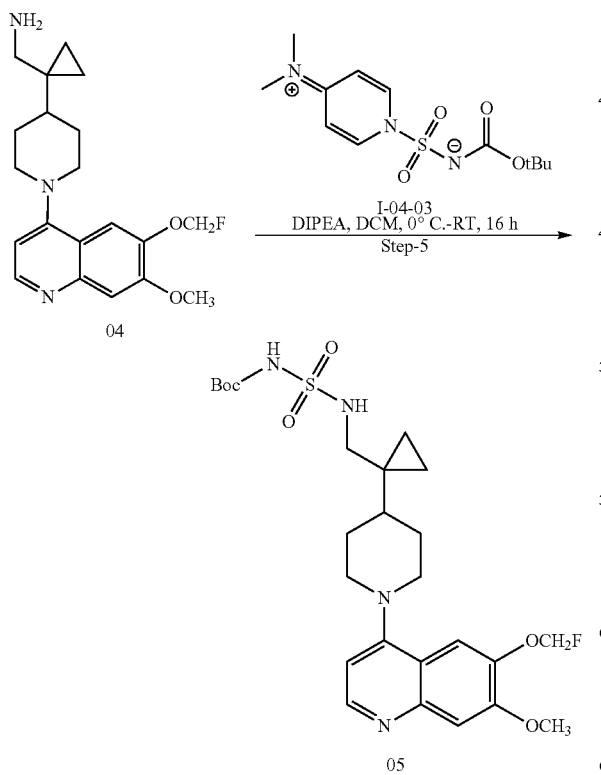

To a stirred solution of (1-(1-(6-(fluoromethoxy)-7-methoxyquinolin-4-yl)piperidin-4-yl)cyclopropyl)methanamine (04) (480 mg; 45% purity, 1.33 mmol, 1 eq) in DCM (5 mL) at 0° C. was added DIPEA (0.4 mL, 2.0 mmol, 1.5 eq), (tert-butoxycarbonyl)((4-(dimethyliminio)pyridin-1(4H)-yl)sulfonyl)amide (I-04-03) (547 mg, 1.60 mmol, 1.2 eq) and stirred at room temperature for 16 h. After completion of reaction by TLC, diluted with water and extracted with DCM (2×50 mL). The combined organic layers were washed with brine solution (40 mL) dried over sodium sulfate and concentrated under reduced pressure to get crude compound. The crude compound was purified by silica gel (60-120 mesh) column chromatography [eluted with EtOAc] to afford tert-butyl (N-((1-(1-(6-(fluoromethoxy)-7-methoxyquinolin-4-yl)piperidin-4-yl)cyclopropyl)methyl)sulfamoyl)carbamate (05) (280 mg, 39% purity) as a yellow solid. TLC system: MeOH:DCM (5:95), R$_f$ value: 0.3; LCMS (m/z): 539.3 (M+H)$^+$.

Synthesis of N-((1-(1-(6-(fluoromethoxy)-7-methoxyquinolin-4-yl)piperidin-4-yl)cyclopropyl)methyl)sulfuricdiamide (I-37)

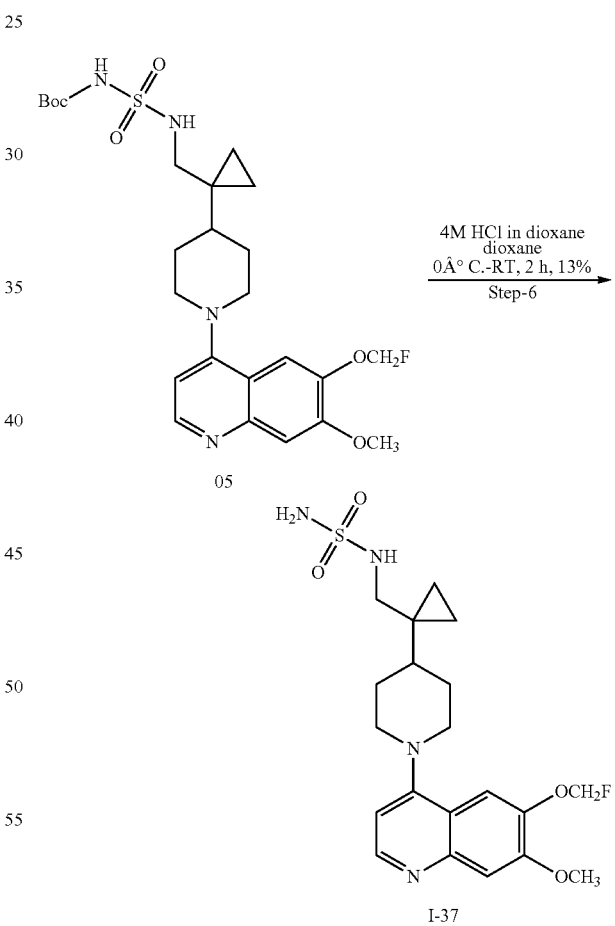

To a stirred solution of tert-butyl (N-((1-(1-(6-(fluoromethoxy)-7-methoxyquinolin-4-yl)piperidin-4-yl)cyclopropyl)methyl)sulfamoyl)carbamate (05) (280 mg, 0.52 mmol, 1 eq) in 1,4 Dioxane (5 mL) at 0° C. was added 4M Dioxane.HCl (1 mL) slowly drop-wise and stirred at room temperature for 2 h. After completion of reaction by TLC, reaction mixture was concentrated to afford crude. The crude compound was purified by prep-HPLC provided I-37 with 95% purity. Material was further triturated with acetonitrile and diethyl ether to afford N-((1-(1-(6-(fluoromethoxy)-7-methoxyquinolin-4-yl)piperidin-4-yl)cyclopropyl)methyl) sulfuricdiamide (I-37) (16 mg, yield: 13%) as an off-white solid. TLC system MeOH:DCM (5:95), $R_f$ value: 0.1; LCMS (m/z): 439.3 (M+H)$^+$, $^1$HNMR (400 MHz, DMSO-d$_6$) δ 8.54 (d, J=6.8 Hz, 1H), 7.59 (s, 1H), 7.39 (s, 1H), 7.08 (d, J=6.8 Hz, 1H), 6.49-6.45 (m, 3H), 6.02 (d, J=53.6 Hz, 2H), 4.08-4.05 (m, 2H), 3.99 (s, 3H), 3.24-3.21 (m, 2H), 2.85-2.83 (m, 2H), 1.81-1.78 (m, 2H), 1.69-1.66 (m, 1H) 1.56-1.50 (m, 2H), 0.40-0.39 (m, 4H).

Experimental Biology

1. ENPP1 Inhibition Assay
Materials:
Assay Buffer: 1 mM CaCl$_2$, 0.2 mM ZnCl$_2$, 50 mM Tris, pH 9.0
Substrate: 8 mM Thymidine 5'-monophosphate p-nitrophenol ester sodium salt (Sigma Cat #T4510)
Enzyme: 5 ng/µL Recombinant Human ENPP-1 Protein (R&D Cat #6136-EN-010) DMSO
96-well clear assay plates
Methods:
An eight point serial dilution of drugs was prepared in 10× in assay buffer with the final assay concentrations starting at 10 µM, 3 µM, 1 µM, 0.3 µM . . . 0 µM. A dilution of DMSO was included as a control. The assay plate was set up as follows with each well in duplicate: 81 µL assay buffer+10 µL ENPP1 inhibitor or DMSO+5 µL Substrate+4 µL Enzyme. Both the enzyme and substrate were added to opposite sides of the well to ensure that there was no interaction until all wells had both components. The plate was then centrifuged gently for 10 seconds, followed by an incubation at 37° C. for 45 minutes. The reaction was quantified by measuring absorbance at 405 nm using the Envision.

IC$_{50}$ Calculation:

IC$_{50}$ values are determined using GraphPad Prism 5 software. The data were entered as an X-Y plot into the software as percent inhibition for each concentration of the drug. The concentration values of the drug were log transformed and the nonlinear regression was carried out using the "sigmoidal dose-response (variable slope)" option within the GraphPad software to model the data and calculate IC$_{50}$ values. The IC$_{50}$ values reported are the concentration of drug at which 50% inhibition was reached.

The results of this experiment are shown in Table 1. Table 1 demonstrates that compounds I-01 through I-04 and I-06 through I-37 were effective in inhibiting the activity of ENPP1.

Thermal Shift Binding Assay.

The Thermal Shift Assays were implemented to study thermal stabilization of ENPP1 proteins upon ENPP1 inhibitor or ligand binding. These assays were used extensively on purified ENPP1 protein. In a 384-well plate, 1 µg of ENPP1 protein was incubated with 100 µM of the corresponding drug for 5 minutes. Each well was exposed to increasing temperatures to determine an unfolding temperature of the protein. As indicated, wells exposed to ENPP1 inhibitors showed increased unfolding temperatures and therefore increase stability of the protein. 2'3' cGAMP was used as a positive control, as it is a substrate of ENPP1.

TABLE 1

List of compound structures, molecular weight, IC$_{50}$ (nM) ENPP1 and Thermal Shift

| Compd. ID | Chemical name | Mol. Wt | ENPP1 (IC$_{50}$) (nM) | *Thermal Shift (Δ TmD) |
|---|---|---|---|---|
| I-01 | N-(2-(1-(6,7-dimethoxyquinazolin-4-yl)piperidin-4-yl)propyl)sulfonamide urea | 410.4 (M + H)$^+$ | 2.79 | 5.5 |
| I-02 | N-(2-(1-(6,7-dimethoxyquinolin-4-yl)piperidin-4-yl)propyl)sulfamoylcarbamate | 409.4 (M + H)$^+$ | 5.95 | 5.0 |
| I-03 | sodium 7-methoxy-4-(4-(2-(sulfamoylamino)ethyl)piperidin-1-yl)quinazolin-6-yl phosphate | 462.2 ([M − 2Na] + H)$^+$ | 2874 | ND |
| I-04 | N-(2-(1-(6,7-dimethoxyquinazolin-4-yl)piperidin-4-yl)ethyl)sulfonamide | 395.48 | 3.91 | 5.8 |
| I-06 | 2,5-dimethoxy-N-(quinolin-3-yl)benzenesulfonamide | 344.39 | 5147 | 1.6 |
| I-07 | N-(2-(1-(7-methoxyquinolin-4-yl)piperidin-4-yl)propyl)aminosulfonamide | 424.52 | 250 | ND |
| I-08 | N-(2-(1-(6-methoxyquinolin-4-yl)piperidin-4-yl)propyl)aminosulfonamide | 414.95 | 224 | ND |
| I-09 | N-(N-(2-(1-(6-hydroxy-7-methoxyquinolin-4-yl)piperidin-4-yl)propyl)sulfuricdiamide formate salt | 440.52 | 1879 | ND |
| I-10 | N-(2-(1-(7-methoxy-6-(2-methoxyethoxy)quinolin-4-yl)piperidin-4-yl)propyl)aninosulfonamide formate salt | 498.5 | 156 | ND |
| I-11 | N-(2-(1-(6-(2-hydroxyethoxy)-7-methoxyquinolin-4-yl)piperidin-4-yl)propyl)aminosulfonamide formate salt | 484.57 | 4486 | ND |

TABLE 1-continued

List of compound structures, molecular weight,
IC$_{50}$ (nM) ENPP1 and Thermal Shift

| Compd. ID | Chemical name | Mol. Wt | ENPP1 (IC$_{50}$) (nM) | *Thermal Shift (Δ TmD) |
|---|---|---|---|---|
| I-12 | N-(N-(2-(1-(7-methoxy-6-morpholinoquinolin-4-yl)piperidin-4-yl)propyl)sulfuricdiamide | 463.59 | 835 | 3.6 |
| I-13 | N-(2-(1-(6,7-dimethoxyquinolin-4-yl)piperidin-4-yl)butyl)sulfuricdiamide | 422.54 | 4.55 | 4.0 |
| I-14 | N-(2-(1-(6,7-dimethoxyquinolin-4-yl)piperidin-4-yl)-2-methylpropyl)sulfuricdiamide | 459 | 35.2 | ND |
| I-15 | N-(2-(1-(6,7-dimethoxyquinolin-4-yl)piperidin-4-yl)propyl)Methyaminosulfonamide | 422.54 | 3482 | ND |
| I-16 | N-cyclopropyl-N-(2-(1-(6,7-dimethoxyquinolin-4-yl)piperidin-4-yl)propyl)aminosulfonamide formate salt | 494.6 | 409 | ND |
| I-17 | 6,7-dimethoxy-4-(1-(aminosulfonyl)-[3,4'-bipiperidin]-1'-yl)quinoline formate salt | 480.58 | 75.79 | ND |
| I-18 | N-(1-cyanocyclopropyl)-1-(6,7-dimethoxyquinolin-4-yl)piperidine-4-carboxamide | 380.45 | >10,000 | ND |
| I-19 | N-(2-(1-(6,7-dimethoxyquinolin-4-yl)piperidin-4-yl)propyl)methanesulfonamide | 407.53 | 3813 | ND |
| I-20 | N-(2-(4-(6,7-dimethoxyquinolin-4-yl)piperazin-1-yl)propyl)aminosulfonamide formate salt | 455.5 | 13.95 | ND |
| I-21 | (R)-N-(2-(4-(6,7-dimethoxyquinolin-4-yl)-2-methylpiperazin-1-yl)ethyl)aminosulfonamide | 455.5 | 344 | ND |
| I-22 | N-(N-((1-(1-(6,7-dimethoxyquinolin-4-yl)piperidin-4-yl)cyclopropyl)methyl)sulfamoyl)acetamide | 466.55 | 9.09 | ND |
| I-23 | N-(N-(1-(6,7-dimethoxyquinolin-4-yl)piperidin-4-yl)sulfuricdiamide formate salt | 412.46 | 897 | ND |
| I-24 | N-(N-cyclopropyl-N-(1-(6,7-dimethoxyquinolin-4-yl)piperidin-4-yl)sulfuricdiamide formate salt | 452.53 | 953 | ND |
| I-25 | N-(N-(2-(1-(6,7-dimethoxyquinazolin-4-yl)piperidin-4-yl)butyl)sulfuricdiamide formate salt | 469.56 | 5.05 | ND |
| I-26 | N-(2-(1-(6,7-dimethoxyquinazolin-4-y)piperidin-4-yl)-2-methylpropyl)sulfuricdiamide formate salt | 469.56 | 2.39 | ND |
| I-27 | N-(N-((1-(1-(6,7-dimethoxyquinazolin-4-yl)piperidin-4-yl)cyclopropyl)methyl)sulfuricdiamide formate salt | 467.54 | 11.49 | ND |
| I-28 | N-(N-(2-(1-(7-methoxy-6-(methoxymethoxy)quinazolin-4-yl)piperidin-4-yl)propyl)sulfuricdiamide | 439.53 | 26.23 | ND |
| I-29 | N-(N-(1-(6,7-dimethoxyquinazolin-4-yl)piperidin-4-yl)sulfuricdiamide formate salt | 413.45 | 420 | ND |
| I-30 | N-(N-cyclopropyl-N-(1-(6,7-dimethoxyquinazolin-4-yl)piperidin-4-yl)sulfuricdiamide | 407.49 | 5606 | ND |
| I-31 | N-((1-(4-(6,7-dimethoxyquinolin-4-yl)piperazin-1-yl)cyclopropyl)methyl)sulfuricdiamide | 518.53 | 23.71 | ND |
| I-32 | N-((1-(4-(6,7-dimethoxyquinazolin-4-yl)piperazin-1-yl)cyclopropyl)methyl)sulfuricdiamide | 422.5 | 55.65 | ND |
| I-33 | N-((1-(4-(7-methoxy-6-(methoxymethoxy)quinazolin-4-yl)piperazin-1-yl)cyclopropyl)methyl)sulfuricdiamide | 452.53 | 157.8 | ND |

TABLE 1-continued

List of compound structures, molecular weight,
IC$_{50}$ (nM) ENPP1 and Thermal Shift

| Compd. ID | Chemical name | Mol. Wt | ENPP1 (IC$_{50}$) (nM) | *Thermal Shift (Δ TmD) |
|---|---|---|---|---|
| I-34 | N-((1-(4-(6-(fluoromethoxy)-7-methoxyquinazolin-4-yl)piperazin-1-yl)cyclopropyl)methyl)sulfuricdiamide | 440.49 | 133 | ND |
| I-35 | N-((1-(1-(7-methoxy-6-(methoxymethoxy)quinazolin-4-yl)piperidin-4-yl)cyclopropyl)methyl)sulfuricdiamide | 451.54 | 49.17 | ND |
| I-36 | N-(2-(1-(7-methoxy-6-(methoxymethoxy)quinazolin-4-yl)piperidin-4-yl)-2-methylpropyl)sulfuricdiamide | 453.56 | 52.62 | ND |
| I-37 | N-((1-(1-(6-(fluoromethoxy)-7-methoxyquinolin-4-yl)piperidin-4-yl)cyclopropyl)methyl)sulfuricdiamide | 438.52 | 1.09 | ND |

*ND: Not Determined

Prophetic Pharmaceutical Composition Examples

"Active ingredient" as used throughout these examples relates to one or more of the compounds of the invention, or a pharmaceutically acceptable salt, solvate, polymorph, hydrate and the stereochemically isomeric form thereof. The following examples of the formulation of the compounds of the present invention in tablets, suspension, injectables and ointments are prophetic.

Typical examples of recipes for the formulation of the invention are as given below. Various other dosage forms can be applied herein such as a filled gelatin capsule, liquid emulsion/suspension, ointments, suppositories or chewable tablet form employing the disclosed compounds in desired dosage amounts in accordance with the present invention. Various conventional techniques for preparing suitable dosage forms can be used to prepare the prophetic pharmaceutical compositions, such as those disclosed herein and in standard reference texts, for example the British and US Pharmacopoeias, Remington's Pharmaceutical Sciences (Mack Publishing Co.) and Martindale The Extra Pharmacopoeia (London The Pharmaceutical Press). The disclosure of this reference is hereby incorporated herein by reference.

a. Pharmaceutical Composition for Oral Administration

A tablet can be prepared as follows:

| Component | Amount |
|---|---|
| Active ingredient | 10 to 500 mg |
| Lactose | 100 mg |
| Crystalline cellulose | 60 mg |
| Magnesium stearate | 5 |
| Starch (e.g. potato starch) | Amount necessary to yield total weight indicated below |
| Total (per capsule) | 1000 mg |

Alternatively, about 100 mg of a disclosed compound, 50 mg of lactose (monohydrate), 50 mg of maize starch (native), 10 mg of polyvinylpyrrolidone (PVP 25) (e.g. from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is moulded using a customary tablet press (e.g. tablet format: diameter 8 mm, curvature radius 12 mm). The moulding force applied is typically about 15 kN.

Alternatively, a disclosed compound can be administered in a suspension formulated for oral use. For example, about 100-5000 mg of the desired disclosed compound, 1000 mg of ethanol (96%), 400 mg of xanthan gum, and 99 g of water are combined with stirring. A single dose of about 10-500 mg of the desired disclosed compound according can be provided by 10 ml of oral suspension.

In these Examples, active ingredient can be replaced with the same amount of any of the compounds according to the present invention, in particular by the same amount of any of the exemplified compounds. In some circumstances it may be desirable to use a capsule, e.g. a filled gelatin capsule, instead of a tablet form. The choice of tablet or capsule will depend, in part, upon physicochemical characteristics of the particular disclosed compound used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound per tablet for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

b. Pharmaceutical Composition for Injectable Use

A parenteral composition can be prepared as follows:

| Component | Amount |
|---|---|
| Active ingredient | 10 to 500 mg |
| Sodium carbonate | 560 mg* |

209
-continued

| Component | Amount |
|---|---|
| Sodium hydroxide | 80 mg* |
| Distilled, sterile water | Quantity sufficient to prepare total volumen indicated below. |
| Total (per capsule) | 10 ml per ampule |

*Amount adjusted as required to maintain physiological pH in the context of the amount of active ingredient, and form of active ingredient, e.g. a particular salt form of the active ingredient.

Alternatively, a pharmaceutical composition for intravenous injection can be used, with composition comprising about 100-5000 mg of a disclosed compound, 15 g polyethyleneglycol 400 and 250 g water in saline with optionally up to about 15% Cremophor EL, and optionally up to 15% ethyl alcohol, and optionally up to 2 equivalents of a pharmaceutically suitable acid such as citric acid or hydrochloric acid are used. The preparation of such an injectable composition can be accomplished as follows: The disclosed compound and the polyethyleneglycol 400 are dissolved in the water with stirring. The solution is sterile filtered (pore size 0.22 μm) and filled into heat sterilized infusion bottles under aseptic conditions. The infusion bottles are sealed with rubber seals.

In a further example, a pharmaceutical composition for intravenous injection can be used, with composition comprising about 10-500 mg of a disclosed compound, standard saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid. Preparation can be accomplished as follows: a desired disclosed compound is dissolved in the saline solution with stirring. Optionally Cremophor EL, ethyl alcohol or acid are added. The solution is sterile filtered (pore size 0.22 μm) and filled into heat sterilized infusion bottles under aseptic conditions. The infusion bottles are sealed with rubber seals.

In this Example, active ingredient can be replaced with the same amount of any of the compounds according to the present invention, in particular by the same amount of any of the exemplified compounds.

The amount of a disclosed compound per ampule for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 1000 mg of a disclosed compound per dosage unit.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

210

What is claimed is:

1. A compound selected from the group consisting of:

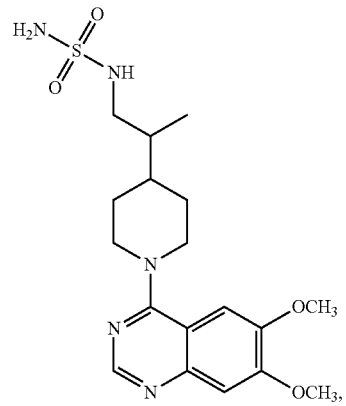

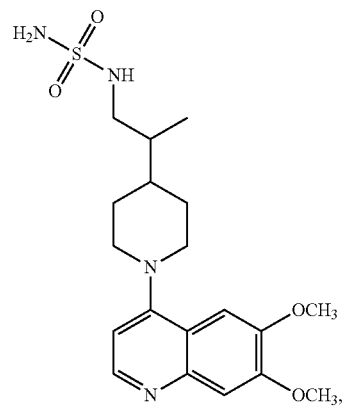

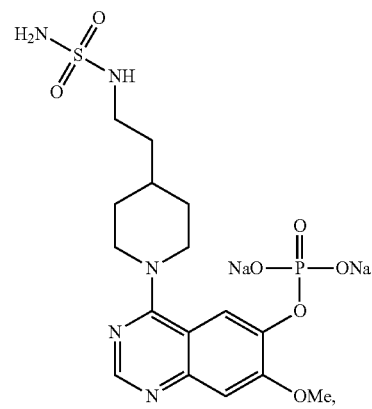

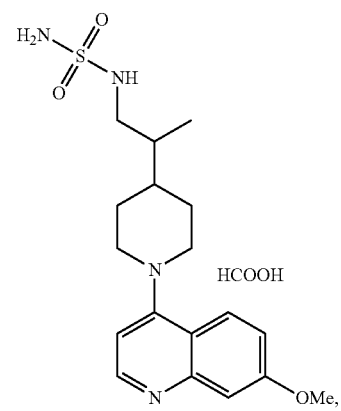

211
-continued
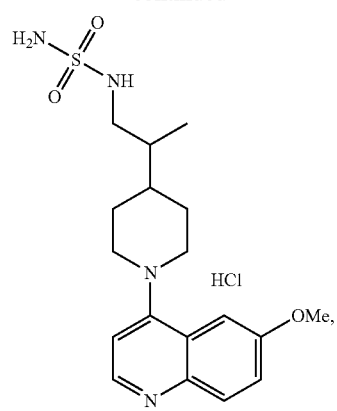
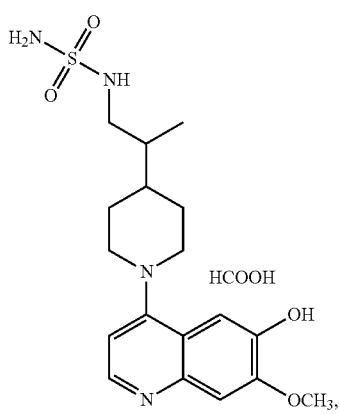
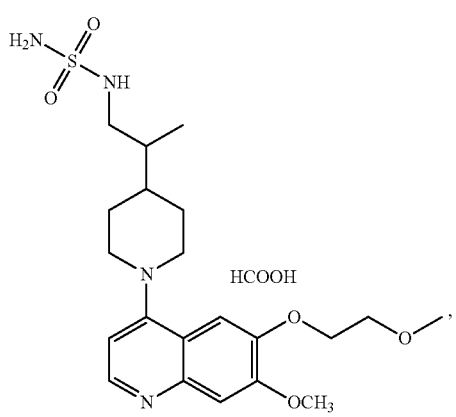
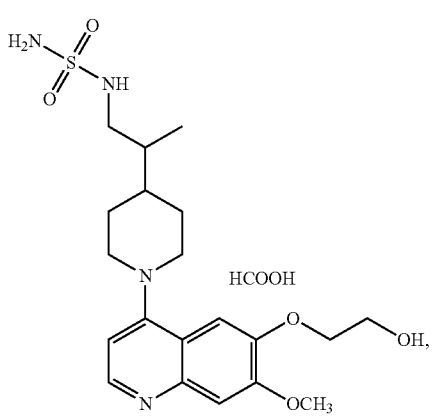
212
-continued
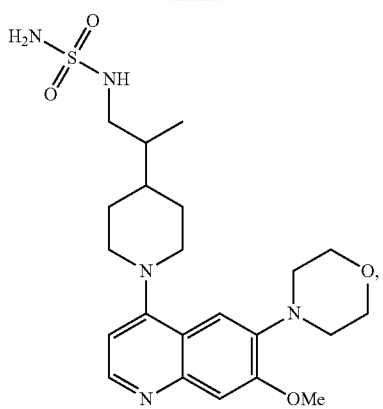
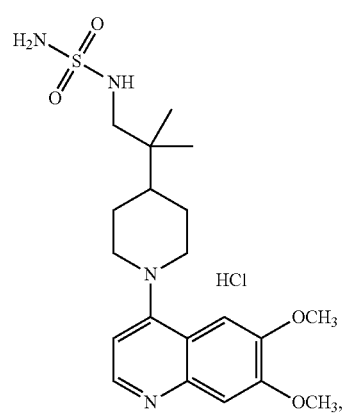
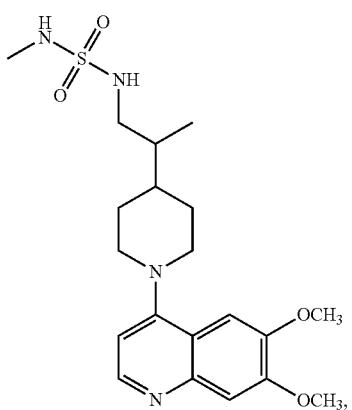
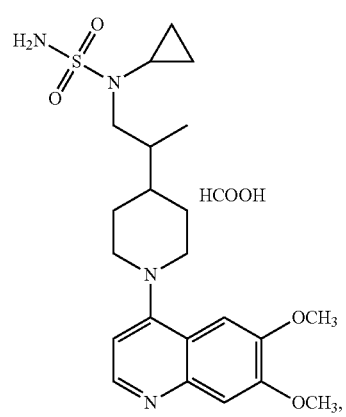

213
-continued
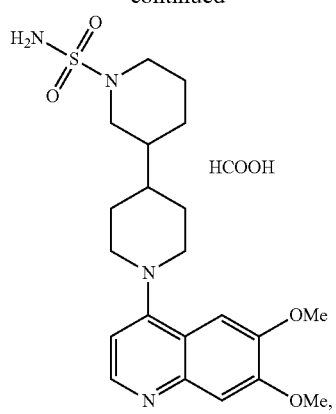
HCOOH
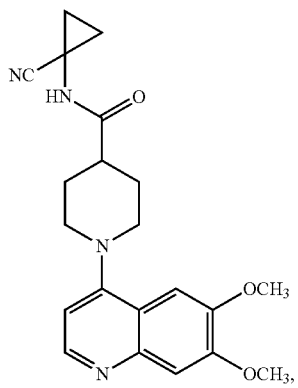
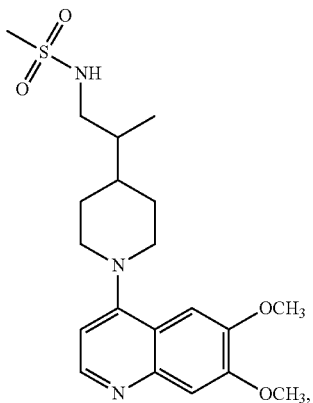
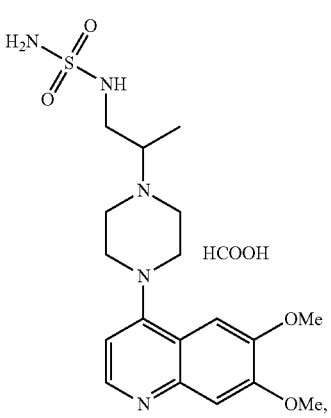
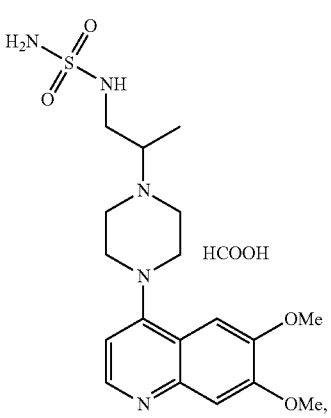
HCOOH
214
-continued
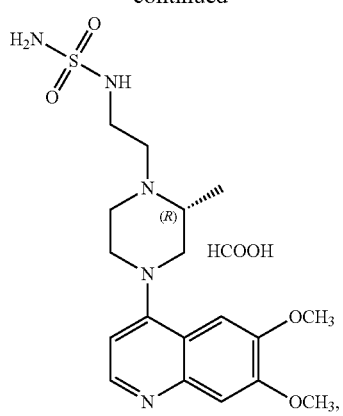
HCOOH
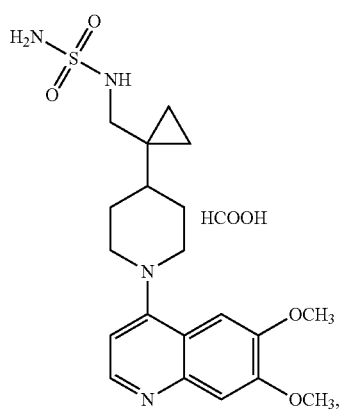
HCOOH
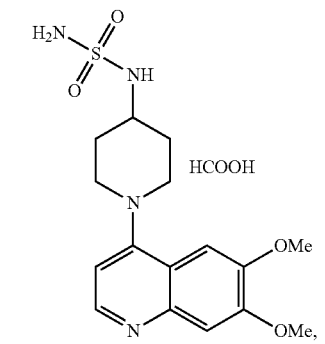
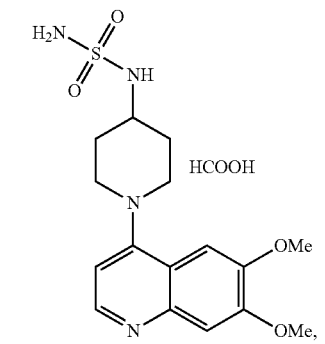
HCOOH
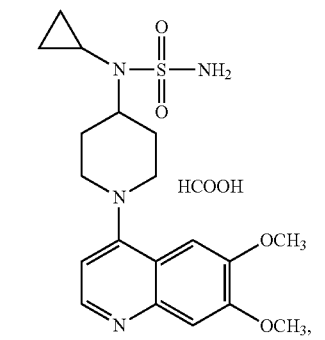
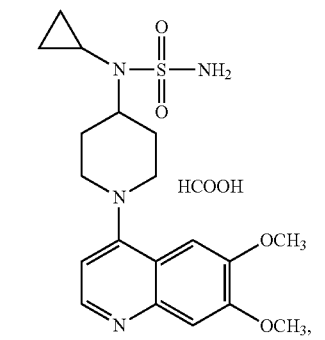
HCOOH
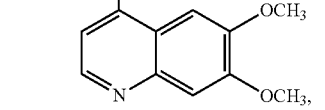

215
-continued
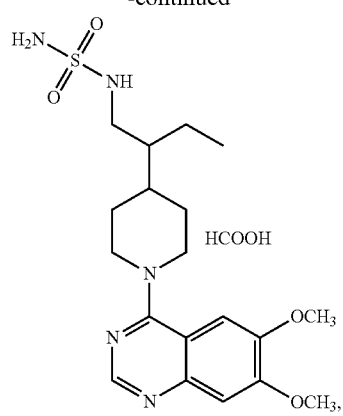
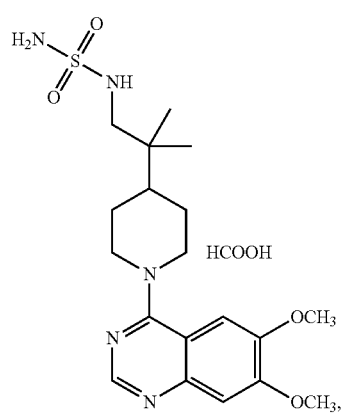
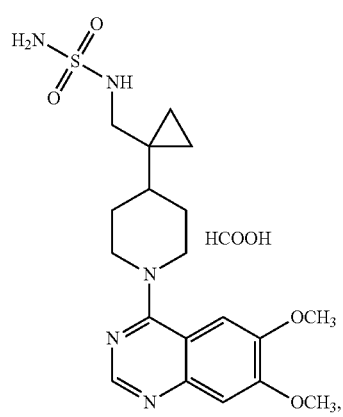
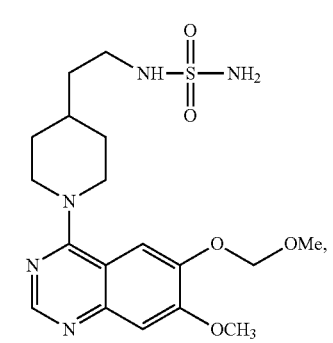
216
-continued
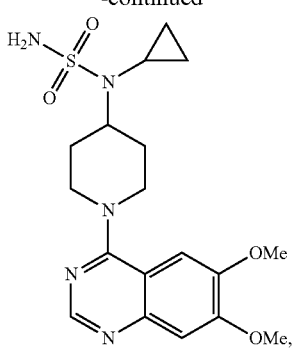
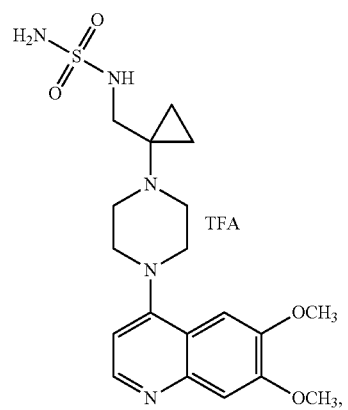
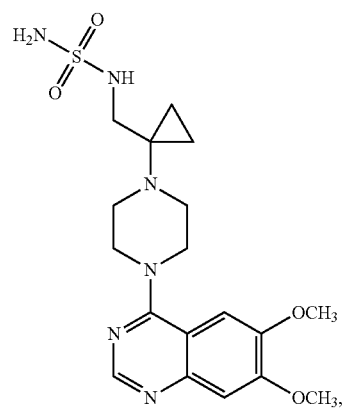
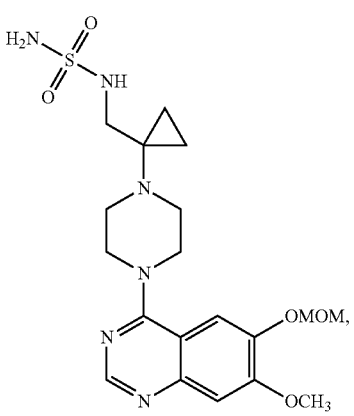

-continued

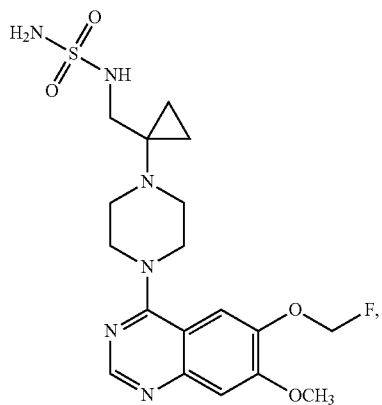

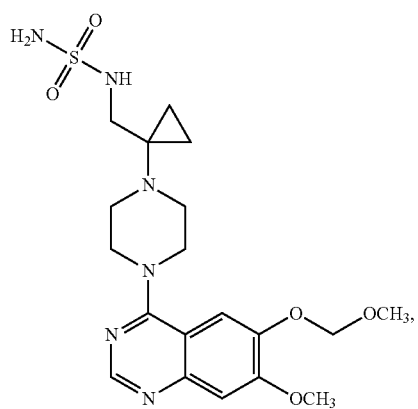

-continued

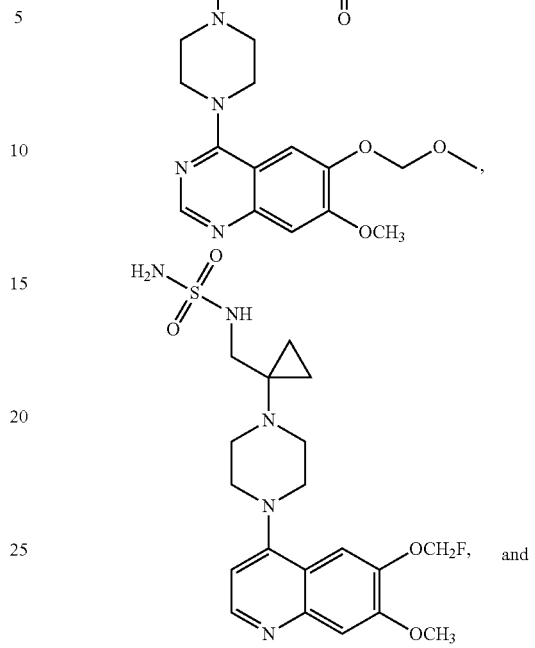

pharmaceutically acceptable salts thereof.

2. A pharmaceutical composition comprising a therapeutically effective amount of a compound of claim 1 and a pharmaceutically acceptable carrier.

3. A method for treating cancer in a mammal wherein the cancer is characterized by overexpression of ENPP1, the method comprising the step of administering to the mammal a therapeutically effective amount of a compound of claim 1.

* * * * *